US006656731B1

(12) United States Patent
Eckstein et al.

(10) Patent No.: US 6,656,731 B1
(45) Date of Patent: Dec. 2, 2003

(54) NUCLEIC ACID CATALYSTS WITH ENDONUCLEASE ACTIVITY

(75) Inventors: Fritz Eckstein, Gottingen (DE); Janos Ludwig, Gottingen (DE); Leonid Beigelman, Longmont, CO (US)

(73) Assignees: Max Planck Gesellschaft zur Forderung der Wissenschaften E.V., Munich (DE); Sirna Therapeutics, Boulder, CO (US)

( * ) Notice: Subject to any disclaimer, the term of this patent is extended or adjusted under 35 U.S.C. 154(b) by 0 days.

(21) Appl. No.: 09/479,005

(22) Filed: Jan. 7, 2000

Related U.S. Application Data

(63) Continuation-in-part of application No. 09/444,209, filed on Nov. 19, 1999, which is a continuation-in-part of application No. 09/159,274, filed on Sep. 22, 1998, now Pat. No. 6,127,173.
(60) Provisional application No. 60/059,473, filed on Sep. 22, 1997.

(51) Int. Cl.[7] .............................. C12N 5/00; C12N 5/02; C12N 15/00; C12Q 1/68; C07H 21/04

(52) U.S. Cl. ........................... 435/375; 435/6; 435/91.1; 435/91.31; 435/320.1; 435/325; 536/23.1; 536/23.2; 536/24.5

(58) Field of Search ..................... 435/6, 91.31, 91.1, 435/325, 375, 91.5, 320.1; 536/23.1, 23.2, 24.5; 514/44

(56) References Cited

U.S. PATENT DOCUMENTS

| 5,334,711 A | 8/1994 | Sproat et al. ............... 536/24.5 |
| 5,610,052 A | 3/1997 | Thompson et al. ............ 514/44 |
| 5,624,803 A | 4/1997 | Noonberg et al. ............. 435/6 |
| 5,801,158 A | 9/1998 | Thompson et al. ......... 435/366 |

FOREIGN PATENT DOCUMENTS

| WO | WO8902439 | 3/1989 |
| WO | WO9103162 | 3/1991 |
| WO | WO9118624 | 12/1991 |
| WO | WO9118625 | 12/1991 |
| WO | WO9118913 | 12/1991 |
| WO | WO9207065 | 4/1992 |
| WO | WO9315187 | 8/1993 |
| WO | WO9323569 | 11/1993 |
| WO | WO9402595 | 2/1994 |
| WO | WO9506731 | 3/1995 |
| WO | WO9511910 | 5/1995 |
| WO | WO9610390 | 4/1996 |
| WO | WO9610391 | 4/1996 |
| WO | WO9610392 | 4/1996 |
| WO | WO9618736 | 6/1996 |
| WO | WO9710328 | 3/1997 |
| WO | WO9726270 | 7/1997 |

OTHER PUBLICATIONS

Stanley Crooke, Antisense Research and Applications, Chapter 1, Basic Principles of Antisense Therapeutics, Springer–Verlag Press, Berlin, Heidelberg, New York, p. 3, Jul. 1998.*

Abelson, "Pharmaceuticals Based on Biotechnology," *Science* 273:719 (1996).

Baidya, "A Kinetic and Thermodynamic Analysis of Cleavage Site Mutations in the Hammerhead Ribozyme," *Biochemistry* 36, 1108–14 (1997).

Barbacid et al, "ras Genes," *Annu. Rev. Biochem.* 56:779–827 (1997).

Bartel and Szostak, "Isolation of New Ribozymes From a Large Pool of Random Sequences," *Science* 261:1411–1418 (1993).

Beaucage and Iyer, "The Functionalization of Oligonucleotides Via Phosphoramidite Derivatives," *Tetrahedron* 49:1925–1963 (1993).

Beaudry and Joyce, "Directed Evolution of an RNA Enzyme," *Science* 257:635–641 (1992).

Beaudry and Joyce, "Minimum Secondary Structure Requirements for Catalytic Activity of a Self–Splicing Group I Intron," *Biochemistry* 29:6534–6539 (1990).

Been et al., "Secondary Structure of the Self–Cleaving RNA of Hepatitis Delta Virus: Applications of Catalytic RNA Design," *Biochemistry* 31:11843–11852 (1992).

Beigleman et al., "Chemical Modification of Hammerhead Ribozymes," *J. Biol. Chem.* 270:25702–25708 (1995).

Beigelman et al., "Synthesis of 1–Deoxy–D–Ribofuranose Phosphoramidite & The Incorporation of Abasic Nucleotides in Stem–Loop II of a Hammerhead Ribozyme," *Bioorganic & Medicinal Chemistry Letters* 4:1715–1720 (1994).

Bellon et al., "Amino–Linked Ribozymes: Post–Synthetic Conjugation of Half–Ribozymes," *Nucleosides & Nucleotides*, 16:951–954 (1997).

Bellon et al., "Post–synthetically Ligated Ribozymes: An Alternative Approach to Iterative Solid Phase Synthesis," *Bioconjugate Chem.* 8:204–212 (1997).

Benseler et al., "Hammerhead–like Molecules Containing Non–Nucleoside Linkers Are Active RNA Catalysts," *J. Am. Chem. Soc.* 115:8483–8484 (1993).

Breaker and Joyce, "Inventing and improving ribozyme function: rational design versus iterative selection methods," *TIBTECH* 12:268–275 (1994).

Breaker, "Are engineered proteins getting competition from RNA?" *Current Opinion in Biotechnology* 7:442–448 (1996).

(List continued on next page.)

Primary Examiner—Sean McGarry
Assistant Examiner—Janet L. Epps-Ford
(74) Attorney, Agent, or Firm—McDonnell Boehnen Hulbert & Berghoff

(57) ABSTRACT

The present invention relates to nucleic acid molecules with new motifs having catalytic activity, methods of syntheses and uses thereof.

50 Claims, 10 Drawing Sheets

OTHER PUBLICATIONS

Breaker, "DNA Enzymes," *Nature Biotechnology* 15:427–431 (1997).

Burgin et al., "Chemically Modified Hammerhead Ribozymes with Improved Catalytic Rates," *Biochemistry* 35:14090–14097 (1996).

Caruthers et al., "Chemical Synthesis of Deoxyoligonucleotides and Deoxyoligonucleotide Analogs," *Methods in Enzymology* 211:3–19 (1992).

Cech, "Ribozyme Engineering," *Current Opinion in Structural Biology* 2:605–609 (1992).

Cech, "Ribozymes and Their Medical Implications," *JAMA* 260:3030–3034 (1988).

Chapman and Szostak, "In vitro Selection of Catalytic RNA's," *Current Opinion in Structural Biology* 4:618–622 (1994).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV-1 Isolates," *Nucleic Acids Research* 20:4581–4589 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Christoffersen and Marr, "Riobozymes as Human Therapeutic Agents," *J. Med. Chem.* 38:2023–2037 (1995).

Christoffersen et al., "Application of computational technologies to ribozyme biotechnology products," *Journal of Molecular Structure (Theochem)* 311:273–284 (1994).

Cload and Schepartz, "Polyether Tetherd Oligonucleotide Probes," *J. Am. Chem. Soc.*. 113:6324–6326 (1991).

Couture and Stinchcomb, "Anti–gene therapy: the use of ribozymes to inhibit gene function," *Trends In Genetics* 12:510–515 (1996).

Dropulic et al., "Functional Characterization of a U5 Ribozyme: Intracellular Suppression of Human Immunodeficiency Virus Type I Expression," *Journal of Virology* 66:1432–1441 (1992).

Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353–6359 (1990).

Ellington et al., "In Vitro selection of RNA molecules that bind specific ligands," *Nature* 346:818–822 (1990).

Ellington et al., "Ribozymes in Wonderland," *Science* 276:546–547 (1997).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Ferentz et al., "Disulfied Cross–Linked Oligonucleotides," *J. Am. Chem. Soc.* 113:4000–4002 (1991).

Forster and Symons, "Self–Cleavage of Plus and Minus RNAs of a Virusoid and a Structural Model for the Active Sites," *Cell* 49:211–220 (1987).

Frank et al., "In vitro selection of Rnase P RNA reveals optimized catalytic activity in a highly conserved structural domain," *RNA* 2:1179–1188 (1996).

Freier et al., "Improved free–energy parameters for predictions of RNA duplex stability," *Proc. Natl. Acad. Sci. USA* 83:9373–9377 (1986).

Gao et al., "Cytoplasmic Expression of a Reporter Gene by Co–Delivery of T7 RNA Polymerase and T7 Promoter Sequence with Cationic Liposomes," *Nucl. Acids Res.* 21:2867–2872 (1993).

Gold et al., Diversity of Oligonucleotide Functions, *Annu. Rev. Biochem.* 64:763–797 (1995).

Good et al., "Expression of small, theraputic RNAs in human nuclei," *Gene Therapy* 4:45–54 (1997).

Guo and Collins, "Efficient trans–cleavage of a stem–loop RNA substrate by a ribozyme derived from Neurospora VS RNA," *EMBO J.* 14:368–276 (1995).

Hendry et al., "Using linkers to investigate the spatial separation of the conserved nucleotides $A_9$ and $G_{12}$ in the Hammerhead Ribozyme," *Biochimica et Biophysica Acta* 1219:405–412 (1994).

Hertel et al., "A Kinetic Thermodynamic Framework for the Hammerhead Ribozyme Reaction," *Biochemistry* 33:374–3385 (1994).

Hertel et al., "Numbering System for the Hammerhead," *Nucl. Acids Res.* 20:3252 (1992).

Igloi et al., "Interaction of tRNAs and of Phosphorothioate–Substituted Nucleic Acids with an Organomercurial, Probing the Chemical Environment of Thiolated Residues by Affinity Electrophoresis," *Biochemistry* 27:3842–3849 (1988).

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995).

Ishizaka et al., "Isolation of Active Ribozymes from an RNA Pool of Random Sequences Using an Anchored Substrate RNA," *Biochemical and Biophysical Research Communication* 214(2):403–409 (1995).

Izant and Weintraub, "Constitutive and Conditional Suppression of Exogenous and Endogeneous Genes by Anti–Sense RNA," *Science* 229:345–352 (1985).

Jaeger et al., "Improved Predictions of Secondary Structures for RNA," *Proc. Natl. Acad. Sci. USA* 86:7706–7710 (1989).

Hodgson et al., "Probing the hammerhead robyzme structure with ribonucleases," *Nucleic Acids Research* 22:1620–1625 (1994).

Jaschke et al., "Automated Incorporation of Polyethylene Glycol into Synthetic Oligonucleotides," *Tetrahedron Letters* 34:301–304 (1993).

Jeffries and Symons, "A Catalytic 13–mer Ribozyme," *Nucleic Acids Research* 17:1371–1377 (1989) (also referred to as Jeffries).

Joseph and Burke, "Optimization of an Anti–HIV Hairpin Ribozyme by in Vitro Selection," *J. Biol. Chem.* 268:24515–24518 (1993).

Joseph et al., "Substrate selection rules for the hairpin ribozyme determined by in vitro selection, mutation, and analysis of mismatched substrates," *Genes & Development* 7:130–138 (1993).

Joyce et al., "Amplification, mutation and selection of catalytic RNA," *Gene* 82:83–87 (1989).

Joyce, "Directed Molecular Evolution," *Scientific American* 267:90–97 (1992).

Kashani–Sabet et al., "Reversal of the Malignant Phenotype by an Anti–ras Ribozyme," *Antisense Research & Development* 2:3–15 (1992).

Kumar and Ellington, "Artificial evolution and natural ribozymes," *FASEB J.* 9:183–1195 (1995).

Lasic and Needham "The 'Stealth' Liposome: A Protypical Biomaterial," *Chemical Reviews* 95:2601–2627 (1995).

Lasic and Papahadjopoulos, "Liposomes Revisited," *Science* 267:1275–1276 (1995).

L'Huillier et al., "Cytoplasmic Delivery of Ribozymes Leads to Efficient Reduction in α–Lactalbumin mRNA Levels in C1271 Mouse," *EMBO J.* 11:4411–4418 (1992).

Lieber et al., "Stable High–Level Gene Expression in Mammalian Cells by T7 Phase RNA Polymerase," *Methods in Enzymol.* 217:47–66 (1993).

Limbach et al., "Summary: the modified nucleosides of RNA," *Nucleic Acids Research* 22(12):2183–2196 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004(1993).

Liu et al., "Cationic Liposome–mediated Intravenous Gene Delivery," *J. Biol. Chem.* 270(42):24864–24870 (1995).

Long and Uhlenbeck, "Kinetic characterization of intramolecular and intermolecular hammerhead RNAs with stem II deletions," *Proc. Natl. Acad. Sci. USA* 91:6977–6981 (1994).

Loria and Pan, "Domain Structure of the ribozyme from eubacterial ribonuclease P," *RNA* 2:551–563 (1996).

Ma et al., "Design and Synthesis of RNA Miniduplexes via a Synthetic Linker Approach. 2. Generation of Covalently Closed, Double–Stranded Cyclic HIV–1 TAR RNA Analogs with High Tat–Binding Affinity," *Nucleic Acids Research* 21:2585–2589 (1993).

Ma et al., "Design and Synthesis of RNA Miniduplexes via a Synthetic Linker Approach," *Biochemistry* 32:1751–1758 (1993).

McCall et al., "Minimal sequence requirements for ribozyme activity," *Proc. Natl. Acad. Sci. USA* 89:5710–5714 (1992).

McCurdy et al., "Deoxyoligonucleotides with Inverted Polarity: Synthesis and Use in Triple–Helix Formation" *Nucleosides Nucleotides* 10:287–290 (1991).

McGarry and Lindquist, "Inhibition of heat shock protein synthesis by heat–inducible antisense RNA," *Proc. Natl. Acad. Sci. USA* 83:399–403 (1986).

Michels and Pyle, "Conversion of a Group II Intron into a New Multiple–Turnover Ribozyme that Selectively Cleaves Oligonucleotides: Elucidatin of Reaction Mechanism and Structure/Function Relationships," *Biochemistry* 34:2965–2977 (1995).

Milligan and Uhlenbeck, "Synthesis of Small RNAs Using T7 RNA Polymerase," *Methods Enzymol.* 180:51–62 (1989).

Moore and Sharp, "Site–Specific Modification of Pre–mRNA: The 2'–Hydroxyl Groups at the Splice Sites," *Science* 256:992–996 (1992).

Nakamaye and Eckstein, "AUA–Cleaving Hammerhead Ribozymes: Attempted Selection for Improved Cleavage," *Biochemistry* 33:1271–1277 (1994).

Nathans and Smith, "Restriction Endonucleases in the Analysis and Restructuring of DNA Molecules," *Ann. Rev. Biochem.* 44:273–293 (1975).

Noonberg et al., In vivo generation of highly abundant sequence–specific oligonucleotides for antisense and triplex gene regulation, *Nucleic Acids Research* 22(14):2830–2836 (1994).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Oku et al., "Real–time analysis of liposomal trafficking in tumor–bearing mice by use of positron emission tomography," *Biochimica et Biophysica Acta* 1238:86–90 (1995).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914–9921 (1991).

Orgel, "Selection in vitro," *Proc: R. Soc. London B.* 205:435–442 (1979).

Pan et al., "Properties of an In Vitro Selected Pb$^{2+}$ Cleavage Motif," *Biochemistry* 33:9561–9565 (1994).

Perreault et al., "Mixed Deoxyribo–and Ribo–Oligonucleotides with Catalytic Activity," *Nature* 344:565–567 (1990).

Pieken et al., "Kinetic Characterization of Ribonuclease–Resistant 2'–Modified Hammerhead Ribozymes," *Science* 253:314–317 (1991).

Pley et al., "Three–dimensional structure of a hammerhead ribozyme," *Nature* 372:68–74 (1994).

Richardson and Schepartz, "Tethered Oligonucleotide Probes. A Strategy for the Recognition of Structured RNA," *J. Am. Chem. Soc.* 113:5109–5111 (1991).

Robertson and Joyce. 1990. "Selection in vitro of an RNA Enzyme that Specifically Cleaves Single–Stranded DNA," *Nature* 344:467–468.

Ruffner et al., "Sequence Requirements of the Hammerhead RNA Self–Cleavage Reaction," *Biochemistry* 29:10695–10702 (1990).

Sarver et al., "Ribozymes as Potential Anti–HIV–1 Therapeutic Agents" *Science* 247:1222–1225 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucleic Acids Research* 18:5433–5441 (1990).

Scott et al., "Capturing the Structure of a Catalytic RNA Intermediate: The Hammerhead Ribzoyme," *Science* 274:2065–2069 (1996).

Seela and Kaiser, "Oligodeoxyribonucleotides containing 1,3–propanediol as nucleoside substitute," *Nucleic Acids Research* 15:3113–3129 (1987).

Shabarova et al., "Chemical ligation of DNA: The first non–enyzmatic assembly of a biologically active gene," *Nucleic Acids Research* 19:4247–4251 (1991).

Sugiyama et al., "Catalytic activities of hammerhead ribozymes with a triterpenoid linker insteade of stem/loop II," *FEBS Letters* 392:215–219 (1996).

Sullenger and Cech, "Tethering Ribozymes to a Retroviral Packaging Signal for Destruction of Viral RNA," *Science* 262:1566–1569 (1993).

Szostak et al., "Ch. 20—In Vitro Selection of Functioal RNA Sequences," in *The RNA World*, edited by Gesteland and Atkins, Cold Spring Harbor Laboratory Press, pp. 511–533 (1993).

Szostak, "In Vitro Genes," *TIBS* 17:89–93 (1993).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tang et al., "Examination of the Catalytic Fitness of the Hammerhead Ribozyme by in vitor Selection," *RNA* 3:914–925 (1997).

Thompson et al., "Improved accumulation and activity of ribozymes expressed from a tRNA–based RNA polymerase III promoter," *Nucleic Acids Research* 23:2259–2268 (1995).

Thomson et al., "In vitro selection of hammerhead ribozymes containing a bulged nucleotide in stem II," *Nucl. Acids Res.* 24:4401–4406 (1996).

Tuerk et al., "Systematic Evolution of Ligands by Exponential Enrichment: RNA Ligands to Bacteriophage T4 DNA Polymerase," *Science* 249:505–510 (1990).

Turner et al., "Free Energy Increments for Hydrogen Bonds in Nucleic Acid Base Pairs," *J. Am. Chem. Soc.* 109:3783–3785 (1987).

Turner et al., "Improved Parameters for Prediction of RNA Structure," *Cold Spring Harbor Symposia on Quantitative Biology*, vol. LII, pp. 123–133 (1987).

Usman and Cedergren, "Exploiting the chemical synthesis of RNA," *TIBS* 17:334–339 (1992).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Syposium Series* 31:163–164 (1994).

Vaish et al, "In vitro Selection of a Purine Nucleotide–Specific Hammerhead–Like Ribozyme," *Proc. Natl. Acad. Sci.* 95:2158–2162 (1998).

Vaish et al., "Isolation of Hammerhead Ribozymes with Altered Core Sequences by in Vitro Selection," *Biochemistry* 36:6495–6501 (1997).

Ventura et al., "Activation of HIV–Specific Ribozyme Activity by Self–Cleavage," *Nucleic Acids Research* 21:3249–3255 (1993).

Weerasinghe et al., "Resistance of Human Immunodeficiency Virus Type I (HIV–1) Infection in Human $CD4^+$ Lymphocyte–Derived Cell Lines Conferred by Using Retroviral Vectors Expressing an HIV–1 RNA–Specific Ribozyme," *Journal of Virology* 65:5531–5534 (1994).

Wincott et al., "Synthesis, deprotection, analysis and purification of RNA and ribozymes," *Nucleic Acids Research* 23(14):2677–2684 (1995).

Wincott et al., "A Practical Method for the Production of RNA and Ribozymes," *Methods in Molecular Biology* 74:59–69 (1997).

Wright et al., "Continuous in Vitro Evolution of Catalytic Function," *Sci.* 276:614–617 (1997).

Yarus, "A Specific Amino Acid Binding Site Composed of RNA," *Science* 240:1751–1758 (1988).

Yu et al., "A Hairpin Ribozyme Inhibits Expression of Diverse Strains of Human Immunodeficiency Virus Type 1," *Proc. Natl. Acad. Sci. USA* 90:6340–6344 (1993).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4259–4537 (1990).

\* cited by examiner

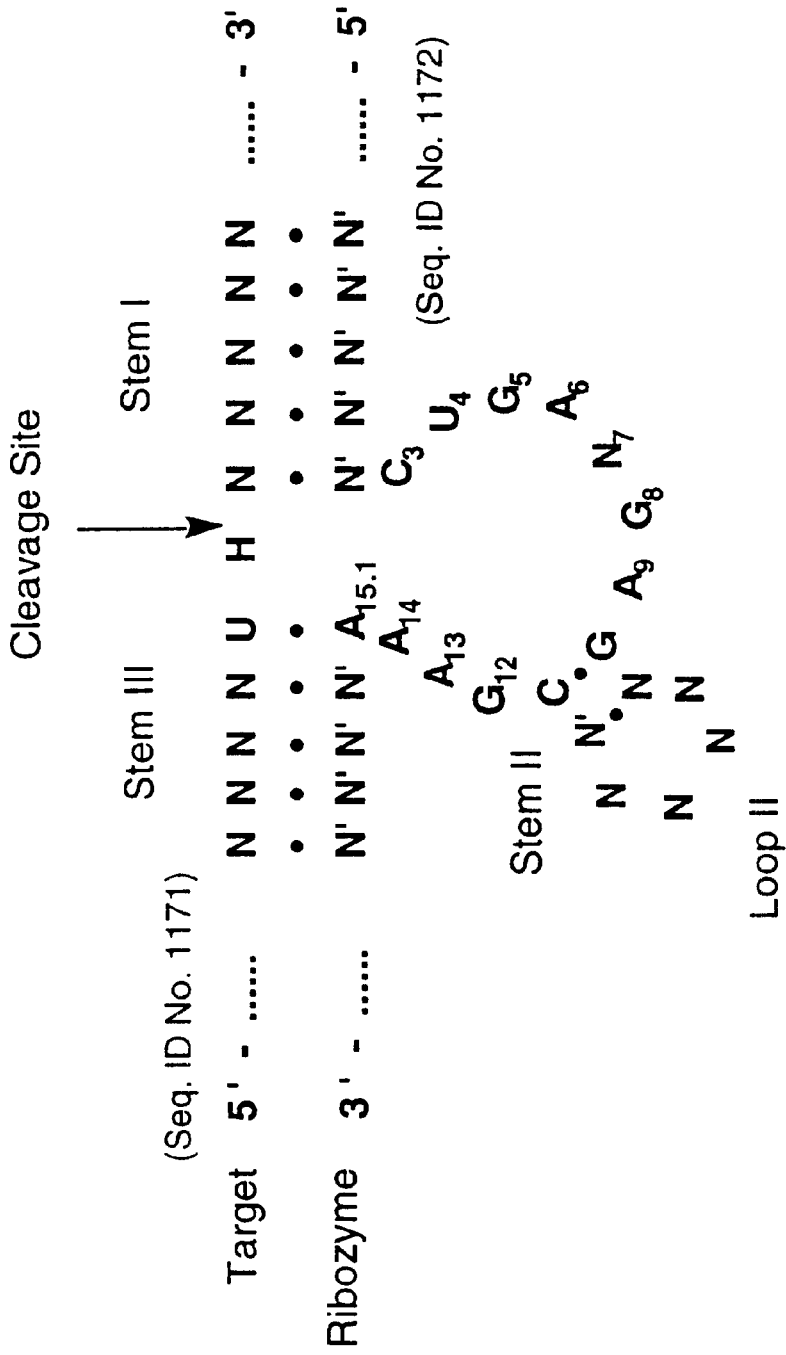
*Figure 1A: Hammerhead Ribozyme*

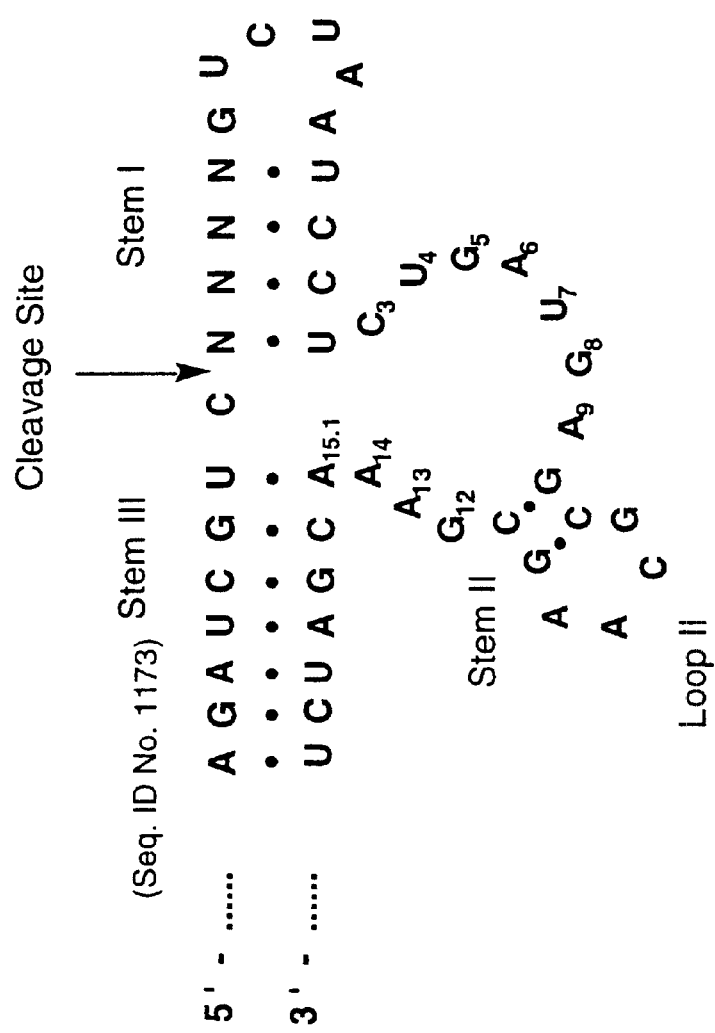
*Figure 1B: Self-Cleaving Hammerhead Ribozyme*

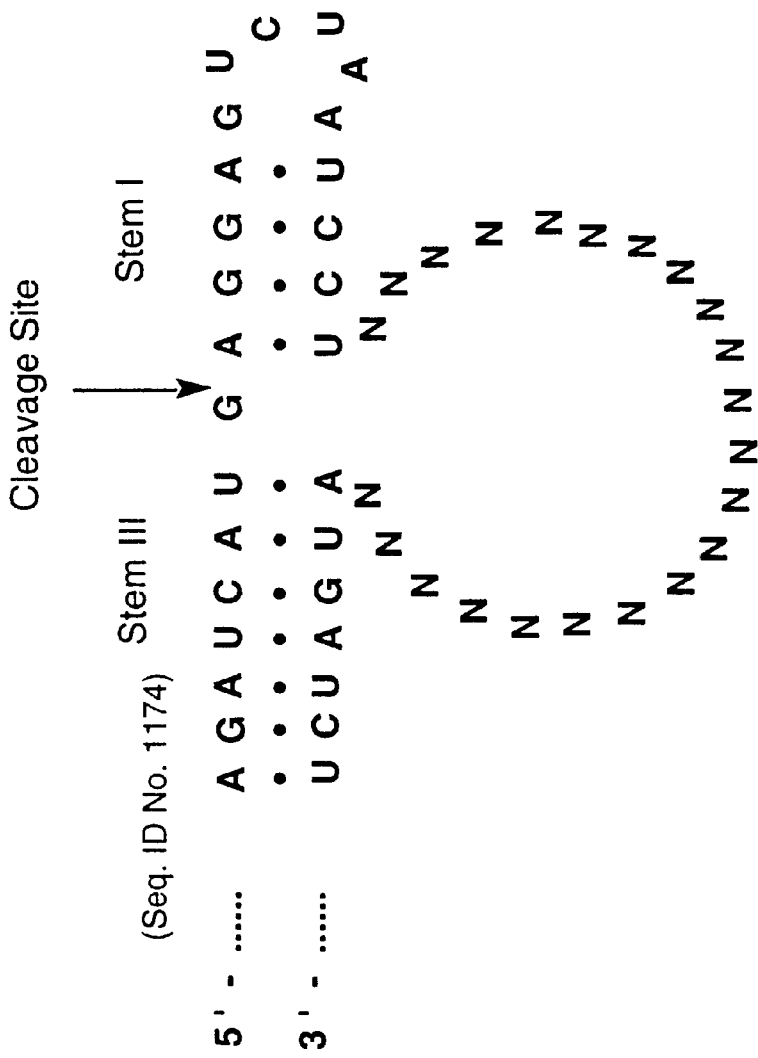
*Figure 1C: Random Pool of Self-Cleaving RNA*

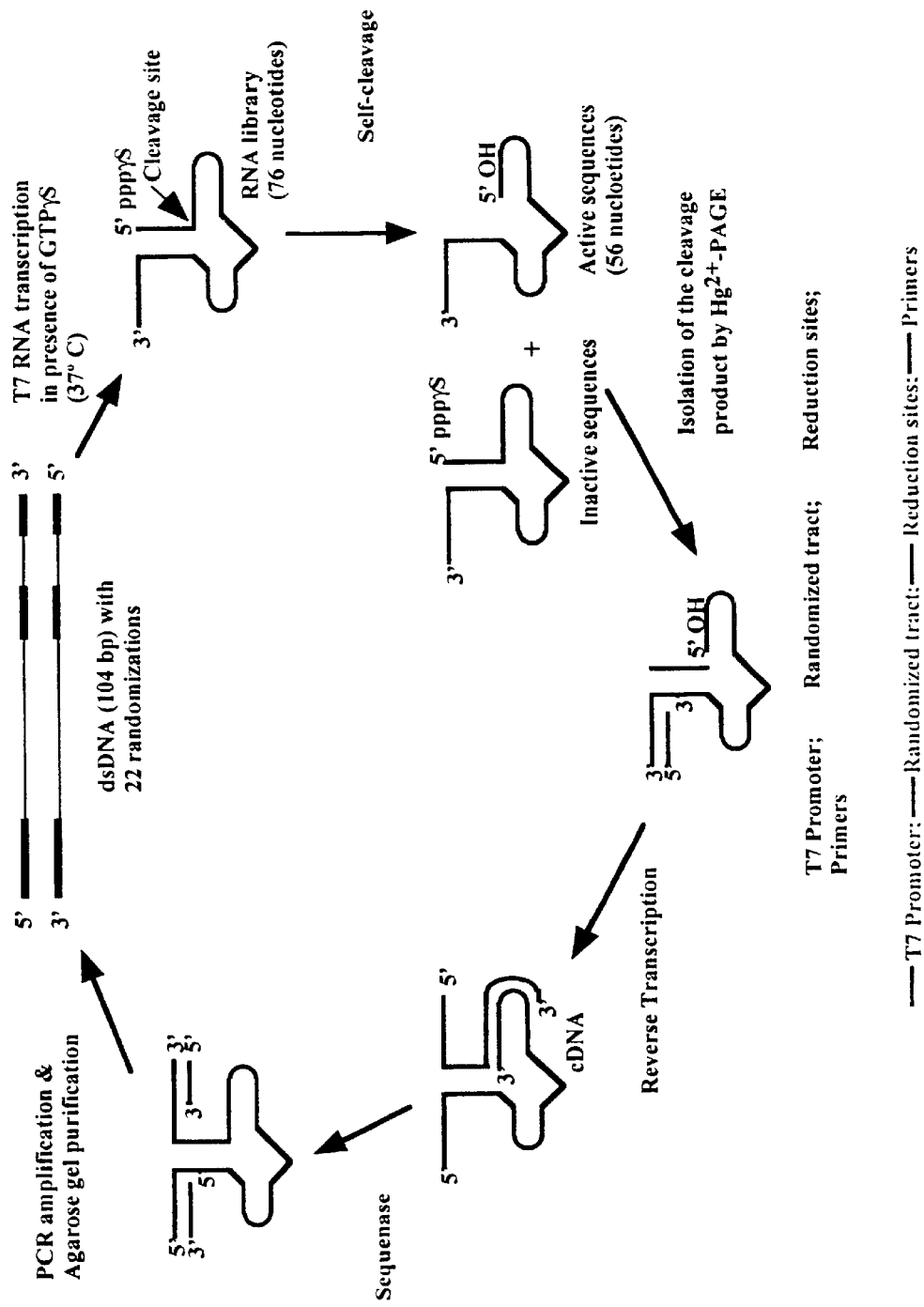

Figure 3: Self-Cleavage Activity of RNA from Positive Clones

5'- GGGAGACUGUCUAGAUCAUGAGGAGUCUAAUCCU NNNNNNN NNNNNNNNNNNN NNN AUGAUCUGCAGG*-3'
(Seq. ID No. 1175)

| Clone No. | | | | | $k_{\text{in-cis}}$ (min-1) | Seq. ID No. |
|---|---|---|---|---|---|---|
| wt hammerhead ribozyme | | CUGAUG | AGCGCAAGC | GAA | 0.66 | 1176 |
| Pool 7 | 14 | GGAAUC | AGCCUGACACCGG | CCC | 0.03 | 1177 |
| Pool 10 | 18 | GGCAUC | CCCGGCAUGGUGC | GCG | 0.06 | 1178 |
| POOL 13 | 31 | AGCAUU | ACCCGGCUGGUGC | GCG | 0.20 | 1179 |
| | 29 (2x) | GCAUCA | CGGGGCAAUCUGC | GCG | 0.16 | 1180 |
| | 18 | AGCAUC | ACCCGGAUGGUGC | GCG | 0.08 | 1181 |
| | 36 (2x) | AGCAUC | ACCCGGCUGGUGC | GCG | 0.08 | 1182 |
| | 39 | AGCGUC | CACGGCAUCGAGC | GCG | 0.04 | 1183 |
| | 19 | UGAUG | GCUUGCACUAAGC | GCG | 0.83 | 1184 |
| | 40 (2X) | UGAUG | GCAUGCACUAUGC | GCG | 0.52 | 1185 |
| | 4 | UGAUG | GCAUGCAGGAUGC | GCG | 0.47 | 1186 |
| | 21 | UGAUG | GCAUGCACCAUGC | GCG | 0.33 | 1187 |
| | 1 | UGAUC | GGAUGCACCAUGC | GCG | 0.24 | 1188 |
| | 3 | UGGGC | CGAUCGCAAGGGC | GCG | 0.03 | 1189 |

Structure Mapping studies on Clone 40

*In trans* constructs of clone 40 with 5 bp in helix I and 6 or 10 bp, respectively, in helix III

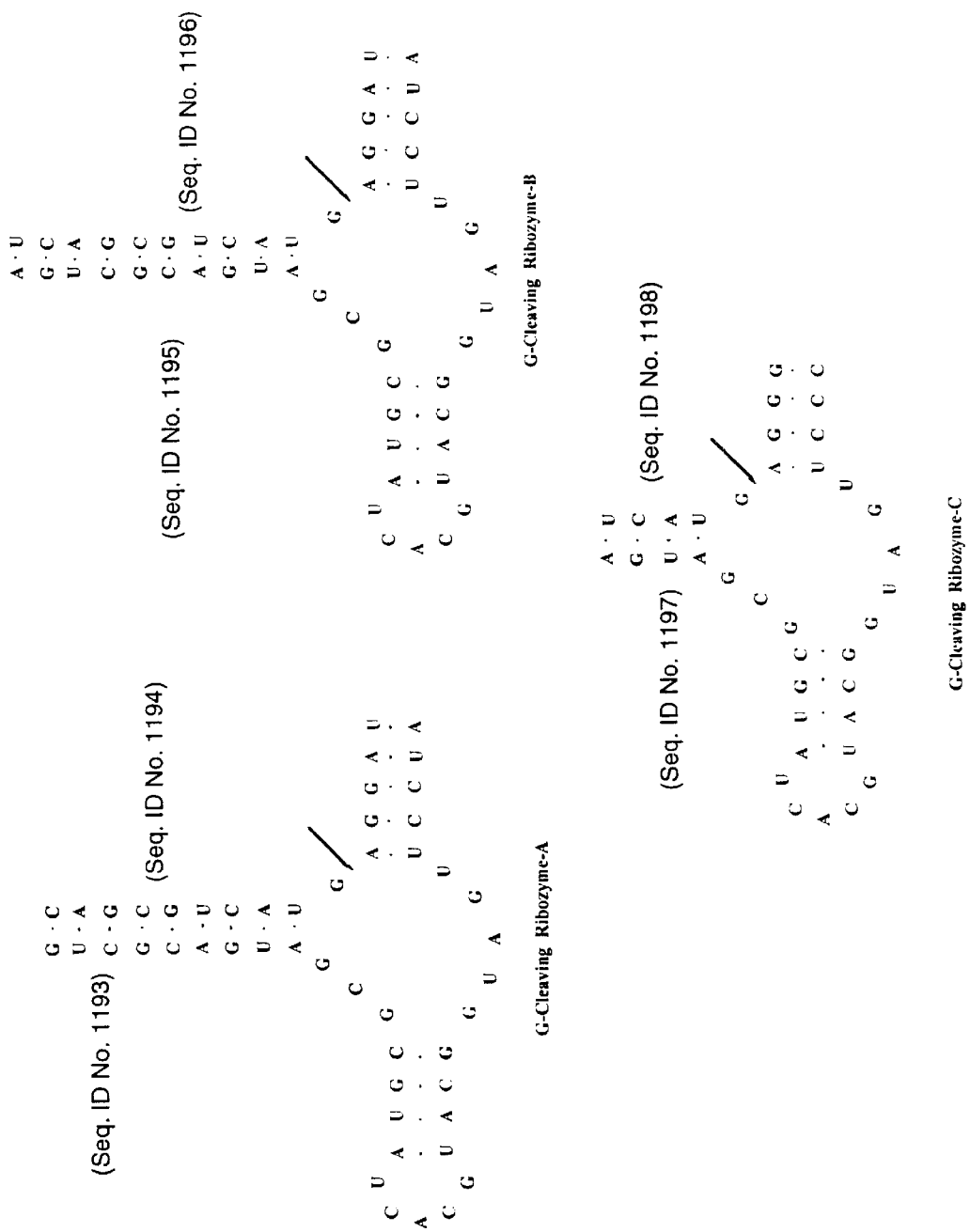
Figure 6: *Trans*-Cleaving Ribozyme-Substrate Complex

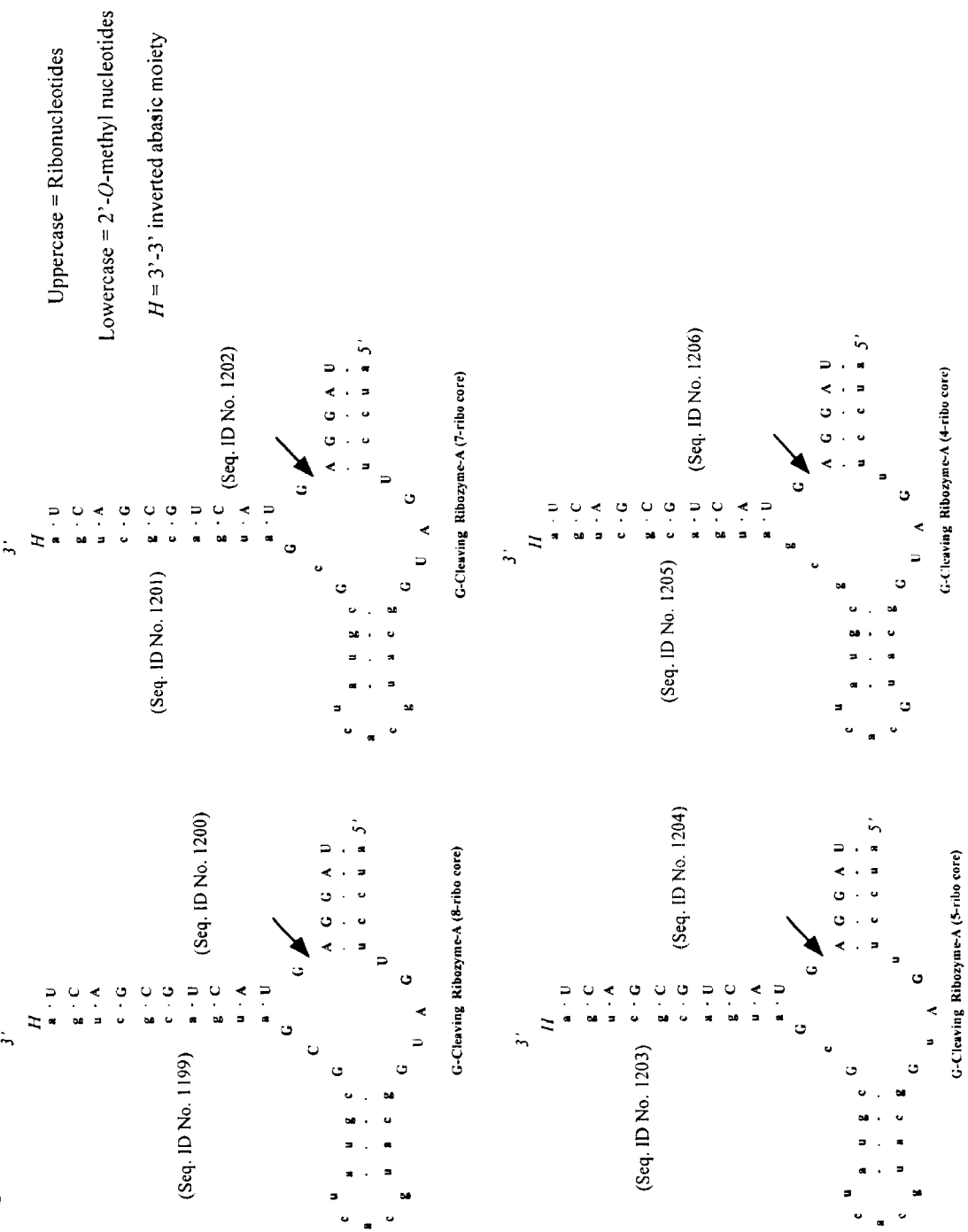
Figure 7: Modified Trans-Cleaving Ribozyme-Substrate Complex

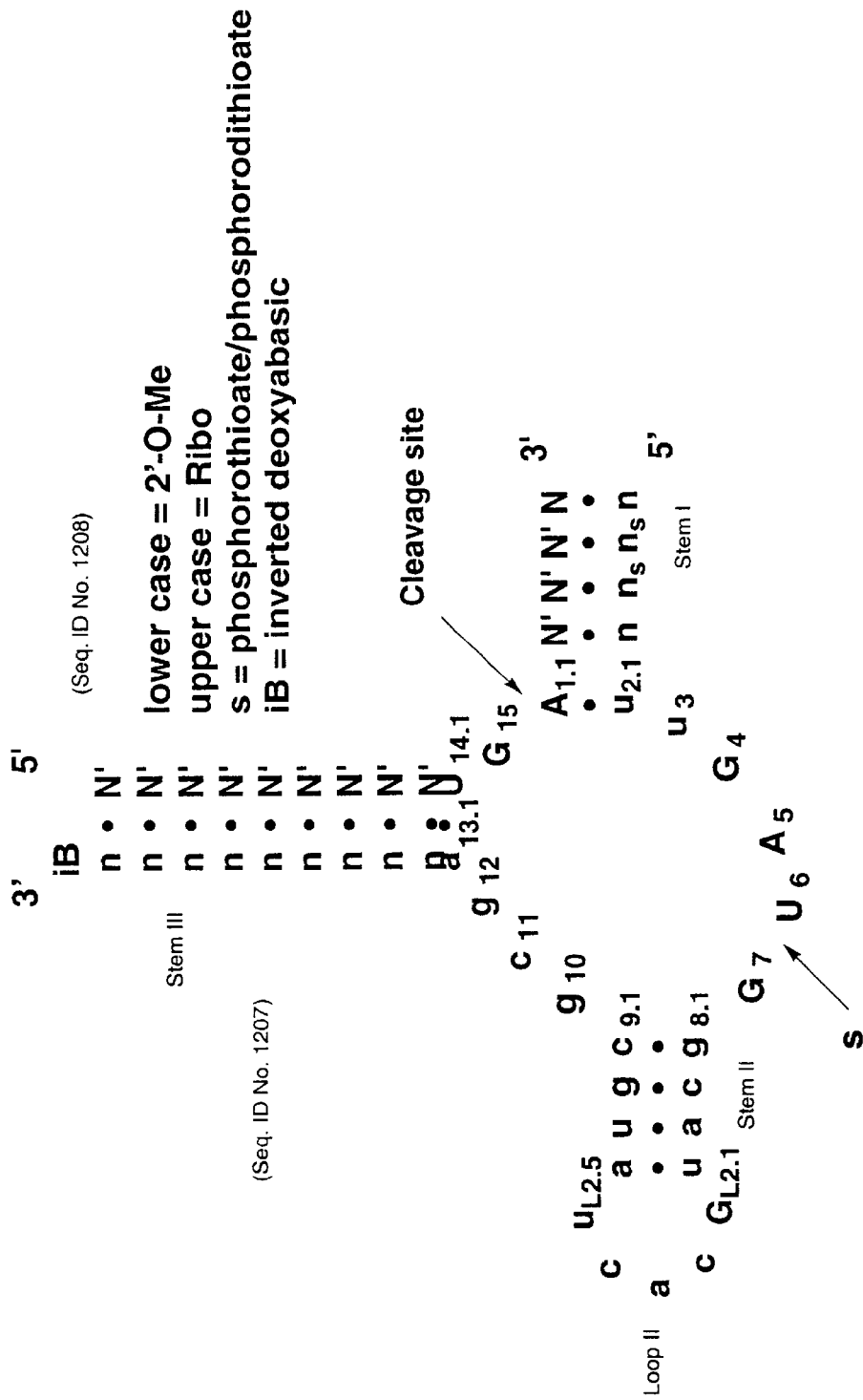
Figure 8: Stablized Trans-Cleaving Ribozyme Substrate Complex

SEQUENCE LISTING

<160> NUMBER OF SEQ ID NOS: 1208

<210> SEQ ID NO 1
<211> LENGTH: 16
<212> TYPE: RNA
<213> ORGANISM: Homo sapiens

<400> SEQUENCE: 1
ggcggcggcc gcggcg                                          16

<210> SEQ ID NO 2
<211> LENGTH: 16
<212> TYPE: RNA
<213> ORGANISM: Homo sapiens

<400> SEQUENCE: 2
uggcggcggc gaaggu                                          16

<210> SEQ ID NO 3
<211> LENGTH: 16
<212> TYPE: RNA
<213> ORGANISM: Homo sapiens

<400> SEQUENCE: 3
cccggccccc gccauu                                          16

<210> SEQ ID NO 4
<211> LENGTH: 16
<212> TYPE: RNA
<213> ORGANISM: Homo sapiens

<400> SEQUENCE: 4
gacugggagc gagcgc                                          16

<210> SEQ ID NO 5
<211> LENGTH: 16
<212> TYPE: RNA
<213> ORGANISM: Homo sapiens

<400> SEQUENCE: 5
gggagcgagc gcggcg                                          16

<210> SEQ ID NO 6
<211> LENGTH: 16
<212> TYPE: RNA
<213> ORGANISM: Homo sapiens

<400> SEQUENCE: 6

-continued cgagcgcggc gcaggc                                               16

<210> SEQ ID NO 7
<211> LENGTH: 16
<212> TYPE: RNA
<213> ORGANISM: Homo sapiens

<400> SEQUENCE: 7
cgcaggcacu gaaggc                                               16

<210> SEQ ID NO 8
<211> LENGTH: 16
<212> TYPE: RNA
<213> ORGANISM: Homo sapiens

<400> SEQUENCE: 8
gcucccaggu gcggga                                               16

<210> SEQ ID NO 9
<211> LENGTH: 16
<212> TYPE: RNA
<213> ORGANISM: Homo sapiens

<400> SEQUENCE: 9
agagaggccu gcugaa                                               16

<210> SEQ ID NO 10
<211> LENGTH: 16
<212> TYPE: RNA
<213> ORGANISM: Homo sapiens

<400> SEQUENCE: 10
gaggccugcu gaaaau                                               16

<210> SEQ ID NO 11
<211> LENGTH: 16
<212> TYPE: RNA
<213> ORGANISM: Homo sapiens

<400> SEQUENCE: 11
ugcugaaaau gacuga                                               16

<210> SEQ ID NO 12
<211> LENGTH: 16
<212> TYPE: RNA
<213> ORGANISM: Homo sapiens

<400> SEQUENCE: 12
gaaaaugacu gaauau                                               16

<210> SEQ ID NO 13
<211> LENGTH: 16
<212> TYPE: RNA
<213> ORGANISM: Homo sapiens

<400> SEQUENCE: 13
augacugaau auaaac                                               16

<210> SEQ ID NO 14
<211> LENGTH: 16
<212> TYPE: RNA
<213> ORGANISM: Homo sapiens

<400> SEQUENCE: 14

```
gacugaauau aaacuu                                              16

<210> SEQ ID NO 15
<211> LENGTH: 16
<212> TYPE: RNA
<213> ORGANISM: Homo sapiens

<400> SEQUENCE: 15
auauaaacuu guggua                                              16

<210> SEQ ID NO 16
<211> LENGTH: 16
<212> TYPE: RNA
<213> ORGANISM: Homo sapiens

<400> SEQUENCE: 16
guuggagcuu guggcg                                              16

<210> SEQ ID NO 17
<211> LENGTH: 16
<212> TYPE: RNA
<213> ORGANISM: Homo sapiens

<400> SEQUENCE: 17
aggcaagagu gccuug                                              16

<210> SEQ ID NO 18
<211> LENGTH: 16
<212> TYPE: RNA
<213> ORGANISM: Homo sapiens

<400> SEQUENCE: 18
agagugccuu gacgau                                              16

<210> SEQ ID NO 19
<211> LENGTH: 16
<212> TYPE: RNA
<213> ORGANISM: Homo sapiens

<400> SEQUENCE: 19
gugccuugac gauaca                                              16

<210> SEQ ID NO 20
<211> LENGTH: 16
<212> TYPE: RNA
<213> ORGANISM: Homo sapiens

<400> SEQUENCE: 20
ccuugacgau acagcu                                              16

<210> SEQ ID NO 21
<211> LENGTH: 16
<212> TYPE: RNA
<213> ORGANISM: Homo sapiens

<400> SEQUENCE: 21
gaaucauuuu guggac                                              16

<210> SEQ ID NO 22
<211> LENGTH: 16
<212> TYPE: RNA
<213> ORGANISM: Homo sapiens
```

-continued

```
<400> SEQUENCE: 22
uuuuguggac gaauau                                               16

<210> SEQ ID NO 23
<211> LENGTH: 16
<212> TYPE: RNA
<213> ORGANISM: Homo sapiens

<400> SEQUENCE: 23
guggacgaau augauc                                               16

<210> SEQ ID NO 24
<211> LENGTH: 16
<212> TYPE: RNA
<213> ORGANISM: Homo sapiens

<400> SEQUENCE: 24
ggacgaauau gaucca                                               16

<210> SEQ ID NO 25
<211> LENGTH: 16
<212> TYPE: RNA
<213> ORGANISM: Homo sapiens

<400> SEQUENCE: 25
auccaacaau agagga                                               16

<210> SEQ ID NO 26
<211> LENGTH: 16
<212> TYPE: RNA
<213> ORGANISM: Homo sapiens

<400> SEQUENCE: 26
aguaguaauu gaugga                                               16

<210> SEQ ID NO 27
<211> LENGTH: 16
<212> TYPE: RNA
<213> ORGANISM: Homo sapiens

<400> SEQUENCE: 27
aguaauugau ggagaa                                               16

<210> SEQ ID NO 28
<211> LENGTH: 16
<212> TYPE: RNA
<213> ORGANISM: Homo sapiens

<400> SEQUENCE: 28
ggagaaaccu gucucu                                               16

<210> SEQ ID NO 29
<211> LENGTH: 16
<212> TYPE: RNA
<213> ORGANISM: Homo sapiens

<400> SEQUENCE: 29
ucucuuggau auucuc                                               16

<210> SEQ ID NO 30
<211> LENGTH: 16
<212> TYPE: RNA
<213> ORGANISM: Homo sapiens
```

<400> SEQUENCE: 30
ggauauucuc gacaca                                                       16

<210> SEQ ID NO 31
<211> LENGTH: 16
<212> TYPE: RNA
<213> ORGANISM: Homo sapiens

<400> SEQUENCE: 31
ggaguacagu gcaaug                                                       16

<210> SEQ ID NO 32
<211> LENGTH: 16
<212> TYPE: RNA
<213> ORGANISM: Homo sapiens

<400> SEQUENCE: 32
acagugcaau gaggga                                                       16

<210> SEQ ID NO 33
<211> LENGTH: 16
<212> TYPE: RNA
<213> ORGANISM: Homo sapiens

<400> SEQUENCE: 33
accaguacau gaggac                                                       16

<210> SEQ ID NO 34
<211> LENGTH: 16
<212> TYPE: RNA
<213> ORGANISM: Homo sapiens

<400> SEQUENCE: 34
ggcuuucuuu guguau                                                       16

<210> SEQ ID NO 35
<211> LENGTH: 16
<212> TYPE: RNA
<213> ORGANISM: Homo sapiens

<400> SEQUENCE: 35
cuuucuuugu guauuu                                                       16

<210> SEQ ID NO 36
<211> LENGTH: 16
<212> TYPE: RNA
<213> ORGANISM: Homo sapiens

<400> SEQUENCE: 36
uuguguauuu gccaua                                                       16

<210> SEQ ID NO 37
<211> LENGTH: 16
<212> TYPE: RNA
<213> ORGANISM: Homo sapiens

<400> SEQUENCE: 37
uauuugccau aaauaa                                                       16

<210> SEQ ID NO 38
<211> LENGTH: 16
<212> TYPE: RNA

-continued

<213> ORGANISM: Homo sapiens

<400> SEQUENCE: 38
ugccauaaau aauacu                                                    16

<210> SEQ ID NO 39
<211> LENGTH: 16
<212> TYPE: RNA
<213> ORGANISM: Homo sapiens

<400> SEQUENCE: 39
cauaaauaau acuaaa                                                    16

<210> SEQ ID NO 40
<211> LENGTH: 16
<212> TYPE: RNA
<213> ORGANISM: Homo sapiens

<400> SEQUENCE: 40
uaaaucauuu gaagau                                                    16

<210> SEQ ID NO 41
<211> LENGTH: 16
<212> TYPE: RNA
<213> ORGANISM: Homo sapiens

<400> SEQUENCE: 41
auuugaagau auucac                                                    16

<210> SEQ ID NO 42
<211> LENGTH: 16
<212> TYPE: RNA
<213> ORGANISM: Homo sapiens

<400> SEQUENCE: 42
ucaccauuau agagaa                                                    16

<210> SEQ ID NO 43
<211> LENGTH: 16
<212> TYPE: RNA
<213> ORGANISM: Homo sapiens

<400> SEQUENCE: 43
uaaggacucu gaagau                                                    16

<210> SEQ ID NO 44
<211> LENGTH: 16
<212> TYPE: RNA
<213> ORGANISM: Homo sapiens

<400> SEQUENCE: 44
cucugaagau guaccu                                                    16

<210> SEQ ID NO 45
<211> LENGTH: 16
<212> TYPE: RNA
<213> ORGANISM: Homo sapiens

<400> SEQUENCE: 45
auguaccuau gguccu                                                    16

<210> SEQ ID NO 46
<211> LENGTH: 16

```
<212> TYPE: RNA
<213> ORGANISM: Homo sapiens

<400> SEQUENCE: 46
aguaggaaau aaaugu                                                      16

<210> SEQ ID NO 47
<211> LENGTH: 16
<212> TYPE: RNA
<213> ORGANISM: Homo sapiens

<400> SEQUENCE: 47
ggaaauaaau gugauu                                                      16

<210> SEQ ID NO 48
<211> LENGTH: 16
<212> TYPE: RNA
<213> ORGANISM: Homo sapiens

<400> SEQUENCE: 48
aaauaaaugu gauuug                                                      16

<210> SEQ ID NO 49
<211> LENGTH: 16
<212> TYPE: RNA
<213> ORGANISM: Homo sapiens

<400> SEQUENCE: 49
aaugugauuu gccuuc                                                      16

<210> SEQ ID NO 50
<211> LENGTH: 16
<212> TYPE: RNA
<213> ORGANISM: Homo sapiens

<400> SEQUENCE: 50
aagaaguuau ggaauu                                                      16

<210> SEQ ID NO 51
<211> LENGTH: 16
<212> TYPE: RNA
<213> ORGANISM: Homo sapiens

<400> SEQUENCE: 51
uccuuuuauu gaaaca                                                      16

<210> SEQ ID NO 52
<211> LENGTH: 16
<212> TYPE: RNA
<213> ORGANISM: Homo sapiens

<400> SEQUENCE: 52
aagacagggu guugau                                                      16

<210> SEQ ID NO 53
<211> LENGTH: 16
<212> TYPE: RNA
<213> ORGANISM: Homo sapiens

<400> SEQUENCE: 53
acaggguguu gaugau                                                      16

<210> SEQ ID NO 54
```

-continued

```
<211> LENGTH: 16
<212> TYPE: RNA
<213> ORGANISM: Homo sapiens

<400> SEQUENCE: 54 gguguugau gaugcc                                                      16

<210> SEQ ID NO 55
<211> LENGTH: 16
<212> TYPE: RNA
<213> ORGANISM: Homo sapiens

<400> SEQUENCE: 55
uguugaugau gccuuc                                                     16

<210> SEQ ID NO 56
<211> LENGTH: 16
<212> TYPE: RNA
<213> ORGANISM: Homo sapiens

<400> SEQUENCE: 56
ugccuucuau acauua                                                     16

<210> SEQ ID NO 57
<211> LENGTH: 16
<212> TYPE: RNA
<213> ORGANISM: Homo sapiens

<400> SEQUENCE: 57
acauuaguuc gagaaa                                                     16

<210> SEQ ID NO 58
<211> LENGTH: 16
<212> TYPE: RNA
<213> ORGANISM: Homo sapiens

<400> SEQUENCE: 58
cgagaaauuc gaaaac                                                     16

<210> SEQ ID NO 59
<211> LENGTH: 16
<212> TYPE: RNA
<213> ORGANISM: Homo sapiens

<400> SEQUENCE: 59
ucgaaaacau aaagaa                                                     16

<210> SEQ ID NO 60
<211> LENGTH: 16
<212> TYPE: RNA
<213> ORGANISM: Homo sapiens

<400> SEQUENCE: 60
aagaaaagau gagcaa                                                     16

<210> SEQ ID NO 61
<211> LENGTH: 16
<212> TYPE: RNA
<213> ORGANISM: Homo sapiens

<400> SEQUENCE: 61
gagcaaagau gguaaa                                                     16
```

-continued

<210> SEQ ID NO 62
<211> LENGTH: 16
<212> TYPE: RNA
<213> ORGANISM: Homo sapiens

<400> SEQUENCE: 62
aagacaaagu guguaa                                                         16

<210> SEQ ID NO 63
<211> LENGTH: 16
<212> TYPE: RNA
<213> ORGANISM: Homo sapiens

<400> SEQUENCE: 63
gacaaagugu guaauu                                                         16

<210> SEQ ID NO 64
<211> LENGTH: 16
<212> TYPE: RNA
<213> ORGANISM: Homo sapiens

<400> SEQUENCE: 64 guguauuau guaaau                                                          16

<210> SEQ ID NO 65
<211> LENGTH: 16
<212> TYPE: RNA
<213> ORGANISM: Homo sapiens

<400> SEQUENCE: 65
uuauguaaau acaauu                                                         16

<210> SEQ ID NO 66
<211> LENGTH: 16
<212> TYPE: RNA
<213> ORGANISM: Homo sapiens

<400> SEQUENCE: 66
aauacaauuu guacuu                                                         16

<210> SEQ ID NO 67
<211> LENGTH: 16
<212> TYPE: RNA
<213> ORGANISM: Homo sapiens

<400> SEQUENCE: 67
cuuaaggcau acuagu                                                         16

<210> SEQ ID NO 68
<211> LENGTH: 16
<212> TYPE: RNA
<213> ORGANISM: Homo sapiens

<400> SEQUENCE: 68
gguaauuuuu guacau                                                         16

<210> SEQ ID NO 69
<211> LENGTH: 16
<212> TYPE: RNA
<213> ORGANISM: Homo sapiens

<400> SEQUENCE: 69
auuagcauuu guuuua                                                         16

-continued

```
<210> SEQ ID NO 70
<211> LENGTH: 16
<212> TYPE: RNA
<213> ORGANISM: Homo sapiens

<400> SEQUENCE: 70 uuuuuuccu gcucca                                                    16

<210> SEQ ID NO 71
<211> LENGTH: 16
<212> TYPE: RNA
<213> ORGANISM: Homo sapiens

<400> SEQUENCE: 71
ccugcuccau gcagac                                                   16

<210> SEQ ID NO 72
<211> LENGTH: 16
<212> TYPE: RNA
<213> ORGANISM: Homo sapiens

<400> SEQUENCE: 72
caugcagacu guuagc                                                   16

<210> SEQ ID NO 73
<211> LENGTH: 16
<212> TYPE: RNA
<213> ORGANISM: Homo sapiens

<400> SEQUENCE: 73
uaccuuaaau gcuuau                                                   16

<210> SEQ ID NO 74
<211> LENGTH: 16
<212> TYPE: RNA
<213> ORGANISM: Homo sapiens

<400> SEQUENCE: 74
auuuuaaaau gacagu                                                   16

<210> SEQ ID NO 75
<211> LENGTH: 16
<212> TYPE: RNA
<213> ORGANISM: Homo sapiens

<400> SEQUENCE: 75
uuuuuuccuc gaagug                                                   16

<210> SEQ ID NO 76
<211> LENGTH: 16
<212> TYPE: RNA
<213> ORGANISM: Homo sapiens

<400> SEQUENCE: 76
uccucgaagu gccagu                                                   16

<210> SEQ ID NO 77
<211> LENGTH: 16
<212> TYPE: RNA
<213> ORGANISM: Homo sapiens

<400> SEQUENCE: 77
uuugguuuuu gaacua                                                   16
```

<210> SEQ ID NO 78
<211> LENGTH: 16
<212> TYPE: RNA
<213> ORGANISM: Homo sapiens

<400> SEQUENCE: 78
aacuagcaau gccugu                                                       16

<210> SEQ ID NO 79
<211> LENGTH: 16
<212> TYPE: RNA
<213> ORGANISM: Homo sapiens

<400> SEQUENCE: 79
agcaaugccu gugaaa                                                       16

<210> SEQ ID NO 80
<211> LENGTH: 16
<212> TYPE: RNA
<213> ORGANISM: Homo sapiens

<400> SEQUENCE: 80
caaugccugu gaaaaa                                                       16

<210> SEQ ID NO 81
<211> LENGTH: 16
<212> TYPE: RNA
<213> ORGANISM: Homo sapiens

<400> SEQUENCE: 81
aaaagaaacu gaauac                                                       16

<210> SEQ ID NO 82
<211> LENGTH: 16
<212> TYPE: RNA
<213> ORGANISM: Homo sapiens

<400> SEQUENCE: 82
gaaacugaau accuaa                                                       16

<210> SEQ ID NO 83
<211> LENGTH: 16
<212> TYPE: RNA
<213> ORGANISM: Homo sapiens

<400> SEQUENCE: 83
uaagauuucu gucuug                                                       16

<210> SEQ ID NO 84
<211> LENGTH: 16
<212> TYPE: RNA
<213> ORGANISM: Homo sapiens

<400> SEQUENCE: 84
gguuuuuggu gcaugc                                                       16

<210> SEQ ID NO 85
<211> LENGTH: 16
<212> TYPE: RNA
<213> ORGANISM: Homo sapiens

<400> SEQUENCE: 85

-continued uuuggugcau gcaguu                            16

<210> SEQ ID NO 86
<211> LENGTH: 16
<212> TYPE: RNA
<213> ORGANISM: Homo sapiens

<400> SEQUENCE: 86
gcaugcaguu gauuac                            16

<210> SEQ ID NO 87
<211> LENGTH: 16
<212> TYPE: RNA
<213> ORGANISM: Homo sapiens

<400> SEQUENCE: 87
cuuaccaagu gugaau                            16

<210> SEQ ID NO 88
<211> LENGTH: 16
<212> TYPE: RNA
<213> ORGANISM: Homo sapiens

<400> SEQUENCE: 88
uaccaagugu gaaugu                            16

<210> SEQ ID NO 89
<211> LENGTH: 16
<212> TYPE: RNA
<213> ORGANISM: Homo sapiens

<400> SEQUENCE: 89
aagugugaau guuggu                            16

<210> SEQ ID NO 90
<211> LENGTH: 16
<212> TYPE: RNA
<213> ORGANISM: Homo sapiens

<400> SEQUENCE: 90
gaauguuggu gugaaa                            16

<210> SEQ ID NO 91
<211> LENGTH: 16
<212> TYPE: RNA
<213> ORGANISM: Homo sapiens

<400> SEQUENCE: 91
auguuggugu gaaaca                            16

<210> SEQ ID NO 92
<211> LENGTH: 16
<212> TYPE: RNA
<213> ORGANISM: Homo sapiens

<400> SEQUENCE: 92
acaaauuaau gaagcu                            16

<210> SEQ ID NO 93
<211> LENGTH: 16
<212> TYPE: RNA
<213> ORGANISM: Homo sapiens

<400> SEQUENCE: 93

-continued ugaagcuuuu gaauca                                              16

<210> SEQ ID NO 94
<211> LENGTH: 16
<212> TYPE: RNA
<213> ORGANISM: Homo sapiens

<400> SEQUENCE: 94
ucccuauucu guguuu                                              16

<210> SEQ ID NO 95
<211> LENGTH: 16
<212> TYPE: RNA
<213> ORGANISM: Homo sapiens

<400> SEQUENCE: 95
ccuauucugu guuuua                                              16

<210> SEQ ID NO 96
<211> LENGTH: 16
<212> TYPE: RNA
<213> ORGANISM: Homo sapiens

<400> SEQUENCE: 96
cuagucacau aaaugg                                              16

<210> SEQ ID NO 97
<211> LENGTH: 16
<212> TYPE: RNA
<213> ORGANISM: Homo sapiens

<400> SEQUENCE: 97
ucacauaaau ggauua                                              16

<210> SEQ ID NO 98
<211> LENGTH: 16
<212> TYPE: RNA
<213> ORGANISM: Homo sapiens

<400> SEQUENCE: 98
aauuucaguu gagacc                                              16

<210> SEQ ID NO 99
<211> LENGTH: 16
<212> TYPE: RNA
<213> ORGANISM: Homo sapiens

<400> SEQUENCE: 99
gguuuuuacu gaaaca                                              16

<210> SEQ ID NO 100
<211> LENGTH: 16
<212> TYPE: RNA
<213> ORGANISM: Homo sapiens

<400> SEQUENCE: 100
cugaaacauu gaggga                                              16

<210> SEQ ID NO 101
<211> LENGTH: 16
<212> TYPE: RNA
<213> ORGANISM: Homo sapiens -continued

```
<400> SEQUENCE: 101
acaaauuuau gggcuu                                                    16

<210> SEQ ID NO 102
<211> LENGTH: 16
<212> TYPE: RNA
<213> ORGANISM: Homo sapiens

<400> SEQUENCE: 102
ugggcuuccu gaugau                                                    16

<210> SEQ ID NO 103
<211> LENGTH: 16
<212> TYPE: RNA
<213> ORGANISM: Homo sapiens

<400> SEQUENCE: 103
gcuuccugau gaugau                                                    16

<210> SEQ ID NO 104
<211> LENGTH: 16
<212> TYPE: RNA
<213> ORGANISM: Homo sapiens

<400> SEQUENCE: 104
uccugaugau gauucu                                                    16

<210> SEQ ID NO 105
<211> LENGTH: 16
<212> TYPE: RNA
<213> ORGANISM: Homo sapiens

<400> SEQUENCE: 105
uaggcaucau guccua                                                    16

<210> SEQ ID NO 106
<211> LENGTH: 16
<212> TYPE: RNA
<213> ORGANISM: Homo sapiens

<400> SEQUENCE: 106
cauguccuau aguuug                                                    16

<210> SEQ ID NO 107
<211> LENGTH: 16
<212> TYPE: RNA
<213> ORGANISM: Homo sapiens

<400> SEQUENCE: 107
ccuauaguuu gucauc                                                    16

<210> SEQ ID NO 108
<211> LENGTH: 16
<212> TYPE: RNA
<213> ORGANISM: Homo sapiens

<400> SEQUENCE: 108
ugucaucccu gaugaa                                                    16

<210> SEQ ID NO 109
<211> LENGTH: 16
<212> TYPE: RNA
<213> ORGANISM: Homo sapiens
```

```
<400> SEQUENCE: 109
caucccugau gaaugu                                                     16

<210> SEQ ID NO 110
<211> LENGTH: 16
<212> TYPE: RNA
<213> ORGANISM: Homo sapiens

<400> SEQUENCE: 110
ccugaugaau guaaag                                                     16

<210> SEQ ID NO 111
<211> LENGTH: 16
<212> TYPE: RNA
<213> ORGANISM: Homo sapiens

<400> SEQUENCE: 111
aaguuacacu guucac                                                     16

<210> SEQ ID NO 112
<211> LENGTH: 16
<212> TYPE: RNA
<213> ORGANISM: Homo sapiens

<400> SEQUENCE: 112
caaagguuuu gucucc                                                     16

<210> SEQ ID NO 113
<211> LENGTH: 16
<212> TYPE: RNA
<213> ORGANISM: Homo sapiens

<400> SEQUENCE: 113
ccuuuccacu gcuauu                                                     16

<210> SEQ ID NO 114
<211> LENGTH: 16
<212> TYPE: RNA
<213> ORGANISM: Homo sapiens

<400> SEQUENCE: 114
uauuagucau ggucac                                                     16

<210> SEQ ID NO 115
<211> LENGTH: 16
<212> TYPE: RNA
<213> ORGANISM: Homo sapiens

<400> SEQUENCE: 115
uccccaaaau auuaua                                                     16

<210> SEQ ID NO 116
<211> LENGTH: 16
<212> TYPE: RNA
<213> ORGANISM: Homo sapiens

<400> SEQUENCE: 116
aaaauauuau auuuuu                                                     16

<210> SEQ ID NO 117
<211> LENGTH: 16
<212> TYPE: RNA
```

<213> ORGANISM: Homo sapiens

<400> SEQUENCE: 117
uuuuuucuau aaaaag                                              16

<210> SEQ ID NO 118
<211> LENGTH: 16
<212> TYPE: RNA
<213> ORGANISM: Homo sapiens

<400> SEQUENCE: 118
agaaaaaaau ggaaaa                                              16

<210> SEQ ID NO 119
<211> LENGTH: 16
<212> TYPE: RNA
<213> ORGANISM: Homo sapiens

<400> SEQUENCE: 119
acaaggcaau ggaaac                                              16

<210> SEQ ID NO 120
<211> LENGTH: 16
<212> TYPE: RNA
<213> ORGANISM: Homo sapiens

<400> SEQUENCE: 120
aaacuauuau aaggcc                                              16

<210> SEQ ID NO 121
<211> LENGTH: 16
<212> TYPE: RNA
<213> ORGANISM: Homo sapiens

<400> SEQUENCE: 121
cacauuagau aaauua                                              16

<210> SEQ ID NO 122
<211> LENGTH: 16
<212> TYPE: RNA
<213> ORGANISM: Homo sapiens

<400> SEQUENCE: 122
aaauuacuau aaagac                                              16

<210> SEQ ID NO 123
<211> LENGTH: 16
<212> TYPE: RNA
<213> ORGANISM: Homo sapiens

<400> SEQUENCE: 123
gacuccuaau agcuuu                                              16

<210> SEQ ID NO 124
<211> LENGTH: 16
<212> TYPE: RNA
<213> ORGANISM: Homo sapiens

<400> SEQUENCE: 124 gcuuuuccu guuaag                                               16

<210> SEQ ID NO 125
<211> LENGTH: 16

```
<212> TYPE: RNA
<213> ORGANISM: Homo sapiens

<400> SEQUENCE: 125
gacccaguau gaaugg                                                   16

<210> SEQ ID NO 126
<211> LENGTH: 16
<212> TYPE: RNA
<213> ORGANISM: Homo sapiens

<400> SEQUENCE: 126
caguaugaau gggauu                                                   16

<210> SEQ ID NO 127
<211> LENGTH: 16
<212> TYPE: RNA
<213> ORGANISM: Homo sapiens

<400> SEQUENCE: 127
ggauuauuau agcaac                                                   16

<210> SEQ ID NO 128
<211> LENGTH: 16
<212> TYPE: RNA
<213> ORGANISM: Homo sapiens

<400> SEQUENCE: 128 uugggcuau auuac                                                     16

<210> SEQ ID NO 129
<211> LENGTH: 16
<212> TYPE: RNA
<213> ORGANISM: Homo sapiens

<400> SEQUENCE: 129
auauuuacau gcuacu                                                   16

<210> SEQ ID NO 130
<211> LENGTH: 16
<212> TYPE: RNA
<213> ORGANISM: Homo sapiens

<400> SEQUENCE: 130
aaauuuuuau aauaau                                                   16

<210> SEQ ID NO 131
<211> LENGTH: 16
<212> TYPE: RNA
<213> ORGANISM: Homo sapiens

<400> SEQUENCE: 131
uuuuuauaau aauuga                                                   16

<210> SEQ ID NO 132
<211> LENGTH: 16
<212> TYPE: RNA
<213> ORGANISM: Homo sapiens

<400> SEQUENCE: 132
uauaauaauu gaaaag                                                   16

<210> SEQ ID NO 133
```

```
<211> LENGTH: 16
<212> TYPE: RNA
<213> ORGANISM: Homo sapiens

<400> SEQUENCE: 133
uaacaaguau aaaaaa                                                      16

<210> SEQ ID NO 134
<211> LENGTH: 16
<212> TYPE: RNA
<213> ORGANISM: Homo sapiens

<400> SEQUENCE: 134
aaauucucau aggaau                                                      16

<210> SEQ ID NO 135
<211> LENGTH: 16
<212> TYPE: RNA
<213> ORGANISM: Homo sapiens

<400> SEQUENCE: 135
ggaauuaaau guaguc                                                      16

<210> SEQ ID NO 136
<211> LENGTH: 16
<212> TYPE: RNA
<213> ORGANISM: Homo sapiens

<400> SEQUENCE: 136
uagucucccu guguca                                                      16

<210> SEQ ID NO 137
<211> LENGTH: 16
<212> TYPE: RNA
<213> ORGANISM: Homo sapiens

<400> SEQUENCE: 137
gucucccugu gucaga                                                      16

<210> SEQ ID NO 138
<211> LENGTH: 16
<212> TYPE: RNA
<213> ORGANISM: Homo sapiens

<400> SEQUENCE: 138
gugucagacu gcucuu                                                      16

<210> SEQ ID NO 139
<211> LENGTH: 16
<212> TYPE: RNA
<213> ORGANISM: Homo sapiens

<400> SEQUENCE: 139
gcucuuucau aguaua                                                      16

<210> SEQ ID NO 140
<211> LENGTH: 16
<212> TYPE: RNA
<213> ORGANISM: Homo sapiens

<400> SEQUENCE: 140
uucauaguau aacuuu                                                      16
```

```
<210> SEQ ID NO 141
<211> LENGTH: 16
<212> TYPE: RNA
<213> ORGANISM: Homo sapiens

<400> SEQUENCE: 141
ucuucaacuu gagucu                                                   16

<210> SEQ ID NO 142
<211> LENGTH: 16
<212> TYPE: RNA
<213> ORGANISM: Homo sapiens

<400> SEQUENCE: 142
uugagucuuu gaagau                                                   16

<210> SEQ ID NO 143
<211> LENGTH: 16
<212> TYPE: RNA
<213> ORGANISM: Homo sapiens

<400> SEQUENCE: 143
cuuugaagau aguuuu                                                   16

<210> SEQ ID NO 144
<211> LENGTH: 16
<212> TYPE: RNA
<213> ORGANISM: Homo sapiens

<400> SEQUENCE: 144
uuuuaauucu gcuugu                                                   16

<210> SEQ ID NO 145
<211> LENGTH: 16
<212> TYPE: RNA
<213> ORGANISM: Homo sapiens

<400> SEQUENCE: 145
aauucugcuu gugaca                                                   16

<210> SEQ ID NO 146
<211> LENGTH: 16
<212> TYPE: RNA
<213> ORGANISM: Homo sapiens

<400> SEQUENCE: 146
uucugcuugu gacauu                                                   16

<210> SEQ ID NO 147
<211> LENGTH: 16
<212> TYPE: RNA
<213> ORGANISM: Homo sapiens

<400> SEQUENCE: 147
ggccaguuau agcuua                                                   16

<210> SEQ ID NO 148
<211> LENGTH: 16
<212> TYPE: RNA
<213> ORGANISM: Homo sapiens

<400> SEQUENCE: 148
cuuauuaggu guugaa                                                   16
```

<210> SEQ ID NO 149
<211> LENGTH: 16
<212> TYPE: RNA
<213> ORGANISM: Homo sapiens

<400> SEQUENCE: 149
auuagguguu gaagag                                                          16

<210> SEQ ID NO 150
<211> LENGTH: 16
<212> TYPE: RNA
<213> ORGANISM: Homo sapiens

<400> SEQUENCE: 150
gaccaagguu gcaagc                                                          16

<210> SEQ ID NO 151
<211> LENGTH: 16
<212> TYPE: RNA
<213> ORGANISM: Homo sapiens

<400> SEQUENCE: 151
gccaggcccu guguga                                                          16

<210> SEQ ID NO 152
<211> LENGTH: 16
<212> TYPE: RNA
<213> ORGANISM: Homo sapiens

<400> SEQUENCE: 152
caggcccugu gugaac                                                          16

<210> SEQ ID NO 153
<211> LENGTH: 16
<212> TYPE: RNA
<213> ORGANISM: Homo sapiens

<400> SEQUENCE: 153
ggcccugugu gaaccu                                                          16

<210> SEQ ID NO 154
<211> LENGTH: 16
<212> TYPE: RNA
<213> ORGANISM: Homo sapiens

<400> SEQUENCE: 154
ugugaaccuu gagcuu                                                          16

<210> SEQ ID NO 155
<211> LENGTH: 16
<212> TYPE: RNA
<213> ORGANISM: Homo sapiens

<400> SEQUENCE: 155
gagcuuucau agagag                                                          16

<210> SEQ ID NO 156
<211> LENGTH: 16
<212> TYPE: RNA
<213> ORGANISM: Homo sapiens

<400> SEQUENCE: 156
uucacagcau ggacug                                                          16

<210> SEQ ID NO 157
<211> LENGTH: 16
<212> TYPE: RNA
<213> ORGANISM: Homo sapiens

<400> SEQUENCE: 157
agcauggacu gugugc                                                     16

<210> SEQ ID NO 158
<211> LENGTH: 16
<212> TYPE: RNA
<213> ORGANISM: Homo sapiens

<400> SEQUENCE: 158
cauggacugu gugccc                                                     16

<210> SEQ ID NO 159
<211> LENGTH: 16
<212> TYPE: RNA
<213> ORGANISM: Homo sapiens

<400> SEQUENCE: 159
uggacugugu gccca                                                      16

<210> SEQ ID NO 160
<211> LENGTH: 16
<212> TYPE: RNA
<213> ORGANISM: Homo sapiens

<400> SEQUENCE: 160 acgucaucc gagugg                                                      16

<210> SEQ ID NO 161
<211> LENGTH: 16
<212> TYPE: RNA
<213> ORGANISM: Homo sapiens

<400> SEQUENCE: 161
ccgagugguu guacga                                                     16

<210> SEQ ID NO 162
<211> LENGTH: 16
<212> TYPE: RNA
<213> ORGANISM: Homo sapiens

<400> SEQUENCE: 162
gugguuguac gaugca                                                     16

<210> SEQ ID NO 163
<211> LENGTH: 16
<212> TYPE: RNA
<213> ORGANISM: Homo sapiens

<400> SEQUENCE: 163
guuguacgau gcauug                                                     16

<210> SEQ ID NO 164
<211> LENGTH: 16
<212> TYPE: RNA
<213> ORGANISM: Homo sapiens

<400> SEQUENCE: 164

-continued agucaaaaau ggggag         16

<210> SEQ ID NO 165
<211> LENGTH: 16
<212> TYPE: RNA
<213> ORGANISM: Homo sapiens

<400> SEQUENCE: 165
caguuuggau agcuca         16

<210> SEQ ID NO 166
<211> LENGTH: 16
<212> TYPE: RNA
<213> ORGANISM: Homo sapiens

<400> SEQUENCE: 166
ucaacaagau acaauc         16

<210> SEQ ID NO 167
<211> LENGTH: 16
<212> TYPE: RNA
<213> ORGANISM: Homo sapiens

<400> SEQUENCE: 167
aucucacucu guggug         16

<210> SEQ ID NO 168
<211> LENGTH: 16
<212> TYPE: RNA
<213> ORGANISM: Homo sapiens

<400> SEQUENCE: 168
uggugguccu gcugac         16

<210> SEQ ID NO 169
<211> LENGTH: 16
<212> TYPE: RNA
<213> ORGANISM: Homo sapiens

<400> SEQUENCE: 169
ugguccugcu gacaaa         16

<210> SEQ ID NO 170
<211> LENGTH: 16
<212> TYPE: RNA
<213> ORGANISM: Homo sapiens

<400> SEQUENCE: 170
caagagcauu gcuuuu         16

<210> SEQ ID NO 171
<211> LENGTH: 16
<212> TYPE: RNA
<213> ORGANISM: Homo sapiens

<400> SEQUENCE: 171
cauugcuuuu guuucu         16

<210> SEQ ID NO 172
<211> LENGTH: 16
<212> TYPE: RNA
<213> ORGANISM: Homo sapiens

<400> SEQUENCE: 172

```
acuuuuaaau auuaac                                         16

<210> SEQ ID NO 173
<211> LENGTH: 16
<212> TYPE: RNA
<213> ORGANISM: Homo sapiens

<400> SEQUENCE: 173
cucaaaaguu gagauu                                         16

<210> SEQ ID NO 174
<211> LENGTH: 16
<212> TYPE: RNA
<213> ORGANISM: Homo sapiens

<400> SEQUENCE: 174
gggugguggu gugcca                                         16

<210> SEQ ID NO 175
<211> LENGTH: 16
<212> TYPE: RNA
<213> ORGANISM: Homo sapiens

<400> SEQUENCE: 175
gugguggugu gccaag                                         16

<210> SEQ ID NO 176
<211> LENGTH: 16
<212> TYPE: RNA
<213> ORGANISM: Homo sapiens

<400> SEQUENCE: 176
uuuaaacaau gaagug                                         16

<210> SEQ ID NO 177
<211> LENGTH: 16
<212> TYPE: RNA
<213> ORGANISM: Homo sapiens

<400> SEQUENCE: 177
acaaugaagu gaaaaa                                         16

<210> SEQ ID NO 178
<211> LENGTH: 16
<212> TYPE: RNA
<213> ORGANISM: Homo sapiens

<400> SEQUENCE: 178
aauuaacauu gcauaa                                         16

<210> SEQ ID NO 179
<211> LENGTH: 16
<212> TYPE: RNA
<213> ORGANISM: Homo sapiens

<400> SEQUENCE: 179
aacauugcau aaacac                                         16

<210> SEQ ID NO 180
<211> LENGTH: 16
<212> TYPE: RNA
<213> ORGANISM: Homo sapiens
```

-continued

<400> SEQUENCE: 180
uuucaagucu gaucca                                                    16

<210> SEQ ID NO 181
<211> LENGTH: 16
<212> TYPE: RNA
<213> ORGANISM: Homo sapiens

<400> SEQUENCE: 181
ucugauccau auuuaa                                                    16

<210> SEQ ID NO 182
<211> LENGTH: 16
<212> TYPE: RNA
<213> ORGANISM: Homo sapiens

<400> SEQUENCE: 182
cauauuuaau aaugcu                                                    16

<210> SEQ ID NO 183
<211> LENGTH: 16
<212> TYPE: RNA
<213> ORGANISM: Homo sapiens

<400> SEQUENCE: 183
auuuaauaau gcuuua                                                    16

<210> SEQ ID NO 184
<211> LENGTH: 16
<212> TYPE: RNA
<213> ORGANISM: Homo sapiens

<400> SEQUENCE: 184
gcuuuaaaau aaaaau                                                    16

<210> SEQ ID NO 185
<211> LENGTH: 16
<212> TYPE: RNA
<213> ORGANISM: Homo sapiens

<400> SEQUENCE: 185
aaauaaaaau aaaaac                                                    16

<210> SEQ ID NO 186
<211> LENGTH: 16
<212> TYPE: RNA
<213> ORGANISM: Homo sapiens

<400> SEQUENCE: 186
caauccuuuu gauaaa                                                    16

<210> SEQ ID NO 187
<211> LENGTH: 16
<212> TYPE: RNA
<213> ORGANISM: Homo sapiens

<400> SEQUENCE: 187
uccuuuugau aaauuu                                                    16

<210> SEQ ID NO 188
<211> LENGTH: 16
<212> TYPE: RNA
<213> ORGANISM: Homo sapiens

```
<400> SEQUENCE: 188
aauuuaaaau guuacu                                                    16

<210> SEQ ID NO 189
<211> LENGTH: 16
<212> TYPE: RNA
<213> ORGANISM: Homo sapiens

<400> SEQUENCE: 189
auuuuaaaau aaauga                                                    16

<210> SEQ ID NO 190
<211> LENGTH: 16
<212> TYPE: RNA
<213> ORGANISM: Homo sapiens

<400> SEQUENCE: 190
uaaaauaaau gaagug                                                    16

<210> SEQ ID NO 191
<211> LENGTH: 16
<212> TYPE: RNA
<213> ORGANISM: Homo sapiens

<400> SEQUENCE: 191
uaaaugaagu gagaug                                                    16

<210> SEQ ID NO 192
<211> LENGTH: 16
<212> TYPE: RNA
<213> ORGANISM: Homo sapiens

<400> SEQUENCE: 192
gaagugagau ggcaug                                                    16

<210> SEQ ID NO 193
<211> LENGTH: 16
<212> TYPE: RNA
<213> ORGANISM: Homo sapiens

<400> SEQUENCE: 193
gagauggcau ggugag                                                    16

<210> SEQ ID NO 194
<211> LENGTH: 16
<212> TYPE: RNA
<213> ORGANISM: Homo sapiens

<400> SEQUENCE: 194
auggcauggu gaggug                                                    16

<210> SEQ ID NO 195
<211> LENGTH: 16
<212> TYPE: RNA
<213> ORGANISM: Homo sapiens

<400> SEQUENCE: 195
auggugaggu gaaagu                                                    16

<210> SEQ ID NO 196
<211> LENGTH: 16
<212> TYPE: RNA
```

<213> ORGANISM: Homo sapiens

<400> SEQUENCE: 196
ggacuagguu guuggu                                                        16

<210> SEQ ID NO 197
<211> LENGTH: 16
<212> TYPE: RNA
<213> ORGANISM: Homo sapiens

<400> SEQUENCE: 197
gguuguuggu gacuua                                                        16

<210> SEQ ID NO 198
<211> LENGTH: 16
<212> TYPE: RNA
<213> ORGANISM: Homo sapiens

<400> SEQUENCE: 198
gguucuagau aggugu                                                        16

<210> SEQ ID NO 199
<211> LENGTH: 16
<212> TYPE: RNA
<213> ORGANISM: Homo sapiens

<400> SEQUENCE: 199
cuagauaggu gucuuu                                                        16

<210> SEQ ID NO 200
<211> LENGTH: 16
<212> TYPE: RNA
<213> ORGANISM: Homo sapiens

<400> SEQUENCE: 200
uuaggacucu gauuuu                                                        16

<210> SEQ ID NO 201
<211> LENGTH: 16
<212> TYPE: RNA
<213> ORGANISM: Homo sapiens

<400> SEQUENCE: 201
cucugauuuu gaggac                                                        16

<210> SEQ ID NO 202
<211> LENGTH: 16
<212> TYPE: RNA
<213> ORGANISM: Homo sapiens

<400> SEQUENCE: 202
auuucuucau guuaaa                                                        16

<210> SEQ ID NO 203
<211> LENGTH: 16
<212> TYPE: RNA
<213> ORGANISM: Homo sapiens

<400> SEQUENCE: 203
uuuacacuau gugauu                                                        16

<210> SEQ ID NO 204
<211> LENGTH: 16

-continued

```
<212> TYPE: RNA
<213> ORGANISM: Homo sapiens

<400> SEQUENCE: 204
uacacuaugu gauuua                                              16

<210> SEQ ID NO 205
<211> LENGTH: 16
<212> TYPE: RNA
<213> ORGANISM: Homo sapiens

<400> SEQUENCE: 205
ugugauuuau auucca                                              16

<210> SEQ ID NO 206
<211> LENGTH: 16
<212> TYPE: RNA
<213> ORGANISM: Homo sapiens

<400> SEQUENCE: 206
ccauuuacau aaggau                                              16

<210> SEQ ID NO 207
<211> LENGTH: 16
<212> TYPE: RNA
<213> ORGANISM: Homo sapiens

<400> SEQUENCE: 207
acauaaggau acacuu                                              16

<210> SEQ ID NO 208
<211> LENGTH: 16
<212> TYPE: RNA
<213> ORGANISM: Homo sapiens

<400> SEQUENCE: 208
acacuuauuu gucaag                                              16

<210> SEQ ID NO 209
<211> LENGTH: 16
<212> TYPE: RNA
<213> ORGANISM: Homo sapiens

<400> SEQUENCE: 209
agcacaaucu guaaau                                              16

<210> SEQ ID NO 210
<211> LENGTH: 16
<212> TYPE: RNA
<213> ORGANISM: Homo sapiens

<400> SEQUENCE: 210
uuuaaccuau guuaca                                              16

<210> SEQ ID NO 211
<211> LENGTH: 16
<212> TYPE: RNA
<213> ORGANISM: Homo sapiens

<400> SEQUENCE: 211
caucuucagu gccagu                                              16

<210> SEQ ID NO 212
```

-continued

```
<211> LENGTH: 16
<212> TYPE: RNA
<213> ORGANISM: Homo sapiens

<400> SEQUENCE: 212
gggcaaaauu gugcaa                                              16

<210> SEQ ID NO 213
<211> LENGTH: 16
<212> TYPE: RNA
<213> ORGANISM: Homo sapiens

<400> SEQUENCE: 213
gcaaaauugu gcaaga                                              16

<210> SEQ ID NO 214
<211> LENGTH: 16
<212> TYPE: RNA
<213> ORGANISM: Homo sapiens

<400> SEQUENCE: 214
ugcaagaggu gaaguu                                              16

<210> SEQ ID NO 215
<211> LENGTH: 16
<212> TYPE: RNA
<213> ORGANISM: Homo sapiens

<400> SEQUENCE: 215
ugaaguuuau auuuga                                              16

<210> SEQ ID NO 216
<211> LENGTH: 16
<212> TYPE: RNA
<213> ORGANISM: Homo sapiens

<400> SEQUENCE: 216
guuuauauuu gaauau                                              16

<210> SEQ ID NO 217
<211> LENGTH: 16
<212> TYPE: RNA
<213> ORGANISM: Homo sapiens

<400> SEQUENCE: 217
auauuugaau auccau                                              16

<210> SEQ ID NO 218
<211> LENGTH: 16
<212> TYPE: RNA
<213> ORGANISM: Homo sapiens

<400> SEQUENCE: 218
cuucuuccau auuagu                                              16

<210> SEQ ID NO 219
<211> LENGTH: 16
<212> TYPE: RNA
<213> ORGANISM: Homo sapiens

<400> SEQUENCE: 219
ccauauuagu gucauc                                              16
```

-continued

```
<210> SEQ ID NO 220
<211> LENGTH: 16
<212> TYPE: RNA
<213> ORGANISM: Homo sapiens

<400> SEQUENCE: 220
gugucaucuu gccucc                                                        16

<210> SEQ ID NO 221
<211> LENGTH: 16
<212> TYPE: RNA
<213> ORGANISM: Homo sapiens

<400> SEQUENCE: 221
ccuuccacau gcccca                                                        16

<210> SEQ ID NO 222
<211> LENGTH: 16
<212> TYPE: RNA
<213> ORGANISM: Homo sapiens

<400> SEQUENCE: 222
caugccccau gacuug                                                        16

<210> SEQ ID NO 223
<211> LENGTH: 16
<212> TYPE: RNA
<213> ORGANISM: Homo sapiens

<400> SEQUENCE: 223
cccaugacuu gaugca                                                        16

<210> SEQ ID NO 224
<211> LENGTH: 16
<212> TYPE: RNA
<213> ORGANISM: Homo sapiens

<400> SEQUENCE: 224
augacuugau gcaguu                                                        16

<210> SEQ ID NO 225
<211> LENGTH: 16
<212> TYPE: RNA
<213> ORGANISM: Homo sapiens

<400> SEQUENCE: 225
caguuuuaau acuugu                                                        16

<210> SEQ ID NO 226
<211> LENGTH: 16
<212> TYPE: RNA
<213> ORGANISM: Homo sapiens

<400> SEQUENCE: 226
uuuaauacuu guaauu                                                        16

<210> SEQ ID NO 227
<211> LENGTH: 16
<212> TYPE: RNA
<213> ORGANISM: Homo sapiens

<400> SEQUENCE: 227
cccuaaccau aagauu                                                        16
```

<210> SEQ ID NO 228
<211> LENGTH: 16
<212> TYPE: RNA
<213> ORGANISM: Homo sapiens

<400> SEQUENCE: 228
aagauuuacu gcugcu                                                    16

<210> SEQ ID NO 229
<211> LENGTH: 16
<212> TYPE: RNA
<213> ORGANISM: Homo sapiens

<400> SEQUENCE: 229
auuuacugcu gcugug                                                    16

<210> SEQ ID NO 230
<211> LENGTH: 16
<212> TYPE: RNA
<213> ORGANISM: Homo sapiens

<400> SEQUENCE: 230
uacugcugcu guggau                                                    16

<210> SEQ ID NO 231
<211> LENGTH: 16
<212> TYPE: RNA
<213> ORGANISM: Homo sapiens

<400> SEQUENCE: 231
ugcuguggau aucucc                                                    16

<210> SEQ ID NO 232
<211> LENGTH: 16
<212> TYPE: RNA
<213> ORGANISM: Homo sapiens

<400> SEQUENCE: 232
auaucuccau gaaguu                                                    16

<210> SEQ ID NO 233
<211> LENGTH: 16
<212> TYPE: RNA
<213> ORGANISM: Homo sapiens

<400> SEQUENCE: 233
uuuucccacu gaguca                                                    16

<210> SEQ ID NO 234
<211> LENGTH: 16
<212> TYPE: RNA
<213> ORGANISM: Homo sapiens

<400> SEQUENCE: 234
caucagaaau gcccua                                                    16

<210> SEQ ID NO 235
<211> LENGTH: 16
<212> TYPE: RNA
<213> ORGANISM: Homo sapiens

<400> SEQUENCE: 235
aagagaaucu gacaga                                                    16

```
<210> SEQ ID NO 236
<211> LENGTH: 16
<212> TYPE: RNA
<213> ORGANISM: Homo sapiens

<400> SEQUENCE: 236 ucgacagau accaua                                                    16

<210> SEQ ID NO 237
<211> LENGTH: 16
<212> TYPE: RNA
<213> ORGANISM: Homo sapiens

<400> SEQUENCE: 237
cagauaccau aaaggg                                                   16

<210> SEQ ID NO 238
<211> LENGTH: 16
<212> TYPE: RNA
<213> ORGANISM: Homo sapiens

<400> SEQUENCE: 238
aaagggauuu gaccua                                                   16

<210> SEQ ID NO 239
<211> LENGTH: 16
<212> TYPE: RNA
<213> ORGANISM: Homo sapiens

<400> SEQUENCE: 239
ggugguggcu gaugcu                                                   16

<210> SEQ ID NO 240
<211> LENGTH: 16
<212> TYPE: RNA
<213> ORGANISM: Homo sapiens

<400> SEQUENCE: 240
gguggcugau gcuuug                                                   16

<210> SEQ ID NO 241
<211> LENGTH: 16
<212> TYPE: RNA
<213> ORGANISM: Homo sapiens

<400> SEQUENCE: 241
cugaugcuuu gaacau                                                   16

<210> SEQ ID NO 242
<211> LENGTH: 16
<212> TYPE: RNA
<213> ORGANISM: Homo sapiens

<400> SEQUENCE: 242
acaucucuuu gcugcc                                                   16

<210> SEQ ID NO 243
<211> LENGTH: 16
<212> TYPE: RNA
<213> ORGANISM: Homo sapiens

<400> SEQUENCE: 243
```

-continued ucucuuugcu gcccaa                                          16

<210> SEQ ID NO 244
<211> LENGTH: 16
<212> TYPE: RNA
<213> ORGANISM: Homo sapiens

<400> SEQUENCE: 244
auccauuagc gacagu                                          16

<210> SEQ ID NO 245
<211> LENGTH: 16
<212> TYPE: RNA
<213> ORGANISM: Homo sapiens

<400> SEQUENCE: 245
acccugguau gaauag                                          16

<210> SEQ ID NO 246
<211> LENGTH: 16
<212> TYPE: RNA
<213> ORGANISM: Homo sapiens

<400> SEQUENCE: 246
ugguaugaau agacag                                          16

<210> SEQ ID NO 247
<211> LENGTH: 16
<212> TYPE: RNA
<213> ORGANISM: Homo sapiens

<400> SEQUENCE: 247
agaauuuaau aaagau                                          16

<210> SEQ ID NO 248
<211> LENGTH: 16
<212> TYPE: RNA
<213> ORGANISM: Homo sapiens

<400> SEQUENCE: 248
uaauaaagau agugca                                          16

<210> SEQ ID NO 249
<211> LENGTH: 16
<212> TYPE: RNA
<213> ORGANISM: Homo sapiens

<400> SEQUENCE: 249
uaaagauagu gcagaa                                          16

<210> SEQ ID NO 250
<211> LENGTH: 16
<212> TYPE: RNA
<213> ORGANISM: Homo sapiens

<400> SEQUENCE: 250
gguaaucuau aacuag                                          16

<210> SEQ ID NO 251
<211> LENGTH: 16
<212> TYPE: RNA
<213> ORGANISM: Homo sapiens

<400> SEQUENCE: 251
uaacaguaau acauuc                                                             16

<210> SEQ ID NO 252
<211> LENGTH: 16
<212> TYPE: RNA
<213> ORGANISM: Homo sapiens

<400> SEQUENCE: 252
acauuccauu guuuua                                                             16

<210> SEQ ID NO 253
<211> LENGTH: 16
<212> TYPE: RNA
<213> ORGANISM: Homo sapiens

<400> SEQUENCE: 253
aaaucuucau gcaaug                                                             16

<210> SEQ ID NO 254
<211> LENGTH: 16
<212> TYPE: RNA
<213> ORGANISM: Homo sapiens

<400> SEQUENCE: 254
uucaugcaau gaaaaa                                                             16

<210> SEQ ID NO 255
<211> LENGTH: 16
<212> TYPE: RNA
<213> ORGANISM: Homo sapiens

<400> SEQUENCE: 255
aaugaaaaau acuuua                                                             16

<210> SEQ ID NO 256
<211> LENGTH: 16
<212> TYPE: RNA
<213> ORGANISM: Homo sapiens

<400> SEQUENCE: 256
uuuaauucau gaagcu                                                             16

<210> SEQ ID NO 257
<211> LENGTH: 16
<212> TYPE: RNA
<213> ORGANISM: Homo sapiens

<400> SEQUENCE: 257
uuuuuuuggu gucaga                                                             16

<210> SEQ ID NO 258
<211> LENGTH: 16
<212> TYPE: RNA
<213> ORGANISM: Homo sapiens

<400> SEQUENCE: 258
ucagagucuc gcucuu                                                             16

<210> SEQ ID NO 259
<211> LENGTH: 16
<212> TYPE: RNA
<213> ORGANISM: Homo sapiens -continued

```
<400> SEQUENCE: 259
ucucgcucuu gucacc                                                    16

<210> SEQ ID NO 260
<211> LENGTH: 16
<212> TYPE: RNA
<213> ORGANISM: Homo sapiens

<400> SEQUENCE: 260
aggcuggaau gcagug                                                    16

<210> SEQ ID NO 261
<211> LENGTH: 16
<212> TYPE: RNA
<213> ORGANISM: Homo sapiens

<400> SEQUENCE: 261
augcaguggc gccauc                                                    16

<210> SEQ ID NO 262
<211> LENGTH: 16
<212> TYPE: RNA
<213> ORGANISM: Homo sapiens

<400> SEQUENCE: 262
ucagcucacu gcaacc                                                    16

<210> SEQ ID NO 263
<211> LENGTH: 16
<212> TYPE: RNA
<213> ORGANISM: Homo sapiens

<400> SEQUENCE: 263
agguucaagc gauucu                                                    16

<210> SEQ ID NO 264
<211> LENGTH: 16
<212> TYPE: RNA
<213> ORGANISM: Homo sapiens

<400> SEQUENCE: 264
cgauucucgu gccucg                                                    16

<210> SEQ ID NO 265
<211> LENGTH: 16
<212> TYPE: RNA
<213> ORGANISM: Homo sapiens

<400> SEQUENCE: 265
ucggccuccu gaguag                                                    16

<210> SEQ ID NO 266
<211> LENGTH: 16
<212> TYPE: RNA
<213> ORGANISM: Homo sapiens

<400> SEQUENCE: 266
uuacaggcgu gugcac                                                    16

<210> SEQ ID NO 267
<211> LENGTH: 16
<212> TYPE: RNA
<213> ORGANISM: Homo sapiens
```

```
<400> SEQUENCE: 267
acaggcgugu gcacua                                                    16

<210> SEQ ID NO 268
<211> LENGTH: 16
<212> TYPE: RNA
<213> ORGANISM: Homo sapiens

<400> SEQUENCE: 268
acuaauuuuu guauuu                                                    16

<210> SEQ ID NO 269
<211> LENGTH: 16
<212> TYPE: RNA
<213> ORGANISM: Homo sapiens

<400> SEQUENCE: 269
gguuucaccu guuggc                                                    16

<210> SEQ ID NO 270
<211> LENGTH: 16
<212> TYPE: RNA
<213> ORGANISM: Homo sapiens

<400> SEQUENCE: 270
ggcuggucuc gaacuc                                                    16

<210> SEQ ID NO 271
<211> LENGTH: 16
<212> TYPE: RNA
<213> ORGANISM: Homo sapiens

<400> SEQUENCE: 271
ucgaacuccu gaccuc                                                    16

<210> SEQ ID NO 272
<211> LENGTH: 16
<212> TYPE: RNA
<213> ORGANISM: Homo sapiens

<400> SEQUENCE: 272
gaccucaagu gauuca                                                    16

<210> SEQ ID NO 273
<211> LENGTH: 16
<212> TYPE: RNA
<213> ORGANISM: Homo sapiens

<400> SEQUENCE: 273
uuggccucau aaaccu                                                    16

<210> SEQ ID NO 274
<211> LENGTH: 16
<212> TYPE: RNA
<213> ORGANISM: Homo sapiens

<400> SEQUENCE: 274
ucauaaaccu guuuug                                                    16

<210> SEQ ID NO 275
<211> LENGTH: 16
<212> TYPE: RNA
```

```
<213> ORGANISM: Homo sapiens

<400> SEQUENCE: 275
aaccuguuuu gcagaa                                                        16

<210> SEQ ID NO 276
<211> LENGTH: 16
<212> TYPE: RNA
<213> ORGANISM: Homo sapiens

<400> SEQUENCE: 276
uucagcaaau auuuau                                                        16

<210> SEQ ID NO 277
<211> LENGTH: 16
<212> TYPE: RNA
<213> ORGANISM: Homo sapiens

<400> SEQUENCE: 277
aauauuuauu gagugc                                                        16

<210> SEQ ID NO 278
<211> LENGTH: 16
<212> TYPE: RNA
<213> ORGANISM: Homo sapiens

<400> SEQUENCE: 278
uuuauugagu gccuac                                                        16

<210> SEQ ID NO 279
<211> LENGTH: 16
<212> TYPE: RNA
<213> ORGANISM: Homo sapiens

<400> SEQUENCE: 279
ccuaccagau gccagu                                                        16

<210> SEQ ID NO 280
<211> LENGTH: 16
<212> TYPE: RNA
<213> ORGANISM: Homo sapiens

<400> SEQUENCE: 280
gccagucacc gcacaa                                                        16

<210> SEQ ID NO 281
<211> LENGTH: 16
<212> TYPE: RNA
<213> ORGANISM: Homo sapiens

<400> SEQUENCE: 281 cacugguau auggua                                                         16

<210> SEQ ID NO 282
<211> LENGTH: 16
<212> TYPE: RNA
<213> ORGANISM: Homo sapiens

<400> SEQUENCE: 282
cuggguauau gguauc                                                        16

<210> SEQ ID NO 283
<211> LENGTH: 16
```

<212> TYPE: RNA
<213> ORGANISM: Homo sapiens

<400> SEQUENCE: 283
caagagacau aauccc                                                        16

<210> SEQ ID NO 284
<211> LENGTH: 16
<212> TYPE: RNA
<213> ORGANISM: Homo sapiens

<400> SEQUENCE: 284
cuuagguacu gcuagu                                                        16

<210> SEQ ID NO 285
<211> LENGTH: 16
<212> TYPE: RNA
<213> ORGANISM: Homo sapiens

<400> SEQUENCE: 285
uacugcuagu gugguc                                                        16

<210> SEQ ID NO 286
<211> LENGTH: 16
<212> TYPE: RNA
<213> ORGANISM: Homo sapiens

<400> SEQUENCE: 286
aguguggucu guaaua                                                        16

<210> SEQ ID NO 287
<211> LENGTH: 16
<212> TYPE: RNA
<213> ORGANISM: Homo sapiens

<400> SEQUENCE: 287
ggucuguaau aucuua                                                        16

<210> SEQ ID NO 288
<211> LENGTH: 16
<212> TYPE: RNA
<213> ORGANISM: Homo sapiens

<400> SEQUENCE: 288
ccuuugguau acgacc                                                        16

<210> SEQ ID NO 289
<211> LENGTH: 16
<212> TYPE: RNA
<213> ORGANISM: Homo sapiens

<400> SEQUENCE: 289
uuugguauac gaccca                                                        16

<210> SEQ ID NO 290
<211> LENGTH: 16
<212> TYPE: RNA
<213> ORGANISM: Homo sapiens

<400> SEQUENCE: 290
acccagagau aacacg                                                        16

<210> SEQ ID NO 291

-continued

```
<211> LENGTH: 16
<212> TYPE: RNA
<213> ORGANISM: Homo sapiens

<400> SEQUENCE: 291
gagauaacac gaugcg                                              16

<210> SEQ ID NO 292
<211> LENGTH: 16
<212> TYPE: RNA
<213> ORGANISM: Homo sapiens

<400> SEQUENCE: 292
auaacacgau gcguau                                              16

<210> SEQ ID NO 293
<211> LENGTH: 16
<212> TYPE: RNA
<213> ORGANISM: Homo sapiens

<400> SEQUENCE: 293
uuuuaguuuu gcaaag                                              16

<210> SEQ ID NO 294
<211> LENGTH: 16
<212> TYPE: RNA
<213> ORGANISM: Homo sapiens

<400> SEQUENCE: 294
uuuggucucu gugcca                                              16

<210> SEQ ID NO 295
<211> LENGTH: 16
<212> TYPE: RNA
<213> ORGANISM: Homo sapiens

<400> SEQUENCE: 295
uggucucugu gccagc                                              16

<210> SEQ ID NO 296
<211> LENGTH: 16
<212> TYPE: RNA
<213> ORGANISM: Homo sapiens

<400> SEQUENCE: 296
ccagcucuau aauugu                                              16

<210> SEQ ID NO 297
<211> LENGTH: 16
<212> TYPE: RNA
<213> ORGANISM: Homo sapiens

<400> SEQUENCE: 297
cucuauaauu guuuug                                              16

<210> SEQ ID NO 298
<211> LENGTH: 16
<212> TYPE: RNA
<213> ORGANISM: Homo sapiens

<400> SEQUENCE: 298
uaauuguuuu gcuacg                                              16
```

```
<210> SEQ ID NO 299
<211> LENGTH: 16
<212> TYPE: RNA
<213> ORGANISM: Homo sapiens

<400> SEQUENCE: 299
guuuugcuac gauucc                                                      16

<210> SEQ ID NO 300
<211> LENGTH: 16
<212> TYPE: RNA
<213> ORGANISM: Homo sapiens

<400> SEQUENCE: 300
cgauuccacu gaaacu                                                      16

<210> SEQ ID NO 301
<211> LENGTH: 16
<212> TYPE: RNA
<213> ORGANISM: Homo sapiens

<400> SEQUENCE: 301
gaaacucuuc gaucaa                                                      16

<210> SEQ ID NO 302
<211> LENGTH: 16
<212> TYPE: RNA
<213> ORGANISM: Homo sapiens

<400> SEQUENCE: 302
gcuacuuuau guaaau                                                      16

<210> SEQ ID NO 303
<211> LENGTH: 16
<212> TYPE: RNA
<213> ORGANISM: Homo sapiens

<400> SEQUENCE: 303
ucacuucauu guuuua                                                      16

<210> SEQ ID NO 304
<211> LENGTH: 16
<212> TYPE: RNA
<213> ORGANISM: Homo sapiens

<400> SEQUENCE: 304
uuaaaggaau aaacuu                                                      16

<210> SEQ ID NO 305
<211> LENGTH: 16
<212> TYPE: RNA
<213> ORGANISM: Homo sapiens

<400> SEQUENCE: 305
gaauaaacuu gauuau                                                      16

<210> SEQ ID NO 306
<211> LENGTH: 16
<212> TYPE: RNA
<213> ORGANISM: Homo sapiens

<400> SEQUENCE: 306
acuugauuau auuguu                                                      16
```

<210> SEQ ID NO 307
<211> LENGTH: 16
<212> TYPE: RNA
<213> ORGANISM: Homo sapiens

<400> SEQUENCE: 307
ugauuauauu guuuuu                                                         16

<210> SEQ ID NO 308
<211> LENGTH: 16
<212> TYPE: RNA
<213> ORGANISM: Homo sapiens

<400> SEQUENCE: 308
uauuuggcau aacugu                                                         16

<210> SEQ ID NO 309
<211> LENGTH: 16
<212> TYPE: RNA
<213> ORGANISM: Homo sapiens

<400> SEQUENCE: 309
uggcauaacu gugauu                                                         16

<210> SEQ ID NO 310
<211> LENGTH: 16
<212> TYPE: RNA
<213> ORGANISM: Homo sapiens

<400> SEQUENCE: 310
gcauaacugu gauucu                                                         16

<210> SEQ ID NO 311
<211> LENGTH: 16
<212> TYPE: RNA
<213> ORGANISM: Homo sapiens

<400> SEQUENCE: 311
gacaauuacu guacac                                                         16

<210> SEQ ID NO 312
<211> LENGTH: 16
<212> TYPE: RNA
<213> ORGANISM: Homo sapiens

<400> SEQUENCE: 312
acauuaaggu guaugu                                                         16

<210> SEQ ID NO 313
<211> LENGTH: 16
<212> TYPE: RNA
<213> ORGANISM: Homo sapiens

<400> SEQUENCE: 313
uaagguguau gucaga                                                         16

<210> SEQ ID NO 314
<211> LENGTH: 16
<212> TYPE: RNA
<213> ORGANISM: Homo sapiens

<400> SEQUENCE: 314
uaugucagau auucau                                                         16

<210> SEQ ID NO 315
<211> LENGTH: 16
<212> TYPE: RNA
<213> ORGANISM: Homo sapiens

<400> SEQUENCE: 315
agauauucau auugac                                               16

<210> SEQ ID NO 316
<211> LENGTH: 16
<212> TYPE: RNA
<213> ORGANISM: Homo sapiens

<400> SEQUENCE: 316
uauucauauu gaccca                                               16

<210> SEQ ID NO 317
<211> LENGTH: 16
<212> TYPE: RNA
<213> ORGANISM: Homo sapiens

<400> SEQUENCE: 317
ugacccaaau guguaa                                               16

<210> SEQ ID NO 318
<211> LENGTH: 16
<212> TYPE: RNA
<213> ORGANISM: Homo sapiens

<400> SEQUENCE: 318
acccaaaugu guaaua                                               16

<210> SEQ ID NO 319
<211> LENGTH: 16
<212> TYPE: RNA
<213> ORGANISM: Homo sapiens

<400> SEQUENCE: 319
aauguguaau auucca                                               16

<210> SEQ ID NO 320
<211> LENGTH: 16
<212> TYPE: RNA
<213> ORGANISM: Homo sapiens

<400> SEQUENCE: 320
aguuuucucu gcauaa                                               16

<210> SEQ ID NO 321
<211> LENGTH: 16
<212> TYPE: RNA
<213> ORGANISM: Homo sapiens

<400> SEQUENCE: 321
uucucugcau aaguaa                                               16

<210> SEQ ID NO 322
<211> LENGTH: 16
<212> TYPE: RNA
<213> ORGANISM: Homo sapiens

<400> SEQUENCE: 322
uaauuaaaau auacuu 16

<210> SEQ ID NO 323
<211> LENGTH: 16
<212> TYPE: RNA
<213> ORGANISM: Homo sapiens

<400> SEQUENCE: 323
auuaaaauau acuuaa 16

<210> SEQ ID NO 324
<211> LENGTH: 16
<212> TYPE: RNA
<213> ORGANISM: Homo sapiens

<400> SEQUENCE: 324
aaaaauuaau aguuuu 16

<210> SEQ ID NO 325
<211> LENGTH: 16
<212> TYPE: RNA
<213> ORGANISM: Homo sapiens

<400> SEQUENCE: 325
ggguacaaau aaacag 16

<210> SEQ ID NO 326
<211> LENGTH: 16
<212> TYPE: RNA
<213> ORGANISM: Homo sapiens

<400> SEQUENCE: 326
aauaaacagu gccuga 16

<210> SEQ ID NO 327
<211> LENGTH: 16
<212> TYPE: RNA
<213> ORGANISM: Homo sapiens

<400> SEQUENCE: 327
aacagugccu gaacua 16

<210> SEQ ID NO 328
<211> LENGTH: 16
<212> TYPE: RNA
<213> ORGANISM: Homo sapiens

<400> SEQUENCE: 328
aaacuucuau guaaaa 16

<210> SEQ ID NO 329
<211> LENGTH: 16
<212> TYPE: RNA
<213> ORGANISM: Homo sapiens

<400> SEQUENCE: 329
aaaucacuau gauuuc 16

<210> SEQ ID NO 330
<211> LENGTH: 16
<212> TYPE: RNA
<213> ORGANISM: Homo sapiens

<400> SEQUENCE: 330

-continued uaugauuucu gaauug 16

<210> SEQ ID NO 331
<211> LENGTH: 16
<212> TYPE: RNA
<213> ORGANISM: Homo sapiens

<400> SEQUENCE: 331
uuucugaauu gcuaug 16

<210> SEQ ID NO 332
<211> LENGTH: 16
<212> TYPE: RNA
<213> ORGANISM: Homo sapiens

<400> SEQUENCE: 332
gaauugcuau gugaaa 16

<210> SEQ ID NO 333
<211> LENGTH: 16
<212> TYPE: RNA
<213> ORGANISM: Homo sapiens

<400> SEQUENCE: 333
auugcuaugu gaaacu 16

<210> SEQ ID NO 334
<211> LENGTH: 16
<212> TYPE: RNA
<213> ORGANISM: Homo sapiens

<400> SEQUENCE: 334
uuggaacacu guuuag 16

<210> SEQ ID NO 335
<211> LENGTH: 16
<212> TYPE: RNA
<213> ORGANISM: Homo sapiens

<400> SEQUENCE: 335
uagguagggu guuaag 16

<210> SEQ ID NO 336
<211> LENGTH: 16
<212> TYPE: RNA
<213> ORGANISM: Homo sapiens

<400> SEQUENCE: 336
guuaagacuu gacaca 16

<210> SEQ ID NO 337
<211> LENGTH: 16
<212> TYPE: RNA
<213> ORGANISM: Homo sapiens

<400> SEQUENCE: 337
agaaagaaau ggccau 16

<210> SEQ ID NO 338
<211> LENGTH: 16
<212> TYPE: RNA
<213> ORGANISM: Homo sapiens

```
<400> SEQUENCE: 338
aaauggccau acuuca                                                    16

<210> SEQ ID NO 339
<211> LENGTH: 16
<212> TYPE: RNA
<213> ORGANISM: Homo sapiens

<400> SEQUENCE: 339
uucaggaacu gcagug                                                    16

<210> SEQ ID NO 340
<211> LENGTH: 16
<212> TYPE: RNA
<213> ORGANISM: Homo sapiens

<400> SEQUENCE: 340
gaacugcagu gcuuau                                                    16

<210> SEQ ID NO 341
<211> LENGTH: 16
<212> TYPE: RNA
<213> ORGANISM: Homo sapiens

<400> SEQUENCE: 341
cagugcuuau gagggg                                                    16

<210> SEQ ID NO 342
<211> LENGTH: 16
<212> TYPE: RNA
<213> ORGANISM: Homo sapiens

<400> SEQUENCE: 342
augaggggau auuuag                                                    16

<210> SEQ ID NO 343
<211> LENGTH: 16
<212> TYPE: RNA
<213> ORGANISM: Homo sapiens

<400> SEQUENCE: 343
uaggccucuu gaauuu                                                    16

<210> SEQ ID NO 344
<211> LENGTH: 16
<212> TYPE: RNA
<213> ORGANISM: Homo sapiens

<400> SEQUENCE: 344
uugaauuuuu gaugua                                                    16

<210> SEQ ID NO 345
<211> LENGTH: 16
<212> TYPE: RNA
<213> ORGANISM: Homo sapiens

<400> SEQUENCE: 345
aauuuuugau guagau                                                    16

<210> SEQ ID NO 346
<211> LENGTH: 16
<212> TYPE: RNA
<213> ORGANISM: Homo sapiens
```

<400> SEQUENCE: 346
ugauguagau gggcau                                           16

<210> SEQ ID NO 347
<211> LENGTH: 16
<212> TYPE: RNA
<213> ORGANISM: Homo sapiens

<400> SEQUENCE: 347
uuaccuuuau gugaac                                           16

<210> SEQ ID NO 348
<211> LENGTH: 16
<212> TYPE: RNA
<213> ORGANISM: Homo sapiens

<400> SEQUENCE: 348
accuuuaugu gaacuu                                           16

<210> SEQ ID NO 349
<211> LENGTH: 16
<212> TYPE: RNA
<213> ORGANISM: Homo sapiens

<400> SEQUENCE: 349
ugugaacuuu gaaugg                                           16

<210> SEQ ID NO 350
<211> LENGTH: 16
<212> TYPE: RNA
<213> ORGANISM: Homo sapiens

<400> SEQUENCE: 350
aacuuugaau gguuua                                           16

<210> SEQ ID NO 351
<211> LENGTH: 16
<212> TYPE: RNA
<213> ORGANISM: Homo sapiens

<400> SEQUENCE: 351
caaaagauuu guuuuu                                           16

<210> SEQ ID NO 352
<211> LENGTH: 16
<212> TYPE: RNA
<213> ORGANISM: Homo sapiens

<400> SEQUENCE: 352
auuuguuuuu guagag                                           16

<210> SEQ ID NO 353
<211> LENGTH: 16
<212> TYPE: RNA
<213> ORGANISM: Homo sapiens

<400> SEQUENCE: 353
uucuagaaau aaaugu                                           16

<210> SEQ ID NO 354
<211> LENGTH: 16
<212> TYPE: RNA

```
<213> ORGANISM: Homo sapiens

<400> SEQUENCE: 354
agaaauaaau guuacc                                                    16

<210> SEQ ID NO 355
<211> LENGTH: 16
<212> TYPE: RNA
<213> ORGANISM: Homo sapiens

<400> SEQUENCE: 355
aaaaauccuu guugaa                                                    16

<210> SEQ ID NO 356
<211> LENGTH: 16
<212> TYPE: RNA
<213> ORGANISM: Homo sapiens

<400> SEQUENCE: 356
aauccuuguu gaaguu                                                    16

<210> SEQ ID NO 357
<211> LENGTH: 16
<212> TYPE: RNA
<213> ORGANISM: Homo sapiens

<400> SEQUENCE: 357
uaaauuacau agacuu                                                    16

<210> SEQ ID NO 358
<211> LENGTH: 16
<212> TYPE: RNA
<213> ORGANISM: Homo sapiens

<400> SEQUENCE: 358
gcauuaacau guuugu                                                    16

<210> SEQ ID NO 359
<211> LENGTH: 16
<212> TYPE: RNA
<213> ORGANISM: Homo sapiens

<400> SEQUENCE: 359
uaacauguuu guggaa                                                    16

<210> SEQ ID NO 360
<211> LENGTH: 16
<212> TYPE: RNA
<213> ORGANISM: Homo sapiens

<400> SEQUENCE: 360
guggaagaau auagca                                                    16

<210> SEQ ID NO 361
<211> LENGTH: 16
<212> TYPE: RNA
<213> ORGANISM: Homo sapiens

<400> SEQUENCE: 361
ggaagaauau agcaga                                                    16

<210> SEQ ID NO 362
<211> LENGTH: 16
```

<212> TYPE: RNA
<213> ORGANISM: Homo sapiens

<400> SEQUENCE: 362
gcagacguau auugua                                                    16

<210> SEQ ID NO 363
<211> LENGTH: 16
<212> TYPE: RNA
<213> ORGANISM: Homo sapiens

<400> SEQUENCE: 363
gacguauauu guauca                                                    16

<210> SEQ ID NO 364
<211> LENGTH: 16
<212> TYPE: RNA
<213> ORGANISM: Homo sapiens

<400> SEQUENCE: 364
uguaucauuu gaguga                                                    16

<210> SEQ ID NO 365
<211> LENGTH: 16
<212> TYPE: RNA
<213> ORGANISM: Homo sapiens

<400> SEQUENCE: 365 ucauugagu gaaugu                                                     16

<210> SEQ ID NO 366
<211> LENGTH: 16
<212> TYPE: RNA
<213> ORGANISM: Homo sapiens

<400> SEQUENCE: 366
uugagugaau guuccc                                                    16

<210> SEQ ID NO 367
<211> LENGTH: 16
<212> TYPE: RNA
<213> ORGANISM: Homo sapiens

<400> SEQUENCE: 367
cuauuuaacu gaguca                                                    16

<210> SEQ ID NO 368
<211> LENGTH: 16
<212> TYPE: RNA
<213> ORGANISM: Homo sapiens

<400> SEQUENCE: 368
gagucacacu gcauag                                                    16

<210> SEQ ID NO 369
<211> LENGTH: 16
<212> TYPE: RNA
<213> ORGANISM: Homo sapiens

<400> SEQUENCE: 369
cacacugcau aggaau                                                    16

<210> SEQ ID NO 370

```
<211> LENGTH: 16
<212> TYPE: RNA
<213> ORGANISM: Homo sapiens

<400> SEQUENCE: 370
uaacuuuuau agguua                                                    16

<210> SEQ ID NO 371
<211> LENGTH: 16
<212> TYPE: RNA
<213> ORGANISM: Homo sapiens

<400> SEQUENCE: 371
uaucaaaacu guuguc                                                    16

<210> SEQ ID NO 372
<211> LENGTH: 16
<212> TYPE: RNA
<213> ORGANISM: Homo sapiens

<400> SEQUENCE: 372
caaaacuguu gucacc                                                    16

<210> SEQ ID NO 373
<211> LENGTH: 16
<212> TYPE: RNA
<213> ORGANISM: Homo sapiens

<400> SEQUENCE: 373
ugucaccauu gcacaa                                                    16

<210> SEQ ID NO 374
<211> LENGTH: 16
<212> TYPE: RNA
<213> ORGANISM: Homo sapiens

<400> SEQUENCE: 374
gcacaauuuu guccua                                                    16

<210> SEQ ID NO 375
<211> LENGTH: 16
<212> TYPE: RNA
<213> ORGANISM: Homo sapiens

<400> SEQUENCE: 375
uuguccuaau auauac                                                    16

<210> SEQ ID NO 376
<211> LENGTH: 16
<212> TYPE: RNA
<213> ORGANISM: Homo sapiens

<400> SEQUENCE: 376
guccuaauau auacau                                                    16

<210> SEQ ID NO 377
<211> LENGTH: 16
<212> TYPE: RNA
<213> ORGANISM: Homo sapiens

<400> SEQUENCE: 377
ccuaauauau acauag                                                    16
```

```
<210> SEQ ID NO 378
<211> LENGTH: 16
<212> TYPE: RNA
<213> ORGANISM: Homo sapiens

<400> SEQUENCE: 378
auauauacau agaaac                                              16

<210> SEQ ID NO 379
<211> LENGTH: 16
<212> TYPE: RNA
<213> ORGANISM: Homo sapiens

<400> SEQUENCE: 379
uagaaacuuu gugggg                                              16

<210> SEQ ID NO 380
<211> LENGTH: 16
<212> TYPE: RNA
<213> ORGANISM: Homo sapiens

<400> SEQUENCE: 380 ugugggcau guuaag                                               16

<210> SEQ ID NO 381
<211> LENGTH: 16
<212> TYPE: RNA
<213> ORGANISM: Homo sapiens

<400> SEQUENCE: 381
guuacaguuu gcacaa                                              16

<210> SEQ ID NO 382
<211> LENGTH: 16
<212> TYPE: RNA
<213> ORGANISM: Homo sapiens

<400> SEQUENCE: 382
caucucauuu guauuc                                              16

<210> SEQ ID NO 383
<211> LENGTH: 16
<212> TYPE: RNA
<213> ORGANISM: Homo sapiens

<400> SEQUENCE: 383
guauuccauu gauuuu                                              16

<210> SEQ ID NO 384
<211> LENGTH: 16
<212> TYPE: RNA
<213> ORGANISM: Homo sapiens

<400> SEQUENCE: 384
aaaacaguau auauaa                                              16

<210> SEQ ID NO 385
<211> LENGTH: 16
<212> TYPE: RNA
<213> ORGANISM: Homo sapiens

<400> SEQUENCE: 385
aacaguauau auaacu                                              16
```

<210> SEQ ID NO 386
<211> LENGTH: 16
<212> TYPE: RNA
<213> ORGANISM: Homo sapiens

<400> SEQUENCE: 386
caguauauau aacuuu                                                         16

<210> SEQ ID NO 387
<211> LENGTH: 16
<212> TYPE: RNA
<213> ORGANISM: Homo sapiens

<400> SEQUENCE: 387
aaaacuaucu gaagau                                                         16

<210> SEQ ID NO 388
<211> LENGTH: 16
<212> TYPE: RNA
<213> ORGANISM: Homo sapiens

<400> SEQUENCE: 388
auuuccauuu gucaaa                                                         16

<210> SEQ ID NO 389
<211> LENGTH: 16
<212> TYPE: RNA
<213> ORGANISM: Homo sapiens

<400> SEQUENCE: 389
aaaaaguaau gauuuc                                                         16

<210> SEQ ID NO 390
<211> LENGTH: 16
<212> TYPE: RNA
<213> ORGANISM: Homo sapiens

<400> SEQUENCE: 390
augauuucuu gauaau                                                         16

<210> SEQ ID NO 391
<211> LENGTH: 16
<212> TYPE: RNA
<213> ORGANISM: Homo sapiens

<400> SEQUENCE: 391
auuucuugau aauugu                                                         16

<210> SEQ ID NO 392
<211> LENGTH: 16
<212> TYPE: RNA
<213> ORGANISM: Homo sapiens

<400> SEQUENCE: 392
cuugauaauu guguag                                                         16

<210> SEQ ID NO 393
<211> LENGTH: 16
<212> TYPE: RNA
<213> ORGANISM: Homo sapiens

<400> SEQUENCE: 393
ugauaauugu guagug                                                         16

<210> SEQ ID NO 394
<211> LENGTH: 16
<212> TYPE: RNA
<213> ORGANISM: Homo sapiens

<400> SEQUENCE: 394 auguguagu gaaugu                                                      16

<210> SEQ ID NO 395
<211> LENGTH: 16
<212> TYPE: RNA
<213> ORGANISM: Homo sapiens

<400> SEQUENCE: 395
uguagugaau guuuuu                                                     16

<210> SEQ ID NO 396
<211> LENGTH: 16
<212> TYPE: RNA
<213> ORGANISM: Homo sapiens

<400> SEQUENCE: 396
caguuaccuu gaaagc                                                     16

<210> SEQ ID NO 397
<211> LENGTH: 16
<212> TYPE: RNA
<213> ORGANISM: Homo sapiens

<400> SEQUENCE: 397
cuugaaagcu gaauuu                                                     16

<210> SEQ ID NO 398
<211> LENGTH: 16
<212> TYPE: RNA
<213> ORGANISM: Homo sapiens

<400> SEQUENCE: 398
cugaauuuau auuuag                                                     16

<210> SEQ ID NO 399
<211> LENGTH: 16
<212> TYPE: RNA
<213> ORGANISM: Homo sapiens

<400> SEQUENCE: 399
aguaacuucu guguua                                                     16

<210> SEQ ID NO 400
<211> LENGTH: 16
<212> TYPE: RNA
<213> ORGANISM: Homo sapiens

<400> SEQUENCE: 400
uaacuucugu guuaau                                                     16

<210> SEQ ID NO 401
<211> LENGTH: 16
<212> TYPE: RNA
<213> ORGANISM: Homo sapiens

<400> SEQUENCE: 401

-continued cuguguuaau acugga 16

<210> SEQ ID NO 402
<211> LENGTH: 16
<212> TYPE: RNA
<213> ORGANISM: Homo sapiens

<400> SEQUENCE: 402
aauacuggau agcaug 16

<210> SEQ ID NO 403
<211> LENGTH: 16
<212> TYPE: RNA
<213> ORGANISM: Homo sapiens

<400> SEQUENCE: 403
uggauagcau gaauuc 16

<210> SEQ ID NO 404
<211> LENGTH: 16
<212> TYPE: RNA
<213> ORGANISM: Homo sapiens

<400> SEQUENCE: 404
caugaauucu gcauug 16

<210> SEQ ID NO 405
<211> LENGTH: 16
<212> TYPE: RNA
<213> ORGANISM: Homo sapiens

<400> SEQUENCE: 405
auucugcauu gagaaa 16

<210> SEQ ID NO 406
<211> LENGTH: 16
<212> TYPE: RNA
<213> ORGANISM: Homo sapiens

<400> SEQUENCE: 406
uugagaaacu gaauag 16

<210> SEQ ID NO 407
<211> LENGTH: 16
<212> TYPE: RNA
<213> ORGANISM: Homo sapiens

<400> SEQUENCE: 407
gaaacugaau agcugu 16

<210> SEQ ID NO 408
<211> LENGTH: 16
<212> TYPE: RNA
<213> ORGANISM: Homo sapiens

<400> SEQUENCE: 408
cugaauagcu gucaua 16

<210> SEQ ID NO 409
<211> LENGTH: 16
<212> TYPE: RNA
<213> ORGANISM: Homo sapiens

<400> SEQUENCE: 409
uagcugucau aaaaug                                                  16

<210> SEQ ID NO 410
<211> LENGTH: 16
<212> TYPE: RNA
<213> ORGANISM: Homo sapiens

<400> SEQUENCE: 410
gucauaaaau gcuuc                                                   16

<210> SEQ ID NO 411
<211> LENGTH: 16
<212> TYPE: RNA
<213> ORGANISM: Homo sapiens

<400> SEQUENCE: 411
aaagaaagau acucac                                                  16

<210> SEQ ID NO 412
<211> LENGTH: 16
<212> TYPE: RNA
<213> ORGANISM: Homo sapiens

<400> SEQUENCE: 412
auacucacau gaguuc                                                  16

<210> SEQ ID NO 413
<211> LENGTH: 16
<212> TYPE: RNA
<213> ORGANISM: Homo sapiens

<400> SEQUENCE: 413
augaguucuu gaagaa                                                  16

<210> SEQ ID NO 414
<211> LENGTH: 16
<212> TYPE: RNA
<213> ORGANISM: Homo sapiens

<400> SEQUENCE: 414
cuugaagaau agucau                                                  16

<210> SEQ ID NO 415
<211> LENGTH: 16
<212> TYPE: RNA
<213> ORGANISM: Homo sapiens

<400> SEQUENCE: 415
gaauagucau aacuag                                                  16

<210> SEQ ID NO 416
<211> LENGTH: 16
<212> TYPE: RNA
<213> ORGANISM: Homo sapiens

<400> SEQUENCE: 416
auuaagaucu guguuu                                                  16

<210> SEQ ID NO 417
<211> LENGTH: 16
<212> TYPE: RNA
<213> ORGANISM: Homo sapiens -continued

<400> SEQUENCE: 417
uaagaucugu guuuua                                                    16

<210> SEQ ID NO 418
<211> LENGTH: 16
<212> TYPE: RNA
<213> ORGANISM: Homo sapiens

<400> SEQUENCE: 418
uuaguuuaau aguuug                                                    16

<210> SEQ ID NO 419
<211> LENGTH: 16
<212> TYPE: RNA
<213> ORGANISM: Homo sapiens

<400> SEQUENCE: 419
uuaauaguuu gaagug                                                    16

<210> SEQ ID NO 420
<211> LENGTH: 16
<212> TYPE: RNA
<213> ORGANISM: Homo sapiens

<400> SEQUENCE: 420
aguuugaagu gccugu                                                    16

<210> SEQ ID NO 421
<211> LENGTH: 16
<212> TYPE: RNA
<213> ORGANISM: Homo sapiens

<400> SEQUENCE: 421
ugaagugccu guuugg                                                    16

<210> SEQ ID NO 422
<211> LENGTH: 16
<212> TYPE: RNA
<213> ORGANISM: Homo sapiens

<400> SEQUENCE: 422
uguuugggau aaugau                                                    16

<210> SEQ ID NO 423
<211> LENGTH: 16
<212> TYPE: RNA
<213> ORGANISM: Homo sapiens

<400> SEQUENCE: 423
uugggauaau gauagg                                                    16

<210> SEQ ID NO 424
<211> LENGTH: 16
<212> TYPE: RNA
<213> ORGANISM: Homo sapiens

<400> SEQUENCE: 424
ggauaaugau agguaa                                                    16

<210> SEQ ID NO 425
<211> LENGTH: 16
<212> TYPE: RNA
<213> ORGANISM: Homo sapiens

<400> SEQUENCE: 425
uaauuuagau gaauuu                                            16

<210> SEQ ID NO 426
<211> LENGTH: 16
<212> TYPE: RNA
<213> ORGANISM: Homo sapiens

<400> SEQUENCE: 426
aaaguuaucu gcaguu                                            16

<210> SEQ ID NO 427
<211> LENGTH: 16
<212> TYPE: RNA
<213> ORGANISM: Homo sapiens

<400> SEQUENCE: 427
cugcaguuau guugag                                            16

<210> SEQ ID NO 428
<211> LENGTH: 16
<212> TYPE: RNA
<213> ORGANISM: Homo sapiens

<400> SEQUENCE: 428
caguuauguu gagggc                                            16

<210> SEQ ID NO 429
<211> LENGTH: 16
<212> TYPE: RNA
<213> ORGANISM: Homo sapiens

<400> SEQUENCE: 429
ggguuacagu guuuua                                            16

<210> SEQ ID NO 430
<211> LENGTH: 16
<212> TYPE: RNA
<213> ORGANISM: Homo sapiens

<400> SEQUENCE: 430
uguuuuaucc gaaagu                                            16

<210> SEQ ID NO 431
<211> LENGTH: 16
<212> TYPE: RNA
<213> ORGANISM: Homo sapiens

<400> SEQUENCE: 431
caauuccacu gucuug                                            16

<210> SEQ ID NO 432
<211> LENGTH: 16
<212> TYPE: RNA
<213> ORGANISM: Homo sapiens

<400> SEQUENCE: 432
ccacugucuu guguuu                                            16

<210> SEQ ID NO 433
<211> LENGTH: 16
<212> TYPE: RNA

<213> ORGANISM: Homo sapiens

<400> SEQUENCE: 433 acugcuugu guuuuc                                                    16

<210> SEQ ID NO 434
<211> LENGTH: 16
<212> TYPE: RNA
<213> ORGANISM: Homo sapiens

<400> SEQUENCE: 434
guguuuucau guugaa                                                   16

<210> SEQ ID NO 435
<211> LENGTH: 16
<212> TYPE: RNA
<213> ORGANISM: Homo sapiens

<400> SEQUENCE: 435
uuuucauguu gaaaau                                                   16

<210> SEQ ID NO 436
<211> LENGTH: 16
<212> TYPE: RNA
<213> ORGANISM: Homo sapiens

<400> SEQUENCE: 436
uguugaaaau acuuuu                                                   16

<210> SEQ ID NO 437
<211> LENGTH: 16
<212> TYPE: RNA
<213> ORGANISM: Homo sapiens

<400> SEQUENCE: 437
aaauacuuuu gcauuu                                                   16

<210> SEQ ID NO 438
<211> LENGTH: 16
<212> TYPE: RNA
<213> ORGANISM: Homo sapiens

<400> SEQUENCE: 438
uuuuuccuuu gagugc                                                   16

<210> SEQ ID NO 439
<211> LENGTH: 16
<212> TYPE: RNA
<213> ORGANISM: Homo sapiens

<400> SEQUENCE: 439
uccuuugagu gccaau                                                   16

<210> SEQ ID NO 440
<211> LENGTH: 16
<212> TYPE: RNA
<213> ORGANISM: Homo sapiens

<400> SEQUENCE: 440
auuucuuaau guaaca                                                   16

<210> SEQ ID NO 441
<211> LENGTH: 16

```
<212> TYPE: RNA
<213> ORGANISM: Homo sapiens

<400> SEQUENCE: 441
aauguaacau guuuac                                                     16

<210> SEQ ID NO 442
<211> LENGTH: 16
<212> TYPE: RNA
<213> ORGANISM: Homo sapiens

<400> SEQUENCE: 442
uaccuggccu gucuuu                                                     16

<210> SEQ ID NO 443
<211> LENGTH: 16
<212> TYPE: RNA
<213> ORGANISM: Homo sapiens

<400> SEQUENCE: 443
aacuauuuuu guauag                                                     16

<210> SEQ ID NO 444
<211> LENGTH: 16
<212> TYPE: RNA
<213> ORGANISM: Homo sapiens

<400> SEQUENCE: 444
auuuuuguau agugua                                                     16

<210> SEQ ID NO 445
<211> LENGTH: 16
<212> TYPE: RNA
<213> ORGANISM: Homo sapiens

<400> SEQUENCE: 445
uuuguauagu guaaac                                                     16

<210> SEQ ID NO 446
<211> LENGTH: 16
<212> TYPE: RNA
<213> ORGANISM: Homo sapiens

<400> SEQUENCE: 446
aguguaaacu gaaaca                                                     16

<210> SEQ ID NO 447
<211> LENGTH: 16
<212> TYPE: RNA
<213> ORGANISM: Homo sapiens

<400> SEQUENCE: 447
acugaaacau gcacau                                                     16

<210> SEQ ID NO 448
<211> LENGTH: 16
<212> TYPE: RNA
<213> ORGANISM: Homo sapiens

<400> SEQUENCE: 448
ugcacauuuu guacau                                                     16

<210> SEQ ID NO 449
```

```
<211> LENGTH: 16
<212> TYPE: RNA
<213> ORGANISM: Homo sapiens

<400> SEQUENCE: 449
uuuguacauu gugcuu                                                        16

<210> SEQ ID NO 450
<211> LENGTH: 16
<212> TYPE: RNA
<213> ORGANISM: Homo sapiens

<400> SEQUENCE: 450
uguacauugu gcuuuc                                                        16

<210> SEQ ID NO 451
<211> LENGTH: 16
<212> TYPE: RNA
<213> ORGANISM: Homo sapiens

<400> SEQUENCE: 451
gcuuucuuuu gugggu                                                        16

<210> SEQ ID NO 452
<211> LENGTH: 16
<212> TYPE: RNA
<213> ORGANISM: Homo sapiens

<400> SEQUENCE: 452
ugugggucau augcag                                                        16

<210> SEQ ID NO 453
<211> LENGTH: 16
<212> TYPE: RNA
<213> ORGANISM: Homo sapiens

<400> SEQUENCE: 453
ugggucauau gcagug                                                        16

<210> SEQ ID NO 454
<211> LENGTH: 16
<212> TYPE: RNA
<213> ORGANISM: Homo sapiens

<400> SEQUENCE: 454
cauaugcagu gugauc                                                        16

<210> SEQ ID NO 455
<211> LENGTH: 16
<212> TYPE: RNA
<213> ORGANISM: Homo sapiens

<400> SEQUENCE: 455
uaugcagugu gaucca                                                        16

<210> SEQ ID NO 456
<211> LENGTH: 16
<212> TYPE: RNA
<213> ORGANISM: Homo sapiens

<400> SEQUENCE: 456
ugauccaguu guuuuc                                                        16
```

<210> SEQ ID NO 457
<211> LENGTH: 16
<212> TYPE: RNA
<213> ORGANISM: Homo sapiens

<400> SEQUENCE: 457
ucauuugguu gcgcug                                                         16

<210> SEQ ID NO 458
<211> LENGTH: 16
<212> TYPE: RNA
<213> ORGANISM: Homo sapiens

<400> SEQUENCE: 458
auuugguugc gcugac                                                         16

<210> SEQ ID NO 459
<211> LENGTH: 16
<212> TYPE: RNA
<213> ORGANISM: Homo sapiens

<400> SEQUENCE: 459
ugguugcgcu gaccua                                                         16

<210> SEQ ID NO 460
<211> LENGTH: 16
<212> TYPE: RNA
<213> ORGANISM: Homo sapiens

<400> SEQUENCE: 460
accuaggaau guuggu                                                         16

<210> SEQ ID NO 461
<211> LENGTH: 16
<212> TYPE: RNA
<213> ORGANISM: Homo sapiens

<400> SEQUENCE: 461
uguuggucau aucaaa                                                         16

<210> SEQ ID NO 462
<211> LENGTH: 16
<212> TYPE: RNA
<213> ORGANISM: Homo sapiens

<400> SEQUENCE: 462
cauuaaaaau gaccac                                                         16

<210> SEQ ID NO 463
<211> LENGTH: 16
<212> TYPE: RNA
<213> ORGANISM: Homo sapiens

<400> SEQUENCE: 463 cucuuuaau gaaauu                                                          16

<210> SEQ ID NO 464
<211> LENGTH: 16
<212> TYPE: RNA
<213> ORGANISM: Homo sapiens

<400> SEQUENCE: 464
acuuuuaaau guuuau                                                         16

<210> SEQ ID NO 465
<211> LENGTH: 16
<212> TYPE: RNA
<213> ORGANISM: Homo sapiens

<400> SEQUENCE: 465
aaauguuuau aggagu                                                    16

<210> SEQ ID NO 466
<211> LENGTH: 16
<212> TYPE: RNA
<213> ORGANISM: Homo sapiens

<400> SEQUENCE: 466
auaggaguau gugcug                                                    16

<210> SEQ ID NO 467
<211> LENGTH: 16
<212> TYPE: RNA
<213> ORGANISM: Homo sapiens

<400> SEQUENCE: 467
aggaguaugu gcugug                                                    16

<210> SEQ ID NO 468
<211> LENGTH: 16
<212> TYPE: RNA
<213> ORGANISM: Homo sapiens

<400> SEQUENCE: 468
aguaugugcu gugaag                                                    16

<210> SEQ ID NO 469
<211> LENGTH: 16
<212> TYPE: RNA
<213> ORGANISM: Homo sapiens

<400> SEQUENCE: 469
uaugugcugu gaagug                                                    16

<210> SEQ ID NO 470
<211> LENGTH: 16
<212> TYPE: RNA
<213> ORGANISM: Homo sapiens

<400> SEQUENCE: 470
gcugugaagu gaucua                                                    16

<210> SEQ ID NO 471
<211> LENGTH: 16
<212> TYPE: RNA
<213> ORGANISM: Homo sapiens

<400> SEQUENCE: 471
ucuaaaauuu guaaua                                                    16

<210> SEQ ID NO 472
<211> LENGTH: 16
<212> TYPE: RNA
<213> ORGANISM: Homo sapiens

<400> SEQUENCE: 472
aauuuguaau auuuuu                                                    16

<210> SEQ ID NO 473
<211> LENGTH: 16
<212> TYPE: RNA
<213> ORGANISM: Homo sapiens

<400> SEQUENCE: 473
uaauauuuuu gucaug                                                          16

<210> SEQ ID NO 474
<211> LENGTH: 16
<212> TYPE: RNA
<213> ORGANISM: Homo sapiens

<400> SEQUENCE: 474
uuuuugucau gaacug                                                          16

<210> SEQ ID NO 475
<211> LENGTH: 16
<212> TYPE: RNA
<213> ORGANISM: Homo sapiens

<400> SEQUENCE: 475
gucaugaacu guacua                                                          16

<210> SEQ ID NO 476
<211> LENGTH: 16
<212> TYPE: RNA
<213> ORGANISM: Homo sapiens

<400> SEQUENCE: 476
ccuaauuauu guaaug                                                          16

<210> SEQ ID NO 477
<211> LENGTH: 16
<212> TYPE: RNA
<213> ORGANISM: Homo sapiens

<400> SEQUENCE: 477
uuauuguaau guaaua                                                          16

<210> SEQ ID NO 478
<211> LENGTH: 16
<212> TYPE: RNA
<213> ORGANISM: Homo sapiens

<400> SEQUENCE: 478
guaauguaau aaaaau                                                          16

<210> SEQ ID NO 479
<211> LENGTH: 16
<212> TYPE: RNA
<213> ORGANISM: Homo sapiens

<400> SEQUENCE: 479
uaauaaaaau aguuac                                                          16

<210> SEQ ID NO 480
<211> LENGTH: 16
<212> TYPE: RNA
<213> ORGANISM: Homo sapiens

<400> SEQUENCE: 480

-continued uaguuacagu gacuau    16

<210> SEQ ID NO 481
<211> LENGTH: 16
<212> TYPE: RNA
<213> ORGANISM: Homo sapiens

<400> SEQUENCE: 481
cagugacuau gagugu    16

<210> SEQ ID NO 482
<211> LENGTH: 16
<212> TYPE: RNA
<213> ORGANISM: Homo sapiens

<400> SEQUENCE: 482
gacuaugagu guguau    16

<210> SEQ ID NO 483
<211> LENGTH: 16
<212> TYPE: RNA
<213> ORGANISM: Homo sapiens

<400> SEQUENCE: 483
cuaugagugu guauuu    16

<210> SEQ ID NO 484
<211> LENGTH: 16
<212> TYPE: RNA
<213> ORGANISM: Homo sapiens

<400> SEQUENCE: 484
auuuauucau gcaaau    16

<210> SEQ ID NO 485
<211> LENGTH: 16
<212> TYPE: RNA
<213> ORGANISM: Homo sapiens

<400> SEQUENCE: 485
augcaaauuu gaacug    16

<210> SEQ ID NO 486
<211> LENGTH: 16
<212> TYPE: RNA
<213> ORGANISM: Homo sapiens

<400> SEQUENCE: 486
aauuugaacu guuugc    16

<210> SEQ ID NO 487
<211> LENGTH: 16
<212> TYPE: RNA
<213> ORGANISM: Homo sapiens

<400> SEQUENCE: 487
ugaacuguuu gccccg    16

<210> SEQ ID NO 488
<211> LENGTH: 16
<212> TYPE: RNA
<213> ORGANISM: Homo sapiens

<400> SEQUENCE: 488

-continued uguuugcccc gaaaug 16

<210> SEQ ID NO 489
<211> LENGTH: 16
<212> TYPE: RNA
<213> ORGANISM: Homo sapiens

<400> SEQUENCE: 489
gccccgaaau ggauau 16

<210> SEQ ID NO 490
<211> LENGTH: 16
<212> TYPE: RNA
<213> ORGANISM: Homo sapiens

<400> SEQUENCE: 490
cgaaauggau auggau 16

<210> SEQ ID NO 491
<211> LENGTH: 16
<212> TYPE: RNA
<213> ORGANISM: Homo sapiens

<400> SEQUENCE: 491
aaauggauau ggauac 16

<210> SEQ ID NO 492
<211> LENGTH: 16
<212> TYPE: RNA
<213> ORGANISM: Homo sapiens

<400> SEQUENCE: 492
ggauauggau acuuua 16

<210> SEQ ID NO 493
<211> LENGTH: 16
<212> TYPE: RNA
<213> ORGANISM: Homo sapiens

<400> SEQUENCE: 493
gauacuuuau aagcca 16

<210> SEQ ID NO 494
<211> LENGTH: 16
<212> TYPE: RNA
<213> ORGANISM: Homo sapiens

<400> SEQUENCE: 494
uauaagccau agacac 16

<210> SEQ ID NO 495
<211> LENGTH: 16
<212> TYPE: RNA
<213> ORGANISM: Homo sapiens

<400> SEQUENCE: 495
uagacacuau aguaua 16

<210> SEQ ID NO 496
<211> LENGTH: 16
<212> TYPE: RNA
<213> ORGANISM: Homo sapiens -continued

<400> SEQUENCE: 496
acuauaguau accagu                                                           16

<210> SEQ ID NO 497
<211> LENGTH: 16
<212> TYPE: RNA
<213> ORGANISM: Homo sapiens

<400> SEQUENCE: 497
guauaccagu gaaucu                                                           16

<210> SEQ ID NO 498
<211> LENGTH: 16
<212> TYPE: RNA
<213> ORGANISM: Homo sapiens

<400> SEQUENCE: 498
aaucuuuuau gcagcu                                                           16

<210> SEQ ID NO 499
<211> LENGTH: 16
<212> TYPE: RNA
<213> ORGANISM: Homo sapiens

<400> SEQUENCE: 499
uaugcagcuu guuaga                                                           16

<210> SEQ ID NO 500
<211> LENGTH: 16
<212> TYPE: RNA
<213> ORGANISM: Homo sapiens

<400> SEQUENCE: 500
ucuaaaaggu gcugug                                                           16

<210> SEQ ID NO 501
<211> LENGTH: 16
<212> TYPE: RNA
<213> ORGANISM: Homo sapiens

<400> SEQUENCE: 501
aaaaggugcu guggau                                                           16

<210> SEQ ID NO 502
<211> LENGTH: 16
<212> TYPE: RNA
<213> ORGANISM: Homo sapiens

<400> SEQUENCE: 502
ugcuguggau auuaug                                                           16

<210> SEQ ID NO 503
<211> LENGTH: 16
<212> TYPE: RNA
<213> ORGANISM: Homo sapiens

<400> SEQUENCE: 503
uggauauuau guaaag                                                           16

<210> SEQ ID NO 504
<211> LENGTH: 16
<212> TYPE: RNA
<213> ORGANISM: Homo sapiens

<400> SEQUENCE: 504
guaaaggcgu guuugc                                                16

<210> SEQ ID NO 505
<211> LENGTH: 16
<212> TYPE: RNA
<213> ORGANISM: Homo sapiens

<400> SEQUENCE: 505
aggcguguuu gcuuaa                                                16

<210> SEQ ID NO 506
<211> LENGTH: 16
<212> TYPE: RNA
<213> ORGANISM: Homo sapiens

<400> SEQUENCE: 506
aauuuuccau auuuag                                                16

<210> SEQ ID NO 507
<211> LENGTH: 16
<212> TYPE: RNA
<213> ORGANISM: Homo sapiens

<400> SEQUENCE: 507
agaaguagau gcaaaa                                                16

<210> SEQ ID NO 508
<211> LENGTH: 16
<212> TYPE: RNA
<213> ORGANISM: Homo sapiens

<400> SEQUENCE: 508
aaacaaaucu gccuuu                                                16

<210> SEQ ID NO 509
<211> LENGTH: 16
<212> TYPE: RNA
<213> ORGANISM: Homo sapiens

<400> SEQUENCE: 509
cugccuuuau gacaaa                                                16

<210> SEQ ID NO 510
<211> LENGTH: 16
<212> TYPE: RNA
<213> ORGANISM: Homo sapiens

<400> SEQUENCE: 510
acaaaaaaau aggaua                                                16

<210> SEQ ID NO 511
<211> LENGTH: 16
<212> TYPE: RNA
<213> ORGANISM: Homo sapiens

<400> SEQUENCE: 511
aaaauaggau aacauu                                                16

<210> SEQ ID NO 512
<211> LENGTH: 16
<212> TYPE: RNA

```
<213> ORGANISM: Homo sapiens

<400> SEQUENCE: 512
uuuuaucaau aaggua                                                   16

<210> SEQ ID NO 513
<211> LENGTH: 16
<212> TYPE: RNA
<213> ORGANISM: Homo sapiens

<400> SEQUENCE: 513
uaagguaauu gauaca                                                   16

<210> SEQ ID NO 514
<211> LENGTH: 16
<212> TYPE: RNA
<213> ORGANISM: Homo sapiens

<400> SEQUENCE: 514
gguaauugau acacaa                                                   16

<210> SEQ ID NO 515
<211> LENGTH: 16
<212> TYPE: RNA
<213> ORGANISM: Homo sapiens

<400> SEQUENCE: 515
cacaacaggu gacuug                                                   16

<210> SEQ ID NO 516
<211> LENGTH: 16
<212> TYPE: RNA
<213> ORGANISM: Homo sapiens

<400> SEQUENCE: 516
caacauuaau aaugga                                                   16

<210> SEQ ID NO 517
<211> LENGTH: 16
<212> TYPE: RNA
<213> ORGANISM: Homo sapiens

<400> SEQUENCE: 517
cauuaauaau ggaaau                                                   16

<210> SEQ ID NO 518
<211> LENGTH: 16
<212> TYPE: RNA
<213> ORGANISM: Homo sapiens

<400> SEQUENCE: 518
uaauggaaau aauuga                                                   16

<210> SEQ ID NO 519
<211> LENGTH: 16
<212> TYPE: RNA
<213> ORGANISM: Homo sapiens

<400> SEQUENCE: 519
ggaaauaauu gaauag                                                   16

<210> SEQ ID NO 520
<211> LENGTH: 16
```

<212> TYPE: RNA
<213> ORGANISM: Homo sapiens

<400> SEQUENCE: 520
auaauugaau aguuag                                                    16

<210> SEQ ID NO 521
<211> LENGTH: 16
<212> TYPE: RNA
<213> ORGANISM: Homo sapiens

<400> SEQUENCE: 521
aguuaguuau guaugu                                                    16

<210> SEQ ID NO 522
<211> LENGTH: 16
<212> TYPE: RNA
<213> ORGANISM: Homo sapiens

<400> SEQUENCE: 522
aguuauguau guuaau                                                    16

<210> SEQ ID NO 523
<211> LENGTH: 16
<212> TYPE: RNA
<213> ORGANISM: Homo sapiens

<400> SEQUENCE: 523
guauguuaau gccagu                                                    16

<210> SEQ ID NO 524
<211> LENGTH: 16
<212> TYPE: RNA
<213> ORGANISM: Homo sapiens

<400> SEQUENCE: 524
cagaaguaau gacucc                                                    16

<210> SEQ ID NO 525
<211> LENGTH: 16
<212> TYPE: RNA
<213> ORGANISM: Homo sapiens

<400> SEQUENCE: 525
augacuccau acauau                                                    16

<210> SEQ ID NO 526
<211> LENGTH: 16
<212> TYPE: RNA
<213> ORGANISM: Homo sapiens

<400> SEQUENCE: 526
cuccauacau auuauu                                                    16

<210> SEQ ID NO 527
<211> LENGTH: 16
<212> TYPE: RNA
<213> ORGANISM: Homo sapiens

<400> SEQUENCE: 527
uuauuucuau aacuac                                                    16

<210> SEQ ID NO 528

<210> SEQ ID NO 528
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 528
cgccgugaug gcaugcacua ugcgcgggcc gccgcc                            36

<210> SEQ ID NO 529
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 529
accuuugaug gcaugcacua ugcgcggccg ccgcca                            36

<210> SEQ ID NO 530
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 530
aauggugaug gcaugcacua ugcgcggggg gccggg                            36

<210> SEQ ID NO 531
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 531
gcgcuugaug gcaugcacua ugcgcggcuc ccaguc                            36

<210> SEQ ID NO 532
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 532
cgccgugaug gcaugcacua ugcgcggcuc gcuccc                            36

<210> SEQ ID NO 533
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 533
gccugugaug gcaugcacua ugcgcggccg cgcucg                            36

<210> SEQ ID NO 534
<211> LENGTH: 36

```
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 534
gccuuugaug gcaugcacua ugcgcgagug ccugcg                                   36

<210> SEQ ID NO 535
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 535
ucccgugaug gcaugcacua ugcgcgaccu gggagc                                   36

<210> SEQ ID NO 536
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 536
uucagugaug gcaugcacua ugcgcgaggc cucucu                                   36

<210> SEQ ID NO 537
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 537
auuuuugaug gcaugcacua ugcgcgagca ggccuc                                   36

<210> SEQ ID NO 538
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 538
ucaguugaug gcaugcacua ugcgcgauuu ucagca                                   36

<210> SEQ ID NO 539
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 539
auauuugaug gcaugcacua ugcgcgaguc auuuc                                    36

<210> SEQ ID NO 540
<211> LENGTH: 36
<212> TYPE: RNA
```

```
<213> ORGANISM: Artificial Sequence
<220> FEATURE:
<223> OTHER INFORMATION: Description of Artificial Sequence:  Enzymatic
      Nucleic Acid

<400> SEQUENCE: 540
guuuaugaug gcaugcacua ugcgcgauuc agucau                                   36

<210> SEQ ID NO 541
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 541
aaguuugaug gcaugcacua ugcgcgauau ucaguc                                   36

<210> SEQ ID NO 542
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 542
uaccaugaug gcaugcacua ugcgcgaagu uuauau                                   36

<210> SEQ ID NO 543
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 543
cgccaugaug gcaugcacua ugcgcgaagc uccaac                                   36

<210> SEQ ID NO 544
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 544
caaggugaug gcaugcacua ugcgcgacuc uugccu                                   36

<210> SEQ ID NO 545
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 545
aucguugaug gcaugcacua ugcgcgaagg cacucu                                   36

<210> SEQ ID NO 546
<211> LENGTH: 36
<212> TYPE: RNA
<213> ORGANISM: Artificial Sequence
```

```
<220> FEATURE:
<223> OTHER INFORMATION: Description of Artificial Sequence:  Enzymatic
      Nucleic Acid

<400> SEQUENCE: 546
uguauugaug gcaugcacua ugcgcgguca aggcac                              36

<210> SEQ ID NO 547
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 547
agcugugaug gcaugcacua ugcgcgaucg ucaagg                              36

<210> SEQ ID NO 548
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 548
guccaugaug gcaugcacua ugcgcgaaaa ugauuc                              36

<210> SEQ ID NO 549
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 549
auauuugaug gcaugcacua ugcgcggucc acaaaa                              36

<210> SEQ ID NO 550
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 550
gaucaugaug gcaugcacua ugcgcgauuc guccac                              36

<210> SEQ ID NO 551
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 551
uggauugaug gcaugcacua ugcgcgauau ucgucc                              36

<210> SEQ ID NO 552
<211> LENGTH: 36
<212> TYPE: RNA
<213> ORGANISM: Artificial Sequence
<220> FEATURE:
```

<223> OTHER INFORMATION: Description of Artificial Sequence: Enzymatic
      Nucleic Acid

<400> SEQUENCE: 552
uccucugaug gcaugcacua ugcgcgauug uuggau                                    36

<210> SEQ ID NO 553
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 553
uccauugaug gcaugcacua ugcgcgaauu acuacu                                    36

<210> SEQ ID NO 554
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 554
uucucugaug gcaugcacua ugcgcgauca auuacu                                    36

<210> SEQ ID NO 555
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 555
agagaugaug gcaugcacua ugcgcgaggu uucucc                                    36

<210> SEQ ID NO 556
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 556
gagaaugaug gcaugcacua ugcgcgaucc aagaga                                    36

<210> SEQ ID NO 557
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 557
uguguugaug gcaugcacua ugcgcggaga auaucc                                    36

<210> SEQ ID NO 558
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 558
cauugugaug gcaugcacua ugcgcgacug uacucc                36

<210> SEQ ID NO 559
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 559
ucccuugaug gcaugcacua ugcgcgauug cacugu                36

<210> SEQ ID NO 560
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 560
guccuugaug gcaugcacua ugcgcgaugu acuggu                36

<210> SEQ ID NO 561
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 561
auacaugaug gcaugcacua ugcgcgaaag aaagcc                36

<210> SEQ ID NO 562
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 562
aaauaugaug gcaugcacua ugcgcgacaa agaaag                36

<210> SEQ ID NO 563
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 563
uauggugaug gcaugcacua ugcgcgaaau acacaa                36

<210> SEQ ID NO 564
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

```
<400> SEQUENCE: 564
uuauuugaug gcaugcacua ugcgcgaugg caaaua                        36

<210> SEQ ID NO 565
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 565
aguauugaug gcaugcacua ugcgcgauuu auggca                        36

<210> SEQ ID NO 566
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 566
uuuagugaug gcaugcacua ugcgcgauua uuuaug                        36

<210> SEQ ID NO 567
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 567
aucuuugaug gcaugcacua ugcgcgaaau gauuua                        36

<210> SEQ ID NO 568
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 568
gugaaugaug gcaugcacua ugcgcgaucu ucaaau                        36

<210> SEQ ID NO 569
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 569
uucucugaug gcaugcacua ugcgcgauaa ugguga                        36

<210> SEQ ID NO 570
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid
```

```
<400> SEQUENCE: 570
aucuuugaug gcaugcacua ugcgcgagag uccuua                           36

<210> SEQ ID NO 571
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 571
agguaugaug gcaugcacua ugcgcgaucu ucagag                           36

<210> SEQ ID NO 572
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 572
aggacugaug gcaugcacua ugcgcgauag guacau                           36

<210> SEQ ID NO 573
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 573
acauuugaug gcaugcacua ugcgcgauuu ccuacu                           36

<210> SEQ ID NO 574
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 574
aaucaugaug gcaugcacua ugcgcgauuu auuucc                           36

<210> SEQ ID NO 575
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 575
caaauugaug gcaugcacua ugcgcgacau uuauuu                           36

<210> SEQ ID NO 576
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 576
```
gaaggugaug gcaugcacua ugcgcgaaau cacauu        36

<210> SEQ ID NO 577
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 577
aauucugaug gcaugcacua ugcgcgauaa cuucuu        36

<210> SEQ ID NO 578
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 578
uguuuugaug gcaugcacua ugcgcgaaua aaagga        36

<210> SEQ ID NO 579
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 579
aucaaugaug gcaugcacua ugcgcgaccc ugucuu        36

<210> SEQ ID NO 580
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 580
aucauugaug gcaugcacua ugcgcgaaca cccugu        36

<210> SEQ ID NO 581
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 581
ggcauugaug gcaugcacua ugcgcgauca acaccc        36

<210> SEQ ID NO 582
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 582

```
gaaggugaug gcaugcacua ugcgcgauca ucaaca                               36

<210> SEQ ID NO 583
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 583
uaaugugaug gcaugcacua ugcgcgauag aaggca                              36

<210> SEQ ID NO 584
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 584
uuucuugaug gcaugcacua ugcgcggaac uaaugu                              36

<210> SEQ ID NO 585
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 585
guuuuugaug gcaugcacua ugcgcggaau uucucg                              36

<210> SEQ ID NO 586
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 586
uucuuugaug gcaugcacua ugcgcgaugu uuucga                              36

<210> SEQ ID NO 587
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 587
uugcuugaug gcaugcacua ugcgcgaucu uuucuu                              36

<210> SEQ ID NO 588
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 588
uuuacugaug gcaugcacua ugcgcgaucu uugcuc                              36
```

<210> SEQ ID NO 589
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 589
uuacaugaug gcaugcacua ugcgcgacuu ugucuu                36

<210> SEQ ID NO 590
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 590
aauuaugaug gcaugcacua ugcgcgacac uuuguc                36

<210> SEQ ID NO 591
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 591
auuuaugaug gcaugcacua ugcgcgauaa uuacac                36

<210> SEQ ID NO 592
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 592 aaugugaug gcaugcacua ugcgcgauuu acauaa                 36

<210> SEQ ID NO 593
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 593
aaguaugaug gcaugcacua ugcgcgaaau uguauu                36

<210> SEQ ID NO 594
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 594
acuagugaug gcaugcacua ugcgcgaugc cuuaag                36

<210> SEQ ID NO 595
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 595
auguaugaug gcaugcacua ugcgcgaaaa auuacc                36

<210> SEQ ID NO 596
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 596
uaaaaugaug gcaugcacua ugcgcgaaau gcuaau                36

<210> SEQ ID NO 597
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 597
uggagugaug gcaugcacua ugcgcgagga aaaaaa                36

<210> SEQ ID NO 598
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 598
gucugugaug gcaugcacua ugcgcgaugg agcagg                36

<210> SEQ ID NO 599
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 599
gcuaaugaug gcaugcacua ugcgcgaguc ugcaug                36

<210> SEQ ID NO 600
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 600
auaagugaug gcaugcacua ugcgcgauuu aaggua                36

```
<210> SEQ ID NO 601
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 601
acuguugaug gcaugcacua ugcgcgauuu uaaaau                              36

<210> SEQ ID NO 602
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 602
cacuuugaug gcaugcacua ugcgcggagg aaaaaa                              36

<210> SEQ ID NO 603
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 603
acuggugaug gcaugcacua ugcgcgacuu cgagga                              36

<210> SEQ ID NO 604
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 604
uaguuugaug gcaugcacua ugcgcgaaaa accaaa                              36

<210> SEQ ID NO 605
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 605
acaggugaug gcaugcacua ugcgcgauug cuaguu                              36

<210> SEQ ID NO 606
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 606
uuucaugaug gcaugcacua ugcgcgaggc auugcu                              36

<210> SEQ ID NO 607
```

```
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 607
uuuuuugaug gcaugcacua ugcgcgacag gcauug                                 36

<210> SEQ ID NO 608
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 608
guauuugaug gcaugcacua ugcgcgaguu ucuuuu                                 36

<210> SEQ ID NO 609
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 609
uuaggugaug gcaugcacua ugcgcgauuc aguuuc                                 36

<210> SEQ ID NO 610
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 610
caagaugaug gcaugcacua ugcgcgagaa aucuua                                 36

<210> SEQ ID NO 611
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 611
gcaugugaug gcaugcacua ugcgcgacca aaaacc                                 36

<210> SEQ ID NO 612
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 612
aacugugaug gcaugcacua ugcgcgaugc accaaa                                 36

<210> SEQ ID NO 613
<211> LENGTH: 36
```

```
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 613
guaauugaug gcaugcacua ugcgcgaacu gcaugc                              36

<210> SEQ ID NO 614
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 614
auucaugaug gcaugcacua ugcgcgacuu gguaag                              36

<210> SEQ ID NO 615
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 615
acauuugaug gcaugcacua ugcgcgacac uuggua                              36

<210> SEQ ID NO 616
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 616
accaaugaug gcaugcacua ugcgcgauuc acacuu                              36

<210> SEQ ID NO 617
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 617
uuucaugaug gcaugcacua ugcgcgacca acauuc                              36

<210> SEQ ID NO 618
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 618
uguuuugaug gcaugcacua ugcgcgacac caacau                              36

<210> SEQ ID NO 619
<211> LENGTH: 36
<212> TYPE: RNA
```

<213> ORGANISM: Artificial Sequence
<220> FEATURE:
<223> OTHER INFORMATION: Description of Artificial Sequence: Enzymatic
      Nucleic Acid

<400> SEQUENCE: 619
agcuuugaug gcaugcacua ugcgcgauua auuugu                                36

<210> SEQ ID NO 620
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 620
ugauuugaug gcaugcacua ugcgcgaaaa gcuuca                                36

<210> SEQ ID NO 621
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 621
aaacaugaug gcaugcacua ugcgcgagaa uaggga                                36

<210> SEQ ID NO 622
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 622
uaaaaugaug gcaugcacua ugcgcgacag aauagg                                36

<210> SEQ ID NO 623
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 623
ccauuugaug gcaugcacua ugcgcgaugu gacuag                                36

<210> SEQ ID NO 624
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 624
uaaucugaug gcaugcacua ugcgcgauuu auguga                                36

<210> SEQ ID NO 625
<211> LENGTH: 36
<212> TYPE: RNA
<213> ORGANISM: Artificial Sequence

```
<220> FEATURE:
<223> OTHER INFORMATION: Description of Artificial Sequence: Enzymatic
      Nucleic Acid

<400> SEQUENCE: 625
ggucuugaug gcaugcacua ugcgcgaacu gaaauu                                    36

<210> SEQ ID NO 626
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 626
uguuuugaug gcaugcacua ugcgcgagua aaaacc                                    36

<210> SEQ ID NO 627
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 627
ucccuugaug gcaugcacua ugcgcgaaug uuucag                                    36

<210> SEQ ID NO 628
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 628
aagccugaug gcaugcacua ugcgcgauaa auuugu                                    36

<210> SEQ ID NO 629
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 629
aucauugaug gcaugcacua ugcgcgagga agccca                                    36

<210> SEQ ID NO 630
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 630
aucauugaug gcaugcacua ugcgcgauca ggaagc                                    36

<210> SEQ ID NO 631
<211> LENGTH: 36
<212> TYPE: RNA
<213> ORGANISM: Artificial Sequence
<220> FEATURE:
```

```
<223> OTHER INFORMATION: Description of Artificial Sequence:  Enzymatic
      Nucleic Acid

<400> SEQUENCE: 631
agaauugaug gcaugcacua ugcgcgauca ucagga                                 36

<210> SEQ ID NO 632
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 632
uaggaugaug gcaugcacua ugcgcgauga ugccua                                 36

<210> SEQ ID NO 633
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 633
caaacugaug gcaugcacua ugcgcgauag gacaug                                 36

<210> SEQ ID NO 634
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 634
gaugaugaug gcaugcacua ugcgcgaaac uauagg                                 36

<210> SEQ ID NO 635
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 635
uucauugaug gcaugcacua ugcgcgaggg augaca                                 36

<210> SEQ ID NO 636
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 636
acauuugaug gcaugcacua ugcgcgauca gggaug                                 36

<210> SEQ ID NO 637
<211> LENGTH: 36
<212> TYPE: RNA
<213> ORGANISM: Artificial Sequence
<220> FEATURE:
<223> OTHER INFORMATION: Description of Artificial Sequence:  Enzymatic
```

Nucleic Acid

<400> SEQUENCE: 637
cuuuaugaug gcaugcacua ugcgcgauuc aucagg        36

<210> SEQ ID NO 638
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 638
gugaaugaug gcaugcacua ugcgcgagug uaacuu        36

<210> SEQ ID NO 639
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 639
ggagaugaug gcaugcacua ugcgcgaaaa ccuuug        36

<210> SEQ ID NO 640
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 640
aauagugaug gcaugcacua ugcgcgagug gaaagg        36

<210> SEQ ID NO 641
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 641
gugacugaug gcaugcacua ugcgcgauga cuaaua        36

<210> SEQ ID NO 642
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 642
uauaaugaug gcaugcacua ugcgcgauuu ugggga        36

<210> SEQ ID NO 643
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

```
<400> SEQUENCE: 643
aaaaaugaug gcaugcacua ugcgcgauaa uauuuu                         36

<210> SEQ ID NO 644
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 644
cuuuuugaug gcaugcacua ugcgcgauag aaaaaa                         36

<210> SEQ ID NO 645
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 645
uuuucugaug gcaugcacua ugcgcgauuu uuuucu                         36

<210> SEQ ID NO 646
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 646
guuucugaug gcaugcacua ugcgcgauug ccuugu                         36

<210> SEQ ID NO 647
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 647
ggccuugaug gcaugcacua ugcgcgauaa uaguuu                         36

<210> SEQ ID NO 648
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 648
uaauuugaug gcaugcacua ugcgcgaucu aaugug                         36

<210> SEQ ID NO 649
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
```

<400> SEQUENCE: 649
gucuuugaug gcaugcacua ugcgcgauag uaauuu        36

<210> SEQ ID NO 650
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 650
aaagcugaug gcaugcacua ugcgcgauua ggaguc        36

<210> SEQ ID NO 651
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 651
cuuaaugaug gcaugcacua ugcgcgagga aaaagc        36

<210> SEQ ID NO 652
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 652
ccauuugaug gcaugcacua ugcgcgauac ugdguc        36

<210> SEQ ID NO 653
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 653
aauccugaug gcaugcacua ugcgcgauuc auacug        36

<210> SEQ ID NO 654
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 654
guugcugaug gcaugcacua ugcgcgauaa uaaucc        36

<210> SEQ ID NO 655
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 655
guaaaugaug gcaugcacua ugcgcgauag ccccaa         36

<210> SEQ ID NO 656
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 656
aguagugaug gcaugcacua ugcgcgaugu aaauau         36

<210> SEQ ID NO 657
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 657
auuauugaug gcaugcacua ugcgcgauaa aaauuu         36

<210> SEQ ID NO 658
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 658
ucaauugaug gcaugcacua ugcgcgauua uaaaaa         36

<210> SEQ ID NO 659
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 659
cuuuuugaug gcaugcacua ugcgcgaauu auuaua         36

<210> SEQ ID NO 660
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 660
uuuuuugaug gcaugcacua ugcgcgauac uuguua         36

<210> SEQ ID NO 661
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 661

```
auuccugaug gcaugcacua ugcgcgauga gaauuu                    36

<210> SEQ ID NO 662
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 662
gacuaugaug gcaugcacua ugcgcgauuu aauucc                    36

<210> SEQ ID NO 663
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 663
ugacaugaug gcaugcacua ugcgcgaggg agacua                    36

<210> SEQ ID NO 664
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 664
ucugaugaug gcaugcacua ugcgcgacag ggagac                    36

<210> SEQ ID NO 665
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 665
aagagugaug gcaugcacua ugcgcgaguc ugacac                    36

<210> SEQ ID NO 666
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 666
uauacugaug gcaugcacua ugcgcgauga aagagc                    36

<210> SEQ ID NO 667
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 667
aaaguugaug gcaugcacua ugcgcgauac uaugaa                    36
```

<210> SEQ ID NO 668
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 668
agacuugaug gcaugcacua ugcgcgaagu ugaaga          36

<210> SEQ ID NO 669
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 669
aucuuugaug gcaugcacua ugcgcgaaag acucaa          36

<210> SEQ ID NO 670
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 670
aaaacugaug gcaugcacua ugcgcgaucu ucaaag          36

<210> SEQ ID NO 671
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 671
acaagugaug gcaugcacua ugcgcgagaa uuaaaa          36

<210> SEQ ID NO 672
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 672
ugucaugaug gcaugcacua ugcgcgaagc agaauu          36

<210> SEQ ID NO 673
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 673
aauguugaug gcaugcacua ugcgcgacaa gcagaa          36

<210> SEQ ID NO 674
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 674
uaagcugaug gcaugcacua ugcgcgauaa cuggcc                                    36

<210> SEQ ID NO 675
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 675
uucaaugaug gcaugcacua ugcgcgaccu aauaag                                    36

<210> SEQ ID NO 676
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 676
cucuuugaug gcaugcacua ugcgcgaaca ccuaau                                    36

<210> SEQ ID NO 677
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 677
gcuugugaug gcaugcacua ugcgcgaacc uugguc                                    36

<210> SEQ ID NO 678
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 678
ucacaugaug gcaugcacua ugcgcgaggg ccuggc                                    36

<210> SEQ ID NO 679
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 679
guucaugaug gcaugcacua ugcgcgacag ggccug                                    36

<210> SEQ ID NO 680
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 680
agguuugaug gcaugcacua ugcgcgacac agggcc            36

<210> SEQ ID NO 681
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 681
aagcuugaug gcaugcacua ugcgcgaagg uucaca            36

<210> SEQ ID NO 682
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 682
cucucugaug gcaugcacua ugcgcgauga aagcuc            36

<210> SEQ ID NO 683
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 683
cagucugaug gcaugcacua ugcgcgaugc ugugaa            36

<210> SEQ ID NO 684
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 684
gcacaugaug gcaugcacua ugcgcgaguc caugcu            36

<210> SEQ ID NO 685
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 685
gggcaugaug gcaugcacua ugcgcgacag uccaug            36

<210> SEQ ID NO 686

```
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 686 ugggugaug gcaugcacua ugcgcgacac agucca                           36

<210> SEQ ID NO 687
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 687
ccacuugaug gcaugcacua ugcgcgggau gaccgu                          36

<210> SEQ ID NO 688
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 688
ucguaugaug gcaugcacua ugcgcgaacc acucgg                          36

<210> SEQ ID NO 689
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 689
ugcauugaug gcaugcacua ugcgcgguac aaccac                          36

<210> SEQ ID NO 690
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 690
caaugugaug gcaugcacua ugcgcgaucg uacaac                          36

<210> SEQ ID NO 691
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 691
cucccugaug gcaugcacua ugcgcgauuu uugacu                          36

<210> SEQ ID NO 692
<211> LENGTH: 36
```

```
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 692
ugagcugaug gcaugcacua ugcgcgaucc aaacug                                    36

<210> SEQ ID NO 693
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 693
gauugugaug gcaugcacua ugcgcgaucu uguuga                                    36

<210> SEQ ID NO 694
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 694
caccaugaug gcaugcacua ugcgcgagag ugagau                                    36

<210> SEQ ID NO 695
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 695
gucagugaug gcaugcacua ugcgcgagga ccacca                                    36

<210> SEQ ID NO 696
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 696
uuuguugaug gcaugcacua ugcgcgagca ggacca                                    36

<210> SEQ ID NO 697
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 697
aaaagugaug gcaugcacua ugcgcgaaug cucuug                                    36

<210> SEQ ID NO 698
<211> LENGTH: 36
<212> TYPE: RNA
```

```
<213> ORGANISM: Artificial Sequence
<220> FEATURE:
<223> OTHER INFORMATION: Description of Artificial Sequence:  Enzymatic
      Nucleic Acid

<400> SEQUENCE: 698
agaaaugaug gcaugcacua ugcgcgaaaa gcaaug                                    36

<210> SEQ ID NO 699
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 699
guuaaugaug gcaugcacua ugcgcgauuu aaaagu                                    36

<210> SEQ ID NO 700
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 700
aaucuugaug gcaugcacua ugcgcgaacu uuugag                                    36

<210> SEQ ID NO 701
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 701
uggcaugaug gcaugcacua ugcgcgacca ccaccc                                    36

<210> SEQ ID NO 702
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 702
cuuggugaug gcaugcacua ugcgcgacac caccac                                    36

<210> SEQ ID NO 703
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 703
cacuuugaug gcaugcacua ugcgcgauug uuuaaa                                    36

<210> SEQ ID NO 704
<211> LENGTH: 36
<212> TYPE: RNA
<213> ORGANISM: Artificial Sequence
```

```
<220> FEATURE:
<223> OTHER INFORMATION: Description of Artificial Sequence:  Enzymatic
      Nucleic Acid

<400> SEQUENCE: 704
uuuuuugaug gcaugcacua ugcgcgacuu cauugu                              36

<210> SEQ ID NO 705
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 705
uuaugugaug gcaugcacua ugcgcgaaug uuaauu                              36

<210> SEQ ID NO 706
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 706
guguuugaug gcaugcacua ugcgcgaugc aauguu                              36

<210> SEQ ID NO 707
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 707
uggauugaug gcaugcacua ugcgcgagac uugaaa                              36

<210> SEQ ID NO 708
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 708
uuaaaugaug gcaugcacua ugcgcgaugg aucaga                              36

<210> SEQ ID NO 709
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 709
agcauugaug gcaugcacua ugcgcgauua aauaug                              36

<210> SEQ ID NO 710
<211> LENGTH: 36
<212> TYPE: RNA
<213> ORGANISM: Artificial Sequence
<220> FEATURE:
```

```
<223> OTHER INFORMATION: Description of Artificial Sequence:  Enzymatic
      Nucleic Acid

<400> SEQUENCE: 710
uaaagugaug gcaugcacua ugcgcgauua uuaaau                                 36

<210> SEQ ID NO 711
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 711
auuuuugaug gcaugcacua ugcgcgauuu uaaagc                                 36

<210> SEQ ID NO 712
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 712
guuuuugaug gcaugcacua ugcgcgauuu uuauuu                                 36

<210> SEQ ID NO 713
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 713
uuuauugaug gcaugcacua ugcgcgaaaa ggauug                                 36

<210> SEQ ID NO 714
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 714
aaauuugaug gcaugcacua ugcgcgauca aaagga                                 36

<210> SEQ ID NO 715
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 715
aguaaugaug gcaugcacua ugcgcgauuu uaaauu                                 36

<210> SEQ ID NO 716
<211> LENGTH: 36
<212> TYPE: RNA
<213> ORGANISM: Artificial Sequence
<220> FEATURE:
<223> OTHER INFORMATION: Description of Artificial Sequence:  Enzymatic
```

Nucleic Acid

<400> SEQUENCE: 716
ucauuugaug gcaugcacua ugcgcgauuu uaaaau          36

<210> SEQ ID NO 717
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 717
cacuuugaug gcaugcacua ugcgcgauuu auuuua          36

<210> SEQ ID NO 718
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 718
caucuugaug gcaugcacua ugcgcgacuu cauuua          36

<210> SEQ ID NO 719
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 719
caugcugaug gcaugcacua ugcgcgaucu cacuuc          36

<210> SEQ ID NO 720
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 720
cucacugaug gcaugcacua ugcgcgaugc caucuc          36

<210> SEQ ID NO 721
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 721
caccuugaug gcaugcacua ugcgcgacca ugccau          36

<210> SEQ ID NO 722
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 722
acuuuugaug gcaugcacua ugcgcgaccu caccau                36

<210> SEQ ID NO 723
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 723
accaaugaug gcaugcacua ugcgcgaacc uagucc                36

<210> SEQ ID NO 724
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 724
uaaguugaug gcaugcacua ugcgcgacca acaacc                36

<210> SEQ ID NO 725
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 725
acaccugaug gcaugcacua ugcgcgaucu agaacc                36

<210> SEQ ID NO 726
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 726
aaagaugaug gcaugcacua ugcgcgaccu aucuag                36

<210> SEQ ID NO 727
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 727
aaaauugaug gcaugcacua ugcgcgagag uccuaa                36

<210> SEQ ID NO 728
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 728
guccuugaug gcaugcacua ugcgcgaaaa ucagag                                36

<210> SEQ ID NO 729
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 729
uuuaaugaug gcaugcacua ugcgcgauga agaaau                                36

<210> SEQ ID NO 730
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 730
aaucaugaug gcaugcacua ugcgcgauag uguaaa                                36

<210> SEQ ID NO 731
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 731
uaaauugaug gcaugcacua ugcgcgacau agugua                                36

<210> SEQ ID NO 732
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 732
uggaaugaug gcaugcacua ugcgcgauaa aucaca                                36

<210> SEQ ID NO 733
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 733
auccuugaug gcaugcacua ugcgcgaugu aaaugg                                36

<210> SEQ ID NO 734
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 734
aagugugaug gcaugcacua ugcgcgaucc uuaugu          36

<210> SEQ ID NO 735
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 735
cuugaugaug gcaugcacua ugcgcgaaau aagugu          36

<210> SEQ ID NO 736
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 736
auuuaugaug gcaugcacua ugcgcgagau ugugcu          36

<210> SEQ ID NO 737
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 737
uguaaugaug gcaugcacua ugcgcgauag guuaaa          36

<210> SEQ ID NO 738
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 738
acuggugaug gcaugcacua ugcgcgacug aagaug          36

<210> SEQ ID NO 739
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 739
uugcaugaug gcaugcacua ugcgcgaauu uugccc          36

<210> SEQ ID NO 740
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 740

-continued ucuugugaug gcaugcacua ugcgcgacaa uuuugc                36

<210> SEQ ID NO 741
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 741
aacuuugaug gcaugcacua ugcgcgaccu cuugca                36

<210> SEQ ID NO 742
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 742
ucaaaugaug gcaugcacua ugcgcgauaa acuuca                36

<210> SEQ ID NO 743
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 743
auauuugaug gcaugcacua ugcgcgaaau auaaac                36

<210> SEQ ID NO 744
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 744
auggaugaug gcaugcacua ugcgcgauuc aaauau                36

<210> SEQ ID NO 745
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 745
acuaaugaug gcaugcacua ugcgcgaugg aagaag                36

<210> SEQ ID NO 746
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 746
gaugaugaug gcaugcacua ugcgcgacua auaugg                36

<210> SEQ ID NO 747
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 747
ggaggugaug gcaugcacua ugcgcgaaga ugacac        36

<210> SEQ ID NO 748
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 748 ugggugaug gcaugcacua ugcgcgaugu ggaagg        36

<210> SEQ ID NO 749
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 749
caaguugaug gcaugcacua ugcgcgaugg ggcaug        36

<210> SEQ ID NO 750
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 750
ugcauugaug gcaugcacua ugcgcgaagu cauggg        36

<210> SEQ ID NO 751
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 751
aacugugaug gcaugcacua ugcgcgauca agucau        36

<210> SEQ ID NO 752
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 752
acaagugaug gcaugcacua ugcgcgauua aaacug        36

```
<210> SEQ ID NO 753
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 753
aauuaugaug gcaugcacua ugcgcgaagu auuaaa                                   36

<210> SEQ ID NO 754
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 754
aaucuugaug gcaugcacua ugcgcgaugg uuaggg                                   36

<210> SEQ ID NO 755
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 755
agcagugaug gcaugcacua ugcgcgagua aaucuu                                   36

<210> SEQ ID NO 756
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 756
cacagugaug gcaugcacua ugcgcgagca guaaau                                   36

<210> SEQ ID NO 757
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 757
auccaugaug gcaugcacua ugcgcgagca gcagua                                   36

<210> SEQ ID NO 758
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 758
ggagaugaug gcaugcacua ugcgcgaucc acagca                                   36
```

```
<210> SEQ ID NO 759
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 759
aacuuugaug gcaugcacua ugcgcgaugg agauau                                      36

<210> SEQ ID NO 760
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 760
ugacuugaug gcaugcacua ugcgcgagug ggaaaa                                      36

<210> SEQ ID NO 761
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 761
uagggugaug gcaugcacua ugcgcgauuu cugaug                                      36

<210> SEQ ID NO 762
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 762
ucuguugaug gcaugcacua ugcgcgagau ucucuu                                      36

<210> SEQ ID NO 763
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 763
uauggugaug gcaugcacua ugcgcgaucu gucaga                                      36

<210> SEQ ID NO 764
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 764
cccuuugaug gcaugcacua ugcgcgaugg uaucug                                      36

<210> SEQ ID NO 765
```

```
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 765
uagguugaug gcaugcacua ugcgcgaaau cccuuu                                   36

<210> SEQ ID NO 766
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 766
agcauugaug gcaugcacua ugcgcgagcc accacc                                   36

<210> SEQ ID NO 767
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 767
caaagugaug gcaugcacua ugcgcgauca gccacc                                   36

<210> SEQ ID NO 768
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 768
auguuugaug gcaugcacua ugcgcgaaag caucag                                   36

<210> SEQ ID NO 769
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 769
ggcagugaug gcaugcacua ugcgcgaaag agaugu                                   36

<210> SEQ ID NO 770
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 770
uugggugaug gcaugcacua ugcgcgagca aagaga                                   36

<210> SEQ ID NO 771
<211> LENGTH: 36
```

```
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 771
acuguugaug gcaugcacua ugcgcggcua auggau                               36

<210> SEQ ID NO 772
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 772
cuauuugaug gcaugcacua ugcgcgauac cagggu                               36

<210> SEQ ID NO 773
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 773
cugucugaug gcaugcacua ugcgcgauuc auacca                               36

<210> SEQ ID NO 774
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 774
aucuuugaug gcaugcacua ugcgcgauua aauucu                               36

<210> SEQ ID NO 775
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 775
ugcacugaug gcaugcacua ugcgcgaucu uuauua                               36

<210> SEQ ID NO 776
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 776
uucugugaug gcaugcacua ugcgcgacua ucuuua                               36

<210> SEQ ID NO 777
<211> LENGTH: 36
<212> TYPE: RNA
```

```
<213> ORGANISM: Artificial Sequence
<220> FEATURE:
<223> OTHER INFORMATION: Description of Artificial Sequence:  Enzymatic
      Nucleic Acid

<400> SEQUENCE: 777
cuaguugaug gcaugcacua ugcgcgauag auuacc                                36

<210> SEQ ID NO 778
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 778
gaaugugaug gcaugcacua ugcgcgauua cuguua                                36

<210> SEQ ID NO 779
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 779
uaaaaugaug gcaugcacua ugcgcgaaug gaaugu                                36

<210> SEQ ID NO 780
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 780
cauugugaug gcaugcacua ugcgcgauga agauuu                                36

<210> SEQ ID NO 781
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 781
uuuuuugaug gcaugcacua ugcgcgauug caugaa                                36

<210> SEQ ID NO 782
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 782
uaaagugaug gcaugcacua ugcgcgauuu uucauu                                36

<210> SEQ ID NO 783
<211> LENGTH: 36
<212> TYPE: RNA
<213> ORGANISM: Artificial Sequence
```

```
<220> FEATURE:
<223> OTHER INFORMATION: Description of Artificial Sequence:  Enzymatic
      Nucleic Acid

<400> SEQUENCE: 783
agcuuugaug gcaugcacua ugcgcgauga auuaaa                              36

<210> SEQ ID NO 784
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 784
ucugaugaug gcaugcacua ugcgcgacca aaaaaa                              36

<210> SEQ ID NO 785
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 785
aagagugaug gcaugcacua ugcgcggaga cucuga                              36

<210> SEQ ID NO 786
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 786
ggugaugaug gcaugcacua ugcgcgaaga gcgaga                              36

<210> SEQ ID NO 787
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 787
cacugugaug gcaugcacua ugcgcgauuc cagccu                              36

<210> SEQ ID NO 788
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 788
gauggugaug gcaugcacua ugcgcggcca cugcau                              36

<210> SEQ ID NO 789
<211> LENGTH: 36
<212> TYPE: RNA
<213> ORGANISM: Artificial Sequence
<220> FEATURE:
```

<223> OTHER INFORMATION: Description of Artificial Sequence: Enzymatic
      Nucleic Acid

<400> SEQUENCE: 789
gguugugaug gcaugcacua ugcgcgagug agcuga                                 36

<210> SEQ ID NO 790
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 790
agaauugaug gcaugcacua ugcgcggcuu gaaccu                                 36

<210> SEQ ID NO 791
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 791
cgaggugaug gcaugcacua ugcgcgacga gaaucg                                 36

<210> SEQ ID NO 792
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 792
cuacuugaug gcaugcacua ugcgcgagga ggccga                                 36

<210> SEQ ID NO 793
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 793
gugcaugaug gcaugcacua ugcgcgacgc cuguaa                                 36

<210> SEQ ID NO 794
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 794
uagugugaug gcaugcacua ugcgcgacac gccugu                                 36

<210> SEQ ID NO 795
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 795
aaauaugaug gcaugcacua ugcgcgaaaa auuagu        36

<210> SEQ ID NO 796
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 796
gccaaugaug gcaugcacua ugcgcgaggu gaaacc        36

<210> SEQ ID NO 797
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 797
gaguuugaug gcaugcacua ugcgcggaga ccagcc        36

<210> SEQ ID NO 798
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 798
gagguugaug gcaugcacua ugcgcgagga guucga        36

<210> SEQ ID NO 799
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 799
ugaauugaug gcaugcacua ugcgcgacuu gagguc        36

<210> SEQ ID NO 800
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 800
agguuugaug gcaugcacua ugcgcgauga ggccaa        36

<210> SEQ ID NO 801
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

```
<400> SEQUENCE: 801
caaaaugaug gcaugcacua ugcgcgaggu uuauga                                 36

<210> SEQ ID NO 802
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 802
uucugugaug gcaugcacua ugcgcgaaaa cagguu                                 36

<210> SEQ ID NO 803
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 803
auaaaugaug gcaugcacua ugcgcgauuu gcugaa                                 36

<210> SEQ ID NO 804
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 804
gcacuugaug gcaugcacua ugcgcgaaua aauauu                                 36

<210> SEQ ID NO 805
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 805
guaggugaug gcaugcacua ugcgcgacuc aauaaa                                 36

<210> SEQ ID NO 806
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 806
acuggugaug gcaugcacua ugcgcgaucu gguagg                                 36

<210> SEQ ID NO 807
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid
```

```
<400> SEQUENCE: 807
uugugugaug gcaugcacua ugcgcgggug acuggc                    36

<210> SEQ ID NO 808
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 808
uaccaugaug gcaugcacua ugcgcgauac ccagug                    36

<210> SEQ ID NO 809
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 809
gauacugaug gcaugcacua ugcgcgauau acccag                    36

<210> SEQ ID NO 810
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 810
gggauugaug gcaugcacua ugcgcgaugu cucuug                    36

<210> SEQ ID NO 811
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 811
acuagugaug gcaugcacua ugcgcgagua ccuaag                    36

<210> SEQ ID NO 812
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 812
gaccaugaug gcaugcacua ugcgcgacua gcagua                    36

<210> SEQ ID NO 813
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 813
```
uauuaugaug gcaugcacua ugcgcgagac cacacu        36

<210> SEQ ID NO 814
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 814
uaagaugaug gcaugcacua ugcgcgauua cagacc        36

<210> SEQ ID NO 815
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 815
ggucgugaug gcaugcacua ugcgcgauac caaagg        36

<210> SEQ ID NO 816
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 816
uggguugaug gcaugcacua ugcgcgguau accaaa        36

<210> SEQ ID NO 817
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 817
cguguugaug gcaugcacua ugcgcgaucu cugggu        36

<210> SEQ ID NO 818
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 818
cgcauugaug gcaugcacua ugcgcggugu uaucuc        36

<210> SEQ ID NO 819
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 819

-continued auacgugaug gcaugcacua ugcgcgaucg uguuau          36

<210> SEQ ID NO 820
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 820
cuuugugaug gcaugcacua ugcgcgaaaa cuaaaa          36

<210> SEQ ID NO 821
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 821
uggcaugaug gcaugcacua ugcgcgagag accaaa          36

<210> SEQ ID NO 822
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 822
gcuggugaug gcaugcacua ugcgcgacag agacca          36

<210> SEQ ID NO 823
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 823
acaauugaug gcaugcacua ugcgcgauag agcugg          36

<210> SEQ ID NO 824
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 824
caaaaugaug gcaugcacua ugcgcgaauu auagag          36

<210> SEQ ID NO 825
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 825
cguagugaug gcaugcacua ugcgcgaaaa caauua          36

<210> SEQ ID NO 826
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 826
ggaauugaug gcaugcacua ugcgcgguag caaaac                              36

<210> SEQ ID NO 827
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 827
aguuuugaug gcaugcacua ugcgcgagug gaaucg                              36

<210> SEQ ID NO 828
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 828
uugauugaug gcaugcacua ugcgcggaag aguuuc                              36

<210> SEQ ID NO 829
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 829
auuuaugaug gcaugcacua ugcgcgauaa aguagc                              36

<210> SEQ ID NO 830
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 830
uaaaaugaug gcaugcacua ugcgcgaaug aaguga                              36

<210> SEQ ID NO 831
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 831
aaguuugaug gcaugcacua ugcgcgauuc cuuuaa                              36

```
<210> SEQ ID NO 832
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 832
auaauugaug gcaugcacua ugcgcgaagu uuauuc                                36

<210> SEQ ID NO 833
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 833
aacaaugaug gcaugcacua ugcgcgauaa ucaagu                                36

<210> SEQ ID NO 834
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 834
aaaaaugaug gcaugcacua ugcgcgaaua uaauca                                36

<210> SEQ ID NO 835
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 835
acaguugaug gcaugcacua ugcgcgaugc caaaua                                36

<210> SEQ ID NO 836
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 836
aaucaugaug gcaugcacua ugcgcgaguu augcca                                36

<210> SEQ ID NO 837
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 837
agaauugaug gcaugcacua ugcgcgacag uuaugc                                36
```

```
<210> SEQ ID NO 838
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 838
guguaugaug gcaugcacua ugcgcgagua auuguc                                36

<210> SEQ ID NO 839
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 839
acauaugaug gcaugcacua ugcgcgaccu uaaugu                                36

<210> SEQ ID NO 840
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 840
ucugaugaug gcaugcacua ugcgcgauac accuua                                36

<210> SEQ ID NO 841
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 841
augaaugaug gcaugcacua ugcgcgaucu gacaua                                36

<210> SEQ ID NO 842
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 842
gucaaugaug gcaugcacua ugcgcgauga auaucu                                36

<210> SEQ ID NO 843
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 843
uggguugaug gcaugcacua ugcgcgaaua ugaaua                                36

<210> SEQ ID NO 844
```

<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 844
uuacaugaug gcaugcacua ugcgcgauuu ggguca                                     36

<210> SEQ ID NO 845
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 845
uauuaugaug gcaugcacua ugcgcgacau uugggu                                     36

<210> SEQ ID NO 846
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 846
uggaaugaug gcaugcacua ugcgcgauua cacauu                                     36

<210> SEQ ID NO 847
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 847
uuaugugaug gcaugcacua ugcgcgagag aaaacu                                     36

<210> SEQ ID NO 848
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 848
uuacuugaug gcaugcacua ugcgcgaugc agagaa                                     36

<210> SEQ ID NO 849
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 849
aaguaugaug gcaugcacua ugcgcgauuu uaauua                                     36

<210> SEQ ID NO 850
<211> LENGTH: 36

```
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 850
uuaagugaug gcaugcacua ugcgcgauau uuuaau                             36

<210> SEQ ID NO 851
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 851
aaaacugaug gcaugcacua ugcgcgauua auuuuu                             36

<210> SEQ ID NO 852
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 852
cuguuugaug gcaugcacua ugcgcgauuu guaccc                             36

<210> SEQ ID NO 853
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 853
ucaggugaug gcaugcacua ugcgcgacug uuuauu                             36

<210> SEQ ID NO 854
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 854
uaguuugaug gcaugcacua ugcgcgaggc acuguu                             36

<210> SEQ ID NO 855
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 855
uuuuaugaug gcaugcacua ugcgcgauag aaguuu                             36

<210> SEQ ID NO 856
<211> LENGTH: 36
<212> TYPE: RNA
```

```
<213> ORGANISM: Artificial Sequence
<220> FEATURE:
<223> OTHER INFORMATION: Description of Artificial Sequence:  Enzymatic
      Nucleic Acid

<400> SEQUENCE: 856
gaaauugaug gcaugcacua ugcgcgauag ugauuu                                    36

<210> SEQ ID NO 857
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 857
caauuugaug gcaugcacua ugcgcgagaa aucaua                                    36

<210> SEQ ID NO 858
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 858
cauagugaug gcaugcacua ugcgcgaauu cagaaa                                    36

<210> SEQ ID NO 859
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 859
uuucaugaug gcaugcacua ugcgcgauag caauuc                                    36

<210> SEQ ID NO 860
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 860
aguuuugaug gcaugcacua ugcgcgacau agcaau                                    36

<210> SEQ ID NO 861
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 861
cuaaaugaug gcaugcacua ugcgcgagug uuccaa                                    36

<210> SEQ ID NO 862
<211> LENGTH: 36
<212> TYPE: RNA
<213> ORGANISM: Artificial Sequence
```

```
<220> FEATURE:
<223> OTHER INFORMATION: Description of Artificial Sequence:  Enzymatic
      Nucleic Acid

<400> SEQUENCE: 862
cuuaaugaug gcaugcacua ugcgcgaccc uaccua                                    36

<210> SEQ ID NO 863
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 863
uguguugaug gcaugcacua ugcgcgaagu cuuaac                                    36

<210> SEQ ID NO 864
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 864
auggcugaug gcaugcacua ugcgcgauuu cuuucu                                    36

<210> SEQ ID NO 865
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 865
ugaagugaug gcaugcacua ugcgcgaugg ccauuu                                    36

<210> SEQ ID NO 866
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 866
cacugugaug gcaugcacua ugcgcgaguu ccugaa                                    36

<210> SEQ ID NO 867
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 867
auaagugaug gcaugcacua ugcgcgacug caguuc                                    36

<210> SEQ ID NO 868
<211> LENGTH: 36
<212> TYPE: RNA
<213> ORGANISM: Artificial Sequence
<220> FEATURE:
```

```
<223> OTHER INFORMATION: Description of Artificial Sequence:  Enzymatic
      Nucleic Acid

<400> SEQUENCE: 868
ccccuugaug gcaugcacua ugcgcgauaa gcacug                                     36

<210> SEQ ID NO 869
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 869
cuaaaugaug gcaugcacua ugcgcgaucc ccucau                                     36

<210> SEQ ID NO 870
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 870
aaauuugaug gcaugcacua ugcgcgaaga ggccua                                     36

<210> SEQ ID NO 871
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 871
uacauugaug gcaugcacua ugcgcgaaaa auucaa                                     36

<210> SEQ ID NO 872
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 872
aucuaugaug gcaugcacua ugcgcgauca aaaauu                                     36

<210> SEQ ID NO 873
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 873
augccugaug gcaugcacua ugcgcgaucu acauca                                     36

<210> SEQ ID NO 874
<211> LENGTH: 36
<212> TYPE: RNA
<213> ORGANISM: Artificial Sequence
<220> FEATURE:
<223> OTHER INFORMATION: Description of Artificial Sequence:  Enzymatic
```

Nucleic Acid

<400> SEQUENCE: 874
guucaugaug gcaugcacua ugcgcgauaa agguaa        36

<210> SEQ ID NO 875
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 875
aaguuugaug gcaugcacua ugcgcgacau aaaggu        36

<210> SEQ ID NO 876
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 876
ccauuugaug gcaugcacua ugcgcgaaag uucaca        36

<210> SEQ ID NO 877
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 877
uaaacugaug gcaugcacua ugcgcgauuc aaaguu        36

<210> SEQ ID NO 878
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 878
aaaaaugaug gcaugcacua ugcgcgaaau cuuuug        36

<210> SEQ ID NO 879
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 879
cucuaugaug gcaugcacua ugcgcgaaaa acaaau        36

<210> SEQ ID NO 880
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 880
acauuugaug gcaugcacua ugcgcgauuu cuagaa                36

<210> SEQ ID NO 881
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 881
gguaaugaug gcaugcacua ugcgcgauuu auuucu                36

<210> SEQ ID NO 882
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 882
uucaaugaug gcaugcacua ugcgcgaagg auuuuu                36

<210> SEQ ID NO 883
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 883
aacuuugaug gcaugcacua ugcgcgaaca aggauu                36

<210> SEQ ID NO 884
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 884
aagucugaug gcaugcacua ugcgcgaugu aauuua                36

<210> SEQ ID NO 885
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 885
acaaaugaug gcaugcacua ugcgcgaugu uaaugc                36

<210> SEQ ID NO 886
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

```
<400> SEQUENCE: 886
uuccaugaug gcaugcacua ugcgcgaaac auguua                                    36

<210> SEQ ID NO 887
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 887
ugcuaugaug gcaugcacua ugcgcgauuc uuccac                                    36

<210> SEQ ID NO 888
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 888
ucugcugaug gcaugcacua ugcgcgauau ucuucc                                    36

<210> SEQ ID NO 889
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 889
uacaaugaug gcaugcacua ugcgcgauac gucugc                                    36

<210> SEQ ID NO 890
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 890
ugauaugaug gcaugcacua ugcgcgaaua uacguc                                    36

<210> SEQ ID NO 891
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 891
ucacuugaug gcaugcacua ugcgcgaaau gauaca                                    36

<210> SEQ ID NO 892
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 892
```
acauuugaug gcaugcacua ugcgcgacuc aaauga   36

<210> SEQ ID NO 893
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 893
gggaaugaug gcaugcacua ugcgcgauuc acucaa   36

<210> SEQ ID NO 894
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 894
ugacuugaug gcaugcacua ugcgcgaguu aaauag   36

<210> SEQ ID NO 895
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 895
cuaugugaug gcaugcacua ugcgcgagug ugacuc   36

<210> SEQ ID NO 896
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 896
auuccugaug gcaugcacua ugcgcgaugc agugug   36

<210> SEQ ID NO 897
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 897
uaaccugaug gcaugcacua ugcgcgauaa aaguua   36

<210> SEQ ID NO 898
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 898
gacaaugaug gcaugcacua ugcgcgaguu uugaua                                   36

<210> SEQ ID NO 899
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 899
ggugaugaug gcaugcacua ugcgcgaaca guuuug                                   36

<210> SEQ ID NO 900
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 900
uugugugaug gcaugcacua ugcgcgaaug gugaca                                   36

<210> SEQ ID NO 901
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 901
uaggaugaug gcaugcacua ugcgcgaaaa uugugc                                   36

<210> SEQ ID NO 902
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 902
guauaugaug gcaugcacua ugcgcgauua ggacaa                                   36

<210> SEQ ID NO 903
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 903
auguaugaug gcaugcacua ugcgcgauau uaggac                                   36

<210> SEQ ID NO 904
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 904
cuaugugaug gcaugcacua ugcgcgauau auuagg                                   36

<210> SEQ ID NO 905
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 905
guuucugaug gcaugcacua ugcgcgaugu auauau         36

<210> SEQ ID NO 906
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 906
ccccaugaug gcaugcacua ugcgcgaaag uuucua         36

<210> SEQ ID NO 907
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 907
cuuaaugaug gcaugcacua ugcgcgaugc cccaca         36

<210> SEQ ID NO 908
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 908
uugugugaug gcaugcacua ugcgcgaaac uguaac         36

<210> SEQ ID NO 909
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 909
gaauaugaug gcaugcacua ugcgcgaaau gagaug         36

<210> SEQ ID NO 910
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 910
aaaauugaug gcaugcacua ugcgcgaaug gaauac         36

<210> SEQ ID NO 911
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 911
uuauaugaug gcaugcacua ugcgcgauac uguuuu                36

<210> SEQ ID NO 912
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 912
aguuaugaug gcaugcacua ugcgcgauau acuguu                36

<210> SEQ ID NO 913
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 913
aaaguugaug gcaugcacua ugcgcgauau auacug                36

<210> SEQ ID NO 914
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 914
aucuuugaug gcaugcacua ugcgcgagau aguuuu                36

<210> SEQ ID NO 915
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 915
uuugaugaug gcaugcacua ugcgcgaaau ggaaau                36

<210> SEQ ID NO 916
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 916
gaaauugaug gcaugcacua ugcgcgauua cuuuuu                36

```
<210> SEQ ID NO 917
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 917
auuauugaug gcaugcacua ugcgcgaaga aaucau                                  36

<210> SEQ ID NO 918
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 918
acaauugaug gcaugcacua ugcgcgauca agaaau                                  36

<210> SEQ ID NO 919
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 919
cuacaugaug gcaugcacua ugcgcgaauu aucaag                                  36

<210> SEQ ID NO 920
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 920
cacuaugaug gcaugcacua ugcgcgacaa uuauca                                  36

<210> SEQ ID NO 921
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 921
acauuugaug gcaugcacua ugcgcgacua cacaau                                  36

<210> SEQ ID NO 922
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 922
aaaaaugaug gcaugcacua ugcgcgauuc acuaca                                  36

<210> SEQ ID NO 923
```

```
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 923
gcuuuugaug gcaugcacua ugcgcgaagg uaacug                                 36

<210> SEQ ID NO 924
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 924
aaauuugaug gcaugcacua ugcgcgagcu uucaag                                 36

<210> SEQ ID NO 925
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 925
cuaaaugaug gcaugcacua ugcgcgauaa auucag                                 36

<210> SEQ ID NO 926
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 926
uaacaugaug gcaugcacua ugcgcgagaa guuacu                                 36

<210> SEQ ID NO 927
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 927
auuaaugaug gcaugcacua ugcgcgacag aaguua                                 36

<210> SEQ ID NO 928
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 928
uccagugaug gcaugcacua ugcgcgauua acacag                                 36

<210> SEQ ID NO 929
<211> LENGTH: 36
```

<210> SEQ ID NO 929
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 929
caugcugaug gcaugcacua ugcgcgaucc aguauu        36

<210> SEQ ID NO 930
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 930
gaauuugaug gcaugcacua ugcgcgaugc uaucca        36

<210> SEQ ID NO 931
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 931
caaugugaug gcaugcacua ugcgcgagaa uucaug        36

<210> SEQ ID NO 932
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 932
uuucuugaug gcaugcacua ugcgcgaaug cagaau        36

<210> SEQ ID NO 933
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 933
cuauuugaug gcaugcacua ugcgcgaguu ucucaa        36

<210> SEQ ID NO 934
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 934
acagcugaug gcaugcacua ugcgcgauuc aguuuc        36

<210> SEQ ID NO 935
<211> LENGTH: 36
<212> TYPE: RNA

```
<213> ORGANISM: Artificial Sequence
<220> FEATURE:
<223> OTHER INFORMATION: Description of Artificial Sequence:  Enzymatic
      Nucleic Acid

<400> SEQUENCE: 935
uaugaugaug gcaugcacua ugcgcgagcu auucag                             36

<210> SEQ ID NO 936
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 936
cauuuugaug gcaugcacua ugcgcgauga cagcua                             36

<210> SEQ ID NO 937
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 937
gaaagugaug gcaugcacua ugcgcgauuu uaugac                             36

<210> SEQ ID NO 938
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 938
gugagugaug gcaugcacua ugcgcgaucu uucuuu                             36

<210> SEQ ID NO 939
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 939
gaacuugaug gcaugcacua ugcgcgaugu gaguau                             36

<210> SEQ ID NO 940
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 940
uucuuugaug gcaugcacua ugcgcgaaga acucau                             36

<210> SEQ ID NO 941
<211> LENGTH: 36
<212> TYPE: RNA
<213> ORGANISM: Artificial Sequence
```

```
<220> FEATURE:
<223> OTHER INFORMATION: Description of Artificial Sequence: Enzymatic
      Nucleic Acid

<400> SEQUENCE: 941
augacugaug gcaugcacua ugcgcgauuc uucaag                                  36

<210> SEQ ID NO 942
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 942
cuaguugaug gcaugcacua ugcgcgauga cuauuc                                  36

<210> SEQ ID NO 943
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 943
aaacaugaug gcaugcacua ugcgcgagau cuuaau                                  36

<210> SEQ ID NO 944
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 944
uaaaaugaug gcaugcacua ugcgcgacag aucuua                                  36

<210> SEQ ID NO 945
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 945
caaacugaug gcaugcacua ugcgcgauua aacuaa                                  36

<210> SEQ ID NO 946
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 946
cacuuugaug gcaugcacua ugcgcgaaac uauuaa                                  36

<210> SEQ ID NO 947
<211> LENGTH: 36
<212> TYPE: RNA
<213> ORGANISM: Artificial Sequence
<220> FEATURE:
```

```
<223> OTHER INFORMATION: Description of Artificial Sequence:  Enzymatic
      Nucleic Acid

<400> SEQUENCE: 947
acaggugaug gcaugcacua ugcgcgacuu caaacu                              36

<210> SEQ ID NO 948
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 948
ccaaaugaug gcaugcacua ugcgcgaggc acuuca                              36

<210> SEQ ID NO 949
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 949
aucauugaug gcaugcacua ugcgcgaucc caaaca                              36

<210> SEQ ID NO 950
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 950
ccuauugaug gcaugcacua ugcgcgauua ucccaa                              36

<210> SEQ ID NO 951
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 951
uuaccugaug gcaugcacua ugcgcgauca uuaucc                              36

<210> SEQ ID NO 952
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 952
aaauuugaug gcaugcacua ugcgcgaucu aaauua                              36

<210> SEQ ID NO 953
<211> LENGTH: 36
<212> TYPE: RNA
<213> ORGANISM: Artificial Sequence
<220> FEATURE:
<223> OTHER INFORMATION: Description of Artificial Sequence:  Enzymatic
```

Nucleic Acid

<400> SEQUENCE: 953
aacugugaug gcaugcacua ugcgcgagau aacuuu     36

<210> SEQ ID NO 954
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 954
cucaaugaug gcaugcacua ugcgcgauaa cugcag     36

<210> SEQ ID NO 955
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 955
gcccuugaug gcaugcacua ugcgcgaaca uaacug     36

<210> SEQ ID NO 956
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 956
uaaaaugaug gcaugcacua ugcgcgacug uaaccc     36

<210> SEQ ID NO 957
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 957
acuuuugaug gcaugcacua ugcgcgggau aaaaca     36

<210> SEQ ID NO 958
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 958
caagaugaug gcaugcacua ugcgcgagug gaauug     36

<210> SEQ ID NO 959
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

```
<400> SEQUENCE: 959
aaacaugaug gcaugcacua ugcgcgaaga cagugg                                36

<210> SEQ ID NO 960
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 960
gaaaaugaug gcaugcacua ugcgcgacaa gacagu                                36

<210> SEQ ID NO 961
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 961
uucaaugaug gcaugcacua ugcgcgauga aaacac                                36

<210> SEQ ID NO 962
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 962
auuuuugaug gcaugcacua ugcgcgaaca ugaaaa                                36

<210> SEQ ID NO 963
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 963
aaaagugaug gcaugcacua ugcgcgauuu ucaaca                                36

<210> SEQ ID NO 964
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 964
aaaugugaug gcaugcacua ugcgcgaaaa guauuu                                36

<210> SEQ ID NO 965
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid
```

<400> SEQUENCE: 965
gcacuugaug gcaugcacua ugcgcgaaag gaaaaa         36

<210> SEQ ID NO 966
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 966
auuggugaug gcaugcacua ugcgcgacuc aaagga         36

<210> SEQ ID NO 967
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 967
uguuaugaug gcaugcacua ugcgcgauua agaaau         36

<210> SEQ ID NO 968
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 968
guaaaugaug gcaugcacua ugcgcgaugu uacauu         36

<210> SEQ ID NO 969
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 969
aaagaugaug gcaugcacua ugcgcgaggc caggua         36

<210> SEQ ID NO 970
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 970
cuauaugaug gcaugcacua ugcgcgaaaa auaguu         36

<210> SEQ ID NO 971
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 971
uacacugaug gcaugcacua ugcgcgauac aaaaau                36

<210> SEQ ID NO 972
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 972
guuuaugaug gcaugcacua ugcgcgacua uacaaa                36

<210> SEQ ID NO 973
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 973
uguuuugaug gcaugcacua ugcgcgaguu uacacu                36

<210> SEQ ID NO 974
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 974
augugugaug gcaugcacua ugcgcgaugu uucagu                36

<210> SEQ ID NO 975
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 975
auguaugaug gcaugcacua ugcgcgaaaa ugugca                36

<210> SEQ ID NO 976
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 976
aagcaugaug gcaugcacua ugcgcgaaug uacaaa                36

<210> SEQ ID NO 977
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 977
gaaagugaug gcaugcacua ugcgcgacaa uguaca　　　　　　　　　　　　　　　　36

<210> SEQ ID NO 978
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 978
acccaugaug gcaugcacua ugcgcgaaaa gaaagc　　　　　　　　　　　　　　　　36

<210> SEQ ID NO 979
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 979
cugcaugaug gcaugcacua ugcgcgauga cccaca　　　　　　　　　　　　　　　　36

<210> SEQ ID NO 980
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 980
cacugugaug gcaugcacua ugcgcgauau gaccca　　　　　　　　　　　　　　　　36

<210> SEQ ID NO 981
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 981
gaucaugaug gcaugcacua ugcgcgacug cauaug　　　　　　　　　　　　　　　　36

<210> SEQ ID NO 982
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 982
uggauugaug gcaugcacua ugcgcgacac ugcaua　　　　　　　　　　　　　　　　36

<210> SEQ ID NO 983
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 983
gaaaaugaug gcaugcacua ugcgcgaacu ggauca　　　　　　　　　　　　　　　　36

<210> SEQ ID NO 984
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 984
cagcgugaug gcaugcacua ugcgcgaacc aaauga                36

<210> SEQ ID NO 985
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 985
gucagugaug gcaugcacua ugcgcggcaa ccaaau                36

<210> SEQ ID NO 986
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 986
uagguugaug gcaugcacua ugcgcgagcg caacca                36

<210> SEQ ID NO 987
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 987
accaaugaug gcaugcacua ugcgcgauuc cuaggu                36

<210> SEQ ID NO 988
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 988
uuugaugaug gcaugcacua ugcgcgauga ccaaca                36

<210> SEQ ID NO 989
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 989
gugguugaug gcaugcacua ugcgcgauuu uuaaug                36

<210> SEQ ID NO 990
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 990
aauuuugaug gcaugcacua ugcgcgauua aaagag                                36

<210> SEQ ID NO 991
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 991
auaaaugaug gcaugcacua ugcgcgauuu aaagu                                 36

<210> SEQ ID NO 992
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 992
acuccugaug gcaugcacua ugcgcgauaa acauuu                                36

<210> SEQ ID NO 993
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 993
cagcaugaug gcaugcacua ugcgcgauac uccuau                                36

<210> SEQ ID NO 994
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 994
cacagugaug gcaugcacua ugcgcgacau acuccu                                36

<210> SEQ ID NO 995
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 995
cuucaugaug gcaugcacua ugcgcgagca cauacu                                36

```
<210> SEQ ID NO 996
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 996
cacuuugaug gcaugcacua ugcgcgacag cacaua                                36

<210> SEQ ID NO 997
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 997
uagauugaug gcaugcacua ugcgcgacuu cacagc                                36

<210> SEQ ID NO 998
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 998
uauuaugaug gcaugcacua ugcgcgaaau uuuaga                                36

<210> SEQ ID NO 999
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 999
aaaaaugaug gcaugcacua ugcgcgauua caaauu                                36

<210> SEQ ID NO 1000
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1000
caugaugaug gcaugcacua ugcgcgaaaa auauua                                36

<210> SEQ ID NO 1001
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1001
caguuugaug gcaugcacua ugcgcgauga caaaaa                                36

<210> SEQ ID NO 1002
```

```
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1002
uaguaugaug gcaugcacua ugcgcgaguu caugac                           36

<210> SEQ ID NO 1003
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1003
cauuaugaug gcaugcacua ugcgcgaaua auuagg                           36

<210> SEQ ID NO 1004
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1004
uauuaugaug gcaugcacua ugcgcgauua caauaa                           36

<210> SEQ ID NO 1005
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1005 auuuugaug gcaugcacua ugcgcgauua cauuac                            36

<210> SEQ ID NO 1006
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1006
guaacugaug gcaugcacua ugcgcgauuu uuauua                           36

<210> SEQ ID NO 1007
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1007
auaguugaug gcaugcacua ugcgcgacug uaacua                           36

<210> SEQ ID NO 1008
<211> LENGTH: 36
```

```
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1008
acacuugaug gcaugcacua ugcgcgauag ucacug                              36

<210> SEQ ID NO 1009
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1009
auacaugaug gcaugcacua ugcgcgacuc auaguc                              36

<210> SEQ ID NO 1010
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1010
aaauaugaug gcaugcacua ugcgcgacac ucauag                              36

<210> SEQ ID NO 1011
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1011
auuugugaug gcaugcacua ugcgcgauga auaaau                              36

<210> SEQ ID NO 1012
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1012
caguuugaug gcaugcacua ugcgcgaaau uugcau                              36

<210> SEQ ID NO 1013
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1013 gcaaugaug gcaugcacua ugcgcgaguu caaauu                               36

<210> SEQ ID NO 1014
<211> LENGTH: 36
<212> TYPE: RNA
```

```
<213> ORGANISM: Artificial Sequence
<220> FEATURE:
<223> OTHER INFORMATION: Description of Artificial Sequence:  Enzymatic
      Nucleic Acid

<400> SEQUENCE: 1014
cggggugaug gcaugcacua ugcgcgaaac aguuca                              36

<210> SEQ ID NO 1015
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1015 cauuugaug gcaugcacua ugcgcggggg caaaca                               36

<210> SEQ ID NO 1016
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1016
auaucugaug gcaugcacua ugcgcgauuu cggggc                              36

<210> SEQ ID NO 1017
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1017
auccaugaug gcaugcacua ugcgcgaucc auuucg                              36

<210> SEQ ID NO 1018
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1018
guaucugaug gcaugcacua ugcgcgauau ccauuu                              36

<210> SEQ ID NO 1019
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1019
uaaagugaug gcaugcacua ugcgcgaucc auaucc                              36

<210> SEQ ID NO 1020
<211> LENGTH: 36
<212> TYPE: RNA
<213> ORGANISM: Artificial Sequence
```

```
<220> FEATURE:
<223> OTHER INFORMATION: Description of Artificial Sequence: Enzymatic
      Nucleic Acid

<400> SEQUENCE: 1020
uggcuugaug gcaugcacua ugcgcgauaa aguauc                    36

<210> SEQ ID NO 1021
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1021
gugucugaug gcaugcacua ugcgcgaugg cuuaua                    36

<210> SEQ ID NO 1022
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1022
uauacugaug gcaugcacua ugcgcgauag ugucua                    36

<210> SEQ ID NO 1023
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1023
acuggugaug gcaugcacua ugcgcgauac uauagu                    36

<210> SEQ ID NO 1024
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1024
agauuugaug gcaugcacua ugcgcgacug guauac                    36

<210> SEQ ID NO 1025
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1025
agcugugaug gcaugcacua ugcgcgauaa aagauu                    36

<210> SEQ ID NO 1026
<211> LENGTH: 36
<212> TYPE: RNA
<213> ORGANISM: Artificial Sequence
<220> FEATURE:
```

```
<223> OTHER INFORMATION: Description of Artificial Sequence: Enzymatic
      Nucleic Acid

<400> SEQUENCE: 1026
ucuaaugaug gcaugcacua ugcgcgaagc ugcaua                                36

<210> SEQ ID NO 1027
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1027
cacagugaug gcaugcacua ugcgcgaccu uuuaga                                36

<210> SEQ ID NO 1028
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1028
auccaugaug gcaugcacua ugcgcgagca ccuuuu                                36

<210> SEQ ID NO 1029
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1029
cauaaugaug gcaugcacua ugcgcgaucc acagca                                36

<210> SEQ ID NO 1030
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1030
cuuuaugaug gcaugcacua ugcgcgauaa uaucca                                36

<210> SEQ ID NO 1031
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1031
gcaaaugaug gcaugcacua ugcgcgacgc cuuuac                                36

<210> SEQ ID NO 1032
<211> LENGTH: 36
<212> TYPE: RNA
<213> ORGANISM: Artificial Sequence
<220> FEATURE:
<223> OTHER INFORMATION: Description of Artificial Sequence: Enzymatic
```

```
Nucleic Acid

<400> SEQUENCE: 1032
uuaagugaug gcaugcacua ugcgcgaaac acgccu                                36

<210> SEQ ID NO 1033
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1033
cuaaaugaug gcaugcacua ugcgcgaugg aaaauu                                36

<210> SEQ ID NO 1034
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1034
uuuugugaug gcaugcacua ugcgcgaucu acuucu                                36

<210> SEQ ID NO 1035
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1035
aaaggugaug gcaugcacua ugcgcgagau uuguuu                                36

<210> SEQ ID NO 1036
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1036
uuuguugaug gcaugcacua ugcgcgauaa aggcag                                36

<210> SEQ ID NO 1037
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1037
uauccugaug gcaugcacua ugcgcgauuu uuugu                                 36

<210> SEQ ID NO 1038
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid
```

<400> SEQUENCE: 1038
aauguugaug gcaugcacua ugcgcgaucc uauuuu         36

<210> SEQ ID NO 1039
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1039
uaccuugaug gcaugcacua ugcgcgauug auaaaa         36

<210> SEQ ID NO 1040
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1040
uguauugaug gcaugcacua ugcgcgaauu accuua         36

<210> SEQ ID NO 1041
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1041
uugugugaug gcaugcacua ugcgcgauca auuacc         36

<210> SEQ ID NO 1042
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1042
caaguugaug gcaugcacua ugcgcgaccu guugug         36

<210> SEQ ID NO 1043
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1043
uccauugaug gcaugcacua ugcgcgauua auguug         36

<210> SEQ ID NO 1044
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

```
<400> SEQUENCE: 1044
auuucugaug gcaugcacua ugcgcgauua uuaaug                                36

<210> SEQ ID NO 1045
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1045
ucaauugaug gcaugcacua ugcgcgauuu ccauua                                36

<210> SEQ ID NO 1046
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1046
cuauuugaug gcaugcacua ugcgcgaauu auuucc                                36

<210> SEQ ID NO 1047
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1047
cuaacugaug gcaugcacua ugcgcgauuc aauuau                                36

<210> SEQ ID NO 1048
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1048
acauaugaug gcaugcacua ugcgcgauaa cuaacu                                36

<210> SEQ ID NO 1049
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1049
auuaaugaug gcaugcacua ugcgcgauac auaacu                                36

<210> SEQ ID NO 1050
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1050
```
acuggugaug gcaugcacua ugcgcgauua acauac        36

<210> SEQ ID NO 1051
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1051
ggaguugaug gcaugcacua ugcgcgauua cuucug        36

<210> SEQ ID NO 1052
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1052
auaugugaug gcaugcacua ugcgcgaugg agucau        36

<210> SEQ ID NO 1053
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1053
aauaaugaug gcaugcacua ugcgcgaugu auggag        36

<210> SEQ ID NO 1054
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1054
guaguugaug gcaugcacua ugcgcgauag aaauaa        36

<210> SEQ ID NO 1055
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1055
aacguugaug gcaugcacua ugcgcgaugg cuaggc        36

<210> SEQ ID NO 1056
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1056 aacgugaug gcaugcacua ugcgcgaugg cuaggc                              36

<210> SEQ ID NO 1057
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1057
aacguugaug gcaugcacua ugcgcggugg cuaggc                              36

<210> SEQ ID NO 1058
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1058
aacguugaug gcaugcacua ugcgcguugg cuaggc                              36

<210> SEQ ID NO 1059
<211> LENGTH: 36

```
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1059
aacgaugaug gcaugcacua ugcgcgaugg cuaggc                         36

<210> SEQ ID NO 1060
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 1060
aacgaugaug gcaugcacua ugcgcggugg cuaggc                         36

<210> SEQ ID NO 1061
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1061
aacggugaug gcaugcacua ugcgcggugg cuaggc                         36

<210> SEQ ID NO 1062
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
```

<223> OTHER INFORMATION: 2'-O-Methyl

<400> SEQUENCE: 1062
aacggugaug gcaugcacua ugcgcguugg cuaggc                36

<210> SEQ ID NO 1063
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1063
aacgaugaug gcaugcacua ugcgcguugg cuaggc                36

<210> SEQ ID NO 1064
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1064
aacgcugaug gcaugcacua ugcgcggugg cuaggc                36

<210> SEQ ID NO 1065
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1065
aacgcugaug gcaugcacua ugcgcgaugg cuaggc    36

<210> SEQ ID NO 1066
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1066
aacguugaug gcaugcacua ugcgcgcugg cuaggc    36

<210> SEQ ID NO 1067
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1067
aacggugaug gcaugcacua ugcgcgcugg cuaggc    36

<210> SEQ ID NO 1068
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1068
aacgcugaug gcaugcacua ugcgcguugg cuaggc    36

<210> SEQ ID NO 1069

```
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1069
aacgaugaug gcaugcacua ugcgcgcugg cuaggc                              36

<210> SEQ ID NO 1070
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl

<400> SEQUENCE: 1070
aacgcugaug gcaugcacua ugcgcgcugg cuaggc                              36

<210> SEQ ID NO 1071
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1071
```
agcugugaug gcaugcacua ugcgcgaucg ucaaggn                37

<210> SEQ ID NO 1072
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1072
gaucaugaug gcaugcacua ugcgcgauuc guccacn                37

<210> SEQ ID NO 1073
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1073
uucucugaug gcaugcacua ugcgcgauca auuacun                37

<210> SEQ ID NO 1074
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid

```
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1074
gagaaugaug gcaugcacua ugcgcgaucc aagagan                              37

<210> SEQ ID NO 1075
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1075
ucccuugaug gcaugcacua ugcgcgauug cacugun                              37

<210> SEQ ID NO 1076
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
```

```
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1076
guccuugaug gcaugcacua ugcgcgaugu acuggun                              37

<210> SEQ ID NO 1077
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1077
aguauugaug gcaugcacua ugcgcgauuu auggcan                              37

<210> SEQ ID NO 1078
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage
```

-continued

<400> SEQUENCE: 1078
agguaugaug gcaugcacua ugcgcgaucu ucagagn           37

<210> SEQ ID NO 1079
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1079
aggacugaug gcaugcacua ugcgcgauag guacaun           37

<210> SEQ ID NO 1080
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1080
aaucaugaug gcaugcacua ugcgcgauuu auuuccn           37

<210> SEQ ID NO 1081
<211> LENGTH: 37
<212> TYPE: RNA
<213> ORGANISM: Artificial Sequence
<220> FEATURE:
<223> OTHER INFORMATION: Description of Artificial Sequence:  Enzymatic

```
            Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1081
aauucugaug gcaugcacua ugcgcgauaa cuucuun                           37

<210> SEQ ID NO 1082
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1082
ggcauugaug gcaugcacua ugcgcgauca acacccn                           37

<210> SEQ ID NO 1083
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
```

```
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1083
gaaggugaug gcaugcacua ugcgcgauca ucaacan                              37

<210> SEQ ID NO 1084
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1084
uaaugugaug gcaugcacua ugcgcgauag aaggcan                              37

<210> SEQ ID NO 1085
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage
```

<400> SEQUENCE: 1085
uuuacugaug gcaugcacua ugcgcgaucu uugcucn            37

<210> SEQ ID NO 1086
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1086
auaagugaug gcaugcacua ugcgcgauuu aagguan            37

<210> SEQ ID NO 1087
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1087
acaggugaug gcaugcacua ugcgcgauug cuaguun            37

<210> SEQ ID NO 1088
<211> LENGTH: 37
<212> TYPE: RNA
<213> ORGANISM: Artificial Sequence
<220> FEATURE:

<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1088
aacugugaug gcaugcacua ugcgcgaugc accaaan                                37

<210> SEQ ID NO 1089
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1089
accaaugaug gcaugcacua ugcgcgauuc acacuun                                37

<210> SEQ ID NO 1090
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1090
agcuuugaug gcaugcacua ugcgcgauua auuugun       37

<210> SEQ ID NO 1091
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1091
uaaucugaug gcaugcacua ugcgcgauuu augugan       37

<210> SEQ ID NO 1092
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)

-continued

<223> OTHER INFORMATION: Phosphorothioate 3'-Internucleotide Linkage

<400> SEQUENCE: 1092
aagccugaug gcaugcacua ugcgcgauaa auuugun          37

<210> SEQ ID NO 1093
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1093
aucauugaug gcaugcacua ugcgcgauca ggaagcn          37

<210> SEQ ID NO 1094
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1094
agaauugaug gcaugcacua ugcgcgauca ucaggan          37

<210> SEQ ID NO 1095
<211> LENGTH: 37
<212> TYPE: RNA
<213> ORGANISM: Artificial Sequence

```
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1095
acauuugaug gcaugcacua ugcgcgauca gggaugn                              37

<210> SEQ ID NO 1096
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1096
cuuuaugaug gcaugcacua ugcgcgauuc aucaggn                              37

<210> SEQ ID NO 1097
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
```

```
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1097
guuucugaug gcaugcacua ugcgcgauug ccuugun                              37

<210> SEQ ID NO 1098
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1098
ggccuugaug gcaugcacua ugcgcgauaa uaguuun                              37

<210> SEQ ID NO 1099
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
```

<222> LOCATION: (1)..(1)
<223> OTHER INFORMATION: Phosphorothioate 3'-Internucleotide Linkage

<400> SEQUENCE: 1099
aaagcugaug gcaugcacua ugcgcgauua ggagucn                37

<210> SEQ ID NO 1100
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1100
aauccugaug gcaugcacua ugcgcgauuc auacugn                37

<210> SEQ ID NO 1101
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1101
guugcugaug gcaugcacua ugcgcgauaa uaauccn                37

<210> SEQ ID NO 1102
<211> LENGTH: 37
<212> TYPE: RNA

```
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1102
uaagcugaug gcaugcacua ugcgcgauaa cuggccn                          37

<210> SEQ ID NO 1103
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1103
cucucugaug gcaugcacua ugcgcgauga aagcucn                          37

<210> SEQ ID NO 1104
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
```

```
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1104
cagucugaug gcaugcacua ugcgcgaugc ugugaan                        37

<210> SEQ ID NO 1105
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1105
caaugugaug gcaugcacua ugcgcgaucg uacaacn                        37

<210> SEQ ID NO 1106
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
```

<221> NAME/KEY: misc_feature
<222> LOCATION: (1)..(1)
<223> OTHER INFORMATION: Phosphorothioate 3'-Internucleotide Linkage

<400> SEQUENCE: 1106
ugagcugaug gcaugcacua ugcgcgaucc aaacugn        37

<210> SEQ ID NO 1107
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1107
cacuuugaug gcaugcacua ugcgcgauug uuuaaan        37

<210> SEQ ID NO 1108
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1108
guguuugaug gcaugcacua ugcgcgaugc aauguun        37

<210> SEQ ID NO 1109
<211> LENGTH: 37

```
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1109
uuaaaugaug gcaugcacua ugcgcgaugg aucagan                              37

<210> SEQ ID NO 1110
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1110
caugcugaug gcaugcacua ugcgcgaucu cacuucn                              37

<210> SEQ ID NO 1111
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
```

```
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1111
cucacugaug gcaugcacua ugcgcgaugc caucucn                           37

<210> SEQ ID NO 1112
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1112
acaccugaug gcaugcacua ugcgcgaucu agaaccn                           37

<210> SEQ ID NO 1113
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
```

```
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1113
uuuaaugaug gcaugcacua ugcgcgauga agaaaun                          37

<210> SEQ ID NO 1114
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1114
uggaaugaug gcaugcacua ugcgcgauaa aucacan                          37

<210> SEQ ID NO 1115
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1115
auccuugaug gcaugcacua ugcgcgaugu aaauggn                          37

<210> SEQ ID NO 1116
```

<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1116
aacugugaug gcaugcacua ugcgcgauca agucaun                                    37

<210> SEQ ID NO 1117
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1117
aaucuugaug gcaugcacua ugcgcgaugg uuagggn                                    37

<210> SEQ ID NO 1118
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)

```
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1118
ggagaugaug gcaugcacua ugcgcgaucc acagcan                                37

<210> SEQ ID NO 1119
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1119
aacuuugaug gcaugcacua ugcgcgaugg agauaun                                37

<210> SEQ ID NO 1120
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
```

```
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1120
uagggugaug gcaugcacua ugcgcgauuu cugaugn                              37

<210> SEQ ID NO 1121
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1121
cccuuugaug gcaugcacua ugcgcgaugg uaucugn                              37

<210> SEQ ID NO 1122
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1122
caaagugaug gcaugcacua ugcgcgauca gccaccn                              37
```

```
<210> SEQ ID NO 1123
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1123
cuauuugaug gcaugcacua ugcgcgauac cagggun                              37

<210> SEQ ID NO 1124
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1124
cauugugaug gcaugcacua ugcgcgauga agauuun                              37

<210> SEQ ID NO 1125
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
```

```
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1125
agcuuugaug gcaugcacua ugcgcgauga auuaaan                              37

<210> SEQ ID NO 1126
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1126
cacugugaug gcaugcacua ugcgcgauuc cagccun                              37

<210> SEQ ID NO 1127
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
```

```
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1127
agguuugaug gcaugcacua ugcgcgauga ggccaan                               37

<210> SEQ ID NO 1128
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1128
auaaaugaug gcaugcacua ugcgcgauuu gcugaan                               37

<210> SEQ ID NO 1129
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1129
acuggugaug gcaugcacua ugcgcgaucu gguaggn                               37
```

```
<210> SEQ ID NO 1130
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1130
uaccaugaug gcaugcacua ugcgcgauac ccagugn                              37

<210> SEQ ID NO 1131
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1131
gauacugaug gcaugcacua ugcgcgauau acccagn                              37

<210> SEQ ID NO 1132
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
```

```
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1132
gggauugaug gcaugcacua ugcgcgaugu cucuugn                              37

<210> SEQ ID NO 1133
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1133
ggucgugaug gcaugcacua ugcgcgauac caaaggn                              37

<210> SEQ ID NO 1134
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
```

```
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1134
cguguugaug gcaugcacua ugcgcgaucu cugggun                         37

<210> SEQ ID NO 1135
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1135
auacgugaug gcaugcacua ugcgcgaucg uguuaun                         37

<210> SEQ ID NO 1136
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1136
acaauugaug gcaugcacua ugcgcgauag agcuggn                         37
```

<210> SEQ ID NO 1137
<211> LENGTH: 37
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1137 aaguugaug gcaugcacua ugcgcgauuc cuuuaan                    37

<210> SEQ ID NO 1138
<211> LENGTH: 37
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1138
acaguugaug gcaugcacua ugcgcgaugc caaauan                   37

<210> SEQ ID NO 1139
<211> LENGTH: 37
<212> TYPE: RNA
<213> ORGANISM: Artificial Sequence
<220> FEATURE:
<223> OTHER INFORMATION: Description of Artificial Sequence: Enzymatic Nucleic Acid
<221> NAME/KEY: misc_feature
<222> LOCATION: (37)..(37)

```
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1139
uuacaugaug gcaugcacua ugcgcgauuu gggucan                              37

<210> SEQ ID NO 1140
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1140
uggaaugaug gcaugcacua ugcgcgauua cacauun                              37

<210> SEQ ID NO 1141
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
```

```
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1141
uuacuugaug gcaugcacua ugcgcgaugc agagaan                    37

<210> SEQ ID NO 1142
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1142
cuguuugaug gcaugcacua ugcgcgauuu guacccn                    37

<210> SEQ ID NO 1143
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1143
```
uuucaugaug gcaugcacua ugcgcgauag caauucn                    37

<210> SEQ ID NO 1144
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1144
auggcugaug gcaugcacua ugcgcgauuu cuuucun                    37

<210> SEQ ID NO 1145
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1145
ugaagugaug gcaugcacua ugcgcgaugg ccauuun                    37

<210> SEQ ID NO 1146
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature

```
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1146
augccugaug gcaugcacua ugcgcgaucu acaucan                           37

<210> SEQ ID NO 1147
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1147
guucaugaug gcaugcacua ugcgcgauaa agguaan                           37

<210> SEQ ID NO 1148
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
```

```
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1148
uaaacugaug gcaugcacua ugcgcgauuc aaaguun                      37

<210> SEQ ID NO 1149
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1149
acaaaugaug gcaugcacua ugcgcgaugu uaaugcn                      37

<210> SEQ ID NO 1150
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1150
```
ugcuaugaug gcaugcacua ugcgcgauuc uuccacn                                37

<210> SEQ ID NO 1151
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1151
ucugcugaug gcaugcacua ugcgcgauau ucuuccn                                37

<210> SEQ ID NO 1152
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1152
uacaaugaug gcaugcacua ugcgcgauac gucugcn                                37

<210> SEQ ID NO 1153
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid

```
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1153
gggaaugaug gcaugcacua ugcgcgauuc acucaan                        37

<210> SEQ ID NO 1154
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1154
auuccugaug gcaugcacua ugcgcgaugc agugugn                        37

<210> SEQ ID NO 1155
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
```

```
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1155
caugcugaug gcaugcacua ugcgcgaucc aguauun                              37

<210> SEQ ID NO 1156
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1156
gaauuugaug gcaugcacua ugcgcgaugc uauccan                              37

<210> SEQ ID NO 1157
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage
```

```
<400> SEQUENCE: 1157
acagcugaug gcaugcacua ugcgcgauuc aguuucn                              37

<210> SEQ ID NO 1158
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1158
aucauugaug gcaugcacua ugcgcgaucc caaacan                              37

<210> SEQ ID NO 1159
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1159
ccuauugaug gcaugcacua ugcgcgauua ucccaan                              37

<210> SEQ ID NO 1160
<211> LENGTH: 37
<212> TYPE: RNA
<213> ORGANISM: Artificial Sequence
<220> FEATURE:
<223> OTHER INFORMATION: Description of Artificial Sequence:  Enzymatic
```

Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1160
cucaaugaug gcaugcacua ugcgcgauaa cugcagn                              37

<210> SEQ ID NO 1161
<211> LENGTH: 37
<212> TYPE: RNA
<213> ORGANISM: Artificial Sequence
<220> FEATURE:
<223> OTHER INFORMATION: Description of Artificial Sequence:  Enzymatic
    Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1161
augugugaug gcaugcacua ugcgcgaugu uucagun                              37

<210> SEQ ID NO 1162
<211> LENGTH: 37
<212> TYPE: RNA
<213> ORGANISM: Artificial Sequence
<220> FEATURE:
<223> OTHER INFORMATION: Description of Artificial Sequence:  Enzymatic
    Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature

```
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1162
cugcaugaug gcaugcacua ugcgcgauga cccacan                               37

<210> SEQ ID NO 1163
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1163
cacugugaug gcaugcacua ugcgcgauau gacccan                               37

<210> SEQ ID NO 1164
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage
```

<400> SEQUENCE: 1164
accaaugaug gcaugcacua ugcgcgauuc cuaggun      37

<210> SEQ ID NO 1165
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1165
uuugaugaug gcaugcacua ugcgcgauga ccaacan      37

<210> SEQ ID NO 1166
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (37)..(37)
<223> OTHER INFORMATION: n stands for inverted deoxyabasic derivative
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(14)
<223> OTHER INFORMATION: 2'-O-Methyl
<221> NAME/KEY: misc_feature
<222> LOCATION: (16)..(36)
<223> OTHER INFORMATION: 2'-O-Methyl
<221> NAME/KEY: misc_feature
<222> LOCATION: (9)..(9)
<223> OTHER INFORMATION: Phosphorothioate 3'-Internucleotide Linkage
<221> NAME/KEY: misc_feature
<222> LOCATION: (2)..(2)
<223> OTHER INFORMATION: Phosphorothioate 3'-Internucleotide Linkage
<221> NAME/KEY: misc_feature
<222> LOCATION: (1)..(1)
<223> OTHER INFORMATION: Phosphorothioate 3'-Internucleotide Linkage

<400> SEQUENCE: 1166
cagcaugaug gcaugcacua ugcgcgauac uccuaun      37

<210> SEQ ID NO 1167
<211> LENGTH: 56
<212> TYPE: DNA
<213> ORGANISM: Artificial Sequence
<220> FEATURE:

```
<223> OTHER INFORMATION: Description of Artificial Sequence:  Selection
      Primer 1

<400> SEQUENCE: 1167
tggtgcaagc ttaatacgac tcactatagg gagactgtct agatcatgag gatgct          56

<210> SEQ ID NO 1168
<211> LENGTH: 59
<212> TYPE: DNA
<213> ORGANISM: Artificial Sequence
<220> FEATURE:
<223> OTHER INFORMATION: Description of Artificial Sequence:  Selection
      Primer 2
<221> NAME/KEY: misc_feature
<222> LOCATION: (21)..(42)
<223> OTHER INFORMATION: n stands for any a, g, c, or t

<400> SEQUENCE: 1168
tctcggatcc tgcagatcat nnnnnnnnnn nnnnnnnnnn nnaggattag catcctcat      59

<210> SEQ ID NO 1169
<211> LENGTH: 20
<212> TYPE: DNA
<213> ORGANISM: Artificial Sequence
<220> FEATURE:
<223> OTHER INFORMATION: Description of Artificial Sequence:  Reverse
      transcription primer

<400> SEQUENCE: 1169
tctcggatcc tgcagatcat                                                  20

<210> SEQ ID NO 1170
<211> LENGTH: 23
<212> TYPE: DNA
<213> ORGANISM: Artificial Sequence
<220> FEATURE:
<223> OTHER INFORMATION: Description of Artificial Sequence:  PCR primer

<400> SEQUENCE: 1170
tggtgcaagc ttaatacgac tca                                              23

<210> SEQ ID NO 1171
<211> LENGTH: 11
<212> TYPE: RNA
<213> ORGANISM: Artificial Sequence
<220> FEATURE:
<223> OTHER INFORMATION: Description of Artificial Sequence:
      Miscellaneous substrate
<221> NAME/KEY: misc_feature
<222> LOCATION: (1)..(4)
<223> OTHER INFORMATION: n stands for any a, g, c, or u
<221> NAME/KEY: misc_feature
<222> LOCATION: (7)..(11)
<223> OTHER INFORMATION: n stands for any a, g, c, or u

<400> SEQUENCE: 1171
nnnnuhnnnn n                                                           11

<210> SEQ ID NO 1172
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(5)
<223> OTHER INFORMATION: n stands for any a, g, c, or u
<221> NAME/KEY: misc_feature
```

```
<222> LOCATION: (14)..(19)
<223> OTHER INFORMATION: n stands for any a, g, c, or u
<221> NAME/KEY: misc_feature
<222> LOCATION: (25)..(28)
<223> OTHER INFORMATION: n stands for any a, g, c, or u

<400> SEQUENCE: 1172
nnnnncugan gagnnnnnnc gaaannnn                                28

<210> SEQ ID NO 1173
<211> LENGTH: 47
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid
<221> NAME/KEY: misc_feature
<222> LOCATION: (9)..(12)
<223> OTHER INFORMATION: n stands for any a, g, c, or u

<400> SEQUENCE: 1173
agaucgucnn nngucuaauc cucugaugag cgcaagcgaa acgaucu           47

<210> SEQ ID NO 1174
<211> LENGTH: 51
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid
<221> NAME/KEY: misc_feature
<222> LOCATION: (23)..(44)
<223> OTHER INFORMATION: n stands for any a, g, c, or u

<400> SEQUENCE: 1174
agaucaugag gagucuaauc cunnnnnnnn nnnnnnnnnn nnnnaugauc u      51

<210> SEQ ID NO 1175
<211> LENGTH: 69
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid
<221> NAME/KEY: misc_feature
<222> LOCATION: (35)..(56)
<223> OTHER INFORMATION: n stands for any a, g, c, or u

<400> SEQUENCE: 1175
gggagacugu cuagaucaug aggagucuaa uccunnnnnn nnnnnnnnnn nnnnnnauga    60
ucugcagga                                                           69

<210> SEQ ID NO 1176
<211> LENGTH: 18
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1176
cugaugagcg caagcgaa                                          18

<210> SEQ ID NO 1177
<211> LENGTH: 22
<212> TYPE: RNA
<213> ORGANISM: Artificial Sequence
<220> FEATURE:
```

```
<223> OTHER INFORMATION: Description of Artificial Sequence:
      Self-cleaving Enzymatic Nucleic Acid

<400> SEQUENCE: 1177
ggaaucagcc ugacaccggc cc                                              22

<210> SEQ ID NO 1178
<211> LENGTH: 22
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1178
ggcauccccg gcauggugcg cg                                              22

<210> SEQ ID NO 1179
<211> LENGTH: 22
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1179
agcauuaccc ggcuggugcg cg                                              22

<210> SEQ ID NO 1180
<211> LENGTH: 22
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1180
gcaucacggg gcaaucugcg cg                                              22

<210> SEQ ID NO 1181
<211> LENGTH: 22
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1181
agcaucaccc ggauggugcg cg                                              22

<210> SEQ ID NO 1182
<211> LENGTH: 22
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1182
agcaucaccc ggcuggugcg cg                                              22

<210> SEQ ID NO 1183
<211> LENGTH: 22
<212> TYPE: RNA
<213> ORGANISM: Artificial Sequence
<220> FEATURE:
<223> OTHER INFORMATION: Description of Artificial Sequence:
```

Self-cleaving Enzymatic Nucleic Acid

<400> SEQUENCE: 1183
abcguccacg gcaucgagcg cg                                          22

<210> SEQ ID NO 1184
<211> LENGTH: 21
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1184
ugauggcuug cacuaagcgc g                                           21

<210> SEQ ID NO 1185
<211> LENGTH: 21
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1185
ugauggcaug cacuaugcgc g                                           21

<210> SEQ ID NO 1186
<211> LENGTH: 21
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1186
ugauggcaug caggaugcgc g                                           21

<210> SEQ ID NO 1187
<211> LENGTH: 21
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1187
ugauggcaug caccaugcgc g                                           21

<210> SEQ ID NO 1188
<211> LENGTH: 21
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1188
ugaucggaug caccaugcgc g                                           21

<210> SEQ ID NO 1189
<211> LENGTH: 21
<212> TYPE: RNA
<213> ORGANISM: Artificial Sequence
<220> FEATURE:
<223> OTHER INFORMATION: Description of Artificial Sequence:
      Self-cleaving Enzymatic Nucleic Acid

<400> SEQUENCE: 1189
ugggccgauc gcaagggcgc g                                              21

<210> SEQ ID NO 1190
<211> LENGTH: 75
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1190
gggagacugu cuagaucaug aggaugcuaa uccuugaugg caugcacuau gcgcgaugau    60
cugcaggauc cgaga                                                     75

<210> SEQ ID NO 1191
<211> LENGTH: 36
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1191
auccuugaug gcaugcacua ugcgcgauga ucugca                              36

<210> SEQ ID NO 1192
<211> LENGTH: 16
<212> TYPE: RNA
<213> ORGANISM: Artificial Sequence
<220> FEATURE:
<223> OTHER INFORMATION: Description of Artificial Sequence: Substrate
      Nucleic Acid for SEQ ID NO: 1191

<400> SEQUENCE: 1192
ugcagaucau gaggau                                                    16

<210> SEQ ID NO 1193
<211> LENGTH: 35
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1193
auccuugaug gcaugcacua ugcgcgauga cgcug                               35

<210> SEQ ID NO 1194
<211> LENGTH: 15
<212> TYPE: RNA
<213> ORGANISM: Artificial Sequence
<220> FEATURE:
<223> OTHER INFORMATION: Description of Artificial Sequence: Substrate
      Nucleic Acid for SEQ ID NO: 1193

<400> SEQUENCE: 1194
cagcgucaug aggau                                                     15

<210> SEQ ID NO 1195
<211> LENGTH: 36
<212> TYPE: RNA
<213> ORGANISM: Artificial Sequence
<220> FEATURE:
<223> OTHER INFORMATION: Description of Artificial Sequence: Enzymatic Nucleic Acid

<400> SEQUENCE: 1195
auccuugaug gcaugcacua ugcgcgauga cgcuga        36

<210> SEQ ID NO 1196
<211> LENGTH: 16
<212> TYPE: RNA
<213> ORGANISM: Artificial Sequence
<220> FEATURE:
<223> OTHER INFORMATION: Description of Artificial Sequence: Substrate
      Nucleic Acid for SEQ ID NO: 1195

<400> SEQUENCE: 1196
ucagcgucau gaggau        16

<210> SEQ ID NO 1197
<211> LENGTH: 29
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 1197
cccuugaugg caugcacuau gcgcgauga        29

<210> SEQ ID NO 1198
<211> LENGTH: 9
<212> TYPE: RNA
<213> ORGANISM: Artificial Sequence
<220> FEATURE:
<223> OTHER INFORMATION: Description of Artificial Sequence: Substrate
      Nucleic Acid for SEQ ID NO: 1197

<400> SEQUENCE: 1198 ucaugaggg        9

<210> SEQ ID NO 1199
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(5)
<223> OTHER INFORMATION: 2'-O-methyl
<221> NAME/KEY: misc_feature
<222> LOCATION: (11)..(23)
<223> OTHER INFORMATION: 2'-O-methyl
<221> NAME/KEY: misc_feature
<222> LOCATION: (27)..(36)
<223> OTHER INFORMATION: 2'-O-methyl
<221> NAME/KEY: misc_feature
<222> LOCATION: (37)..(37)
<223> OTHER INFORMATION: n stands for inverted deoxyabasic derivative

<400> SEQUENCE: 1199
auccuugaug gcaugcacua ugcgcgauga cgcugan        37

<210> SEQ ID NO 1200
<211> LENGTH: 16
<212> TYPE: RNA
<213> ORGANISM: Artificial Sequence
<220> FEATURE:
<223> OTHER INFORMATION: Description of Artificial Sequence: Substrate
      Nucleic Acid for SEQ ID NO: 1199

```
<400> SEQUENCE: 1200
ucagcgucau gaggau                                                    16

<210> SEQ ID NO 1201
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(5)
<223> OTHER INFORMATION: 2'-O-methyl
<221> NAME/KEY: misc_feature
<222> LOCATION: (11)..(23)
<223> OTHER INFORMATION: 2'-O-methyl
<221> NAME/KEY: misc_feature
<222> LOCATION: (27)..(36)
<223> OTHER INFORMATION: 2'-O-methyl
<221> NAME/KEY: misc_feature
<222> LOCATION: (37)..(37)
<223> OTHER INFORMATION: n stands for inverted deoxyabasic derivative

<400> SEQUENCE: 1201
auccuugaug gcaugcacua ugcgcgauga cgcugan                              37

<210> SEQ ID NO 1202
<211> LENGTH: 16
<212> TYPE: RNA
<213> ORGANISM: Artificial Sequence
<220> FEATURE:
<223> OTHER INFORMATION: Description of Artificial Sequence:  Substrate
      Nucleic Acid for SEQ ID NO: 1201

<400> SEQUENCE: 1202
ucagcgucau gaggau                                                    16

<210> SEQ ID NO 1203
<211> LENGTH: 36
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-methyl
<221> NAME/KEY: misc_feature
<222> LOCATION: (9)..(9)
<223> OTHER INFORMATION: 2'-O-methyl
<221> NAME/KEY: misc_feature
<222> LOCATION: (11)..(23)
<223> OTHER INFORMATION: 2'-O-methyl
<221> NAME/KEY: misc_feature
<222> LOCATION: (25)..(25)
<223> OTHER INFORMATION: 2'-O-methyl
<221> NAME/KEY: misc_feature
<222> LOCATION: (27)..(36)
<223> OTHER INFORMATION: 2'-O-methyl
<221> NAME/KEY: misc_feature
<222> LOCATION: (37)..(37)
<223> OTHER INFORMATION: n stands for inverted deoxyabasic derivative

<400> SEQUENCE: 1203
auccuugaug gcaugcacua ugcgcgauga cgcuga                               36

<210> SEQ ID NO 1204
<211> LENGTH: 16
<212> TYPE: RNA
<213> ORGANISM: Artificial Sequence
<220> FEATURE:
```

```
<223> OTHER INFORMATION: Description of Artificial Sequence:  Substrate
      Nucleic Acid for SEQ ID NO: 1203

<400> SEQUENCE: 1204
ucagcgucau gaggau                                                          16

<210> SEQ ID NO 1205
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-methyl
<221> NAME/KEY: misc_feature
<222> LOCATION: (11)..(14)
<223> OTHER INFORMATION: 2'-O-methyl
<221> NAME/KEY: misc_feature
<222> LOCATION: (16)..(36)
<223> OTHER INFORMATION: 2'-O-methyl
<221> NAME/KEY: misc_feature
<222> LOCATION: (37)..(37)
<223> OTHER INFORMATION: n stands for inverted deoxyabasic derivative

<400> SEQUENCE: 1205
auccuugaug gcaugcacua ugcgcgauga cgcugan                                   37

<210> SEQ ID NO 1206
<211> LENGTH: 16
<212> TYPE: RNA
<213> ORGANISM: Artificial Sequence
<220> FEATURE:
<223> OTHER INFORMATION: Description of Artificial Sequence:  Substrate
      Nucleic Acid for SEQ ID NO: 1205

<400> SEQUENCE: 1206
ucagcgucau gaggau                                                          16

<210> SEQ ID NO 1207
<211> LENGTH: 37
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(4)
<223> OTHER INFORMATION: n stands for a, c, g, or u
<221> NAME/KEY: misc_feature
<222> LOCATION: (1)..(2)
<223> OTHER INFORMATION: Phosphorothioate/phosphorodithioate
      3'-Internucleotide Linkage
<221> NAME/KEY: misc_feature
<222> LOCATION: (1)..(6)
<223> OTHER INFORMATION: 2'-O-methyl
<221> NAME/KEY: misc_feature
<222> LOCATION: (9)..(9)
<223> OTHER INFORMATION: Phosphorothioate/phosphorodithioate
      3'-Internucleotide Linkage
<221> NAME/KEY: misc_feature
<222> LOCATION: (11)..(14)
<223> OTHER INFORMATION: 2'-O-methyl
<221> NAME/KEY: misc_feature
<222> LOCATION: (16)..(36)
<223> OTHER INFORMATION: 2'-O-methyl
<221> NAME/KEY: misc_feature
<222> LOCATION: (28)..(36)
<223> OTHER INFORMATION: n stands for a, c, g, or u
<221> NAME/KEY: misc_feature
<222> LOCATION: (37)..(37)
<223> OTHER INFORMATION: n stands for inverted deoxyabasic derivative
```

-continued

<400> SEQUENCE: 1207
nnnnuugaug gcaugcacua ugcgcgannn nnnnnnn                37

<210> SEQ ID NO 1208
<211> LENGTH: 16
<212> TYPE: RNA
<213> ORGANISM: Artificial Sequence
<220> FEATURE:
<223> OTHER INFORMATION: Description of Artificial Sequence:  Substrate
      Nucleic Acid for SEQ ID NO: 1207
<221> NAME/KEY: misc_feature
<222> LOCATION: (1)..(9)
<223> OTHER INFORMATION: n stands for a, c, g, or u
<221> NAME/KEY: misc_feature
<222> LOCATION: (13)..(16)
<223> OTHER INFORMATION: n stands for a, c, g, or u

<400> SEQUENCE: 1208
nnnnnnnnnu gannnn                                        16

NUCLEIC ACID CATALYSTS WITH ENDONUCLEASE ACTIVITY

This patent application is a continuation-in-part of Eckstein et al., U.S. Ser. No. 09/444,209 filed Nov. 19, 1999, which is a continuation-in-part of Eckstein et al., U.S. Ser. No. 09/159,274 filed Sep. 22, 1998, now U.S. Pat. No. 6,127,173 which claims the benefit of Eckstein et al., U.S. Ser. No. 60/059,473 filed Sep. 22, 1997, all entitled "NUCLEIC ACID CATALYSTS WITH ENDONUCLEASE ACTIVITY". Each of these applications is hereby incorporated by reference herein in its entirety including the drawings.

The Sequence Listing file named "MBHB00,884-C SequenceListing.txt" (313,506 bytes in size) submitted on Compact Disc-Recordable (CD-R) medium (entitled "010810_1001") in compliance with 37 C.F.R. § 1.52(e) is incorporated herein by reference.

BACKGROUND OF THE INVENTION

This invention relates to nucleic acid molecules with catalytic activity and derivatives thereof.

The following is a brief description of enzymatic nucleic acid molecules. This summary is not meant to be complete but is provided only for understanding of the invention that follows. This summary is not an admission that all of the work described below is prior art to the claimed invention.

Enzymatic nucleic acid molecules (ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, *Nature* 429 1986; Cech, 260 *JAMA* 3030, 1988; and Jefferies et al., 17 *Nucleic Acids Research* 1371, 1989).

Because of their sequence-specificity, trans-cleaving enzymatic nucleic acid molecules show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

There are seven basic varieties of naturally occurring enzymatic RNAs. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

In addition, several in vitro selection (evolution) strategies (Orgel, 1979, *Proc. R. Soc. London*, B 205, 435) have been used to evolve new nucleic acid catalysts capable of catalyzing a variety of reactions, such as cleavage and ligation of phosphodiester linkages and amide linkages, (Joyce, 1989, *Gene*, 82, 83–87; Beaudry et al., 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al, 1995, *FASEB J.*, 9, 1183; Breaker, 1996, *Curr. Op. Biotech.*, 7, 442).

The enzymatic nature of a ribozyme is advantageous over other technologies, since the effective concentration of ribozyme necessary to effect a therapeutic treatment is generally lower than that of an antisense oligonucleotide. This advantage reflects the ability of the ribozyme to act enzymatically, Thus, a single ribozyme (enzymatic nucleic acid) molecule is able to cleave many molecules of target RNA. In addition, the ribozyme is a highly specific inhibitor, with the specificity of inhibition depending not only on the base-pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, it is thought that the specificity of action of a ribozyme is greater than that of antisense oligonucleotide binding the same RNA site.

The development of ribozymes that are optimal for catalytic activity would contribute significantly to any strategy that employs RNA-cleaving ribozymes for the purpose of regulating gene expression. The hammerhead ribozyme functions with a catalytic rate ($k_{cat}$) of ~1 min$^{-1}$ in the presence of saturating (10 mM) concentrations of Mg$^{2+}$ cofactor. However, the rate for this ribozyme in Mg$^{2+}$ concentrations that are closer to those found inside cells (0.5–2 mM) can be 10- to 100-fold slower. In contrast, the RNase P holoenzyme can catalyze pre-tRNA cleavage with a $k_{cat}$ of ~30 min$^{-1}$ under optimal assay conditions. An artificial 'RNA ligase' ribozyme has been shown to catalyze the corresponding self-modification reaction with a rate of ~100 min$^{-1}$. In addition, it is known that certain modified hammerhead ribozymes that have substrate binding arms made of DNA catalyze RNA cleavage with multiple turnover rates that approach 100 min$^{-1}$. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain self-cleaving ribozymes may be optimized to give maximal catalytic activity, or that entirely new RNA motifs can be made that display significantly faster rates for RNA phosphodiester cleavage.

An extensive array of site-directed mutagenesis studies have been conducted with the hammerhead ribozyme to probe relationships between nucleotide sequence and catalytic activity. These systematic studies have made clear that most nucleotides in the conserved core of the hammerhead ribozyme cannot be mutated without significant loss of catalytic activity. In contrast, a combinatorial strategy that simultaneously screens a large pool of mutagenized ribozymes for RNAs that retain catalytic activity could be used more efficiently to define immutable sequences and to identify new ribozyme variants. Although similar in vitro selection experiments have been conducted with the hammerhead ribozyme (Nakamaye & Eckstein, 1994, *Biochemistry* 33, 1271; Long & Uhlenbeck, 1994, *Proc. Natl. Acad. Sci.*, 91, 6977; Ishizaka et al., 1995, *BBRC* 214, 403; Vaish et al., 1997, *Biochemistry* 36, 6495), none of these efforts have successfully screened full-sized hammerhead ribozymes for all possible combinations of sequence variants that encompass the entire catalytic core.

The hammerhead ribozyme is one of the smallest ribozymes known and has thus attracted much attention for the study of structure-function relationships in catalytic. RNAs as well as for its potential for the sequence-specific inhibition of gene expression (Usman et al., supra). The hammerhead cleaves RNA sequence-specifically adjacent to the general triplet sequence NUX, where N is any nucleotide and X can be A, U or C. Cleavage behind a guanosine such as in GUG is very slow ($4.3 \times 10^{-5}$ $min^{-1}$) compared to the triplet substrate GUC (1 $min^{-1}$) (Baidya et al., 1997, *Biochemistry* 36, 1108). Although the X-ray structure of this ribozyme has been solved and a mechanism proposed (Pley et al., 1994 *Nature*, 372, 68; Scott et al., 1996, *Science* 274, 2065), the question of what determines its specificity for the NUX sequence is still largely unresolved. One way of obtaining an insight into this problem might be to compare sequences of hammerhead ribozymes with different triplet cleaving specificities. In previous publications, it was demonstrated, using in vitro selection, that the native hammerhead sequence necessary to cleave a typical cleavage triplet, NUX, can not be altered (Nakamaye & Eckstein, 1994, *Biochemistry* 33, 1271; Long & Uhlenbeck, 1994, *Proc. Natl. Acad. Sci.*, 91, 6977; Ishizaka et al., 1995, *BBRC* 214, 403; Vaish et al., 1997, *Biochemistry* 36, 6495), indicating that nature has evolved a close to perfect GUC cleaver. It was of interest to see what changes have to be imposed on the native hammerhead sequence for it to cleave after AUG, which usually resists cleavage, and thus arrive at a ribozyme with a new specificity. To achieve this, an in vitro selection was undertaken, where the number of randomized positions in the starting pool corresponded to the number of nucleotides typically found in the core and stem-loop II region of a hammerhead ribozyme. This would allow all possible sequence permutations to be explored in the search for a hammerhead which is able to cleave behind AUG (Robertson & Joyce, 1990, *Nature* 344:6265 467–8; Ellington and Szostak, 1990; Tuerk & Gold, 1990; Wright & Joyce, 1997; Carmi et al., 1997; for reviews see Breaker, 1997; Abelson, 1996; Ellington, 1997; Chapman & Szostak, 1994). Tang et al., 1997, RNA 3, 914, reported novel ribozyme sequences with endonuclease activity, where the authors used an in vitro selection approach to isolate these ribozymes.

The platelet derived growth factor (PDGF) system has served as a prototype for the identification of substrates of receptor tyrosine kinases. Certain enzymes become activated by the PDGF receptor kinase, including phospholipase C and phosphatidylinositol 3' kinase, Ras guanosine triphosphate (GTPase) activating protein (GAP) and src-like tyrosine kinases. GAP regulates the function of the Ras protein. It stimulates the GTPase activity of the 21 kD Ras protein (Barbacid. 56 *Ann. Rev. Biochem.* 779, 1987). Microinjection of oncogenically activated Ras into NIH 3T3 cells induces DNA synthesis. Mutations that cause oncogenic activation of ras lead to accumulation of Ras bound to GTP, the active form of the molecule. These mutations block the ability of GAP to convert Ras to the inactive form. Mutations that impair the interactions of Ras with GAP also block the biological function of Ras.

While a number of ras alleles exist (N-ras, K-ras, H-ras) which have been implicated in carcinogenesis, the type most often associated with colon and pancreatic carcinomas is the K-ras. Ribozymes which are targeted to certain regions of the K-ras allelic mRNAs may also prove inhibitory to the function of the other allelic mRNAs of the N-ras and H-ras genes.

Transformation is a cumulative process whereby normal control of cell growth and differentiation is interrupted, usually through the accumulation of mutations affecting the expression of genes that regulate cell growth and differentiation.

Scanlon WO91/18625, WO91/18624, and WO91/18913 describe a specific hammerhead ribozyme effective to cleave RNA from the H-ras gene at codon 12 mutation. This ribozyme is said to inhibit H-ras expression in response to exogenous stimuli.

Thompson et al., U.S. Pat. Nos. 5,610,052 and 5,801,158, describes enzymatic RNA molecules against Ras.

Vaish et al., 1998 *PNAS* 95, 2158–2162, describes the in vitro selection of a hammerhead-like ribozyme with an extended range of cleavable triplets.

The references cited above are distinct from the presently claimed invention since they do not disclose and/or contemplate the catalytic nucleic acid molecules of the instant invention.

SUMMARY OF THE INVENTION

This invention relates to novel nucleic acid molecules with catalytic activity, which are particularly useful for cleavage of RNA or DNA. The nucleic acid catalysts of the instant invention are distinct from other nucleic acid catalysts known in the art. The nucleic acid catalysts of the instant invention do not share sequence homology with other known ribozymes. Specifically, nucleic acid catalysts of the instant invention are capable of catalyzing an intermolecular or intramolecular endonuclease reaction.

In a preferred embodiment, the invention features a nucleic acid molecule with catalytic activity having one of the formulae I–V:

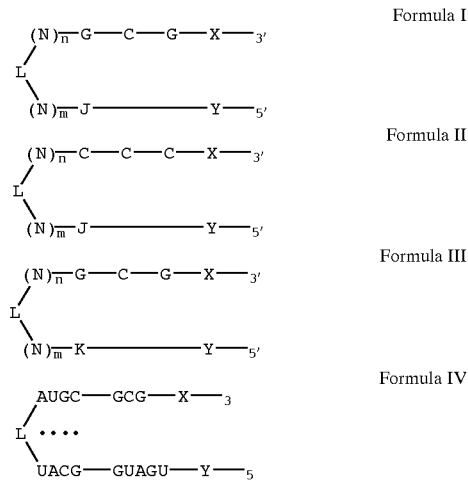

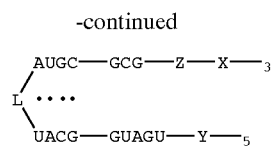

Formula V

In each of the above formulae, N represents independently a nucleotide or a non-nucleotide linker, which may be the same or different; X and Y are independently oligonucleotides of length sufficient to stably interact (e.g., by forming hydrogen bonds with complementary nucleotides in the target) with a target nucleic acid molecule (the target can be an RNA, DNA or RNA/DNA mixed polymers); m and n are integers independently greater than or equal to 1 and preferably less than about 100, wherein if $(N)_m$ and $(N)_n$ are nucleotides, (N)m and (N)n are optionally able to interact by hydrogen bond interaction; J is an oligonucleotide of length 6 or 7 nucleotides; K is an oligonucleotide of length 5 nucleotides; L is a linker which may be present or absent (i.e., the molecule is assembled from two separate molecules), but when present, is a nucleotide and/or a non-nucleotide linker, which may be a single-stranded and/or double-stranded region; and ____ represents a chemical linkage (e.g. a phosphate ester linkage, amide linkage or others known in the art). Z is independently a nucleotide numbered as 13.1 (FIG. 8) which can stably interact with a nucleotide at position 14.1 (FIG. 8) in the target nucleic acid molecule, preferably, the $N^{13.1}$–$N^{14.1}$ interaction is inosine$^{13.1}$-cytidine$^{14.1}$; adenosine$^{13.1}$-uridine$^{14.1}$; guanosine$^{13.1}$-cytidine$^{14.1}$; uridine$^{13.1}$-adenosine$^{14.1}$; or cytidine$^{13.1}$-guanosine$^{14.1}$; and C, G, A, and U represent cytidine, guanosine, adenosine and uridine nucleotides, respectively. The nucleotides in the each of the formulae I–V are unmodified or modified at the sugar, base, and/or phosphate as known in the art.

In a preferred embodiment, the invention features nucleic acid molecules of Formula I, where the sequence of oligonucleotide J is selected from the group comprising 5'-GGCAUCC-3', 5'-AGCAUU-3', 5'-GCAUCA-3', 5'-AGCAUC-3', and 5'-AGCGUC-3'.

In another preferred embodiment, the invention features nucleic acid molecules of Formula II, where the sequence of oligonucleotide J is 5'-GGAAUC-3'.

In a further preferred embodiment, the invention features nucleic acid molecules of Formula III, where the sequence of oligonucleotide K is selected from the group comprising 5'-UGAUG-3', 5'-UGAUC-3', and 5'-UGGGC-3'.

In another embodiment, the nucleotide linker (L) is a nucleic acid sequence selected from the group consisting of 5'-GCACU-3', 5'-GAACU-3', 5'-GCACC-3', 5'-GNACU-3', 5'-GNGCU-3', 5'-GNCCU-3', 5'-GNUCU-3', 5'-GNGUU-3', 5'-GNCUU-3', 5'-GNUUU-3', 5'-GNAUU-3', 5'-GNACA-3', 5'-GNGCA-3', 5'-GNCCA-3', and 5'-GNUCA-3', whereby N can be selected from the group consisting of A, G, C, or U.

In yet another embodiment, the nucleotide linker (L) is a nucleic acid aptamer, such as an ATP aptamer, HIV Rev aptamer (RRE), HIV Tat aptamer (TAR) and others (for a review see Gold et al., 1995, *Annu. Rev. Biochem.*, 64, 763; and Szostak & Ellington, 1993, in *The RNA World*, ed. Gesteland and Atkins, pp. 511, CSH Laboratory Press). A "nucleic acid aptamer" as used herein is meant to indicate a nucleic acid sequence capable of interacting with a ligand. The ligand can be any natural or a synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others.

In yet another embodiment, the non-nucleotide linker (L) is as defined herein. The term "non-nucleotide" as used herein include either abasic nucleotide, polyether, polyamine, polyamide, peptide, carbohydrate, lipid, or polyhydrocarbon compounds. Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al.; *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. Thus, in a preferred embodiment, the invention features an enzymatic nucleic acid molecule having one or more non-nucleotide moieties, and having enzymatic activity to cleave an RNA or DNA molecule. By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenine, guanine, cytosine, uracil or thymine. The terms "abasic" or "abasic nucleotide" as used herein encompass sugar moieties lacking a base or having other chemical groups in place of a base at the 1' position.

In preferred embodiments, the enzymatic nucleic acid includes one or more stretches of RNA, which provide the enzymatic activity of the molecule, linked to the non-nucleotide moiety. The necessary RNA components are known in the art (see for e.g., Usman et al., supra). By RNA is meant a molecule comprising at least one ribonucleotide residue. By "ribonucleotide" is meant a nucleotide with a hydroxyl group at the 2' position of a β-D-ribo-furanose moiety.

Thus, in one preferred embodiment, the invention features ribozymes that inhibit gene expression and/or cell proliferation. These chemically or enzymatically synthesized nucleic acid molecules contain substrate binding domains that bind to accessible regions of specific target nucleic acid molecules. The nucleic acid molecules also contain domains that catalyze the cleavage of target. Upon binding, the enzymatic nucleic acid molecules cleave the target molecules, preventing, for example, translation and protein accumulation. In the absence of the expression of the target gene, cell proliferation, for example, is inhibited. In another aspect of the invention, enzymatic nucleic acid molecules that cleave target molecules are expressed from transcription units inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described below, and persist in target cells. Alternatively, viral vectors may be used that provide for transient expression of ribozymes. Such vectors can be repeatedly administered as necessary. Once expressed, the ribozymes cleave the target mRNA. Delivery of ribozyme expressing vectors can be systemic, such as by intravenous or intramuscular administration, by administration to target cells ex-planted from the patient followed by reintroduction into the patient, or by any other means that would allow for introduction into the desired target cell (for a review, see, Couture and Stinchcomb, 1996, *TIG.*, 12, 510).

As used in herein "cell" is used in its usual biological sense, and does not refer to an entire multicellular organism, e.g., specifically does not refer to a human. The cell may be present in a non-human multicellular organism, e.g., birds, plants and mammals such as cows, sheep, apes, monkeys, swine, dogs, and cats.

In a preferred embodiment, an expression vector comprising a nucleic acid sequence encoding at least one of the nucleic acid catalysts of the instant invention is disclosed. The nucleic acid sequence encoding the nucleic acid catalyst of the instant invention is operable linked in a manner which allows expression of that nucleic acid molecule.

In one embodiment, the expression vector comprises: a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalyst of the instant invention; and wherein said gene is operably linked to said initiation region and said termination region, in a manner which allows expression and/or delivery of said nucleic acid molecule. The vector may optionally include an open reading frame (ORF) for a protein operably linked on the 5' side or the 3'-side of the sequence encoding the nucleic acid catalyst of the invention; and/or an intron (intervening sequences).

By "patient" is meant an organism which is a donor or recipient of explanted cells or the cells themselves. "Patient" also refers to an organism to which enzymatic nucleic acid molecules can be administered. Preferably, a patient is a mammal or mammalian cells. More preferably, a patient is a human or human cells.

By "vectors" is meant any nucleic acid- and/or viral-based technique used to deliver a desired nucleic acid.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase. I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U. S. A.*, 90, 8000–4; Thompson et al., 1995 *Nucleic Acids Res.* 23, 2259; Sullenger & Cech, 1993, *Science* 262, 1566). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In another preferred embodiment, catalytic activity of the molecules described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et. al., International Publication No. WO 93/15187; and Rossi et al., International Publication No. WO 91/03162; Sproat, U.S. Pat. No. 5;334,711; and Burgin et al., supra; all of these describe various chemical modifications that can be made to the base, phosphate and/or sugar moieties of enzymatic RNA molecules). Modifications to the molecules, which enhance their efficacy in cells, and removal of bases from stem loop structures to shorten RNA synthesis times and reduce chemical requirements are desired. All these publications are hereby incorporated by reference herein.

By "enhanced enzymatic activity" is meant to include activity measured in cells and/or in vivo where the activity is a reflection of both catalytic activity and ribozyme stability. In this invention, the product of these properties is increased or not significantly (less than 10-fold) decreased in vivo compared to an all RNA ribozyme.

In yet another preferred embodiment, nucleic acid catalysts having chemical modifications, which maintain or enhance enzymatic activity are provided. Such nucleic acid is also generally more resistant to nucleases than unmodified nucleic acid. Thus, in a cell and/or in vivo the activity may not be significantly lowered. As exemplified herein, such ribozymes are useful in a cell and/or in vivo even if activity over all is reduced 10 fold (Burgin et al., 1996, *Biochemistry*, 35, 14090). Such ribozymes herein are said to "maintain" the enzymatic activity of an all RNA ribozyme.

In yet another aspect the invention features an enzymatic nucleic acid molecule which cleaves mRNA produced from the human K-ras gene (accession NM_004985), H-ras gene (accession NM_005343) or N-ras gene (accession NM_002524). In one nonlimiting example, the enzymatic nucleic acid molecule of the present invention cleaves mRNA molecules associated with the development or maintenance of colon carcinoma. In preferred embodiments, the enzymatic nucleic acid molecules comprise sequences which are complementary to the substrate sequences in Table II. Examples of such enzymatic nucleic acid molecules also are shown in Table II. Examples of such enzymatic nucleic acid molecules consist essentially of sequences defined in Table II.

Other features and advantages of the invention will be apparent from the following description of the preferred embodiments thereof, and from the claims.

DESCRIPTION OF THE PREFERRED EMBODIMENTS

The drawings will first briefly be described.

DRAWINGS

FIG. 1 A) is a diagrammatic representation of the hammerhead ribozyme domain known in the art. Stem II can be 2 base-pairs long. Each N is independently any base or non-nucleotide as used herein; B) is a diagrammatic representation of a self-cleaving hammerhead ribozyme; C) is a diagrammatic representation of a random pool of self-cleaving RNA. N indicates the region with random nucleotides. (SEQ ID NO: 1171–1174)

FIG. 2 is a schematic representation of a non-limiting in vitro selection strategy used to evolve nucleic acid catalysts. (SEQ ID NO: 1175–1189)

FIG. 3 shows sequences of individual RNAs that represent new classes of self-cleaving ribozymes. Also shown are rates of catalysis ($k_{in-cis}$ (min$^{-1}$)) for each of the new self-cleaving RNA sequences. The underlined sequences indicate the regions capable of interacting with each other. (SEQ ID NO: 1175–1189)

FIG. 4 summarizes structure mapping studies on clone 40 RNA. (SEQ ID NO: 1190)

FIG. 6 shows non-limiting examples of trans-cleaving ribozyme-substrate complex of the present invention. (SEQ ID NO: 1193–1198)

FIG. 7 shows non-limiting examples of chemically modified trans-cleaving ribozyme-substrate complex of the present invention. (SEQ ID NO: 1199–1206)

FIG. 8 shows a non-limiting example of a chemically modified trans-cleaving ribozyme-substrate complex of the present invention and the numbering system used for (SEQ ID NO: 1207–1208)

NUCLEIC ACID CATALYSTS

Figure 4:
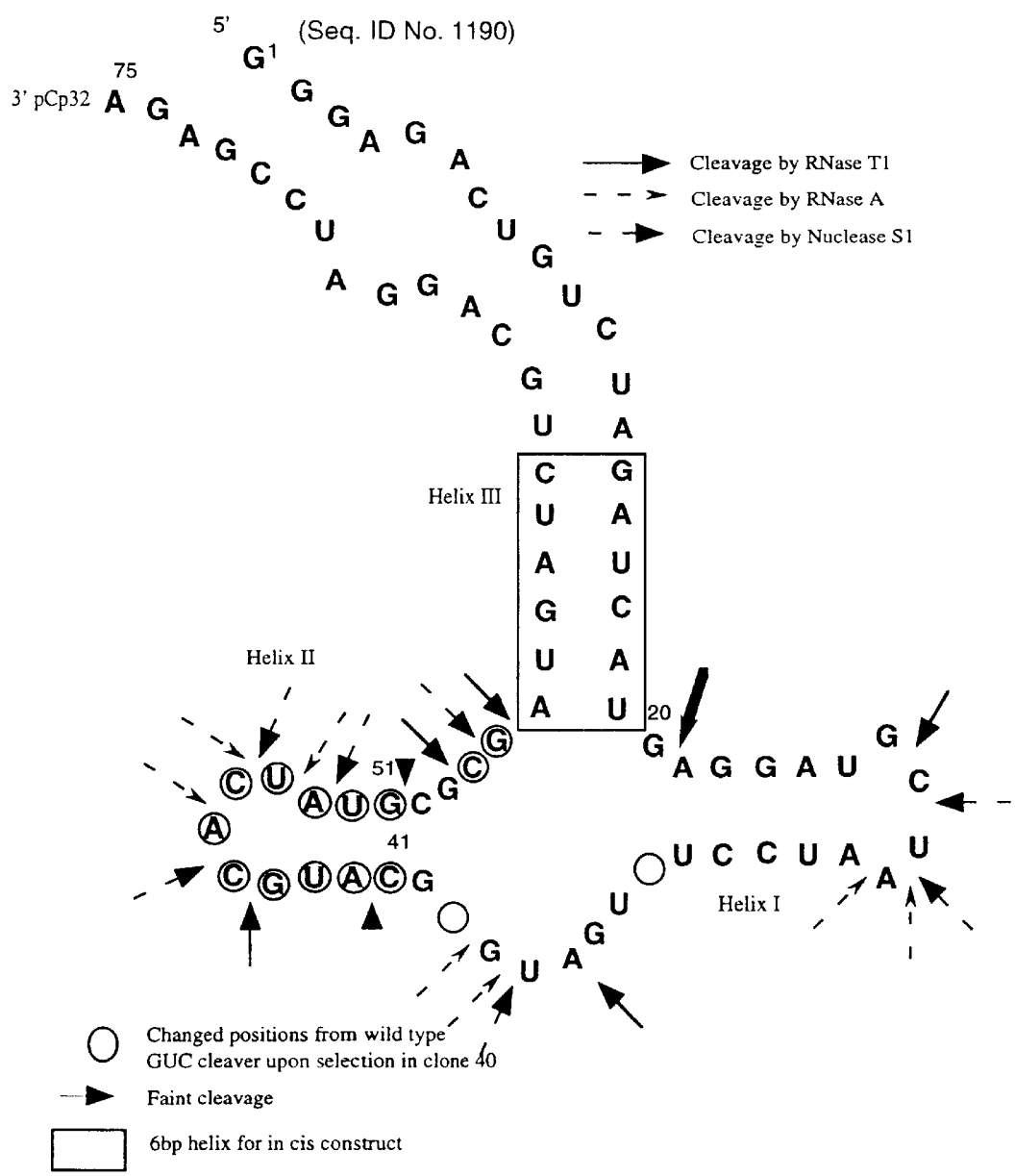

The invention provides nucleic acid catalysts and methods for producing a class of enzymatic nucleic acid cleaving agents which exhibit a high degree of specificity for the nucleic acid sequence of a desired target. The enzymatic nucleic acid molecule is preferably targeted to a highly conserved sequence region of a target such that specific diagnosis and/or treatment of a disease or condition in a variety of biological system can be provided with a single enzymatic nucleic acid. Such enzymatic nucleic acid molecules can be delivered exogenously to specific cells as required. In the preferred hammerhead motif, the small size (less than 60 nucleotides, preferably between 30–40 nucleotides in length) of the molecule allows the cost of treatment to be reduced.

By "nucleic acid catalyst" as used herein is meant a nucleic acid molecule (e.g., the molecule of formulae I–V), capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region (e.g. X and Y in formulae I–V) to a specified-gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, nucleozyme, RNA enzyme, endoribonuclease, endonuclease, minizyme, oligozyme, finderon or nucleic acid catalyst. All of these terminologies describe nucleic acid molecules with enzymatic activity. The specific examples of enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule.

By "nucleic acid molecule" as used herein is meant a molecule having nucleotides. The nucleic acid can be single, double, or multiple stranded and may comprise modified or unmodified nucleotides or non-nucleotides or various mixtures and combinations thereof.

By "complementarity" is meant that a nucleic acid can form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well-known in the art (see, e.g., Turner et al., 1987, *CSH Symp. Quant. Biol.* LII pp.123–133; Frier et al., 1986, *Proc. Nat. Acad. Sci. USA* 83:9373–9377; Turner et al., 1987, *J. Am. Chem. Soc.* 109:3783–3785. A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

The enzymatic nucleic acid molecules of Formulae I–V may independently comprise a cap structure which may independently be present or absent.

By "sufficient length" is meant an oligonucleotide of greater than or equal to 3 nucleotides. For example, for the X and Y portions of the nucleic acid molecules disclosed in formulae I–V "sufficient length" means that the nucleotide length is long enough to provide stable binding to a target site under the expected binding conditions. Preferably, the X and Y portions are not so long as to prevent useful turnover.

By "stably interact" is meant, interaction of the oligonucleotides with target nucleic acid (e.g., by forming hydrogen bonds with complementary nucleotides in the target under physiological conditions).

By "chimeric nucleic acid molecule" or "mixed polymer" is meant that, the molecule may be comprised of both modified or unmodified nucleotides.

By "cap structure" is meant chemical modifications, which have been incorporated at either terminus of the oligonucleotide. These terminal modifications protect the nucleic acid molecule from exonuclease degradation, and may help in delivery and/or localization within a cell. The cap may be present at the 5'-terminus. (5'-cap) or at the 3'-terminus (3'-cap) or may be present on both termini. In non-limiting examples: the 5'-cap is selected from the group comprising inverted abasic residue (moiety); 4',5'-methylene nucleotide; 1-(beta-D-erythrofuranosyl) nucleotide; 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Beigelman et al., International PCT publication No. WO 97/26270, incorporated by reference herein).

In yet another preferred embodiment the 3'-cap is selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details, see, Beaucage and Iyer, 1993, Tetrahedron 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine. The terms "abasic" or "abasic nucleotide" as used herein encompass sugar moieties lacking a base or having other chemical groups in place of base at the 1' position.

By "oligonucleotide" as used herein, is meant a molecule comprising two or more nucleotides.

The specific enzymatic nucleic acid molecules described in the instant application are not limiting in the invention and those skilled in the art will recognize that all that is important in an enzymatic nucleic acid molecule of this invention is that it has a specific substrate binding site (e.g., X and Y of Formulae I–V above) which is complementary to one or more of the target nucleic acid regions, and that it have nucleotide sequences within or surrounding that substrate binding site which impart a nucleic acid cleaving activity to the molecule.

By "enzymatic portion" is meant that part of the ribozyme essential for cleavage of an RNA substrate.

By "substrate binding arm" or "substrate binding domain" is meant that portion of a ribozyme which is complementary to (i.e., able to base-pair with) a portion of its substrate. Generally, such complementarity is 100%, but can be less if desired. For example, as few as 10 nucleotides out of a total of 14 may be base-paired. Such arms are shown generally in FIG. 1A and as X and Y in Formulae I–V. That is, these arms contain sequences within a ribozyme which are intended to bring ribozyme and target RNA together through complementary base-pairing interactions. The ribozyme of the invention may have binding arms that are contiguous or non-contiguous and may be of varying lengths. The length of the binding arm(s) are preferably greater than or equal to four nucleotides; specifically 12–100 nucleotides; more specifically 14–24 nucleotides long. The two binding arms are chosen, such that the length of the binding arms are symmetrical (i.e., each of the binding arms is of the same length; e.g., five and five nucleotides, six and six nucleotides or seven and seven nucleotides long) or asymmetrical (i e., the binding arms are of different length; e.g., six and three nucleotides; three and six nucleotides long; four and five nucleotides long; four and six nucleotides long; four and seven nucleotides long; and the like).

Catalytic activity of the ribozymes described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g. Eckstein et al., International Publication No. WO 92/07065; Perrault et al., 1990 Nature 344, 565; Pieken et al., 1991 Science 253, 314, Usman and Cedergren, 1992 Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. All these publications are hereby incorporated by reference herein.

Therapeutic ribozymes must remain stable within cells until translation of the target RNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 Nucleic Acids Res. 23, 2677; incorporated by reference herein) have expanded the ability to modify ribozymes to enhance their nuclease stability. The term "nucleotide" is used as recognized in the art to include natural bases, and modified bases well known in the art. Such bases are generally located at the 1' position of a sugar moiety. Nucleotides generally comprise a base, sugar and a phosphate group. The nucleotides can be unmodified or modified at the sugar, phosphate and/or base moiety, (see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art. These recently have been summarized by Limbach et al., 1994, Nucleic Acids Res. 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2, 4, 6-trimethoxy benzene, 3-methyluracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, *Biochemistry*, 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

In a preferred embodiment, the invention features modified ribozymes with phosphate backbone modifications comprising one or.more phosphorothioate and/or phosphorodithioate substitutions. A non-limiting, preferred example of a ribozyme of the instant invention utilizing phosphorothioate and/or phosphorodithioate modifications in conjunction with 2'-O-methyl ribonucleotides and conserved ribonucleotide residues is shown in FIG. 8. The incorporation of phosphorothioate and/or phosphorodithioate linkages into the enzymatic nucleic acid of the instant invention results in increased serum stability. Replacement of the 3'-phosphodiester at position 6 with a phosphorothioate or phosphorodithioate linkage (FIG. 8) stabilizes the conserved position 6 ribose moiety, which is prone to nucleolytic cleavage. In a study investigating the serum stability of position 6 modified ribozyme variants which preserve the 2'-hydroxyl function at position 6 (FIG. 8), the relative stability of the modifications were ranked as follows:

3'-Phosphorodithioate>>3'-Phosphorothioate>>4'-Thioribofuranose>Phosphodiester

The preferred incorporation of one to four, but preferably two, phosphorothioate linkages at the 5'-end of the position 6 3'-phosphorothioate ribozyme (FIG. 8) does not significantly affect the cleavage rate of the molecule. In a comparison study, the incorporation of up to four phosphorothioate residues at the 5'-end of this molecule is well tolerated. The incorporation of a 3'-phosphorodithioate residue at.position 6 of the ribozyme results in a 50% reduction in catalytic activity over the corresponding position 6 3'-phosphorothioate derivative. The loss of catalytic activity in the case of the position 6 3'-phosphorodithoate substitution may be offset by the increased serum stability that this modification offers and is likely to enhance the effectiveness of the ribozyme in cells.

In a preferred embodiment, the invention features a 3'-phosphorothioate linkage at position 6 of the nucleic acid molecule of the instant invention (FIG. 8).

In yet another preferred embodiment, the invention features a 3'-phosphorodithioate linkage at position 6 of the nucleic acid molecule (FIG. 8).

In a further preferred embodiment of the instant invention, an inverted deoxy abasic moiety is utilized at the 3' end of the enzymatic nucleic acid molecule.

In particular, the invention features modified ribozymes having a base substitution selected from pyridin-4-one, pyridin-2-one, phenyl, pseudouracil, 2, 4, 6-trimethoxy benzene, 3-methyluracil, dihydrouracil, naphthyl, 6-methyluracil and aminophenyl.

There are several examples in the art describing sugar and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modifications of enzymatic nucleic acid molecules have been extensively described in the art (see Eckstein et al., *International Publication* PCT No. WO 92/07065; Perrault et al. *Nature* 1990, 344, 565–568; Pieken et al. *Science* 1991, 253, 314–317; Usman and Cedergren, *Trends in Biochem. Sci.* 1992, 17, 334–339; Usman et al. *International Publication* PCT No. WO 93/15187; Sproat, U.S. Pat. No. 5,334,711 and Beigelman et al., 1995 *J. Biol. Chem.* 270, 25702).

Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

As the term is used in this application, non-nucleotide-containing enzymatic nucleic acid means a nucleic acid molecule that contains at least one non-nucleotide component which replaces a portion of a ribozyme, e.g., but not limited to, a double-stranded stem, a single-stranded "catalytic core" sequence, a single-stranded loop or a single-stranded recognition sequence. These molecules are able to cleave (preferably, repeatedly cleave) separate RNA or DNA molecules in a nucleotide base sequence specific manner. Such molecules can also act to cleave intramolecularly if that is desired. Such enzymatic molecules can be targeted to virtually any RNA transcript.

The sequences of ribozymes that are chemically synthesized, useful in this invention, are shown in Table II. Those in the art will recognize that these sequences are representative only of many more such sequences where the enzymatic portion of the enzymatic nucleic acid molecule (all but the binding arms) is altered to affect activity. The ribozyme sequences listed in Table II may be formed of ribonucleotides or other nucleotides or non-nucleotides. Such ribozymes with enzymatic activity are equivalent to the ribozymes described specifically in the Table.

Synthesis of Nucleic Acid Molecules

Synthesis of nucleic acids greater than 100 nucleotides in length is difficult using automated methods, and the therapeutic cost of such molecules is prohibitive. In this invention, small nucleic acid motifs ("small refers to nucleic acid motifs no more than 100 nucleotides in length, preferably no more than 80 nucleotides in length, and most preferably no more than 50 nucleotides in length; e.g., antisense oligonucleotides, hammerhead or the hairpin ribozymes) are preferably used for exogenous delivery. The simple structure of these molecules increases the ability of the nucleic acid to invade targeted regions of RNA structure. Exemplary molecules of the instant invention were chemically synthesized, and others can similarly be synthesized. Oligodeoxyribonucleotides were synthesized using standard protocols as described in Caruthers et al., 1992, *Methods in Enzymology* 211,3–19, and is incorporated herein by reference.

The method of synthesis used for normal RNA including certain enzymatic nucleic acid molecules follows the procedure as described in Usman et al., 1987 *J. Am. Chem. Soc.*, 109, 7845; Scaringe et al., 1990 *Nucleic Acids Res.*, 18, 5433; Wincott et al., 1995 *Nucleic Acids Res.* 23, 2677–2684; and Wincott et al., 1997, *Methods Mol. Bio.*, 74, 59, and makes use of common nucleic acid protecting and coupling groups, such as dimethoxytrityl at the 5'-end, and phosphoramidites at the 3'-end. In a non-limiting example, small scale syntheses were conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by calorimetric quantitation of the trityl fractions, were 97.5–99%. Other oligonucleotide, synthesis reagents for the 394 Applied . Biosystems, Inc. synthesizer; detritylation solution was 3% TCA in methylene chloride (ABI); capping was performed with 16% N-methyl imidazole in THF (ABI) and 10% acetic anhydride/10% 2,6-lutidine in THF (ABI); oxidation solution was 16.9 mM $I_2$, 49 mM pyridine, 9% water in THF (PERSEPTIVE™). Burdick & Jackson Synthesis Grade acetonitrile was used directly from the reagent bottle. S-Ethyltetrazole solution (0.25 M in acetonitrile) was made up from the solid obtained from American International Chemical, Inc.

Deprotection of the RNA was performed using either a two-pot or one-pot protocol. For the two-pot protocol, the polymer-bound trityl-on oligoribonucleotide was transferred to a 4 mL glass screw top vial and suspended in a solution of 40% aq. methylamine (1 mL) at 65° C. for 10 min. After cooling to −20° C., the supernatant was removed from the polymer support. The support was washed three times with 1.0 mL of EtOH:MeCN:H2O/3:1:1, vortexed and the supernatant was then added to the first supernatant. The combined supernatants, containing the oligoribonucleotide, were dried to a white powder. The base deprotected oligoribonucleotide was resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 h, the oligomer was quenched with 1.5 M $NH_4HCO_3$.

Alternatively, for the one-pot protocol, the polymer-bound trityl-on oligoribonucleotide was transferred to a 4 mL glass screw top vial and suspended in a solution of 33% ethanolic methylamine/DMSO:1/1 (0.8 mL) at 65° C. for 15 min. The vial was brought to r.t. TEA.3HF (0.1 mL) was added and the vial was heated at 65° C. for 15 min. The sample was cooled at −20° C. and then quenched with 1.5 M $NH_4HCO_3$.

For purification of the trityl-on oligomers, the quenched $NH_4HCO_3$ solution was loaded onto a C-18 containing cartridge that had been prewashed with acetonitrile followed by 50 mM TEAA. After washing the loaded cartridge with water, the RNA was detritylated with 0.5% TFA for 13 min. The cartridge was then washed again with water, salt exchanged with 1 M NaCl and washed with water again. The oligonucleotide was then eluted with 30% acetonitrile.

Inactive hammerhead ribozymes or binding attenuated control (BAC) oligonucleotides) were synthesized by substituting a U for $G_5$ and a U for $A_{14}$ (numbering from Hertel, K. J., et al., 1992, *Nucleic Acids Res.*, 20, 3252). Similarly, one or more nucleotide substitutions can be introduced in other enzymatic nucleic acid molecules to inactivate the molecule and such molecules can serve as a negative control.

The average stepwise coupling yields were >98% (Wincott et al., 1995 *Nucleic Acids Res.* 23, 2677–2684). Those of ordinary skill in the art will recognize that the scale of synthesis can be adapted to be larger or smaller than the example described above including but not limited to 96-well format, all that is important is the ratio of chemicals used in the reaction.

Alternatively, the nucleic acid molecules of the present invention can be synthesized separately and joined together post-synthetically, for example, by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997 *Bioconjugate Chem.* 8, 204).

Ribozymes of the instant invention are also synthesized from DNA templates using bacteriophage T7 RNA polymerase (Milligan and Uhlenbeck, 1989, *Methods Enzymol.* 180, 51).

Ribozymes are purified by gel electrophoresis using general methods or are purified by high pressure liquid chromatography (HPLC; see, Wincott et al., supra; the totality of which is hereby incorporated herein by reference) and are resuspended in water.

Administration of Ribozymes

Sullivan et al., PCT WO 94/02595, describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration, suppositories for rectal administration, sterile solutions, suspensions for injectable administration, and other compositions known in the art.

The present invention also includes pharmaceutically acceptable formulations of the compounds described. These formulations include salts of the above compounds, egg., acid addition salts, for example, salts of hydrochloric, hydrobromic; acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example, oral, transdermal, or by injection. Such forms should not prevent the composition or formulation from reaching, a target cell (i e., a cell to which the negatively charged polymer is desired to be delivered to). For example, pharmacological compositions injected into the blood stream should be soluble. Other factors are known in the art, and include considerations, such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as cancer cells.

The invention also features the use of a composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta*, 1238, 86–90). All of these references are incorporated by reference herein. The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of which are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents may be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. In a one aspect, the invention provides enzymatic nucleic acid molecules that can be delivered exogenously to specific cells as required. The enzymatic nucleic acid molecules are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. Using the methods described herein, other enzymatic nucleic acid molecules that cleave target nucleic acid may be derived and used as described above. Specific examples of nucleic acid catalysts of the instant invention are provided below in the Tables and figures.

Alternatively, the enzymatic nucleic acid molecules of the instant invention can be expressed within cells from eukaryotic promoters (e.g., Izant and Weintraub, 1985 *Science* 229, 345; McGarry and Lindquist, 1986 *Proc. Natl. Acad. Sci. USA* 83, 399; Scanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res.*, 20, 4581–9; Sarver et al., 1990 *Science* 247, 1222–1225; Thompson et al., 1995 *Nucleic Acids Res.* 23, 2259; Good et al., 1997, *Gene Therapy*, 4, 45; all of the references are hereby incorporated by reference herein in their totalities). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO 93/23569, and Sullivan et al., PCT WO 94/02595; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856; all of the references are hereby incorporated by reference herein in their totalities).

In another aspect of the invention, enzymatic nucleic acid molecules that cleave target molecules are expressed from transcription units (see, for example, Couture et al., 1996, *TIG.*, 12, 510) inserted into DNA or RNA vectors. The recombinant vectors are preferably DNA plasmids or viral vectors. Ribozyme expressing viral vectors could be constructed based on, but not limited to, adeno-associated virus, retrovirus, adenovirus, or alphavirus. Preferably, the recombinant vectors capable of expressing the ribozymes are delivered as described above, and persist in target cells. Alternatively, viral vectors may be used that provide for transient expression of ribozymes. Such vectors might be repeatedly administered as necessary. Once expressed, the ribozymes cleave the target mRNA. The active ribozyme contains an enzymatic center or core equivalent to those in the examples, and binding arms able to bind target nucleic acid molecules such that cleavage at the target site occurs. Other sequences may be present which do not interfere with such cleavage. Delivery of ribozyme expressing vectors could be systemic, such as by intravenous or intramuscular administration, by administration to target cells ex-planted from the patient followed by reintroduction into the patient, or by any other means that would allow for introduction into the desired target cell (for a review, see Couture et al., 1996, *TIG.*, 12, 510).

In one aspect, the invention features, an expression vector comprising a nucleic acid sequence encoding at least one of the nucleic acid catalysts of the instant invention. The nucleic acid sequence encoding the nucleic acid catalyst of the instant invention is operable linked in a manner which allows expression of that nucleic acid molecule.

In another aspect the invention features, an expression vector comprising: a transcription initiation region (e.g., eukaryotic pol I, II or III initiation region); b) a transcription termination region (e.g. eukaryotic pol I, II or III termination region); c) a nucleic acid sequence encoding at least one of the nucleic acid catalyst of the instant invention; and wherein said sequence is operably linked to said initiation region and said termination region, in a manner which allows expression and/or delivery of said nucleic acid molecule. The vector may optionally include an open reading frame (ORF) for a protein operably linked on the 5' side or the 3' side of the sequence encoding the nucleic acid catalyst of the invention; and/or an intron (intervening sequences).

Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). All of these references are incorporated by reference herein. Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U.S.A.*, 90, 8000–4; Thompson et al., 1995 *Nucleic Acids Res.* 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as ribozymes in cells (Thompson et al., supra; Couture and Stinchcomb, 1996, supra; Noonberg et al., 1994, *Nucleic Acid Res.*, 22, 2830; Noonberg et al., U.S. Pat. No. 5,624,803; Good et al., 1997, *Gene Ther.* 4, 45; Beigelman et al., International PCT Publication No. WO 96/18736; all of these publications are incorporated by reference herein). Examples of transcription units suitable for expression of ribozymes of the instant invention are shown in FIG. 15. The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review, see Couture and Stinchcomb, 1996, supra).

In yet another aspect the invention features an expression vector comprising a nucleic acid sequence encoding at least one of the catalytic nucleic acid molecules of the invention, in-a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule. In another preferred embodiment the expression vector comprises: a) a transcription initiation region; b) a transcription termination region; c) an open reading frame; d) a sequence encoding at least one said nucleic acid molecule, wherein said gene is operably linked to the 3'-end of said open reading frame; and wherein said gene is operably linked to said initiation region, said open reading frame and said termination region, in a manner which allows expression and/or delivery of said nucleic acid molecule. In yet another embodiment the expression vector comprises: a) a transcription initiation region; b) a transcription termination region; c) an intron; d) a nucleic acid sequence encoding at least one said nucleic acid molecule; and wherein said sequence is operably linked to said initiation region, said intron and said termination region, in a manner which allows expression and/or delivery of said nucleic acid molecule. In another embodiment, the expression vector comprises: a) a transcription initiation region; b) a transcription termination region; c) an intron; d) an open reading frame; e) a nucleic acid sequence encoding at least one said nucleic acid molecule, wherein said sequence is operably linked to the 3'-end of said open reading frame; and wherein said sequence is operably linked to said initiation region, said intron, said open reading frame and said termination region, in a manner which allows expression and/or delivery of said nucleic acid molecule.

By "consists essentially of" is meant that the active ribozyme contains an enzymatic center or core equivalent to those in the examples, and binding arms able to bind target nucleic acid molecules such that cleavage at the target site occurs. Other sequences may be present which do not interfere with such cleavage.

EXAMPLES

The following are non-limiting examples showing the selection, isolation, synthesis and activity of enzymatic nucleic acids of the instant invention.

An extensive array of site-directed mutagenesis studies have been conducted with the hammerhead to probe relationships between nucleotide sequence and catalytic activity. These systematic studies have made clear that most nucleotides in the conserved core of the hammerhead ribozyme (Forster & Symons, 1987, *Cell*, 49, 211) cannot be mutated without significant loss of catalytic activity. In contrast, a combinatorial strategy that simultaneously screens a large pool of mutagenized ribozymes for RNAs that retain catalytic activity could be used more efficiently to define immutable sequences and to identify new ribozyme variants (Breaker, 1997, supra). For example, Joseph and Burke (1993; *J. Biol. Chem.*, 268, 24515) have used an in vitro selection approach to rapidly screen for sequence variants of the 'hairpin' self-cleaving RNA that show improved catalytic activity. This approach was successful in identifying two mutations in the hairpin ribozyme that together give a 10-fold improvement in catalytic rate. Although similar in vitro selection experiments have been conducted with the hammerhead ribozyme (Nakamaye & Eckstein, 1994, supra; Long & Uhlenbeck, 1994, supra; Ishizaka et al., 1995, supra), none of these efforts have successfully screened full-sized hammerhead ribozymes for all possible combinations of sequence variants that encompass the entire catalytic core.

Applicant employed in vitro selection strategy to comprehensively test whether the natural consensus sequence for the core of the hammerhead ribozyme produces maximal catalytic rates, or whether sequence variants of this ribozyme could catalyze endonuclease reaction similar to or better than the hammerhead ribozyme.

The procedure reported herein to select for intramolecular AUG cleaving sequences is based on Applicant's previously reported selection of alternative GUC cleaving hammerhead sequences (Vaish et al., 1997, *Biochemistry* 36, 6495; incorporated by reference herein).

Example 1

In Vitro Selection of Self-cleaving RNAs From a Random Pool

An initial pool of dsDNAs containing 22 randomized positions flanked by two constant regions was synthesized. These were transcribed, with transcription being initiated with GTPγS, to produce a pool of potential ribozymes. Self-cleavage of active ribozymes occurs during transcription and the cleavage products can then be separated from intact transcripts by means of a mercury gel (Igloi, *Biochemistry* 27, 3842). The recovered cleavage products were then reverse transcribed and amplified by PCR to give a dsDNA pool of selected ribozymes. This selection procedure was repeated for 13 cycles before the dsDNA pool was cloned and sequenced.

Oligodeoxyribonucleotides and oligoribonucleotides were chemically synthesized and purified as previously described (Vaish et al., 1997 *Biochemistry* 36, 6495). Primers used in the selection:
Primer 1:
5'-TGGTGCAAGCTTAATACGACTCACTATAGGGAGACTGTCTAGAT CATGAGGATGCTA-3'(Seq. ID No. 1167);
Primer 2:
5'-TCTCGGATCCTGCAGATCATNNNNNNNNNN NNNNNNNNNNNNAGGATTAGCATCCTCAT-3' (Seq. ID No. 1168).
These two primers were used for the initial Sequenase® reaction, and Primer 2 also functioned as restoration primer for the reintroduction of the lost sequences during cleavage. Reverse transcription (RT)-Primer, 5'-TCTCGGATCCTGCAGATCAT-3' (Seq. ID No. 1169); and polymerase chain reaction (PCR)-Primer, 5'-TGGTGCAAGCTTAATACGACTCA-3' (Seq. ID No. 1170), with HindIII (5'-end) and BamHI and PstI (3'-end) sites in boldface; T7 promoter is underlined; ribozyme cleavage triplet in italics; N, randomized nucleotides. RNA selection was performed as described (Vaish et al., 1997 *Biochemistry* 36, 6495 incorporated by reference herein) with modifications to the initial two cycles of selection. Transcriptions from Pool 0 and Pool 1 were performed on a larger scale (10×500 µl and 1×250 µl, respectively) for 12 h and PCR amplification (Step 5) was omitted in each case. Successive transcriptions were performed at 100 µl volume. Transcription reactions were for decreasing periods of time from 12 h ($1^{st}$ cycle) to 1 min ($13^{th}$ cycle), where reactions for short periods were quenched by addition of EDTA (75 mM final conc.). All transcriptions were performed with 1 µM DNA. DNA template in the PCR mixture was at least $1\times10^{-15}$ M. The minimum concentration of RNA template was $1\times10^{-8}$ M for reverse transcription. The concentrations were determined assuming a molar extinction coefficient of 6600.

A selection pressure was exerted by progressively reducing the time of transcription from 12 h for the first six cycles, to 6 h for the seventh, 1 h for the eighth, 30 min for the ninth and tenth, 5 min for the eleventh, and 1 min for the twelve and thirteenth cycle. White colonies were randomly selected from pools 7 and 10 and those showing self-cleavage upon transcription were sequenced. There was no homology among the sequences.

Cloning and sequencing was performed as described (Vaish et al., 1997, *Biochemistry* 36, 6495) except that the dsDNA was digested with HindIII and BamHI. Clones from pools seven and ten were tested for transcript self-cleavage from linearized plasmids. For clones from Pool 13 plasmid DNA was amplified by PCR, using the RT- and PCR-primers, and then transcribed. Rates of intramolecular cleavage of transcripts were determined as described but with 10 u of enzyme per µl. Active clones were sequenced. A transcript of only 50 nucleotides, without the extra sequences for cloning beyond stem III, showed a $k_{in\text{-}cis}$ of 0.32 $\text{min}^{-1}$.

By "randomized region" is meant a region of completely random sequence and/or partially random sequence. By completely random sequence is meant a sequence wherein theoretically there is equal representation of A, T, G and C nucleotides or modified derivatives thereof, at each position in the sequence. By partially random sequence is meant a sequence wherein there is an unequal representation of A, T, G and C nucleotides or modified derivatives thereof, at each position in the sequence. A partially random sequence can therefore have one or more positions of complete randomness and one or more positions with defined nucleotides.

Characterization of New Self-cleaving Ribozyme Sequences

The intramolecular cleavage rate of the most active sequence of pool 7 was 0.03 $\text{min}^{-1}$ and that of pool 10 was 0.06 $\text{min}^{-1}$ (FIG. 3). Seventy clones from pool thirteen were picked and amplified by PCR. Of these, 20 gave full-length DNA and were transcribed; and, of these, 14 showed intramolecular cleavage. These 14 active ribozymes could be divided into two groups: one group contained transcripts with 22 nucleotides in the randomized region and the second group contained a deletion in this region with only 21 nucleotides being present. Several sequences were represented twice such as those of clones 29, 36 and 40. One of the most active sequences, from clone 13/40, with $k_{in-cis}$ of 0.52 $min^{-1}$ was chosen for further study. In comparison, under these conditions the intramolecular cleavage of the native hammerhead with a GUC triplet was $k_{in-cis}$ of 0.56 $min^{-1}$, indicating that the cleavage activity of the selected ribozyme, Rz13/40, with an AUG triplet is comparable. In order to acquire some information on the secondary structure of Rz13/40, a limited nuclease digest of the 3'-end-labeled, full-length ribozyme was performed. Rz13/40 was prepared by transcription in such a way that cleavage was minimized. A full length transcript for the intramolecularly cleaving ribozyme was generated by transcription at 12° C. for 8 h (Frank et al., 1996, RNA, 2, 1179; incorporated by reference herein) and 3'-end labeled with $^{32}pCp$. Limited nuclease digestions with RNase A, RNase T1 and nuclease S1 were performed as Hodson et al., 1994, Nucleic Acids Res., 22, 1620; Loria et al., 1996, RNA, 2,551; both are incorporated by reference herein). Alkaline hydrolysis of labeled RNA was performed in 50 mM $NaHCO_3$ at 100° C. for 7.5 minutes.

Limited digestion with RNase A and T1 and nuclease S1, which indicates single-stranded regions, gave a digestion pattern consistent with Rz13/40 adopting a hammerhead-type structure, which comprised three base-paired helices surrounding a single-stranded core (FIG. 4). Since the structure of Rz13/40 resembles the hammerhead structure, the same numbering system has been adopted, with positions 3 and 9 in the core being considered vacant.

The data of nuclease digestion corresponded fairly well with the MFOLD structure except for a few discrepancies. MFOLD shows base pairing in the core region between $U^7$ and $G^{14}$; $G^8$ and $C^{13}$; $G^{L2.1}$ and $U^{L2.5}$; and $U^4$ and $G^7$ although there cleavage at these positions by the nucleases.

Ribozyme Engineering

Sequence, chemical and structural variants of ribozymes of the present invention can be engineered using the techniques shown above and known in the art to cleave a separate target RNA or DNA in trans. For example, the size of ribozymes can, be reduced or increased using the techniques known in the art (Zaug et al., 1986, Nature, 324, 429; Ruffner et al., 1990, Biochem., 29, 10695; Beaudry et al., 1990, Biochem., 29, 6534; McCall el al., 1992, Proc. Natl. Acad. Sci., USA., 89, 5710; Long et al., 1994, Supra; Hendry et al., 1994, BBA 1219, 405; Benseler et al., 1993, JACS, 115, 8483; Thompson et al., 1996, Nucl. Acids Res., 24, 4401; Michels et al., 1995, Biochem., 34, 2965; Been et al., 1992, Biochem., 31, 11843; Guo et al., 1995, EMBO. J., 14, 368; Pan et al., 1994, Biochem., 33, 9561; Cech, 1992, Curr. Op. Struc. Bio., 2, 605; Sugiyama et al., 1996, FEBS Lett., 392, 215; Beigelman et al., 1994, Bioorg. Med. Chem., 4, 1715; all are incorporated in its totality by reference herein). For example, the stem-loop II domain of the ribozymes may not be essential for catalytic activity and hence could be systematically reduced in size using a variety of methods known in the art, to the extent that the overall catalytic activity of the ribozyme is not significantly decreased.

Further rounds of in vitro selection strategies described herein and variations thereof can be readily used by a person skilled in the art to evolve additional nucleic acid catalysts and such new catalysts are within the scope of the instant invention.

Example 2

Trans-cleaving Ribozymes

Figure 5:
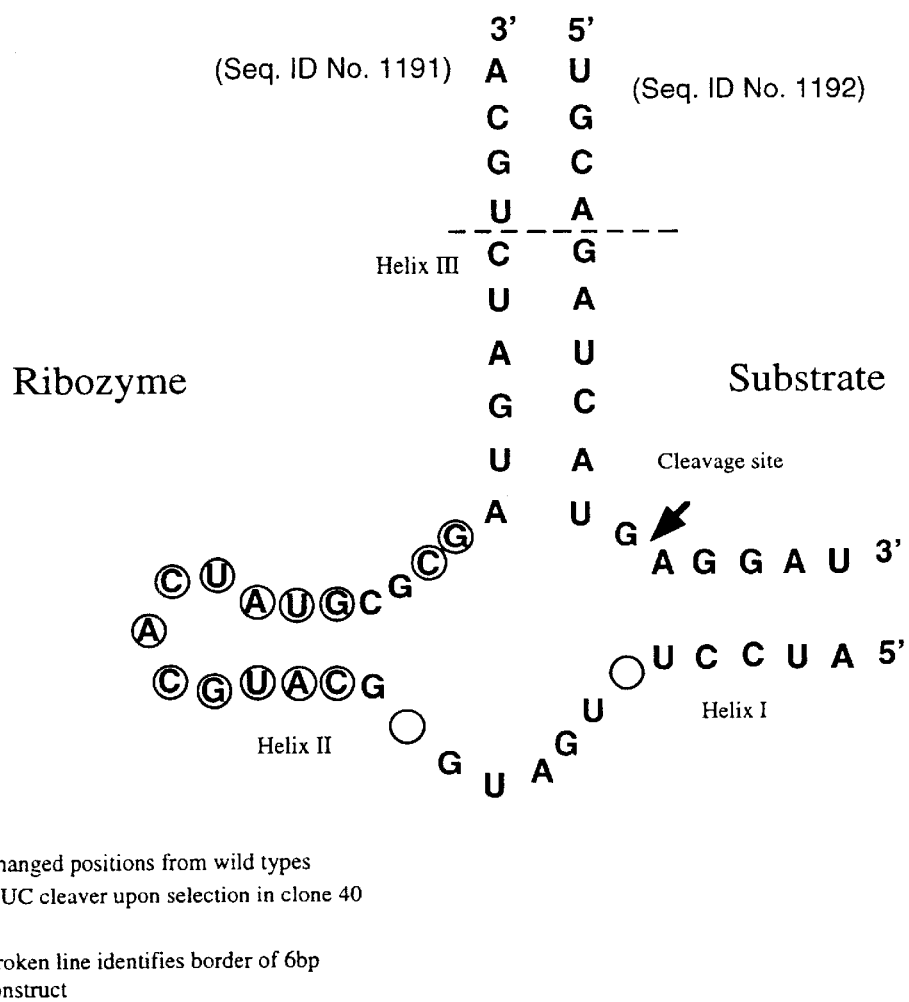
FIG. 5 shows sequence and possible secondary structure of a trans-cleaving ribozyme of the invention. Arrow identifies the site of cleavage. (SEQ ID NO: 1191–1192)

The self-cleaving ribozymes can be divided into separate ribozyme and substrate domains to create a functional bimolecular complex. This ribozyme presumably interacts with the substrate domain by forming base-paired regions that arc analogous to helices I and II of the hammerhead ribozyme (FIG. 1). Likewise, the substrate specificity of ribozymes can presumably be altered by changing the sequences of the substrate-binding arms to complement the sequence of the desired substrate molecule, as was achieved with the ribozyme from clone 40 self-cleaving RNA (FIG. 5). The numbering convention used in Example 2 is taken from Vaish et al., 1998 PNAS 95, 2158–2162.

To further characterize the selected ribozyme for intermolecular cleavage, Rz13/40 was divided into a catalytic portion and the corresponding substrate strand (FIG. 5). The initial ribozyme construct was designed with 5 bp each in stems I and III for annealing to the substrate. Stems of this length were chosen because they had been reported to give reliable kinetic data with the hammerhead. Cleavage kinetics of intramolecularly cleaving ribozymes was performed with chemically synthesized ribozyme and substrate in 50 mM Tris-HCl (pH 8.0), and 10 mM $MgCl_2$ with 50 to 500 nM ribozyme and 25 nM substrate for single turnover, and 50 to 500 nM substrate with 5 to 25 nM ribozyme for multiple turnover kinetics as described (Hertel et al., Biochemistry 33, 3374, 1994). The intermolecular version of Rz13/40 of the present invention gave a very high $K_M$ (1.1 mM) and low $k_{cat}$ (0.1 $min^{-1}$) under single turnover conditions and was inactive under multiple turnover conditions. As there was no doubt about the intramolecular cleavage of Rz13/40, the lack of catalytic activity under multiple turnover conditions must be associated with the design of the intermolecular version. After analysis of the ribozyme-substrate complex by native gel, it was concluded that formation of the complex was inefficient under the conditions used.

A second ribozyme construct was synthesized, where stem III was extended to 10 base-pairs. Native gel analysis confirmed the formation of the ribozyme-substrate complex and the ribozyme cleaved its corresponding substrate efficiently under both single and multiple turnover conditions (Table III). The discrepancy between kcat and kcat' (0.06 and 0.91 $min^{-1}$ respectively) is presumably the result of product inhibition, which is a common effect observed with the native hammerhead. The time course of cleavage was followed for about 12 half-lives under single turnover conditions. Reactions were first order up to 60% cleavage within the first minute and reached a total of 80%. First order end points with the conventional hammerhead are commonly 70 to 75%. Steady state cleavage rates were linear for several turnovers. Although the hammerhead and class I ribozymes cleave at different internucleotide linkages (FIG. 1), both ribozymes appear to proceed by a similar chemical mechanism. The hammerhead ribozyme is known to produce a 2',3'-cyclic phosphate at the terminus of the 5'-cleavage product, thereby leaving a 5'-hydroxyl terminus on the 3'-cleavage fragment.

The site of substrate cleavage was confirmed as being behind G of the AUG cleavage triplet by comparison of the ribozyme cleavage product, obtained under single turnover conditions for 30 min, with the products of a limited alkaline hydrolysis of the 5'-end-labeled substrate and with a partial RNase T1 digest. Reactions were performed in 10 μl containing RNA, 50 mM Tris (pH 8) and CNPase (Sigma Chemicals) (0.62 u to 0.012 u/μl) and incubation at 45° C. for 1.5 h. Product analysis was on a 20% PAGE where the cyclic phosphate-terminated product runs slightly slower than the ring-opened derivative. In addition, the cleavage products were also shown to be the 2', 3'-cyclic phosphate and a 5'-hydroxyl by hydrolysis with CNPase and labeling with T4 PNK respectively. Thus Rz13/40 cleaves in a similar manner to the hammerhead. In order to investigate the properties and sequence requirements of the selected ribozyme Rz13/40, mutations were made on the substrate and ribozyme strands. In the native hammerhead, stem II has been shortened to as few as two base-pairs without significant loss in activity. However, the removal of a single base-pair (10.3/11.3) in Rz13/40 resulted in a 1000-fold loss in activity for the cleavage behind an AUG triplet indicating the stem-loop structure has a wider role in catalysis.

The effect of mutations around the cleavage site has also been investigated under single and multiple turnover conditions (Table III). Surprisingly, the AUA triplet was also cleaved quite efficiently even though it was not selected for, again yielding a 2', 3'-cyclic phosphate. Triplets terminating in a uridine or cytidine were either cleaved extremely slowly or not at all. Thus, this ribozyme is purine nucleoside specific. Whether this indicates a necessity for base pairing between $U^4$ and the nucleotide to be cleaved, as possible with AUG and AUA, is uncertain at present.

As the native hammerhead strictly requires a uridine in the middle of the triplet, it was of interest to test whether this was applicable to Rz13/40. Interestingly the triplet AAG was cleaved with a $k_{cat}$ of 0.57 min$^{-1}$ under single turnover conditions, multiple turnover conditions showed a $k_{cat}$ of 0.09 min$^{-1}$. It was also tested whether the nucleotide next to the cleavage site was of importance. Cleavage of the triplet AUG followed by U or G was found to be only fractionally slower in single turnover than cleavage of AUG-A (Table III).

Inspection of the ribozyme sequences reveals some interesting features. The sequence 5'-GCGCG at positions 11.2 to 14 is present in all ribozymes from pool 10 onwards. This would indicate that this sequence may be an indispensable part for activity just as is the case for the GAA sequence in the conventional hammerhead.

Of the two classes of ribozyme isolated in Pool 13, the ribozymes with a deletion in the randomized region are the more active intramolecular cleavers. These ribozymes appear to have an overall secondary structure which is similar to that of the native hammerhead, but there are significant differences.

Obvious differences include the 'vacancies' at positions 3 and 9 in the core as well as the altered sequence to positions 12 to 14 of the traditional hammerhead ribozyme (FIG. 1) already mentioned. More subtle differences are associated with stem-loop II. In the hammerhead, a variety of structures are tolerated: the stem can be reduced to two base-pairs, and the loop can be of virtually any size and even contain non-nucleotidic linkers. In the selected ribozymes similar to Rz13/40, less variation in the stem-loop structure is observed. In the active ribozymes of this class, the stem-loop II consists of two G:C base-pairs adjacent to the core which are followed by two A:U base-pairs. The stem loop terminates in a five nucleotide loop, where variations at only positions L2.4 and L2.5 of the hammerhead ribozyme have been detected. The length of the stem appears to have a large effect on catalytic efficiency, since the removal of a single base-pair (10.3/11.3) abolishes activity in vitro. The most active sequences in pool 13 have a fully complementary stem II. One mismatch at 10.2/11.2 as in Rz13/1 approximately halves the activity. It is interesting to note that in Pool 13, the more active ribozymes contain a deletion in the randomized region, which is 21 nucleotides instead of 22. Of these only Rz13/31 and 13/29 show reasonable activity. One can draw a secondary structure for these with a stem II with two mismatches and the extra nucleotide in the core region.

Initial experiments to determine cleavage site specificities of ribozymes of the instant invention indicate NR/N as the minimum requirement for ribozyme cleavage, where N represents any nucleotide, R represents any purine nucleotide, and / indicates the site of cleavage. Persons skilled in the art can perform further experiments to determine potential cleavage targets of the ribozymes of the instant invention, such experiments can be performed as described in Ruffner et al., 1990, *Biochem.*, 29, 10695, and Joseph et al., 1993, *Genes and Development.*, 7, 130–138.

The new triplet specificity should be useful for the application of the ribozyme family of the present invention for the inhibition of gene expression in that it expands the targets on a mRNA for cleavage. Although the conventional NUX triplets might be considered sufficient for a wide application, the accessibility of oligodeoxynucleotides to mRNAs is very restricted. Thus the specificity of the new ribozyme for cleavage at purines, apparently independent of the nature of the neighboring nucleotides, should represent a considerable advantage over the native NUX-cleaving ribozyme for this application.

Example 3

Substrate Specificity Variants

An investigation of base pairs at positions 13.1–14.1 of the ribozyme shown in FIG. 9 was undertaken. Six different ribozyme-substrate combinations were synthesized where $N^{13.1}$–$N^{14.1}$ was either adenosine$^{13.1}$-uridine$^{14.1}$ (RZ 1), uridine$^{13.1}$-adenosine$^{14.1}$ (RZ 2), inosine$^{13.1}$-cytidine$^{14.1}$ (RZ 3), guanosine$^{13.1}$-cytidine$^{14.1}$, (Rz 4) cytidine$^{13.1}$-guanosine$^{14.1}$ (RZ 5), or guanosine$^{13.1}$-guanosine$^{14.1}$ (RZ 6). The time course of the cleavage of ribozymes 3–6 in FIG. 9 with non A-U base pairs was determined (FIG. 10). As shown in FIG. 10, no significant difference was observed between cleavage rates of ribozyme substrate complexes containing the $I^{13.1}$-$C^{14.1}$ or $G^{13.1}$-$C^{14.1}$ base pair (0.29 vs. 0.21 min$^{-1}$, FIG. 10). Under comparable conditions the cleavage rate of the AUG substrate was 0.1min$^{-1}$ with the 6 bp stem III and 5 bp stem I ribozyme (Vaish et al., 1998 *PNAS* 95, 2158–2162).

Because the $A^{13.1}$-$U^{14.1}$ pair can be inverted t $U^{13.1}$-$A^{14.1}$ without loss of activity (Example 2 above) it was of interest to study Ribozyme-Substrate complexes containing the $C^{13.1}$-$G^{14.1}$ pair (RZ 5). This inverted $C^{13.1}$-$G^{14.1}$ arrangement retains significant activity (0.09 min$^{-1}$), and it is only 3-fold less active than the corresponding G-C base pair. The use of a G-G base pair (RZ 6) under the specific conditions used in the example caused a significant reduction in the activity of the ribozyme. The $A^{13.1}$-$U^{14.1}$ pair containing ribozyme-substrate complex can cleave a target after an $AU^{14.1}G$ triplet; specificity of this ribozyme can be altered to cleave after $AG^{14.1}G$ triplets with a $G^{13.1}$ to $C^{13.1}$ substitution. The $AU^{14.1}G$ triplet recognizing ribozyme can therefore be engineered to cleavage after $AA^{14.1}G$ (see, Example 2), $AC^{14.1}G$ and $AG^{14.1}G$ triplets.

Since the original $AU^{14.1}G$ cleaving ribozymes have nonspecific requirements for the 1.1 nucleotide (i.e. the nucleotide downstream of G15) and since position 15 may be any purine, the experimental evidence for the acceptance of any nucleoside at the 14.1 position indicates $NR^{15}/N$ as the minimum requirement for ribozyme cleavage, where N represents any nucleotide, R represents any purine nucleotide, and / indicates the site of cleavage. The optimization of these variant ribozyme constructs by modification of stem-loop structures as is known in the art can provide for species with improved cleavage activity.

Example 4

Identification of Potential Target Sites in Human K-ras RNA

The sequence of human K-ras was screened for accessible sites using a computer folding algorithm selecting for AUR/, YG/M, and UG/U target sites where R in any purine, Y is any pyrimidine, M is A or C, and A, U, C, G are adenosine, uridine, cytidine, and guanosine, respectively. Regions of the RNA that did not form secondary folding structures and included cleavage sites for the ribozymes of the instant invention were identified. The sequences of these cleavage sites are shown in Table II.

Example 5

Selection of Enzymatic Nucleic Acid Cleavage Sites in Human K-ras RNA

To test whether the sites predicted by the computer-based RNA-folding algorithm corresponded to accessible sites in K-ras RNA ninety-six ribozyme sites from Table II were selected for further analysis. Ribozyme target sites were chosen by analyzing sequences of Human K-ras, (accession number: NM_004985) and prioritizing the sites on the basis of folding. Ribozymes were designed that could bind each target and were individually analyzed by computer folding (Christoffersen et al., 1994 *J. Mol. Struc. Theochem*, 311, 273; Jaeger et al., 1989, *Proc. Natl. Acad. Sci. USA*, 86, 7706) to assess whether the ribozyme sequences fold into the appropriate secondary structure. Those ribozymes with unfavorable intramolecular interactions between the binding arms and the catalytic core were eliminated from consideration. As noted below, varying binding arm lengths can be chosen to optimize activity. Generally, at least 5 bases on each arm are able to bind to, or otherwise interact with, the target RNA.

Example 6

Chemical Synthesis and Purification of Ribozymes for Efficient Cleavage of K-ras RNA Ribozymes were designed to anneal to various sites in the RNA message. The binding arms are complementary to the target site sequences described above. The ribozymes were chemically synthesized. The method of synthesis used followed the procedure for normal RNA synthesis as described above and in Usman et al., (1987 *J. Am. Chem. Soc.*, 109, 7845), Scaringe et al., (1990 *Nucleic Acids Res.*, 18, 5433) and Wincott et al., supra, and made use of common nucleic acid protecting and coupling groups, such as dimethoxytrityl at the 5'-end, and phosphoramidites at the 3'-end. The average stepwise coupling yields were >98%.

On instrument dithioate linkage formation via PADS/3-picoline: All processes were performed on an ABI (PE Biosystems) 394 DNA/RNA Synthesizer. Phosphorodithioate containing ribozymes were synthesized using PADS (Phenoxy acetyl disulfide), 3-Picoline, Acetonitrile, 5'-O-DMT-2'-O-TBDMS-Uridine-3'-thiophosphoramidite, and standard synthesis reagents and phosphoramidites. A 0.2 M solution of PADS was prepared in 1:1 acetonitrile:3-picoline. This solution was placed on the instrument and substituted for the normal oxidizing reagent to create the phosphorodithioate triester bond. The thio-amidite (0.1 M in ACN) was coupled for 450 seconds using a standard cycle. At the oxidation step, the PADS solution was delivered for 7.5s at a flow rate of 5 mL/min. and with a 300s wait time after delivery. After completion of the synthesis, the oligo was deprotected and purified in the standard manner (MA/$H_2O$, 3HF.TEA, $NH_4HCO_3$ quench, T-on solid phase purification).

Example 7

Ribozyme Cleavage of K-ras RNA Target in Vitro

Ribozymes targeted to the human K-ras RNA are designed and synthesized as described above. These ribozymes can be tested for cleavage activity in vitro, for example using the following procedure. The target sequences and the nucleotide location within the K-ras RNA are given in Table II.

Cleavage Reactions: Full-length or partially full-length, internally-labeled target RNA for ribozyme cleavage assay is prepared by in vitro transcription in the presence of [$\alpha$-$^{32}$p] CTP, passed over a G 50 Sephadex® column by spin chromatography and used as substrate RNA without further purification. Alternately, substrates are 5'-$^{32}$P-end labeled using T4 polynucleotide kinase enzyme. Assays are performed by pre-warming a 2× concentration of purified ribozyme in ribozyme cleavage buffer (50 mM Tris-HCl, pH 7.5 at 37° C., 10 mM $MgCl_2$) and the cleavage reaction was initiated by adding the 2× ribozyme mix to an equal volume of substrate RNA (maximum of 1–5 nM) that was also pre-warmed in cleavage buffer. As an initial screen, assays are carried out for 1 hour at 37° C. using a final concentration of either 40 nM or 1 mM ribozyme, i.e., ribozyme excess. The reaction is quenched by the addition of an equal volume of 95% formamide, 20 mM EDTA, 0.05% bromophenol blue and 0.05% xylene cyanol after which the sample is heated to 95° C. for 2 minutes, quick chilled and loaded onto a denaturing polyacrylamide gel. Substrate RNA and the specific RNA cleavage products generated by ribozyme cleavage are visualized on an autoradiograph of the gel. The percentage of cleavage is determined by Phosphor Imager® quantitation of bands representing the intact substrate and the cleavage products.

Example 8

Cleavage Reactions for Determining Substrate Specificity of Stabilized Ribozymes (Table IV)

Substrates are 5'-$^{32}$P-end labeled using T4 polynucleotide kinase enzyme. Assays are performed by pre-warming a 2× concentration of purified ribozyme in ribozyme cleavage buffer (50 mM Tris-HCl, pH 8.0 at 37° C., 10 mM $MgCl_2$) and the cleavage reaction is initiated by adding the 2× ribozyme mix to an equal volume of substrate RNA (maximum of 1–5 nM) that was also pre-warmed in cleavage buffer. Assays are carried out for 1 hour at 37° C. using a final concentration of 500 nM ribozyme, i.e., ribozyme excess. The reaction is quenched at specific time points by the addition of an equal volume of 95% formamide, 20 mM EDTA, 0.05% bromophenol blue and 0.05% xylene cyanol after which the time points are heated to 95° C. for 1 minute and loaded onto a denaturing polyacrylamide gel. Substrate RNA and the specific RNA cleavage products generated by ribozyme cleavage are visualized by scanning a Phosphor Imager® screen which has been exposed to the assay gel. The percentage of cleavage is determined by Phosphor Imager® quantitation of bands representing the intact substrate and the cleavage products. Table IV lists the substrate specificity rate constants for stabilized G-cleaver Ribozymes.

Example 9

Ribozyme Stability Assay

A mixture of 1.5 µg 5'-$^{32}$P-end labeled ribozyme and 13 µg unlabeled (cold) ribozyme is dried down and resuspended in 20 µL human serum. The suspension is incubated at 37° C. for 24 hours. Aliquots of the reaction are quenched at specific time points by removal into a 2.5-fold excess of 95% formamide, 20 mM EDTA, 0.05% bromophenol blue and 0.05% xylene cyanol on ice. A portion of each time point is counted on a scintillation counter for normalizing counts per lane. The time points are heated to 95° C. for 1 minute and loaded onto a denaturing polyacrylamide gel at 750 k cpm per lane. Intact ribozyme and the specific RNA degradation products generated by exposure to ribonucleases in the serum are visualized by scanning a Phosphor Imager® screen which has been exposed to the assay gel. The percentage of full-length ribozyme at each time point is determined by Phosphor Imager® quantitation of bands representing the intact ribozyme and the degradation products. A non-limiting example of a ribozyme of the instant invention utilizing phosphorothioate and/or phosphorodithioate modifications in a stabilized 2'-O-methyl ribonucleotide background with essential "core ribonucleotides" is shown in FIG. 8. The incorporation of phosphorothioate and/or phosphorodithioate linkages into the enzymatic nucleic acid of the instant invention results in increased serum stability. Replacement of the 3'-phosphodiester at position 6 with a phosphorothioate or phosphorodithioate linkage (FIG. 8) stabilizes the conserved position 6 ribose moiety, which is prone to nucleolytic cleavage. In a study investigating the serum stability of position 6 modified ribozyme variants which preserve the 2'-hydroxyl function at position 6 (FIG. 8), the relative stability of the modifications were ranked as follows:

3'-Phosphorodithioate>>3'-Phosphorothioate>>4'-Thioribofuranose>Phosphodiester

Example 10

Cell Culture Models

A selected group of 96 G-cleaver ribozymes targeting K-ras RNA (Table V) were tested in human colorectal cancer cells with a mutated K-ras allele (DLD-1), ovarian cancer cells with a mutated K-ras allele (SKOV3), and human colorectal cancer cells with a mutated K-ras allele (SW680). Cells were plated into four 96 well plates at 15000 cells/well. The 96 ribozymes were split into four groups (on four plates) to be able to include the appropriate controls on each plate. The ribozymes were transfected at 100 nM concentration with 5 µg/ml of GSV and incubated overnight Total RNA was prepared 24 hr after transfection using a Quiagen 96 well Rneasy® kit. An additional DNaseI treatment to remove traces of DNA was introduced. RT reactions were prepared using 4 µl of the RNA eluate with a Clontech RT-kit. Analyses were performed using a Multiplex Taqman® assay (PE ABI Prism® 7700 Sequence Detection System User Bulletin #5, © Copyright 1998, The Perkin-Elmer Corporation) using actin as a control. Results indicate that ribozyme (RPI No. 12819, Table V) reduced K-ras mRNA levels by 50% in DLD-1 cells and SKOV3 cells.

Diagnostic Uses

Enzymatic nucleic acids of this invention may be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These experiments will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by determining the presence of a cleavage product after treatment with a ribozyme using standard methodology.

In a specific example, ribozymes which can cleave only wild-type or mutant forms of the target RNA are used for the assay. The first ribozyme is used to identify wild-type RNA present in the sample and the second ribozyme will be used to identify mutant RNA in the sample. As reaction controls, synthetic substrates of both wild-type and mutant RNA will be cleaved by both ribozymes to demonstrate the relative ribozyme efficiencies in the reactions and the absence of cleavage of the "non-targeted" RNA species. The cleavage products from the synthetic substrates will also serve to generate size markers for the analysis of wild-type and mutant RNAs in the sample population. Thus, each analysis can involve two ribozymes, two substrates and one unknown sample which will be combined into six reactions. The presence of cleavage products will be determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential usefulness of sequence-specific enzymatic nucleic acid molecules of the instant invention can have many of the same applications for the study of RNA that DNA restriction endonucleases have for the study of DNA (Nathans et al., 1975 *Ann. Rev. Biochem.* 44:273). For example, the pattern of restriction fragments could be used to establish sequence relationships between two related RNAs, and large RNAs could be specifically cleaved to fragments of a size more useful for study. The ability to engineer sequence specificity of the ribozyme is ideal for cleavage of RNAs of unknown sequence.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terns and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

TABLE I

| Reagent | Equivalents | Amount | Wait Time* | Wait Time* |
|---|---|---|---|---|
| A. 2.5 μmol Synthesis Cycle ABI 394 Instrument | | | | |
| | | | 2'-O-methyl | RNA |
| Phosphoramidites | 6.5 | 163 μL | 2.5 min | 7.5 |
| S-Ethyl Tetrazole | 23.8 | 238 μL | 2.5 min | 7.5 |
| Acetic Anhydride | 100 | 233 μL | 5 sec | 5 sec |
| N-Methyl Imidazole | 186 | 233 μL | 5 sec | 5 sec |
| TCA | 110.1 | 2.3 mL | 21 sec | 21 sec |
| Iodine | 11.2 | 1.7 mL | 45 sec | 45 sec |
| Acetonitrile | NA | 6.67 mL | NA | NA |
| B. 0.2 μmol Synthesis Cycle ABI 394 Instrument | | | | |
| | | | 2'-O-methyl | RNA |
| Phosphoramidites | 15 | 31 μL | 233 sec | 465 sec |
| S-Ethyl Tetrazole | 38.7 | 31 μL | 233 min | 465 sec |
| Acetic Anhydride | 655 | 124 μL | 5 sec | 5 sec |
| N-Methyl Imidazole | 1245 | 124 μL | 5 sec | 5 sec |
| TCA | 700 | 732 μL | 10 sec | 10 sec |
| Iodine | 20.6 | 244 μL | 15 sec | 15 sec |
| Acetonitrile | NA | 2.64 mL | NA | NA |
| C. 0.2 μmol Synthesis Cycle 96 well Instrument | | | | |
| | 2'-O-methyl/ Ribo | 2'-O-methyl/ Ribo | 2'-O-methyl | Ribo |
| Phosphoramidites | 33/66 | 60/120 μL | 233 sec | 465 sec |
| S-Ethyl Tetrazole | 75/150 | 60/120 μL | 233 min | 465 sec |
| Acetic Anhydride | 50/50 | 50/50 μL | 10 sec | 10 sec |
| N-Methyl Imidazole | 502/502 | 50/50 μL | 10 sec | 10 sec |
| TCA | 16,000/16,000 | 500/500 μL | 15 sec | 15 sec |
| Iodine | 6.8/6.8 | 80/80 μL | 30 sec | 30 sec |
| Acetonitrile | NA | 850/850 μL | NA | NA |

* Wait time does not include contact time during delivery.

TABLE II

Human K-ras Ribozyme and Target Sequence

| Nt. Position | Substrate Sequence | | Seq. ID Nos. | Ribozyme Sequence | | Seq. ID Nos. |
|---|---|---|---|---|---|---|
| 16 | GGCGGCGGCC | G CGGCG | 1 | CGCCG UGAUGGCAUGCACUAUGCGCG | GGCCGCCGCC | 528 |
| 57 | UGGCGGCGGC | G AAGGU | 2 | ACCUU UGAUGGCAUGCACUAUGCGCG | GCCGCCGCCA | 529 |
| 94 | CCCGGCCCCC | G CCAUU | 3 | AAUGG UGAUGGCAUGCACUAUGCGCG | GGGGGCCGGG | 530 |
| 113 | GACUGGGAGC | G AGCGC | 4 | GCGCU UGAUGGCAUGCACUAUGCGCG | GCUCCCAGUC | 531 |
| 117 | GGGAGCGAGC | G CGGCG | 5 | CGCCG UGAUGGCAUGCACUAUGCGCG | GCUCGCUCCC | 532 |
| 122 | CGAGCGCGGC | G CAGGC | 6 | GCCUG UGAUGGCAUGCACUAUGCGCG | GCCGCGCUCG | 533 |
| 131 | CGCAGGCACU | G AAGGC | 7 | GCCUU UGAUGGCAUGCACUAUGCGCG | AGUGCCUGCG | 534 |
| 171 | GCUCCCAGGU | G CGGGA | 8 | UCCCG UGAUGGCAUGCACUAUGCGCG | ACCUGGGAGC | 535 |
| 186 | AGAGAGGCCU | G CUGAA | 9 | UUCAG UGAUGGCAUGCACUAUGCGCG | AGGCCUCUCU | 536 |
| 189 | GAGGCCUGCU | G AAAAU | 10 | AUUUU UGAUGGCAUGCACUAUGCGCG | AGCAGGCCUC | 537 |
| 195 | UGCUGAAAAU | G ACUGA | 11 | UCAGU UGAUGGCAUGCACUAUGCGCG | AUUUUCAGCA | 538 |
| 199 | GAAAAUGACU | G AAUAU | 12 | AUAUU UGAUGGCAUGCACUAUGCGCG | AGUCAUUUUC | 539 |
| 203 | AUGACUGAAU | A UAAAC | 13 | GUUUA UGAUGGCAUGCACUAUGCGCG | AUUCAGUCAU | 540 |
| 205 | GACUGAAUAU | A AACUU | 14 | AAGUU UGAUGGCAUGCACUAUGCGCG | AUAUUCAGUC | 541 |
| 211 | AUAUAAACUU | G UGGUA | 15 | UACCA UGAUGGCAUGCACUAUGCGCG | AAGUUUAUAU | 542 |

TABLE II-continued

Human K-ras Ribozyme and Target Sequence

| Nt. Position | Substrate Sequence | Seq. ID Nos. | Ribozyme Sequence | Seq. ID Nos. |
|---|---|---|---|---|
| 227 | GUUGGAGCUU G UGGCG | 16 | CGCCA UGAUGGCAUGCACUAUGCGCG AAGCUCCAAC | 543 |
| 244 | AGGCAAGAGU G CCUUG | 17 | CAAGG UGAUGGCAUGCACUAUGCGCG ACUCUUGCCU | 544 |
| 249 | AGAGUGCCUU G ACGAU | 18 | AUCGU UGAUGGCAUGCACUAUGCGCG AAGGCACUCU | 545 |
| 252 | GUGCCUUGAC G AUACA | 19 | UGUAU UGAUGGCAUGCACUAUGCGCG GUCAAGGCAC | 546 |
| 255 | CCUUGACGAU A CAGCU | 20 | AGCUG UGAUGGCAUGCACUAUGCGCG AUCGUCAAGG | 547 |
| 277 | GAAUCAUUUU G UGGAC | 21 | GUCCA UGAUGGCAUGCACUAUGCGCG AAAAUGAUUC | 548 |
| 283 | UUUUGUGGAC G AAUAU | 22 | AUAUU UGAUGGCAUGCACUAUGCGCG GUCCACAAAA | 549 |
| 287 | GUGGACGAAU A UGAUC | 23 | GAUCA UGAUGGCAUGCACUAUGCGCG AUUCGUCCAC | 550 |
| 289 | GGACGAAUAU G AUCCA | 24 | UGGAU UGAUGGCAUGCACUAUGCGCG AUAUUCGUCC | 551 |
| 300 | AUCCAACAAU G AGGA | 25 | UCCUC UGAUGGCAUGCACUAUGCGCG AUUGUUGGAU | 552 |
| 331 | AGUAGUAAUU G AUGGA | 26 | UCCAU UGAUGGCAUGCACUAUGCGCG AAUUACUACU | 553 |
| 334 | AGUAAUUGAU G GAGAA | 27 | UUCUC UGAUGGCAUGCACUAUGCGCG AUCAAUUACU | 554 |
| 344 | GGAGAAACCU G UCUCU | 28 | AGAGA UGAUGGCAUGCACUAUGCGCG AGGUUUCUCC | 555 |
| 355 | UCUCUUGGAU A UUCUC | 29 | GAGAA UGAUGGCAUGCACUAUGCGCG AUCCAAGAGA | 556 |
| 361 | GGAUAUUCUC G ACACA | 30 | UGUGU UGAUGGCAUGCACUAUGCGCG GAGAAUAUCC | 557 |
| 388 | GGAGUACAGU G CAAUG | 31 | CAUUG UGAUGGCAUGCACUAUGCGCG ACUGUACUCC | 558 |
| 393 | ACAGUGCAAU G AGGGA | 32 | UCCCU UGAUGGCAUGCACUAUGCGCG AUUGCACUGU | 559 |
| 408 | ACCAGUACAU G AGGAC | 33 | GUCCU UGAUGGCAUGCACUAUGCGCG AUGUACUGGU | 560 |
| 431 | GGCUUUCUUU G UGUAU | 34 | AUACA UGAUGGCAUGCACUAUGCGCG AAAGAAAGCC | 561 |
| 433 | CUUUCUUUGU G UAUUU | 35 | AAAUA UGAUGGCAUGCACUAUGCGCG ACAAAGAAAG | 562 |
| 439 | UUGUGUAUUU G CCAUA | 36 | UAUGG UGAUGGCAUGCACUAUGCGCG AAAUACACAA | 563 |
| 444 | UAUUUGCCAU A AAUAA | 37 | UUAUU UGAUGGCAUGCACUAUGCGCG AUGGCAAAUA | 564 |
| 448 | UGCCAUAAAU A AUACU | 38 | AGUAU UGAUGGCAUGCACUAUGCGCG AUUUAUGGCA | 565 |
| 451 | CAUAAAUAAU A CUAAA | 39 | UUUAG UGAUGGCAUGCACUAUGCGCG AUUAUUUAUG | 566 |
| 463 | UAAAUCAUUU G AAGAU | 40 | AUCUU UGAUGGCAUGCACUAUGCGCG AAAUGAUUUA | 567 |
| 469 | AUUUGAAGAU A UUCAC | 41 | GUGAA UGAUGGCAUGCACUAUGCGCG AUCUUCAAAU | 568 |
| 481 | UCACCAUUAU A GAGAA | 42 | UUCUC UGAUGGCAUGCACUAUGCGCG AUAAUGGUGA | 569 |
| 511 | UAAGGACUCU G AAGAU | 43 | AUCUU UGAUGGCAUGCACUAUGCGCG AGAGUCCUUA | 570 |
| 517 | CUCUGAAGAU G UACCU | 44 | AGGUA UGAUGGCAUGCACUAUGCGCG AUCUUCAGAG | 571 |
| 525 | AUGUACCUAU G GUCCU | 45 | AGGAC UGAUGGCAUGCACUAUGCGCG AUAGGUACAU | 572 |
| 541 | AGUAGGAAAU A AAUGU | 46 | ACAUU UGAUGGCAUGCACUAUGCGCG AUUUCCUACU | 573 |
| 545 | GGAAAUAAAU G UGAUU | 47 | AAUCA UGAUGGCAUGCACUAUGCGCG AUUUAUUUCC | 574 |
| 547 | AAAUAAAUGU G AUUUG | 48 | CAAAU UGAUGGCAUGCACUAUGCGCG ACAUUUAUUU | 575 |
| 552 | AAUGUGAUUU G CCUUC | 49 | GAAGG UGAUGGCAUGCACUAUGCGCG AAAUCACAUU | 576 |
| 604 | AAGAAGUUAU G GAAUU | 50 | AAUUC UGAUGGCAUGCACUAUGCGCG AUAACUUCUU | 577 |
| 619 | UCCUUUUAUU G AAACA | 51 | UGUUU UGAUGGCAUGCACUAUGCGCG AAUAAAAGGA | 578 |
| 646 | AAGACAGGGU G UUGAU | 52 | AUCAA UGAUGGCAUGCACUAUGCGCG ACCCUGUCUU | 579 |
| 649 | ACAGGGUGUU G AUGAU | 53 | AUCAU UGAUGGCAUGCACUAUGCGCG AACACCCUGU | 580 |
| 652 | GGGUGUUGAU G AUGCC | 54 | GGCAU UGAUGGCAUGCACUAUGCGCG AUCAACACCC | 581 |
| 655 | UGUUGAUGAU G CCUUC | 55 | GAAGG UGAUGGCAUGCACUAUGCGCG AUCAUCAACA | 582 |
| 664 | UGCCUUCUAU A CAUUA | 56 | UAAUG UGAUGGCAUGCACUAUGCGCG AUAGAAGGCA | 583 |
| 674 | ACAUUAGUUC G AGAAA | 57 | UUUCU UGAUGGCAUGCACUAUGCGCG GAACUAAUGU | 584 |
| 683 | CGAGAAAUUC G AAAAC | 58 | GUUUU UGAUGGCAUGCACUAUGCGCG GAAUUUCUCG | 585 |
| 691 | UCGAAAACAU A AAGAA | 59 | UUCUU UGAUGGCAUGCACUAUGCGCG AUGUUUUCGA | 586 |
| 702 | AAGAAAAGAU G AGCAA | 60 | UUGCU UGAUGGCAUGCACUAUGCGCG AUCUUUUCUU | 587 |
| 712 | GAGCAAAGAU G GUAAA | 61 | UUUAC UGAUGGCAUGCACUAUGCGCG AUCUUUGCUC | 588 |
| 746 | AAGACAAAGU G UGUAA | 62 | UUACA UGAUGGCAUGCACUAUGCGCG ACACUUGUCUU | 589 |
| 748 | GACAAAGUGU G UAAUU | 63 | AAUUA UGAUGGCAUGCACUAUGCGCG ACACUUUGUC | 590 |
| 756 | GUGUAAUUAU G UAAAU | 64 | AUUUA UGAUGGCAUGCACUAUGCGCG AUAAUUACAC | 591 |
| 762 | UUAUGUAAAU A CAAUU | 65 | AAUUG UGAUGGCAUGCACUAUGCGCG AUUUACAUAA | 592 |
| 769 | AAUACAAUUU G UACUU | 66 | AAGUA UGAUGGCAUGCACUAUGCGCG AAAUUGUAUU | 593 |
| 789 | CUUAAGGCAU A CUAGU | 67 | ACUAG UGAUGGCAUGCACUAUGCGCG AUGCCUUAAG | 594 |
| 811 | GGUAAUUUUU G UACAU | 68 | AUGUA UGAUGGCAUGCACUAUGCGCG AAAAAUUACC | 595 |
| 838 | AUUAGCAUUU G UUUUA | 69 | UAAAA UGAUGGCAUGCACUAUGCGCG AAAUGCUAAU | 596 |
| 865 | UUUUUUUCCU G CUCCA | 70 | UGGAG UGAUGGCAUGCACUAUGCGCG AGGAAAAAAA | 597 |
| 872 | CCUGCUCCAU G CAGAC | 71 | GUCUG UGAUGGCAUGCACUAUGCGCG AUGGAGCAGG | 598 |
| 879 | CAUGCAGACU G UUAGC | 72 | GCUAA UGAUGGCAUGCACUAUGCGCG AGUCUGCAUG | 599 |
| 898 | UACCUAAAAU G CUUAU | 73 | AUAAG UGAUGGCAUGCACUAUGCGCG AUUUAAGGUA | 600 |
| 912 | AUUUUAAAAU G ACAGU | 74 | ACUGU UGAUGGCAUGCACUAUGCGCG AUUUUAAAAU | 601 |
| 936 | UUUUUUCCUC G AAGUG | 75 | CACUU UGAUGGCAUGCACUAUGCGCG GAGGAAAAAA | 602 |
| 941 | UCCUCGAAGU G CCAGU | 76 | ACUGG UGAUGGCAUGCACUAUGCGCG ACUUCGAGGA | 603 |
| 968 | UUUGGUUUUU G AACUA | 77 | UAGUU UGAUGGCAUGCACUAUGCGCG AAAAACCAAA | 604 |
| 979 | AACUAGCAAU G CCUGU | 78 | ACAGG UGAUGGCAUGCACUAUGCGCG AUUGCUAGUU | 605 |
| 983 | AGCAAUGCCU G UGAAA | 79 | UUUCA UGAUGGCAUGCACUAUGCGCG AGGCAUUGCU | 606 |
| 985 | CAAUGCCUGU G AAAAA | 80 | UUUUU UGAUGGCAUGCACUAUGCGCG ACAGGCAUUG | 607 |
| 997 | AAAAGAAACU G AAUAC | 81 | GUAUU UGAUGGCAUGCACUAUGCGCG AGUUUCUUUU | 608 |
| 1001 | GAAACUGAAU A CCUAA | 82 | UUAGG UGAUGGCAUGCACUAUGCGCG AUUCAGUUUC | 609 |
| 1014 | UAAGAUUUCU G UCUUG | 83 | CAAGA UGAUGGCAUGCACUAUGCGCG AGAAAUCUUA | 610 |
| 1031 | GGUUUUUGGU G CAUGC | 84 | GCAUG UGAUGGCAUGCACUAUGCGCG ACCAAAAACC | 611 |
| 1035 | UUUGGUGCAU G CAGUU | 85 | AACUG UGAUGGCAUGCACUAUGCGCG AUGCACCAAA | 612 |
| 1041 | GCAUGCAGUU G AUUAC | 86 | GUAAU UGAUGGCAUGCACUAUGCGCG AACUGCAUGC | 613 |
| 1068 | CUUACCAAGU G UGAAU | 87 | AUUCA UGAUGGCAUGCACUAUGCGCG ACUUGGUAAG | 614 |
| 1070 | UACCAAGUGU G AAUGU | 88 | ACAUU UGAUGGCAUGCACUAUGCGCG ACACUUGGUA | 615 |
| 1074 | AAGUGUGAAU G UUGGU | 89 | ACCAA UGAUGGCAUGCACUAUGCGCG AUUCACACUU | 616 |

TABLE II-continued

Human K-ras Ribozyme and Target Sequence

| Nt. Position | Substrate Sequence | Seq. ID Nos. | Ribozyme Sequence | Seq. ID Nos. |
|---|---|---|---|---|
| 1080 | GAAUGUUGGU G UGAAA | 90 | UUUCA UGAUGGCAUGCACUAUGCGCG ACCAACAUUC | 617 |
| 1082 | AUGUUGGUGU G AAACA | 91 | UGUUU UGAUGGCAUGCACUAUGCGCG ACACCAACAU | 618 |
| 1095 | ACAAAUUAAU G AAGCU | 92 | AGCUU UGAUGGCAUGCACUAUGCGCG AUUAAUUUGU | 619 |
| 1104 | UGAAGCUUUU G AAUCA | 93 | UGAUU UGAUGGCAUGCACUAUGCGCG AAAAGCUUCA | 620 |
| 1120 | UCCCUAUUCU G UGUUU | 94 | AAACA UGAUGGCAUGCACUAUGCGCG AGAAUAGGGA | 621 |
| 1122 | CCUAUUCUGU G UUUUA | 95 | UAAAA UGAUGGCAUGCACUAUGCGCG ACAGAAUAGG | 622 |
| 1139 | CUAGUCACAU A AAUGG | 96 | CCAUU UGAUGGCAUGCACUAUGCGCG AUGUGACUAG | 623 |
| 1143 | UCACAUAAAU G GAUUA | 97 | UAAUC UGAUGGCAUGCACUAUGCGCG AUUUAUGUGA | 624 |
| 1165 | AAUUUCAGUU G AGACC | 98 | GGUCU UGAUGGCAUGCACUAUGCGCG AACUGAAAUU | 625 |
| 1189 | GGUUUUUACU G AAACA | 99 | UGUUU UGAUGGCAUGCACUAUGCGCG AGUAAAAACC | 626 |
| 1197 | CUGAAACAUU G AGGGA | 100 | UCCCU UGAUGGCAUGCACUAUGCGCG AAUGUUUCAG | 627 |
| 1214 | ACAAAUUUAU G GGCUU | 101 | AAGCC UGAUGGCAUGCACUAUGCGCG AUAAAUUUGU | 628 |
| 1223 | UGGGCUUCCU G AUGAU | 102 | AUCAU UGAUGGCAUGCACUAUGCGCG AGGAAGCCCA | 629 |
| 1226 | GCUUCCUGAU G AUGAU | 103 | AUCAU UGAUGGCAUGCACUAUGCGCG AUCAGGAAGC | 630 |
| 1229 | UCCUGAUGAU G AUUCU | 104 | AGAAU UGAUGGCAUGCACUAUGCGCG AUCAUCAGGA | 631 |
| 1247 | UAGGCAUCAU G UCCUA | 105 | UAGGA UGAUGGCAUGCACUAUGCGCG AUGAUGCCUA | 632 |
| 1254 | CAUGUCCUAU A GUUUG | 106 | CAAAC UGAUGGCAUGCACUAUGCGCG AUAGGACAUG | 633 |
| 1259 | CCUAUAGUUU G UCAUC | 107 | GAUGA UGAUGGCAUGCACUAUGCGCG AAACUAUAGG | 634 |
| 1268 | UGUCAUCCCU G AUGAA | 108 | UUCAU UGAUGGCAUGCACUAUGCGCG AGGGAUGACA | 635 |
| 1271 | CAUCCCUGAU G AAUGU | 109 | ACAUU UGAUGGCAUGCACUAUGCGCG AUCAGGGAUG | 636 |
| 1275 | CCUGAUGAAU G UAAAG | 110 | CUUUA UGAUGGCAUGCACUAUGCGCG AUUCAUCAGG | 637 |
| 1288 | AAGUUACACU G UUCAC | 111 | GUGAA UGAUGGCAUGCACUAUGCGCG AGUGUAACUU | 638 |
| 1303 | CAAAGGUUUU G UCUCC | 112 | GGAGA UGAUGGCAUGCACUAUGCGCG AAAACCUUUG | 639 |
| 1317 | CCUUUCCACU G CUAUU | 113 | AAUAG UGAUGGCAUGCACUAUGCGCG AGUGGAAAGG | 640 |
| 1329 | UAUUAGUCAU G GUCAC | 114 | GUGAC UGAUGGCAUGCACUAUGCGCG AUGACUAAUA | 641 |
| 1347 | UCCCCAAAAU A UUAUA | 115 | UAUAA UGAUGGCAUGCACUAUGCGCG AUUUUGGGGA | 642 |
| 1352 | AAAAUAUUAU A UUUUU | 116 | AAAAA UGAUGGCAUGCACUAUGCGCG AUAAUAUUUU | 643 |
| 1363 | UUUUUUCUAU A AAAAG | 117 | CUUUU UGAUGGCAUGCACUAUGCGCG AUAGAAAAAA | 644 |
| 1377 | AGAAAAAAGU G GAAAA | 118 | UUUUC UGAUGGCAUGCACUAUGCGCG AUUUUUUUCU | 645 |
| 1398 | ACAAGGCAAU G GAAAC | 119 | GUUUC UGAUGGCAUGCACUAUGCGCG AUUGCCUUGU | 646 |
| 1410 | AAACUAUUAU A AGGCC | 120 | GGCCU UGAUGGCAUGCACUAUGCGCG AUAAUAGUUU | 647 |
| 1436 | CACAUUAGAU A AAUUA | 121 | UAAUU UGAUGGCAUGCACUAUGCGCG AUCUAAUGUG | 648 |
| 1446 | AAAUUACUAU A AAGAC | 122 | GUCUU UGAUGGCAUGCACUAUGCGCG AUAGUAAUUU | 649 |
| 1459 | GACUCCUAAU A GCUUU | 123 | AAAGC UGAUGGCAUGCACUAUGCGCG AUUAGGAGUC | 650 |
| 1470 | GCUUUUUCCU G UUAAG | 124 | CUUAA UGAUGGCAUGCACUAUGCGCG AGGAAAAAGC | 651 |
| 1489 | GACCCAGUAU G AAUGG | 125 | CCAUU UGAUGGCAUGCACUAUGCGCG AUACUGGGUC | 652 |
| 1493 | CAGUAUGAAU G GGAUU | 126 | AAUCC UGAUGGCAUGCACUAUGCGCG AUUCAUACUG | 653 |
| 1504 | GGAUUAUUAU A GCAAC | 127 | GUUGC UGAUGGCAUGCACUAUGCGCG AUAAUAAUCC | 654 |
| 1524 | UUGGGGCUAU A UUUAC | 128 | GUAAA UGAUGGCAUGCACUAUGCGCG AUAGCCCCAA | 655 |
| 1532 | AUAUUUACAU G CUACU | 129 | AGUAG UGAUGGCAUGCACUAUGCGCG AUGUAAAUAU | 656 |
| 1548 | AAAUUUUUAU A AUAAU | 130 | AUUAU UGAUGGCAUGCACUAUGCGCG AUAAAAAUUU | 657 |
| 1551 | UUUUUAUAAU A AUUGA | 131 | UCAAU UGAUGGCAUGCACUAUGCGCG AUUAUAAAAA | 658 |
| 1555 | UAUAAUAAUU G AAAAG | 132 | CUUUU UGAUGGCAUGCACUAUGCGCG AAUUAUUAUA | 659 |
| 1575 | UAACAAGUAU G AAAAA | 133 | UUUUU UGAUGGCAUGCACUAUGCGCG AUACUUGUUA | 660 |
| 1589 | AAAUUCUCAU A GGAAU | 134 | AUUCC UGAUGGCAUGCACUAUGCGCG AUGAGAAUUU | 661 |
| 1600 | GGAAUUAAAU G UAGUC | 135 | GACUA UGAUGGCAUGCACUAUGCGCG AUUUAAUUCC | 662 |
| 1611 | UAGUCUCCCU G UGUCA | 136 | UGACA UGAUGGCAUGCACUAUGCGCG AGGGAGACUA | 663 |
| 1613 | GUCUCCCUGU G UCAGA | 137 | UCUGA UGAUGGCAUGCACUAUGCGCG ACAGGGAGAC | 664 |
| 1621 | GUGUCAGACU G CUCUU | 138 | AAGAG UGAUGGCAUGCACUAUGCGCG AGUCUGACAC | 665 |
| 1631 | GCUCUUUCAU A GUAUA | 139 | UAUAC UGAUGGCAUGCACUAUGCGCG AUGAAAGAGC | 666 |
| 1636 | UUCAUAGUAU A ACUUU | 140 | AAAGU UGAUGGCAUGCACUAUGCGCG AUACUAUGAA | 667 |
| 1660 | UCUUCAACUU G AGUCU | 141 | AGACU UGAUGGCAUGCACUAUGCGCG AAGUUGAAGA | 668 |
| 1668 | UUGAGUCUUU G AAGAU | 142 | AUCUU UGAUGGCAUGCACUAUGCGCG AAAGACUCAA | 669 |
| 1674 | CUUUGAAGAU A GUUUU | 143 | AAAAC UGAUGGCAUGCACUAUGCGCG AUCUUCAAAG | 670 |
| 1686 | UUUUAAUUCU G CUUGU | 144 | ACAAG UGAUGGCAUGCACUAUGCGCG AGAAUUAAAA | 671 |
| 1690 | AAUUCUGCUU G UGACA | 145 | UGUCA UGAUGGCAUGCACUAUGCGCG AAGCAGAAUU | 672 |
| 1692 | UUCUGCUUGU G ACAUU | 146 | AAUGU UGAUGGCAUGCACUAUGCGCG ACAAGCAGAA | 673 |
| 1721 | GGCCAGUUAU A GCUUA | 147 | UAAGC UGAUGGCAUGCACUAUGCGCG AUAACUGGCC | 674 |
| 1733 | CUUAUUAGGU G UUGAA | 148 | UUCAA UGAUGGCAUGCACUAUGCGCG ACCUAAUAAG | 675 |
| 1736 | AUUAGGUGUU G AAGAG | 149 | CUCUU UGAUGGCAUGCACUAUGCGCG AACACCUAAU | 676 |
| 1751 | GACCAAGGUU G CAAGC | 150 | GCUUG UGAUGGCAUGCACUAUGCGCG AACCUUGGUC | 677 |
| 1765 | GCCAGGCCCU G UGUGA | 151 | UCACA UGAUGGCAUGCACUAUGCGCG AGGGCCUGGC | 678 |
| 1767 | CAGGCCCUGU G UGAAC | 152 | GUUCA UGAUGGCAUGCACUAUGCGCG ACAGGGCCUG | 679 |
| 1769 | GGCCCUGUGU G AACCU | 153 | AGGUU UGAUGGCAUGCACUAUGCGCG ACACAGGGCC | 680 |
| 1776 | UGUGAACCUU G AGCUU | 154 | AAGCU UGAUGGCAUGCACUAUGCGCG AAGGUUCACA | 681 |
| 1786 | GAGCUUUCAU A GAGAG | 155 | CUCUC UGAUGGCAUGCACUAUGCGCG AUGAAAGCUC | 682 |
| 1803 | UUCACAGCAU G GACUG | 156 | CAGUC UGAUGGCAUGCACUAUGCGCG AUGCUGUGAA | 683 |
| 1808 | AGCAUGGACU G UGUGC | 157 | GCACA UGAUGGCAUGCACUAUGCGCG AGUCCAUGCU | 684 |
| 1810 | CAUGGACUGU G UGCCC | 158 | GGGCA UGAUGGCAUGCACUAUGCGCG ACAGUCCAUG | 685 |
| 1812 | UGGACUGUGU G CCCCA | 159 | UGGGG UGAUGGCAUGCACUAUGCGCG ACACAGUCCA | 686 |
| 1827 | ACGUCAUCC G AGUGG | 160 | CCACU UGAUGGCAUGCACUAUGCGCG GGAUGACGU | 687 |
| 1835 | CCGAGUGGUU G UACGA | 161 | UCGUA UGAUGGCAUGCACUAUGCGCG AACCACUCGG | 688 |
| 1839 | GUGGUUGUAC G AUGCA | 162 | UGCAU UGAUGGCAUGCACUAUGCGCG GUACAACCAC | 689 |
| 1842 | GUUGUACGAU G CAUUG | 163 | CAAUG UGAUGGCAUGCACUAUGCGCG AUCGUACAAC | 690 |

TABLE II-continued

Human K-ras Ribozyme and Target Sequence

| Nt. Position | Substrate Sequence | Seq. ID Nos. | Ribozyme Sequence | Seq. ID Nos. |
|---|---|---|---|---|
| 1861 | AGUCAAAAAU G GGGAG | 164 | CUCCC UGAUGGCAUGCACUAUGCGCG AUUUUUGACU | 691 |
| 1886 | CAGUUUGGAU A GCUCA | 165 | UGAGC UGAUGGCAUGCACUAUGCGCG AUCCAAACUG | 692 |
| 1899 | UCAACAAGAU A CAAUC | 166 | GAUUG UGAUGGCAUGCACUAUGCGCG AUCUUGUUGA | 693 |
| 1912 | AUCUCACUCU G UGGUG | 167 | CACCA UGAUGGCAUGCACUAUGCGCG AGAGUGAGAU | 694 |
| 1923 | UGGUGGUCCU G CUGAC | 168 | GUCAG UGAUGGCAUGCACUAUGCGCG AGGACCACCA | 695 |
| 1926 | UGGUCCUGCU G ACAAA | 169 | UUUGU UGAUGGCAUGCACUAUGCGCG AGCAGGACCA | 696 |
| 1943 | CAAGAGCAUU G CUUUU | 170 | AAAAG UGAUGGCAUGCACUAUGCGCG AAUGCUCUUG | 697 |
| 1949 | CAUUGCUUUU G UUUCU | 171 | AGAAA UGAUGGCAUGCACUAUGCGCG AAAAGCAAUG | 698 |
| 1993 | ACUUUUAAAU A UUAAC | 172 | GUUAA UGAUGGCAUGCACUAUGCGCG AUUUAAAAGU | 699 |
| 2008 | CUCAAAAGUU G AGAUU | 173 | AAUCU UGAUGGCAUGCACUAUGCGCG AACUUUUGAG | 700 |
| 2027 | GGGUGGUGGU G UGCCA | 174 | UGGCA UGAUGGCAUGCACUAUGCGCG ACCACCACCC | 701 |
| 2029 | GUGGUGUGU G CCAAG | 175 | CUUGG UGAUGGCAUGCACUAUGCGCG ACACCACCAC | 702 |
| 2059 | UUUAAACAAU G AAGUG | 176 | CACUU UGAUGGCAUGCACUAUGCGCG AUUGUUUAAA | 703 |
| 2064 | ACAAUGAAGU G AAAAA | 177 | UUUUU UGAUGGCAUGCACUAUGCGCG ACUUCAUUGU | 704 |
| 2124 | AAUUAACAUU G CAUAA | 178 | UUAUG UGAUGGCAUGCACUAUGCGCG AAUGUUAAUU | 705 |
| 2128 | AACAUUGCAU A AACAC | 179 | GUGUU UGAUGGCAUGCACUAUGCGCG AUGCAAUGUU | 706 |
| 2145 | UUUCAAGUCU G AUCCA | 180 | UGGAU UGAUGGCAUGCACUAUGCGCG AGACUUGAAA | 707 |
| 2152 | UCUGAUCCAU A UUUAA | 181 | UUAAA UGAUGGCAUGCACUAUGCGCG AUGGAUCAGA | 708 |
| 2159 | CAUAUUUAAU A AUGCU | 182 | AGCAU UGAUGGCAUGCACUAUGCGCG AUUAAAUAUG | 709 |
| 2162 | AUUUAAUAAU G CUUUA | 183 | UAAAG UGAUGGCAUGCACUAUGCGCG AUUAUUAAAU | 710 |
| 2172 | GCUUUAAAAU A AAAAU | 184 | AUUUU UGAUGGCAUGCACUAUGCGCG AUUUUAAAGC | 711 |
| 2178 | AAAUAAAAAU A AAAAC | 185 | GUUUU UGAUGGCAUGCACUAUGCGCG AUUUUUAUUU | 712 |
| 2193 | CAAUCCUUUU G AUAAA | 186 | UUUAU UGAUGGCAUGCACUAUGCGCG AAAAGGAUUG | 713 |
| 2196 | UCCUUUUGAU A AAUUU | 187 | AAAUU UGAUGGCAUGCACUAUGCGCG AUCAAAAGGA | 714 |
| 2207 | AAUUUAAAAU G UUACU | 188 | AGUAA UGAUGGCAUGCACUAUGCGCG AUUUUAAAUU | 715 |
| 2224 | AUUUUAAAAU A AAUGA | 189 | UCAUU UGAUGGCAUGCACUAUGCGCG AUUUUAAAAU | 716 |
| 2228 | UAAAAUAAAU G AAGUG | 190 | CACUU UGAUGGCAUGCACUAUGCGCG AUUUAUUUUA | 717 |
| 2233 | UAAAUGAAGU G AGAUG | 191 | CAUCU UGAUGGCAUGCACUAUGCGCG ACUUCAUUUA | 718 |
| 2238 | GAAGUGAGAU G GCAUG | 192 | CAUGC UGAUGGCAUGCACUAUGCGCG AUCUCACUUC | 719 |
| 2243 | GAGAUGGCAU G GUGAG | 193 | CUCAC UGAUGGCAUGCACUAUGCGCG AUGCCAUCUC | 720 |
| 2246 | AUGGCAUGGU G AGGUG | 194 | CACCU UGAUGGCAUGCACUAUGCGCG ACCAUGCCAU | 721 |
| 2251 | AUGGUGAGGU G AAAGU | 195 | ACUUU UGAUGGCAUGCACUAUGCGCG ACCUCACCAU | 722 |
| 2273 | GGACUAGGUU G UUGGU | 196 | ACCAA UGAUGGCAUGCACUAUGCGCG AACCUAGUCC | 723 |
| 2279 | GGUUGUUGGU G ACUUA | 197 | UAAGU UGAUGGCAUGCACUAUGCGCG ACCAACAACC | 724 |
| 2295 | GGUUCUAGAU A GGUGU | 198 | ACACC UGAUGGCAUGCACUAUGCGCG AUCUAGAACC | 725 |
| 2299 | CUAGAUAGGU G UCUUU | 199 | AAAGA UGAUGGCAUGCACUAUGCGCG ACCUAUCUAG | 726 |
| 2314 | UUAGGACUCU G AUUUU | 200 | AAAAU UGAUGGCAUGCACUAUGCGCG AGAGUCCUAA | 727 |
| 2320 | CUCUGAUUUU G AGGAC | 201 | GUCCU UGAUGGCAUGCACUAUGCGCG AAAAUCAGAG | 728 |
| 2350 | AUUUCUUCAU G UUAAA | 202 | UUUAA UGAUGGCAUGCACUAUGCGCG AUGAAGAAAU | 729 |
| 2397 | UUUACACUAU G UGAUU | 203 | AAUCA UGAUGGCAUGCACUAUGCGCG AUAGUGUAAA | 730 |
| 2399 | UACACUAUGU G AUUUA | 204 | UAAAU UGAUGGCAUGCACUAUGCGCG ACAUAGUGUA | 731 |
| 2406 | UGUGAUUUAU A UUCCA | 205 | UGGAA UGAUGGCAUGCACUAUGCGCG AUAAAUCACA | 732 |
| 2419 | CCAUUUACAU A AGGAU | 206 | AUCCU UGAUGGCAUGCACUAUGCGCG AUGUAAAUGG | 733 |
| 2425 | ACAUAAGGAU A CACUU | 207 | AAGUG UGAUGGCAUGCACUAUGCGCG AUCCUUAUGU | 734 |
| 2435 | ACACUAUUU G UCAAG | 208 | CUUGA UGAUGGCAUGCACUAUGCGCG AAAUAAGUGU | 735 |
| 2454 | AGCACAAUCU G UAAAU | 209 | AUUUA UGAUGGCAUGCACUAUGCGCG AGAUUGUGCU | 736 |
| 2471 | UUUAACCUAU G UUACA | 210 | UGUAA UGAUGGCAUGCACUAUGCGCG AUAGGUUAAA | 737 |
| 2488 | CAUCUUCAGU G CCAGU | 211 | ACUGG UGAUGGCAUGCACUAUGCGCG ACUGAAGAUG | 738 |
| 2507 | GGGCAAAAUU G UGCAA | 212 | UUGCA UGAUGGCAUGCACUAUGCGCG AAUUUUGCCC | 739 |
| 2509 | GCAAAAUUGU G CAAGA | 213 | UCUUG UGAUGGCAUGCACUAUGCGCG ACAAUUUUGC | 740 |
| 2518 | UGCAAGAGGU G AAGUU | 214 | AACUU UGAUGGCAUGCACUAUGCGCG ACCUCUUGCA | 741 |
| 2527 | UGAAGUUUAU A UUUGA | 215 | UCAAA UGAUGGCAUGCACUAUGCGCG AUAAACUUCA | 742 |
| 2531 | GUUUAUAUUU G AAUAU | 216 | AUAUU UGAUGGCAUGCACUAUGCGCG AAAUAUAAAC | 743 |
| 2535 | AUAUUUGAAU A UCCAU | 217 | AUGGA UGAUGGCAUGCACUAUGCGCG AUUCAAAUAU | 744 |
| 2566 | CUUCUUCCAU A UUAGU | 218 | ACUAA UGAUGGCAUGCACUAUGCGCG AUGGAAGAAG | 745 |
| 2572 | CCAUAUUAGU G UCAUC | 219 | GAUGA UGAUGGCAUGCACUAUGCGCG ACUAAUAUGG | 746 |
| 2580 | GUGUCAUCUU G CCUCC | 220 | GGAGG UGAUGGCAUGCACUAUGCGCG AAGAUGACAC | 747 |
| 2599 | CCUCCACAUU G CCCCA | 221 | UGGGG UGAUGGCAUGCACUAUGCGCG AUGUGGAAGG | 748 |
| 2606 | CAUGCCCCAU G ACUUG | 222 | CAAGU UGAUGGCAUGCACUAUGCGCG AUGGGGCAUG | 749 |
| 2611 | CCCAUGACUU G AUGCA | 223 | UGCAU UGAUGGCAUGCACUAUGCGCG AAGUCAUGGG | 750 |
| 2614 | AUGACUUGAU G CAGUU | 224 | AACUG UGAUGGCAUGCACUAUGCGCG AUCAAGUCAU | 751 |
| 2625 | CAGUUUUAAU A CUUGU | 225 | ACAAG UGAUGGCAUGCACUAUGCGCG AUUAAAACUG | 752 |
| 2629 | UUUAAUACUU G UAAUU | 226 | AAUUA UGAUGGCAUGCACUAUGCGCG AAGUAUUAAA | 753 |
| 2646 | CCCUAACCAU A AGAUU | 227 | AAUCU UGAUGGCAUGCACUAUGCGCG AUGGUUAGGG | 754 |
| 2656 | AAGAUUUACU G CUGCU | 228 | AGCAG UGAUGGCAUGCACUAUGCGCG AGUAAAUCUU | 755 |
| 2659 | AUUUACUGCU G CUGUG | 229 | CACAG UGAUGGCAUGCACUAUGCGCG AGCAGUAAAU | 756 |
| 2662 | UACUGCUGCU G UGGAU | 230 | AUCCA UGAUGGCAUGCACUAUGCGCG AGCAGCAGUA | 757 |
| 2668 | UGCUGUGGAU A UCUCC | 231 | GGAGA UGAUGGCAUGCACUAUGCGCG AUCCACAGCA | 758 |
| 2676 | AUAUCUCCAU A AGUU | 232 | AACUU UGAUGGCAUGCACUAUGCGCG AUGGAGAUAU | 759 |
| 2690 | UUUCCCACU G AGUCA | 233 | UGACU UGAUGGCAUGCACUAUGCGCG AGUGGGAAAA | 760 |
| 2706 | CAUCAGAAAU G CCCUA | 234 | UAGGG UGAUGGCAUGCACUAUGCGCG AUUUCUGAUG | 761 |
| 2744 | AAGAGAAUCU G ACAGA | 235 | UCUGU UGAUGGCAUGCACUAUGCGCG AGAUUCUCUU | 762 |
| 2751 | UCUGACAGAU A CCAUA | 236 | UAUGG UGAUGGCAUGCACUAUGCGCG AUCUGUCAGA | 763 |
| 2756 | CAGAUACCAU A AAGGG | 237 | CCCUU UGAUGGCAUGCACUAUGCGCG AUGGUAUCUG | 764 |

TABLE II-continued

Human K-ras Ribozyme and Target Sequence

| Nt. Position | Substrate Sequence | Seq. ID Nos. | Ribozyme Sequence | Seq. ID Nos. |
|---|---|---|---|---|
| 2766 | AAAGGGAUUU G ACCUA | 238 | UAGGU UGAUGGCAUGCACUAUGCGCG AAAUCCCUUU | 765 |
| 2796 | GGUGGUGGCU G AUGCU | 239 | AGCAU UGAUGGCAUGCACUAUGCGCG AGCCACCACC | 766 |
| 2799 | GGUGGCUGAU G CUUUG | 240 | CAAAG UGAUGGCAUGCACUAUGCGCG AUCAGCCACC | 767 |
| 2804 | CUGAUGCUUU G AACAU | 241 | AUGUU UGAUGGCAUGCACUAUGCGCG AAAGCAUCAG | 768 |
| 2816 | ACAUCUCUUU G CUGCC | 242 | GGCAG UGAUGGCAUGCACUAUGCGCG AAAGAGAUGU | 769 |
| 2819 | UCUCUUUGCU G CCCAA | 243 | UUGGG UGAUGGCAUGCACUAUGCGCG AGCAAAGAGA | 770 |
| 2834 | AUCCAUUAGC G ACAGU | 244 | ACUGU UGAUGGCAUGCACUAUGCGCG GCUAAUGGAU | 771 |
| 2861 | ACCCUGGUAU G AAUAG | 245 | CUAUU UGAUGGCAUGCACUAUGCGCG AUACCAGGGU | 772 |
| 2865 | UGGUAUGAAU A GACAG | 246 | CUGUC UGAUGGCAUGCACUAUGCGCG AUUCAUACCA | 773 |
| 2900 | AGAAUUUAAU A AAGAU | 247 | AUCUU UGAUGGCAUGCACUAUGCGCG AUUAAAUUCU | 774 |
| 2906 | UAAUAAAGAU A GUGCA | 248 | UGCAC UGAUGGCAUGCACUAUGCGCG AUCUUUAUUA | 775 |
| 2909 | UAAAGAUAGU G CAGAA | 249 | UUCUG UGAUGGCAUGCACUAUGCGCG ACUAUCUUUA | 776 |
| 2936 | GGUAAUCUAU A ACUAG | 250 | CUAGU UGAUGGCAUGCACUAUGCGCG AUAGAUUACC | 777 |
| 2964 | UAACAGUAAU G CAUUC | 251 | GAAUG UGAUGGCAUGCACUAUGCGCG AUUACGUUA | 778 |
| 2974 | ACAUUCCAUU G UUUUA | 252 | UAAAA UGAUGGCAUGCACUAUGCGCG AAUGGAAUGU | 779 |
| 2998 | AAAUCUUCAU G CAAUG | 253 | CAUUG UGAUGGCAUGCACUAUGCGCG AUGAAGAUUU | 780 |
| 3003 | UUCAUGCAAU G AAAAA | 254 | UUUUU UGAUGGCAUGCACUAUGCGCG AUUGCAUGAA | 781 |
| 3010 | AAUGAAAAAU A CUUUA | 255 | UAAAG UGAUGGCAUGCACUAUGCGCG AUUUUCAUU | 782 |
| 3022 | UUUAAUUCAU G AAGCU | 256 | AGCUU UGAUGGCAUGCACUAUGCGCG AUGAAUUAAA | 783 |
| 3046 | UUUUUUUGGU G UCAGA | 257 | UCUGA UGAUGGCAUGCACUAUGCGCG ACCAAAAAAA | 784 |
| 3057 | UCAGAGUCUC G CUCUU | 258 | AAGAG UGAUGGCAUGCACUAUGCGCG GAGACUCUGA | 785 |
| 3063 | UCUCGCUCUU G UCACC | 259 | GGUGA UGAUGGCAUGCACUAUGCGCG AAGAGCGAGA | 786 |
| 3080 | AGGCUGGAAU G CAGUG | 260 | CACUG UGAUGGCAUGCACUAUGCGCG AUUCCAGCCU | 787 |
| 3088 | AUGCAGUGGC G CCAUC | 261 | GAUGG UGAUGGCAUGCACUAUGCGCG GCCACUGCAU | 788 |
| 3104 | UCAGCUCACU G CAACC | 262 | GGUUG UGAUGGCAUGCACUAUGCGCG AGUGAGCUGA | 789 |
| 3132 | AGGUUCAAGC G AUUCU | 263 | AGAAU UGAUGGCAUGCACUAUGCGCG GCUUGAACCU | 790 |
| 3141 | CGAUUCUCGU G CCUCG | 264 | CGAGG UGAUGGCAUGCACUAUGCGCG ACGAGAAUCG | 791 |
| 3154 | UCGGCCUCCU G AGUAG | 265 | CUACU UGAUGGCAUGCACUAUGCGCG AGGAGGCCGA | 792 |
| 3176 | UUACAGGCGU G UGCAC | 266 | GUGCA UGAUGGCAUGCACUAUGCGCG ACGCCUGUAA | 793 |
| 3178 | ACAGGCGUGU G CACUA | 267 | UAGUG UGAUGGCAUGCACUAUGCGCG ACACGCCUGU | 794 |
| 3200 | ACUAAUUUUU G UAUUU | 268 | AAAUA UGAUGGCAUGCACUAUGCGCG AAAAAUUAGU | 795 |
| 3229 | GGUUUCACCU G UUGGC | 269 | GCCAA UGAUGGCAUGCACUAUGCGCG AGGUGAAACC | 796 |
| 3247 | GGCUGGUCUC G AACUC | 270 | GAGUU UGAUGGCAUGCACUAUGCGCG GAGACCAGCC | 797 |
| 3255 | UCGAACUCCU G ACCUC | 271 | GAGGU UGAUGGCAUGCACUAUGCGCG AGGAGUUCGA | 798 |
| 3265 | GACCUCAAGU G AUUCA | 272 | UGAAU UGAUGGCAUGCACUAUGCGCG ACUUGAGGUC | 799 |
| 3287 | UUGGCCUCAU A AACCU | 273 | AGGUU UGAUGGCAUGCACUAUGCGCG AUGAGGCCAA | 800 |
| 3293 | UCAUAAACCU G UUUUG | 274 | CAAAA UGAUGGCAUGCACUAUGCGCG AGGUUUAUGA | 801 |
| 3298 | AACCUGUUUU G CAGAA | 275 | UUCUG UGAUGGCAUGCACUAUGCGCG AAAACAGGUU | 802 |
| 3322 | UUCAGCAAAU A UUUAU | 276 | AUAAA UGAUGGCAUGCACUAUGCGCG AUUUGCUGAA | 803 |
| 3329 | AAUAUUUAUU G AGUGC | 277 | GCACU UGAUGGCAUGCACUAUGCGCG AAUAAAUAUU | 804 |
| 3333 | UUUAUUGAGU G CCUAC | 278 | GUAGG UGAUGGCAUGCACUAUGCGCG ACUCAAUAAA | 805 |
| 3344 | CCUACCAGAU G CCAGU | 279 | ACUGG UGAUGGCAUGCACUAUGCGCG AUCUGGUAGG | 806 |
| 3354 | GCCAGUCACC G CACAA | 280 | UUGUG UGAUGGCAUGCACUAUGCGCG GGUGACUGGC | 807 |
| 3372 | CACUGGGUAU A UGGUAU | 281 | UACCA UGAUGGCAUGCACUAUGCGCG AUACCCAGUG | 808 |
| 3374 | CUGGGUAUAU G GUAUC | 282 | GAUAC UGAUGGCAUGCACUAUGCGCG AUAUACCCAG | 809 |
| 3396 | CAAGAGACAU A AUCCC | 283 | GGGAU UGAUGGCAUGCACUAUGCGCG AUGUCUCUUG | 810 |
| 3416 | CUUAGGUACU G CUAGU | 284 | ACUAG UGAUGGCAUGCACUAUGCGCG AGUACCUAAG | 811 |
| 3422 | UACUGCUAGU G UGGUC | 285 | GACCA UGAUGGCAUGCACUAUGCGCG ACUAGCAGUA | 812 |
| 3429 | AGUGUGGUCU G UAAUA | 286 | UAUUA UGAUGGCAUGCACUAUGCGCG AGACCACACU | 813 |
| 3434 | GGUCUGUAAU A UCUUA | 287 | UAAGA UGAUGGCAUGCACUAUGCGCG AUUACAGACC | 814 |
| 3456 | CCUUUGGUAU A CGACC | 288 | GGUCG UGAUGGCAUGCACUAUGCGCG AUACCAAAGG | 815 |
| 3458 | UUUGGUAUAC G ACCCA | 289 | UGGGU UGAUGGCAUGCACUAUGCGCG GUAUACCAAA | 816 |
| 3469 | ACCCAGAGAU A ACACG | 290 | CGUGU UGAUGGCAUGCACUAUGCGCG AUCUCUGGGU | 817 |
| 3474 | GAGAUAACAC G AUGCG | 291 | CGCAU UGAUGGCAUGCACUAUGCGCG GUGUUAUCUC | 818 |
| 3477 | AUAACACGAU G CGUAU | 292 | AUACG UGAUGGCAUGCACUAUGCGCG AUCGUGUUAU | 819 |
| 3492 | UUUUAGUUUU G CAAAG | 293 | CUUUG UGAUGGCAUGCACUAUGCGCG AAAACUAAAA | 820 |
| 3514 | UUUGGUCUCU G UGCCA | 294 | UGGCA UGAUGGCAUGCACUAUGCGCG AGAGACCAAA | 821 |
| 3516 | UGGUCUCUGU G CCAGC | 295 | GCUGG UGAUGGCAUGCACUAUGCGCG ACAGAGACCA | 822 |
| 3527 | CCAGCUCUAU A AUUGU | 296 | ACAAU UGAUGGCAUGCACUAUGCGCG AUAGAGCUGG | 823 |
| 3531 | CUCUAUAAUU G UUUUG | 297 | CAAAA UGAUGGCAUGCACUAUGCGCG AAUUAUAGAG | 824 |
| 3536 | UAAUUGUUUU G CUACG | 298 | CGUAG UGAUGGCAUGCACUAUGCGCG AAAACAAUUA | 825 |
| 3541 | GUUUUGCUAC G AUUCC | 299 | GGAAU UGAUGGCAUGCACUAUGCGCG GUAGCAAAAC | 826 |
| 3550 | CGAUUCCACU G AAACU | 300 | AGUUU UGAUGGCAUGCACUAUGCGCG AGUGGAAUCG | 827 |
| 3560 | GAAACUCUUC G AUCAA | 301 | UUGAU UGAUGGCAUGCACUAUGCGCG GAAGAGUUUC | 828 |
| 3576 | GCUACUUUAU G UAAAU | 302 | AUUUA UGAUGGCAUGCACUAUGCGCG AUAAAGUAGC | 829 |
| 3591 | UCACUUCAUU G UUUUA | 303 | UAAAA UGAUGGCAUGCACUAUGCGCG AAUGAAGUGA | 830 |
| 3604 | UUAAGGAAU A AACUU | 304 | AAGUU UGAUGGCAUGCACUAUGCGCG AUUCCUUAA | 831 |
| 3610 | GAAUAAACUU G AUUAU | 305 | AUAAU UGAUGGCAUGCACUAUGCGCG AAGUUUAUUC | 832 |
| 3616 | ACUUGAUUAU G UUGUU | 306 | AACAA UGAUGGCAUGCACUAUGCGCG AUAAUCAAGU | 833 |
| 3619 | UGAUUAUAUU G UUUUU | 307 | AAAAA UGAUGGCAUGCACUAUGCGCG AAUAUAAUCA | 834 |
| 3636 | UAUUUGGCAU A ACUGU | 308 | ACAGU UGAUGGCAUGCACUAUGCGCG AUGCCAAAUA | 835 |
| 3640 | UGGCAUAACU G UGAUU | 309 | AAUCA UGAUGGCAUGCACUAUGCGCG AGUUAUGCCA | 836 |
| 3642 | GCAUAACUGU G AUUCU | 310 | AGAAU UGAUGGCAUGCACUAUGCGCG ACAGUUAUGC | 837 |
| 3663 | GACAAUUACU G UACAC | 311 | GUGUA UGAUGGCAUGCACUAUGCGCG AGUAAUUGUC | 838 |

TABLE II-continued

Human K-ras Ribozyme and Target Sequence

| Nt. Position | Substrate Sequence | Seq. ID Nos. | Ribozyme Sequence | Seq. ID Nos. |
|---|---|---|---|---|
| 3677 | ACAUUAAGGU G UAUGU | 312 | ACAUA UGAUGGCAUGCACUAUGCGCG ACCUUAAUGU | 839 |
| 3681 | UAAGGUGUAU G UCAGA | 313 | UCUGA UGAUGGCAUGCACUAUGCGCG AUACACCUUA | 840 |
| 3688 | UAUGUCAGAU A UUCAU | 314 | AUGAA UGAUGGCAUGCACUAUGCGCG AUCUGACAUA | 841 |
| 3694 | AGAUAUUCAU A UUGAC | 315 | GUCAA UGAUGGCAUGCACUAUGCGCG AUGAAUAUCU | 842 |
| 3697 | UAUUCAUAUU G ACCCA | 316 | UGGGU UGAUGGCAUGCACUAUGCGCG AAUAUGAAUA | 843 |
| 3706 | UGACCCAAAU G UGUAA | 317 | UUACA UGAUGGCAUGCACUAUGCGCG AUUUGGGUCA | 844 |
| 3708 | ACCCAAAUGU G UAAUA | 318 | UAUUA UGAUGGCAUGCACUAUGCGCG ACAUUUGGGU | 845 |
| 3713 | AAUGUGUAAU A UUCCA | 319 | UGGAA UGAUGGCAUGCACUAUGCGCG AUUACACAUU | 846 |
| 3728 | AGUUUUCUCU G CAUAA | 320 | UUAUG UGAUGGCAUGCACUAUGCGCG AGAGAAAACU | 847 |
| 3732 | UUCUCUGCAU A AGUAA | 321 | UUACU UGAUGGCAUGCACUAUGCGCG AUGCAGAGAA | 848 |
| 3745 | UAAUUAAAAU A UACUU | 322 | AAGUA UGAUGGCAUGCACUAUGCGCG AUUUUAAUUA | 849 |
| 3747 | AUUAAAAUAU A CUUAA | 323 | UUAAG UGAUGGCAUGCACUAUGCGCG AUAUUUUAAU | 850 |
| 3761 | AAAAAUUAAU A GUUUU | 324 | AAAAC UGAUGGCAUGCACUAUGCGCG AUUAAUUUUU | 851 |
| 3781 | GGGUACAAAU A AACAG | 325 | CUGUU UGAUGGCAUGCACUAUGCGCG AUUUGUACCC | 852 |
| 3788 | AAUAAACAGU G CCUGA | 326 | UCAGG UGAUGGCAUGCACUAUGCGCG ACUGUUUAUU | 853 |
| 3792 | AACAGUGCCU G AACUA | 327 | UAGUU UGAUGGCAUGCACUAUGCGCG AGGCACUGUU | 854 |
| 3823 | AAACUUCUAU G UAAAA | 328 | UUUUA UGAUGGCAUGCACUAUGCGCG AUAGAAGUUU | 855 |
| 3837 | AAAUCACUAU G AUUUC | 329 | GAAAU UGAUGGCAUGCACUAUGCGCG AUAGUGAUUU | 856 |
| 3844 | UAUGAUUUCU G AAUUG | 330 | CAAUU UGAUGGCAUGCACUAUGCGCG AGAAAUCAUA | 857 |
| 3849 | UUUCUGAAUU G CUAUG | 331 | CAUAG UGAUGGCAUGCACUAUGCGCG AAUUCAGAAA | 858 |
| 3854 | GAAUUGCUAU G UGAAA | 332 | UUUCA UGAUGGCAUGCACUAUGCGCG AUAGCAAUUC | 859 |
| 3856 | AUUGCUAUGU G AAACU | 333 | AGUUU UGAUGGCAUGCACUAUGCGCG ACAUAGCAAU | 860 |
| 3880 | UUGGAACACU G UUUAG | 334 | CUAAA UGAUGGCAUGCACUAUGCGCG AGUGUUCCAA | 861 |
| 3893 | UAGGUAGGGU G UUAAG | 335 | CUUAA UGAUGGCAUGCACUAUGCGCG ACCCUACCUA | 862 |
| 3903 | GUUAAGACUU G ACACA | 336 | UGUGU UGAUGGCAUGCACUAUGCGCG AAGUCUUAAC | 863 |
| 3938 | AGAAAGAAAU G GCCAU | 337 | AUGGC UGAUGGCAUGCACUAUGCGCG AUUUCUUUCU | 864 |
| 3944 | AAAUGGCCAU A CUUCA | 338 | UGAAG UGAUGGCAUGCACUAUGCGCG AUGGCCAUUU | 865 |
| 3956 | UUCAGGAACU G CAGUG | 339 | CACUG UGAUGGCAUGCACUAUGCGCG AGUUCCUGAA | 866 |
| 3961 | GAACUGCAGU G CUUAU | 340 | AUAAG UGAUGGCAUGCACUAUGCGCG ACUGCAGUUC | 867 |
| 3967 | CAGUGCUUAU G AGGGG | 341 | CCCCU UGAUGGCAUGCACUAUGCGCG AUAAGCACUG | 868 |
| 3975 | AUGAGGGGAU A UUUAG | 342 | CUAAA UGAUGGCAUGCACUAUGCGCG AUCCCCUCAU | 869 |
| 3988 | UAGGCCUCUU G AAUUU | 343 | AAAUU UGAUGGCAUGCACUAUGCGCG AAGAGGCCUA | 870 |
| 3996 | UUGAAUUUUU G AUGUA | 344 | UACAU UGAUGGCAUGCACUAUGCGCG AAAAAUUCAA | 871 |
| 3999 | AAUUUUUGAU G UAGAU | 345 | AUCUA UGAUGGCAUGCACUAUGCGCG AUCAAAAAUU | 872 |
| 4005 | UGAUGUAGAU G GCAU | 346 | AUGCC UGAUGGCAUGCACUAUGCGCG AUCUACAUCA | 873 |
| 4041 | UUACCUUUAU G UGAAC | 347 | GUUCA UGAUGGCAUGCACUAUGCGCG AUAAAGGUAA | 874 |
| 4043 | ACCUUUAUGU G AACUU | 348 | AAGUU UGAUGGCAUGCACUAUGCGCG ACAUAAAGGU | 875 |
| 4050 | UGUGAACUUU G AAUGG | 349 | CCAUU UGAUGGCAUGCACUAUGCGCG AAAGUUCACA | 876 |
| 4054 | AACUUUGAAU G GUUUA | 350 | UAAAC UGAUGGCAUGCACUAUGCGCG AUUCAAGUU | 877 |
| 4071 | CAAAAGAUUU G UUUUU | 351 | AAAAA UGAUGGCAUGCACUAUGCGCG AAAUCUUUUG | 878 |
| 4077 | AUUUGUUUUU G UAGAG | 352 | CUCUA UGAUGGCAUGCACUAUGCGCG AAAAACAAAU | 879 |
| 4110 | UUCUAGAAAU A AAUGU | 353 | ACAUU UGAUGGCAUGCACUAUGCGCG AUUUCUAGAA | 880 |
| 4114 | AGAAAUAAAU G UUACC | 354 | GGUAA UGAUGGCAUGCACUAUGCGCG AUUUAUUUCU | 881 |
| 4152 | AAAAUCCUU G UUGAA | 355 | UUCAA UGAUGGCAUGCACUAUGCGCG AAGGAUUUUU | 882 |
| 4155 | AAUCCUUGUU G AAGUU | 356 | AACUU UGAUGGCAUGCACUAUGCGCG AACAAGGAUU | 883 |
| 4186 | UAAAUUACAU A GACUU | 357 | AAGUC UGAUGGCAUGCACUAUGCGCG AUGUAAUUUA | 884 |
| 4204 | GCAUUAACAU G UUUGU | 358 | ACAAA UGAUGGCAUGCACUAUGCGCG AUGUUAAUGC | 885 |
| 4208 | UAACAUGUUU G UGGAA | 359 | UUCCA UGAUGGCAUGCACUAUGCGCG AAACAUGUUA | 886 |
| 4218 | GUGGAAGAAU A UAGCA | 360 | UGCUA UGAUGGCAUGCACUAUGCGCG AUUCUUCCAC | 887 |
| 4220 | GGAAGAAUAU A GCAGA | 361 | UCUGC UGAUGGCAUGCACUAUGCGCG AUAUUCUUCC | 888 |
| 4231 | GCAGACGUAU A UUGUA | 362 | UACAA UGAUGGCAUGCACUAUGCGCG AUACGUCUGC | 889 |
| 4234 | GACGUAUAUU A UCAA | 363 | UGAUA UGAUGGCAUGCACUAUGCGCG AAUAUACGUC | 890 |
| 4243 | UGUAUCAUUU G AGUGA | 364 | UCACU UGAUGGCAUGCACUAUGCGCG AAAUGAUACA | 891 |
| 4247 | UCAUUUGAGU G AAUGU | 365 | ACAUU UGAUGGCAUGCACUAUGCGCG ACUCAAAUGA | 892 |
| 4251 | UUGAGUGAAU G UUCCC | 366 | GGGAA UGAUGGCAUGCACUAUGCGCG AUUCACUCAA | 893 |
| 4285 | CUAUUUAACU G AGUCA | 367 | UGACU UGAUGGCAUGCACUAUGCGCG AGUUAAAUAG | 894 |
| 4295 | GAGUCACACU G CAUAG | 368 | CUAUG UGAUGGCAUGCACUAUGCGCG AGUGUGACUC | 895 |
| 4299 | CACACUGCAU A GGAAU | 369 | AUUCC UGAUGGCAUGCACUAUGCGCG AUGCAGUGUG | 896 |
| 4323 | UAACUUUUAU A GGUUA | 370 | UAACC UGAUGGCAUGCACUAUGCGCG AUAAAAGUUA | 897 |
| 4337 | UAUCAAAACU G UUGUC | 371 | GACAA UGAUGGCAUGCACUAUGCGCG AGUUUUGAUA | 898 |
| 4340 | CAAAACUGUU G UCACC | 372 | GGUGA UGAUGGCAUGCACUAUGCGCG AACAGUUUUG | 899 |
| 4349 | UGUCACCAUU G CACAA | 373 | UUGUG UGAUGGCAUGCACUAUGCGCG AAUGGUGACA | 900 |
| 4359 | GCACAAUUUU G UCCUA | 374 | UAGGA UGAUGGCAUGCACUAUGCGCG AAAAUUGUGC | 901 |
| 4367 | UUGUCCUAUU G UAUAC | 375 | GUAUA UGAUGGCAUGCACUAUGCGCG AUUAGGACAA | 902 |
| 4369 | GUCCUAUAUU G UACAU | 376 | AUGUA UGAUGGCAUGCACUAUGCGCG AUAUUAGGAC | 903 |
| 4371 | CCUAUAUAUU G CAUAG | 377 | CUAUG UGAUGGCAUGCACUAUGCGCG AUAUAUUAGG | 904 |
| 4375 | AUAUAUACAU A GAAAC | 378 | GUUUC UGAUGGCAUGCACUAUGCGCG AUGUAUAUAU | 905 |
| 4384 | UAGAAACUUU G UGGGG | 379 | CCCCA UGAUGGCAUGCACUAUGCGCG AAAGUUUCUA | 906 |
| 4393 | UGUGGGGCAU G UUAAG | 380 | CUUAA UGAUGGCAUGCACUAUGCGCG AUGCCCCACA | 907 |
| 4408 | GUUACAGUUU G CACAA | 381 | UUGUG UGAUGGCAUGCACUAUGCGCG AAACUGUAAC | 908 |
| 4427 | CAUCUCAUUU G UAUUC | 382 | GAAUA UGAUGGCAUGCACUAUGCGCG AAAUGAGAUG | 909 |
| 4437 | GUAUUCCAUU G AUUUU | 383 | AAAAU UGAUGGCAUGCACUAUGCGCG AAUGGAAUAC | 910 |
| 4480 | AAACAGUAUA A UAUAA | 384 | UUAUA UGAUGGCAUGCACUAUGCGCG AUACUGUUUU | 911 |
| 4482 | AACAGUAUAU A UAACU | 385 | AGUUA UGAUGGCAUGCACUAUGCGCG AUAUACUGUU | 912 |

TABLE II-continued

Human K-ras Ribozyme and Target Sequence

| Nt. Position | Substrate Sequence | Seq. ID Nos. | Ribozyme Sequence | Seq. ID Nos. |
|---|---|---|---|---|
| 4484 | CAGUAUAUAU A ACUUU | 386 | AAAGU UGAUGGCAUGCACUAUGCGCG AUAUAUACUG | 913 |
| 4527 | AAAACUAUCU A AAGAU | 387 | AUCUU UGAUGGCAUGCACUAUGCGCG AGAUAGUUUU | 914 |
| 4541 | AUUUCCAUUU G UCAAA | 388 | UUUGA UGAUGGCAUGCACUAUGCGCG AAAUGGAAAU | 915 |
| 4554 | AAAAGUAAU G AUUUC | 389 | GAAAU UGAUGGCAUGCACUAUGCGCG AUUACUUUUU | 916 |
| 4562 | AUGAUUCUU G AUAAU | 390 | AUUAU UGAUGGCAUGCACUAUGCGCG AAGAAAUCAU | 917 |
| 4565 | AUUUCUUGAU A AUUGU | 391 | ACAAU UGAUGGCAUGCACUAUGCGCG AUCAAGAAAU | 918 |
| 4569 | CUUGAUAAUU G UGUAG | 392 | CUACA UGAUGGCAUGCACUAUGCGCG AAUUAUCAAG | 919 |
| 4571 | UGAUAAUUGU G UAGUG | 393 | CACUA UGAUGGCAUGCACUAUGCGCG ACAAUUAUCA | 920 |
| 4576 | AUUGUGUAGU G AAUGU | 394 | ACAUU UGAUGGCAUGCACUAUGCGCG ACUACACAAU | 921 |
| 4580 | UGUAGUGAAU G UUUUU | 395 | AAAAA UGAUGGCAUGCACUAUGCGCG AUUCACUACA | 922 |
| 4606 | CAGUUACCUU G AAAGC | 396 | GCUUU UGAUGGCAUGCACUAUGCGCG AAGGUAACUG | 923 |
| 4613 | CUUGAAAGCU G AAUUU | 397 | AAAUU UGAUGGCAUGCACUAUGCGCG AGCUUUCAAG | 924 |
| 4621 | CUGAAUUUAU A UUUAG | 398 | CUAAA UGAUGGCAUGCACUAUGCGCG AUAAAUUCAG | 925 |
| 4635 | AGUAACUUCU G UGUUA | 399 | UAACA UGAUGGCAUGCACUAUGCGCG AGAAGUUACU | 926 |
| 4637 | UAACUUCUGU G UUAAU | 400 | AUUAA UGAUGGCAUGCACUAUGCGCG ACAGAAGUUA | 927 |
| 4643 | CUGUGUUAAU A CUGGA | 401 | UCCAG UGAUGGCAUGCACUAUGCGCG AUUAACACAG | 928 |
| 4650 | AAUACUGGAU A GCAUG | 402 | CAUGC UGAUGGCAUGCACUAUGCGCG AUCCAGUAUU | 929 |
| 4655 | UGGAUAGCAU G AAUUC | 403 | GAAUU UGAUGGCAUGCACUAUGCGCG AUGCUAUCCA | 930 |
| 4662 | CAUGAAUUCU G CAUUG | 404 | CAAUG UGAUGGCAUGCACUAUGCGCG AGAAUUCAUG | 931 |
| 4667 | AUUCUGCAUU G AGAAA | 405 | UUUCU UGAUGGCAUGCACUAUGCGCG AAUGCAGAAU | 932 |
| 4675 | UUGAGAAACU G AAUAG | 406 | CUAUU UGAUGGCAUGCACUAUGCGCG AGUUUCUCAA | 933 |
| 4679 | GAAACUGAAU A GCUGU | 407 | ACAGC UGAUGGCAUGCACUAUGCGCG AUUCAGUUUC | 934 |
| 4683 | CUGAAUAGCU G UCAUA | 408 | UAUGA UGAUGGCAUGCACUAUGCGCG AGCUAUUCAG | 935 |
| 4688 | UAGCUGUCAU A AAAUG | 409 | CAUUU UGAUGGCAUGCACUAUGCGCG AUGACAGCUA | 936 |
| 4693 | GUCAUAAAAU G CUUUC | 410 | GAAAG UGAUGGCAUGCACUAUGCGCG AUUUUAUGAC | 937 |
| 4715 | AAAGAAAGAU A CUCAC | 411 | GUGAG UGAUGGCAUGCACUAUGCGCG AUCUUUCUUU | 938 |
| 4723 | AUACUCACAU G AGUUC | 412 | GAACU UGAUGGCAUGCACUAUGCGCG AUGUGAGUAU | 939 |
| 4731 | AUGAGUUCUU G AAGAA | 413 | UUCUU UGAUGGCAUGCACUAUGCGCG AAGAACUCAU | 940 |
| 4738 | CUUGAAGAAU A GUCAU | 414 | AUGAC UGAUGGCAUGCACUAUGCGCG AUUCUUCAAG | 941 |
| 4744 | GAAUAGUCAU A ACUAG | 415 | CUAGU UGAUGGCAUGCACUAUGCGCG AUGACUAUUC | 942 |
| 4760 | AUUAAGAUCU G UGUUU | 416 | AAACA UGAUGGCAUGCACUAUGCGCG AGAUCUUAAU | 943 |
| 4762 | UAAGAUCUGU G UUUUA | 417 | UAAAA UGAUGGCAUGCACUAUGCGCG ACAGAUCUUA | 944 |
| 4775 | UUAGUUUAAU A GUUUG | 418 | CAAAC UGAUGGCAUGCACUAUGCGCG AUUAAACUAA | 945 |
| 4780 | UUAAUAGUUU G AAGUG | 419 | CACUU UGAUGGCAUGCACUAUGCGCG AAACUAUUAA | 946 |
| 4785 | AGUUUGAAGU G CCUGU | 420 | ACAGG UGAUGGCAUGCACUAUGCGCG ACUUCAAACU | 947 |
| 4789 | UGAAGUGCCU G UUUGG | 421 | CCAAA UGAUGGCAUGCACUAUGCGCG AGGCACUUCA | 948 |
| 4798 | UGUUUGGGAU A AUGAU | 422 | AUCAU UGAUGGCAUGCACUAUGCGCG AUCCCAAACA | 949 |
| 4801 | UUGGGAUAAU G AUAGG | 423 | CCUAU UGAUGGCAUGCACUAUGCGCG AUUAUCCCAA | 950 |
| 4804 | GGAUAAUGAU A GGUAA | 424 | UUACC UGAUGGCAUGCACUAUGCGCG AUCAUUAUCC | 951 |
| 4817 | UAAUUUAGAU G AAUUU | 425 | AAAUU UGAUGGCAUGCACUAUGCGCG AUCUAAAUUA | 952 |
| 4843 | AAAGUUAUCU G CAGUU | 426 | AACUG UGAUGGCAUGCACUAUGCGCG AGAUAACUUU | 953 |
| 4851 | CUGCAGUUAU G UUGAG | 427 | CUCAA UGAUGGCAUGCACUAUGCGCG AUAACUGCAG | 954 |
| 4854 | CAGUUAUGUU G AGGGC | 428 | GCCCU UGAUGGCAUGCACUAUGCGCG AACAUAACUG | 955 |
| 4904 | GGGUUACAGU G UUUUA | 429 | UAAAA UGAUGGCAUGCACUAUGCGCG ACUGUAACCC | 956 |
| 4913 | UGUUUUAUCC G AAAGU | 430 | ACUUU UGAUGGCAUGCACUAUGCGCG GGAUAAAACA | 957 |
| 4932 | CAAUUCCACU G UCUUG | 431 | CAAGA UGAUGGCAUGCACUAUGCGCG AGUGGAAUUG | 958 |
| 4937 | CCACUGUCUU G UGUUU | 432 | AAACA UGAUGGCAUGCACUAUGCGCG AAGACAGUGG | 959 |
| 4939 | ACUGUCUUGU G UUUC | 433 | GAAAA UGAUGGCAUGCACUAUGCGCG ACAAGACAGU | 960 |
| 4947 | GUGUUUUCAU G UUGAA | 434 | UUCAA UGAUGGCAUGCACUAUGCGCG AUGAAAACAC | 961 |
| 4950 | UUUUCAUGUU G AAAAU | 435 | AUUUU UGAUGGCAUGCACUAUGCGCG AACAUGAAAA | 962 |
| 4956 | UGUUGAAAAU A CUUUU | 436 | AAAAG UGAUGGCAUGCACUAUGCGCG AUUUUCAACA | 963 |
| 4962 | AAAAUACUUU G CAUUU | 437 | AAAUG UGAUGGCAUGCACUAUGCGCG AAAAGUAUUU | 964 |
| 4975 | UUUUUCCUUU G AGUGC | 438 | GCACU UGAUGGCAUGCACUAUGCGCG AAAGGAAAAA | 965 |
| 4979 | UCCUUUGAGU G CCAAU | 439 | AUUGG UGAUGGCAUGCACUAUGCGCG ACUCAAAGGA | 966 |
| 5009 | AUUUCUUAAU G UAACA | 440 | UGUUA UGAUGGCAUGCACUAUGCGCG AUUAAGAAAU | 967 |
| 5016 | AAUGUAACAU G UUUAC | 441 | GUAAA UGAUGGCAUGCACUAUGCGCG AUGUUACAUU | 968 |
| 5029 | UACCUGGCCU G UCUUU | 442 | AAAGA UGAUGGCAUGCACUAUGCGCG AGGCCAGGUA | 969 |
| 5046 | AACUAUUUU G UAUAG | 443 | CUAUA UGAUGGCAUGCACUAUGCGCG AAAAAUAGUU | 970 |
| 5050 | AUUUUUGUAU A GUGUA | 444 | UACAC UGAUGGCAUGCACUAUGCGCG AUACAAAAAU | 971 |
| 5053 | UUUGUAUAGU G UAAAC | 445 | GUUUA UGAUGGCAUGCACUAUGCGCG ACUAUACAAA | 972 |
| 5060 | AGUGUAAACU G AAACA | 446 | UGUUU UGAUGGCAUGCACUAUGCGCG AGUUUACACU | 973 |
| 5067 | ACUGAAACAU G CACAU | 447 | AUGUG UGAUGGCAUGCACUAUGCGCG AUGUUUCAGU | 974 |
| 5076 | UGCACAUUUU G UACAU | 448 | AUGUA UGAUGGCAUGCACUAUGCGCG AAAAUGUGCA | 975 |
| 5083 | UUUGUACAUU G UGCUU | 449 | AAGCA UGAUGGCAUGCACUAUGCGCG AAUGUACAAA | 976 |
| 5085 | UGUACAUUGU G CUUUC | 450 | GAAAG UGAUGGCAUGCACUAUGCGCG ACAAUGUACA | 977 |
| 5095 | GCUUUCUUUU G UGGGU | 451 | ACCCA UGAUGGCAUGCACUAUGCGCG AAAAGAAAGC | 978 |
| 5104 | UGUGGGUCAU A UGCAG | 452 | CUGCA UGAUGGCAUGCACUAUGCGCG AUGACCCACA | 979 |
| 5106 | UGGGUCAUAU G CAGUG | 453 | CACUG UGAUGGCAUGCACUAUGCGCG AUAUGACCCA | 980 |
| 5111 | CAUAUGCAGU G UGAUC | 454 | GAUCA UGAUGGCAUGCACUAUGCGCG ACUGCAUAUG | 981 |
| 5113 | UAUGCAGUGU G AUCCA | 455 | UGGAU UGAUGGCAUGCACUAUGCGCG ACACUGCAUA | 982 |
| 5122 | UGAUCCAGUU G UUUUC | 456 | GAAAA UGAUGGCAUGCACUAUGCGCG AACUGGAUCA | 983 |
| 5140 | UCAUUGGUU G CGCUG | 457 | CAGCG UGAUGGCAUGCACUAUGCGCG AACCAAUGA | 984 |
| 5142 | AUUUGGUUGC G CUGAC | 458 | GUCAG UGAUGGCAUGCACUAUGCGCG GCAACCAAAU | 985 |
| 5145 | UGGUUGCGCU G ACCUA | 459 | UAGGU UGAUGGCAUGCACUAUGCGCG AGCGCAACCA | 986 |

TABLE II-continued

Human K-ras Ribozyme and Target Sequence

| Nt. Position | Substrate Sequence | Seq. ID Nos. | Ribozyme Sequence | Seq. ID Nos. |
|---|---|---|---|---|
| 5156 | ACCUAGGAAU G UUGGU | 460 | ACCAA UGAUGGCAUGCACUAUGCGCG AUUCCUAGGU | 987 |
| 5165 | UGUUGGUCAU A UCAAA | 461 | UUUGA UGAUGGCAUGCACUAUGCGCG AUGACCAACA | 988 |
| 5181 | CAUUAAAAAU G ACCAC | 462 | GUGGU UGAUGGCAUGCACUAUGCGCG AUUUUUAAUG | 989 |
| 5196 | CUCUUUUAAU G AAAUU | 463 | AAUUU UGAUGGCAUGCACUAUGCGCG AUUAAAAGAG | 990 |
| 5213 | ACUUUUAAAU G UUUAU | 464 | AUAAA UGAUGGCAUGCACUAUGCGCG AUUUAAAAGU | 991 |
| 5219 | AAAUGUUUAU G GGAGU | 465 | ACUCC UGAUGGCAUGCACUAUGCGCG AUAAACAUUU | 992 |
| 5227 | AUAGGAGUAU G UGCUG | 466 | CAGCA UGAUGGCAUGCACUAUGCGCG AUACUCCUAU | 993 |
| 5229 | AGGAGUAUGU G CUGUG | 467 | CACAG UGAUGGCAUGCACUAUGCGCG ACAUACUCCU | 994 |
| 5232 | AGUAUGUGCU G UGAAG | 468 | CUUCA UGAUGGCAUGCACUAUGCGCG AGCACAUACU | 995 |
| 5234 | UAUGUGCUGU G AAGUG | 469 | CACUU UGAUGGCAUGCACUAUGCGCG ACAGCACAUA | 996 |
| 5239 | GCUGUGAAGU G AUCUA | 470 | UAGAU UGAUGGCAUGCACUAUGCGCG ACUUCACAGC | 997 |
| 5251 | UCUAAAAUUU G UAAUA | 471 | UAUUA UGAUGGCAUGCACUAUGCGCG AAAUUUUAGA | 998 |
| 5256 | AAUUUGUAAU A UUUUU | 472 | AAAAA UGAUGGCAUGCACUAUGCGCG AUUACAAAUU | 999 |
| 5262 | UAAUAUUUUU G UCAUG | 473 | CAUGA UGAUGGCAUGCACUAUGCGCG AAAAAUAUUA | 1000 |
| 5267 | UUUUUGUCAU G AACUG | 474 | CAGUU UGAUGGCAUGCACUAUGCGCG AUGACAAAAA | 1001 |
| 5272 | GUCAUGAACU G UACUA | 475 | UAGUA UGAUGGCAUGCACUAUGCGCG AGUUCAUGAC | 1002 |
| 5290 | CCUAAUUAUU G UAAUG | 476 | CAUUA UGAUGGCAUGCACUAUGCGCG AAUAAUUAGG | 1003 |
| 5295 | UUAUUGUAAU G UAAUA | 477 | UAUUA UGAUGGCAUGCACUAUGCGCG AUUACAUAA | 1004 |
| 5300 | GUAAUGUAAU A AAAAU | 478 | AUUUU UGAUGGCAUGCACUAUGCGCG AUUACAUUAC | 1005 |
| 5306 | UAAUAAAAAU A GUUAC | 479 | GUAAC UGAUGGCAUGCACUAUGCGCG AUUUUUAUUA | 1006 |
| 5315 | UAGUUACAGU G ACUAU | 480 | AUAGU UGAUGGCAUGCACUAUGCGCG ACUGUAACUA | 1007 |
| 5321 | CAGUGACUAU G AGUGU | 481 | ACACU UGAUGGCAUGCACUAUGCGCG AUAGUCACUG | 1008 |
| 5325 | GACUAUGAGU G UGUAU | 482 | AUACA UGAUGGCAUGCACUAUGCGCG ACUCAUAGUC | 1009 |
| 5327 | CUAUGAGUGU G UAUUU | 483 | AAAUA UGAUGGCAUGCACUAUGCGCG ACACUCAUAG | 1010 |
| 5339 | AUUUAUUCAU G CAAAU | 484 | AUUUG UGAUGGCAUGCACUAUGCGCG AUGAAUAAAU | 1011 |
| 5347 | AUGCAAAUUU G AACUG | 485 | CAGUU UGAUGGCAUGCACUAUGCGCG AAAUUUGCAU | 1012 |
| 5352 | AAUUUGAACU G UUUGC | 486 | GCAAA UGAUGGCAUGCACUAUGCGCG AGUUCAAAUU | 1013 |
| 5356 | UGAACUGUUU G CCCCG | 487 | CGGGG UGAUGGCAUGCACUAUGCGCG AAACAGUUCA | 1014 |
| 5361 | UGUUUGCCCC G AAAUG | 488 | CAUUU UGAUGGCAUGCACUAUGCQCG GGGGCAAACA | 1015 |
| 5366 | GCCCCGAAAU G GAUAU | 489 | AUAUC UGAUGGCAUGCACUAUGCGCG AUUUCGGGGC | 1016 |
| 5370 | CGAAAUGGAU A UGGAU | 490 | AUCCA UGAUGGCAUGCACUAUGCGCG AUCCAUUUCG | 1017 |
| 5372 | AAAUGGAUAU G GAUAC | 491 | GUAUC UGAUGGCAUGCACUAUGCGCG AUAUCCAUUU | 1018 |
| 5376 | GGAUAUGGAU A CUUUA | 492 | UAAAG UGAUGGCAUGCACUAUGCGCG AUCCAUAUCC | 1019 |
| 5383 | GAUACUUUAU A AGCCA | 493 | UGGCU UGAUGGCAUGCACUAUGCGCG AUAAAGUAUC | 1020 |
| 5390 | UAUAAGCCAU A GACAC | 494 | GUGUC UGAUGGCAUGCACUAUGCGCG AUGGCUUAUA | 1021 |
| 5399 | UAGACACUAU A GUAUA | 495 | UAUAC UGAUGGCAUGCACUAUGCGCG AUAGUGUCUA | 1022 |
| 5404 | ACUAUAGUAU A CCAGU | 496 | ACUGG UGAUGGCAUGCACUAUGCGCG AUACUAUAGU | 1023 |
| 5410 | GUAUACCAGU G AAUCU | 497 | AGAUU UGAUGGCAUGCACUAUGCGCG ACUGGUAUAC | 1024 |
| 5421 | AAUCUUUUAU G CAGCU | 498 | AGCUG UGAUGGCAUGCACUAUGCGCG AUAAAAGAUU | 1025 |
| 5428 | UAUGCAGCUU G UUAGA | 499 | UCUAA UGAUGGCAUGCACUAUGCGCG AAGCUGCAUA | 1026 |
| 5459 | UCUAAAAGGU G CUGUG | 500 | CACAG UGAUGGCAUGCACUAUGCGCG ACCUUUUAGA | 1027 |
| 5462 | AAAAGGUGCU G UGGAU | 501 | AUCCA UGAUGGCAUGCACUAUGCGCG AGCACCUUUU | 1028 |
| 5468 | UGCUGUGGAU A UUAUG | 502 | CAUAA UGAUGGCAUGCACUAUGCGCG AUCCACAGCA | 1029 |
| 5473 | UGGAUAUUAU G UAAAG | 503 | CUUUA UGAUGGCAUGCACUAUGCGCG AUAAUAUCCA | 1030 |
| 5483 | GUAAAGGCGU G UUUGC | 504 | GCAAA UGAUGGCAUGCACUAUGCGCG ACGCCUUUAC | 1031 |
| 5487 | AGGCGUGUUU G CUUAA | 505 | UUAAG UGAUGGCAUGCACUAUGCGCG AAACACGCCU | 1032 |
| 5505 | AAUUUCCAU A UUUAG | 506 | CUAAA UGAUGGCAUGCACUAUGCGCG AUGGAAAAUU | 1033 |
| 5519 | AGAAGUAGAU G CAAAA | 507 | UUUUG UGAUGGCAUGCACUAUGCGCG AUCUACUUCU | 1034 |
| 5532 | AAACAAAUCU G CCUUU | 508 | AAAGG UGAUGGCAUGCACUAUGCGCG AGAUUUGUUU | 1035 |
| 5540 | CUGCCUUUAU G ACAAA | 509 | UUUGU UGAUGGCAUGCACUAUGCGCG AUAAAGGCAG | 1036 |
| 5551 | ACAAAAAAU A GGAUA | 510 | UAUCC UGAUGGCAUGCACUAUGCGCG AUUUUUUGU | 1037 |
| 5556 | AAAAUAGGAU A ACAUU | 511 | AAUGU UGAUGGCAUGCACUAUGCGCG AUCCUAUUUU | 1038 |
| 5586 | UUUUAUCAAU A AGGUA | 512 | UACCU UGAUGGCAUGCACUAUGCGCG AUUGAUAAAA | 1039 |
| 5595 | UAAGGUAAUU A AUACA | 513 | UGUAU UGAUGGCAUGCACUAUGCGCG AAUUACCUUA | 1040 |
| 5598 | GGUAAUUGAU A CACAA | 514 | UUGUG UGAUGGCAUGCACUAUGCGCG AUCAAUUACC | 1041 |
| 5609 | CACAACAGGU A ACUUG | 515 | CAAGU UGAUGGCAUGCACUAUGCGCG ACCUGUUGUG | 1042 |
| 5650 | CAACAUUAAU A AUGGA | 516 | UCCAU UGAUGGCAUGCACUAUGCGCG AUUAAUGUUG | 1043 |
| 5653 | CAUUAAUAAU A GAAAU | 517 | AUUUC UGAUGGCAUGCACUAUGCGCG AUUAUUAAUG | 1044 |
| 5659 | UAAUGGAAAU A AUUGA | 518 | UCAAU UGAUGGCAUGCACUAUGCGCG AUUUCCAUUA | 1045 |
| 5663 | GGAAAUAAUU A AAUAG | 519 | CUAUU UGAUGGCAUGCACUAUGCGCG AAUUAUUUCC | 1046 |
| 5667 | AUAAUUGAAU A GUUAG | 520 | CUAAC UGAUGGCAUGCACUAUGCGCG AUUCAAUUAU | 1047 |
| 5677 | AGUUAGUUAU G UAUGU | 521 | ACAUA UGAUGGCAUGCACUAUGCGCG AUAACUAACU | 1048 |
| 5681 | AGUAUGUAU G UUAAU | 522 | AUUAA UGAUGGCAUGCACUAUGCGCG AUACAUAACU | 1049 |
| 5687 | GUAUGUUAAU G CCAGU | 523 | ACUGG UGAUGGCAUGCACUAUGCGCG AUUAACAUAC | 1050 |
| 5725 | CAGAAGUAAU G ACUCC | 524 | GGAGU UGAUGGCAUGCACUAUGCGCG AUUACUUCUG | 1051 |
| 5733 | AUGACUCCAU A CAUAU | 525 | AUAUG UGAUGGCAUGCACUAUGCGCG AUGGAGUCAU | 1052 |
| 5737 | CUCCAUACAU A UUAUU | 526 | AAUAA UGAUGGCAUGCACUAUGCGCG AUGUAUGGAG | 1053 |
| 5752 | UUAUUUCUAU A ACUAC | 527 | GUAGU UGAUGGCAUGCACUAUGCGCG AUAGAAAUAA | 1054 |

Input Sequence = KRAS2 Cut Site = AUR/, YG/M or UG/U.
Stem Length = 5/10. Core Sequence = UGAUGGCAUGCACUAUGCGCG
Seq1 = KRAS2 (*Homo sapiens* v-Ki-ras2 Kirsten rat sarcoma 2 viral oncogene homolog (KRAS2) mRNA.; 5775 bp)

TABLE III

Table III. Rate constants for ribozyme 40 cleavage at various triplets with next nucleotide specified. Reaction conditions as in text, na = no activity detectable, single turnover kinetics.

| Cleavable Triplet | $k_{cat}$ (min$^{-1}$) |
|---|---|
| $A_{14.2}U_{14.1}G_{15}/A_{1.1}$ | 0.91 |
| $A_{14.2}U_{14.1}A_{15}/A_{1.1}$ | 0.34 |
| $A_{14.2}U_{14.1}U_{15}/A_{1.1}$ | 0.007 |
| $A_{14.2}A_{14.1}G_{15}/A_{1.1}$ | 0.57 |
| $A_{14.2}U_{14.1}G_{15}/U_{1.1}$ | 0.35 |
| $A_{14.2}U_{14.1}G_{15}/G_{1.1}$ | 0.66 |

/ = site of cleavage
Numbering convention as shown in FIG. 8

TABLE IV

Sequence Specificity and Rate Constants for Stabilized Ribozymes

| Cleavage Site Sequence | RPI # | Corresponding Ribozyme | Seq. ID Nos | k rel to WT |
|---|---|---|---|---|
| WT = UG/A | 13159 | 5'-aac guu GAU$_s$ ggc auG cac uau gcg cga ugg cua ggc-3' | 1055 | 1 |
| UG/C | 12768 | 5'-aac ggu GAU$_s$ ggc auG cac uau gcg cga ugg cua ggc-3' | 1056 | 0.97 |
| CG/A | 13161 | 5'-aac guu GAU$_s$ ggc auG cac uau gcg cgg ugg cua ggc-3' | 1057 | 0.76 |
| AG/A | 12763 | 5'-aac guu GAU$_s$ ggc auG cac uau gcg cgu ugg cua ggc-3' | 1058 | 0.70 |
| UG/U | 12764 | 5'-aac gau GAU$_s$ ggc auG cac uau gcg cga ugg cua ggc-3' | 1059 | 0.35 |
| CG/U | 12766 | 5'-aac gau GAU$_s$ ggc auG cac uau gcg cgg ugg cua ggc-3' | 1060 | 0.12 |
| CG/C | 12770 | 5'-aac ggu GAU$_s$ ggc auG cac uau gcg cgg ugg cua ggc-3' | 1061 | 0.1 |
| AG/C | 12771 | 5'-aac ggu GAU$_s$ ggc auG cac uau gcg cgu ugg cua ggc-3' | 1062 | 0.07 |
| AG/U | 12767 | 5'-aac gau GAU$_s$ ggc auG cac uau gcg cgu ugg cua ggc-3' | 1063 | 0.06 |
| CG/G | 12774 | 5'-aac gcu GAU$_s$ ggc auG cac uau gcg cgg ugg cua ggc-3' | 1064 | 0.06 |
| UG/G | 12772 | 5'-aac gcu GAU$_s$ ggc auG cac uau gcg cga ugg cua ggc-3' | 1065 | 0.04 |
| GG/A | 13160 | 5'-aac guu GAU$_s$ ggc auG cac uau gcg cgc ugg cua ggc-3' | 1066 | 0.02 |
| GG/C | 12769 | 5'-aac ggu GAU$_s$ ggc auG cac uau gcg cgc ugg cua ggc-3' | 1067 | 0.01 |
| AG/G | 12775 | 5'-aac gcu GAU$_s$ ggc auG cac uau gcg cgu ugg cua ggc-3' | 1068 | 0.008 |
| GG/U | 12765 | 5'-aac gau GAU$_s$ ggc auG cac uau gcg cgc ugg cua ggc-3' | 1069 | 0.007 |
| GG/G | 12773 | 5'-aac gcu GAU$_s$ ggc auG cac uau gcg cgc ugg cua ggc-3' | 1070 | 0.002 |

Lower case = 2'-O-Methyl
Upper case = Ribo
$_s$ = phosphorothioate
/= site of cleavage
WT $U_{14.1}G_{15}/A_{1.1}$ (FIG. 8) K obs = 0.266 min$^{-1}$

TABLE V

Human K-ras Ribozyme Sequences

| RPI # | Nt. Position | Alias | Ribozyme Sequence | Seq. ID No. |
|---|---|---|---|---|
| 12779 | 63 | krasM-63 GCl.Rz-5/10 stabl | a$_s$g$_s$cug uGAU$_s$ gcauGcacuaugc gcg aucgucaagg B | 1071 |
| 12780 | 95 | krasM-95 GCl.Rz-5/10 stabl | g$_s$a$_s$uca uGAU$_s$ gcauGcacuaugc gcg auucguccac B | 1072 |
| 12781 | 142 | krasM-142 GCl.Rz-5/10 stabl | u$_s$u$_s$cuc uGAU$_s$ gcauGcacuaugc gcg aucaauuacu B | 1073 |
| 12782 | 163 | krasM-163 GCl.Rz-5/10 stabl | g$_s$a$_s$gaa uGAU$_s$ gcauGcacuaugc gcg auccaagaga B | 1074 |
| 12783 | 201 | krasM-201 GCl.Rz-5/10 stabl | u$_s$c$_s$ccu uGAU$_s$ gcauGcacuaugc gcg auugcacugu B | 1075 |
| 12784 | 216 | krasM-216 GCl.Rz-5/10 stabl | g$_s$u$_s$ccu uGAU$_s$ gcauGcacuaugc gcg auguacuggu B | 1076 |
| 12785 | 256 | krasM-256 GCl.Rz-5/10 stabl | a$_s$g$_s$uau uGAU$_s$ gcauGcacuaugc gcg auuuauggca B | 1077 |
| 12786 | 325 | krasM-325 GCl.Rz-5/10 stabl | a$_s$g$_s$gua uGAU$_s$ gcauGcacuaugc gcg aucuucagag B | 1078 |
| 12787 | 333 | krasM-333 GCl.Rz-5/10 stabl | a$_s$g$_s$gac uGAU$_s$ gcauGcacuaugc gcg auaggguacau B | 1079 |
| 12788 | 353 | krasM-353 GCl.Rz-5/10 stabl | a$_s$a$_s$uca uGAU$_s$ gcauGcacuaugc gcg auuuauuccc B | 1080 |
| 12789 | 412 | krasM-412 GCl.Rz-5/10 stabl | a$_s$a$_s$uuc uGAU$_s$ gcauGcacuaugc gcg auaacuucuu B | 1081 |
| 12790 | 460 | krasM-460 GCl.Rz-5/10 stabl | g$_s$g$_s$cau uGAU$_s$ gcauGcacuaugc gcg aucaacaccc B | 1082 |
| 12791 | 463 | krasM-463 GCl.Rz-5/10 stabl | g$_s$a$_s$agg uGAU$_s$ gcauGcacuaugc gcg aucaucaaca B | 1083 |
| 12792 | 472 | krasM-472 GCl.Rz-5/10 stabl | u$_s$a$_s$aug uGAU$_s$ gcauGcacuaugc gcg auagaaggca B | 1084 |
| 12793 | 520 | krasM-520 GCl.Rz-5/10 stabl | u$_s$s$_s$uac uGAU$_s$ gcauGcacuaugc gcg aucuuugcuc B | 1085 |
| 12794 | 706 | krasM-706 GCl.Rz-5/10 stabl | a$_s$u$_s$aag uGAU$_s$ gcauGcacuaugc gcg auuuaaggua B | 1086 |
| 12795 | 787 | krasM-787 GCl.Rz-5/10 stabl | a$_s$c$_s$agg uGAU$_s$ gcauGcacuaugc gcg auugcuaguu B | 1087 |
| 12796 | 843 | krasM-843 GCl.Rz-5/10 stabl | a$_s$a$_s$cug uGAU$_s$ gcauGcacuaugc gcg augcaccaaa B | 1088 |
| 12797 | 882 | krasM-882 GCl.Rz-5/10 stabl | a$_s$c$_s$caa uGAU$_s$ gcauGcacuaugc gcg auucacacuu B | 1089 |
| 12798 | 903 | krasM-903 GCl.Rz-5/10 stabl | a$_s$g$_s$cuu uGAU$_s$ gcauGcacuaugc gcg auuaauuugu B | 1090 |

TABLE V-continued

Human K-ras Ribozyme Sequences

| RPI # | Nt. Position | Alias | Ribozyme Sequence | Seq. ID No. |
|---|---|---|---|---|
| 12799 | 951 | krasM-951 GCl.Rz-5/10 stab1 | $u_s a_s$auc uGAU$_s$g gcauGcacuaugc gcg auuuauguga B | 1091 |
| 12800 | 1022 | krasM-1022 GCl.Rz-5/10 stab1 | $a_s a_s$gcc uGAU$_s$g gcauGcacuaugc gcg auaaauuugu B | 1092 |
| 12801 | 1034 | krasM-1034 GCl.Rz-5/10 stab1 | $a_s u_s$cau uGAU$_s$g gcauGcacuaugc gcg aucaggaagc B | 1093 |
| 12802 | 1037 | krasM-1037 GCl.Rz-5/10 stab1 | $a_s g_s$aau uGAU$_s$g gcauGcacuaugc gcg aucaucagga B | 1094 |
| 12803 | 1079 | krasM-1079 GCl.Rz-5/10 stab1 | $a_s c_s$auu uGAU$_s$g gcauGcacuaugc gcg aucagggaug B | 1095 |
| 12804 | 1083 | krasM-1083 GCl.Rz-5/10 stab1 | $c_s u_s$uua uGAU$_s$g gcauGcacuaugc gcg auucaucagg B | 1096 |
| 12805 | 1206 | krasM-1206 GCl.Rz-5/10 stab1 | $g_s u_s$uuc uGAU$_s$g gcauGcacuaugc gcg auugccuugu B | 1097 |
| 12806 | 1218 | krasM-1218 GCl.Rz-5/10 stab1 | $g_s g_s$ccu uGAU$_s$g gcauGcacuaugc gcg auaauaguuu B | 1098 |
| 12807 | 1267 | krasM-1267 GCl.Rz-5/10 stab1 | $a_s a_s$agc uGAU$_s$g gcauGcacuaugc gcg auuaggaguc B | 1099 |
| 12808 | 1301 | krasM-1301 GCl.Rz-5/10 stab1 | $a_s a_s$ucc uGAU$_s$g gcauGcacuaugc gcg auucauacug B | 1100 |
| 12809 | 1312 | krasM-1312 GCl.Rz-5/10 stab1 | $g_s u_s$ugc uGAU$_s$g gcauGcacuaugc gcg auaauaaucc B | 1101 |
| 12810 | 1529 | krasM-1529 GCl.Rz-5/10 stab1 | $u_s a_s$agc uGAU$_s$g gcauGcacuaugc gcg auaacuggcc B | 1102 |
| 12811 | 1594 | krasM-1594 GCl.Rz-5/10 stab1 | $c_s u_s$cuc uGAU$_s$g gcauGcacuaugc gcg augaaagcuc B | 1103 |
| 12812 | 1611 | krasM-1611 GCl.Rz-5/10 stab1 | $c_s a_s$guc uGAU$_s$g gcauGcacuaugc gcg augcugugaa B | 1104 |
| 12813 | 1650 | krasM-1650 GCl.Rz-5/10 stab1 | $c_s a_s$aug uGAU$_s$g gcauGcacuaugc gcg aucguacaac B | 1105 |
| 12814 | 1694 | krasM-1694 GCl.Rz-5/10 stab1 | $u_s g_s$agc uGAU$_s$g gcauGcacuaugc gcg auccaaacug B | 1106 |
| 12815 | 1867 | krasM-1867 GCl.Rz-5/10 stab1 | $c_s a_s$cuu uGAU$_s$g gcauGcacuaugc gcg auuguuuaaa B | 1107 |
| 12816 | 1936 | krasM-1936 GCl.Rz-5/10 stab1 | $g_s u_s$guu uGAU$_s$g gcauGcacuaugc gcg augcaauguu B | 1108 |
| 12817 | 1960 | krasM-1960 GCl.Rz-5/10 stab1 | $u_s u_s$aaa uGAU$_s$g gcauGcacuaugc gcg auggaucaga B | 1109 |
| 12818 | 2046 | krasM-2046 GCl.Rz-5/10 stab1 | $c_s a_s$ugc uGAU$_s$g gcauGcacuaugc gcg aucucacuuc B | 1110 |
| 12819 | 2051 | krasM-2051 GCl.Rz-5/10 stab1 | $c_s u_s$cac uGAU$_s$g gcauGcacuaugc gcg augccaucuc B | 1111 |
| 12820 | 2103 | krasM-2103 GCl.Rz-5/10 stab1 | $a_s c_s$acc uGAU$_s$g gcauGcacuaugc gcg aucuagaacc B | 1112 |
| 12821 | 2158 | krasM-2158 GCl.Rz-5/10 stab1 | $u_s u_s$uaa uGAU$_s$g gcauGcacuaugc gcg augaagaaau B | 1113 |
| 12822 | 2214 | krasM-2214 GCl.Rz-5/10 stab1 | $u_s g_s$gaa uGAU$_s$g gcauGcacuaugc gcg auaaaucaca B | 1114 |
| 12823 | 2227 | krasM-2227 GCl.Rz-5/10 stab1 | $a_s u_s$ccu uGAU$_s$g gcauGcacuaugc gcg auguaaaugg B | 1115 |
| 12824 | 2422 | krasM-2422 GCl.Rz-5/10 stab1 | $a_s a_s$cug uGAU$_s$g gcauGcacuaugc gcg aucaagucau B | 1116 |
| 12825 | 2454 | krasM-2454 GCl.Rz-5/10 stab1 | $a_s a_s$ucu uGAU$_s$g gcauGcacuaugc gcg augguuaggg B | 1117 |
| 12826 | 2476 | krasM-2476 GCl.Rz-5/10 stab1 | $g_s g_s$aga uGAU$_s$g gcauGcacuaugc gcg auccacagca B | 1118 |
| 12827 | 2484 | krasM-2484 GCl.Rz-5/10 stab1 | $a_s a_s$cuu uGAU$_s$g gcauGcacuaugc gcg auggagauau B | 1119 |
| 12828 | 2514 | krasM-2514 GCl.Rz-5/10 stab1 | $u_s a_s$ggg uGAU$_s$g gcauGcacuaugc gcg auuucugaug B | 1120 |
| 12829 | 2564 | krasM-2564 GCl Rz-5/10 stab1 | $c_s c_s$cuu uGAU$_s$g gcauGcacuaugc gcg augguaucug B | 1121 |
| 12830 | 2607 | krasM-2607 GCl.Rz-5/10 stab1 | $c_s a_s$aag uGAU$_s$g gcauGcacuaugc gcg aucagccacc B | 1122 |
| 12831 | 2669 | krasM-2669 GCl.Rz-5/10 stab1 | $c_s u_s$auu uGAU$_s$g gcauGcacuaugc gcg auaccagggu B | 1123 |
| 12832 | 2806 | krasM-2806 GCl.Rz-5/10 stab1 | $c_s a_s$uug uGAU$_s$g gcauGcacuaugc gcg augaagauuu B | 1124 |
| 12833 | 2830 | krasM-2830 GCl.Rz-5/10 stab1 | $a_s g_s$ccu uGAU$_s$g gcauGcacuaugc gcg augaauuaaa B | 1125 |
| 12834 | 2888 | krasM-2888 GCl.Rz-5/10 stab1 | $c_s a_s$cug uGAU$_s$g gcauGcacuaugc gcg auuccagccu B | 1126 |
| 12835 | 3095 | krasM-3095 GCl.Rz-5/10 stab1 | $a_s g_s$guu uGAU$_s$g gcauGcacuaugc gcg augaggccaa B | 1127 |
| 12836 | 3130 | krasM-3130 GCl.Rz-5/10 stab1 | $a_s u_s$aaa uGAU$_s$g gcauGcacuaugc gcg auuugcugaa B | 1128 |
| 12837 | 3152 | krasM-3152 GCl.Rz-5/10 stab1 | $a_s c_s$ugg uGAU$_s$g gcauGcacuaugc gcg aucugguagg B | 1129 |
| 12838 | 3180 | krasM-3180 GCl.Rz-5/10 stab1 | $u_s a_s$cca uGAU$_s$g gcauGcacuaugc gcg auacccagug B | 1130 |
| 12839 | 3182 | krasM-3182 GCl.Rz-5/10 stab1 | $g_s a_s$uac uGAU$_s$g gcauGcacuaugc gcg auauacccag B | 1131 |
| 12840 | 3204 | krasM-3204 GCl.Rz-5/10 stab1 | $g_s g_s$gau uGAU$_s$g gcauGcacuaugc gcg augucucuug B | 1132 |
| 12841 | 3264 | krasM-3264 GCl.Rz-5/10 stab1 | $g_s g_s$ucg uGAU$_s$g gcauGcacuaugc gcg auaccaaagg B | 1133 |
| 12842 | 3277 | krasM-3277 GCl.Rz-5/10 stab1 | $c_s g_s$ugu uGAU$_s$g gcauGcacuaugc gcg aucucugggu B | 1134 |
| 12843 | 3285 | krasM-3285 GCl.Rz-5/10 stab1 | $a_s u_s$acg uGAU$_s$g gcauGcacuaugc gcg aucguguuau B | 1135 |
| 12844 | 3335 | krasM-3335 GCl.Rz-5/10 stab1 | $a_s c_s$aau uGAU$_s$g gcauGcacuaugc gcg auagagcugg B | 1136 |
| 12845 | 3412 | krasM-3412 GCl.Rz-5/10 stab1 | $a_s a_s$guu uGAU$_s$g gcauGcacuaugc gcg auuccuuuaa B | 1137 |
| 12846 | 3444 | krasM-3444 GCl.Rz-5/10 stab1 | $a_s c_s$agu uGAU$_s$g gcauGcacuaugc gcg augccaaaua B | 1138 |
| 12847 | 3514 | krasM-3514 GCl.Rz-5/10 stab1 | $u_s u_s$aca uGAU$_s$g gcauGcacuaugc gcg auuugguca B | 1139 |
| 12848 | 3521 | krasM-3521 GCl.Rz-5/10 stab1 | $u_s g_s$gaa uGAU$_s$g gcauGcacuaugc gcg auuacacauu B | 1140 |
| 12849 | 3540 | krasM-3540 GCl.Rz-5/10 stab1 | $u_s u_s$acu uGAU$_s$g gcauGcacuaugc gcg augcagaaa B | 1141 |
| 12850 | 3589 | krasM-3589 GCl.Rz-5/10 stab1 | $c_s a_s$guu uGAU$_s$g gcauGcacuaugc gcg auuuuguaccc B | 1142 |
| 12851 | 3662 | krasM-3662 GCl.Rz-5/10 stab1 | $u_s u_s$uca uGAU$_s$g gcauGcacuaugc gcg auagcaauuc B | 1143 |
| 12852 | 3746 | krasM-3746 GCl.Rz-5/10 stab1 | $a_s u_s$ggc uGAU$_s$g gcauGcacuaugc gcg auuucuuucu B | 1144 |
| 12853 | 3752 | krasM-3752 GCl.Rz-5/10 stab1 | $u_s g_s$aag uGAU$_s$g gcauGcacuaugc gcg auggccauuu B | 1145 |
| 12854 | 3813 | krasM-3813 GCl.Rz-5/10 stab1 | $a_s u_s$cug uGAU$_s$g gcauGcacuaugc gcg aucuacauca B | 1146 |
| 12855 | 3849 | krasM-3849 GCl.Rz-5/10 stab1 | $g_s u_s$uca uGAU$_s$g gcauGcacuaugc gcg auaaagguaa B | 1147 |
| 12856 | 3862 | krasM-3862 GCl.Rz-5/10 stab1 | $u_s a_s$aac uGAU$_s$g gcauGcacuaugc gcg auucaaaguu B | 1148 |
| 12857 | 4012 | krasM-4012 GCl.Rz-5/10 stab1 | $a_s c_s$aaa uGAU$_s$g gcauGcacuaugc gcg auguuaaugc B | 1149 |
| 12858 | 4026 | krasM-4026 GCl.Rz-5/10 stab1 | $u_s g_s$cua uGAU$_s$g gcauGcacuaugc gcg auucuuccac B | 1150 |
| 12859 | 4028 | krasM-4028 GCl.Rz-5/10 stab1 | $u_s c_s$ugc uGAU$_s$g gcauGcacuaugc gcg auauucuucc B | 1151 |
| 12860 | 4039 | krasM-4039 GCl.Rz-5/10 stab1 | $u_s a_s$caa uGAU$_s$g gcauGcacuaugc gcg auacgucugc B | 1152 |
| 12861 | 4059 | krasM-4059 GCl.Rz-5/10 stab1 | $g_s g_s$gaa uGAU$_s$g gcauGcacuaugc gcg auucacucaa B | 1153 |
| 12862 | 4107 | krasM-4107 GCl.Rz-5/10 stab1 | $a_s u_s$ucc uGAU$_s$g gcauGcacuaugc gcg augcagugug B | 1154 |
| 12863 | 4458 | krasM-4458 GCl.Rz-5/10 stab1 | $c_s a_s$ugc uGAU$_s$g gcauGcacuaugc gcg auccaguauu B | 1155 |
| 12864 | 4463 | krasM-4463 GCl.Rz-5/10 stab1 | $g_s a_s$auu uGAU$_s$g gcauGcacuaugc gcg augcuaucca B | 1156 |
| 12865 | 4487 | krasM-4487 GCl.Rz-5/10 stab1 | $a_s c_s$agc uGAU$_s$g gcauGcacuaugc gcg auucaguuc B | 1157 |
| 12866 | 4606 | krasM-4606 GCl.Rz-5/10 stab1 | $a_s u_s$cau uGAU$_s$g gcauGcacuaugc gcg aucccaaaca B | 1158 |
| 12867 | 4609 | krasM-4609 GCl.Rz-5/10 stab1 | $c_s u_s$uau uGAU$_s$g gcauGcacuaugc gcg auuauccaa B | 1159 |
| 12868 | 4659 | krasM-4659 GCl.Rz-5/10 stab1 | $c_s u_s$caa uGAU$_s$g gcauGcacuaugc gcg auaacugcag B | 1160 |
| 12869 | 4875 | krasM-4875 GCl.Rz-5/10 stab1 | $a_s u_s$gug uGAU$_s$g gcauGcacuaugc gcg auguuucagu B | 1161 |
| 12870 | 4912 | krasM-4912 GCl.Rz-5/10 stab1 | $c_s u_s$gca uGAU$_s$g gcauGcacuaugc gcg augacccaca B | 1162 |
| 12871 | 4914 | krasM-4914 GCl.Rz-5/10 stab1 | $c_s a_s$cug uGAU$_s$g gcauGcacuaugc gcg auaugaccca B | 1163 |
| 12872 | 4964 | krasM-4964 GCl.Rz-5/10 stab1 | $a_s c_s$caa uGAU$_s$g gcauGcacuaugc gcg auuccaggu B | 1164 |

TABLE V-continued

Human K-ras Ribozyme Sequences

| RPI # | Nt. Position | Alias | Ribozyme Sequence | Seq. ID No. |
|---|---|---|---|---|
| 12873 | 4973 | krasM-4973 GCl.Rz-5/10 stab1 | u$_s$u$_s$uga uGAU$_s$g gcauGcacuaugc gcg augaccaaca B | 1165 |
| 12874 | 5035 | krasM-5035 GCl.Rz-5/10 stab1 | c$_s$a$_s$gca uGAU$_s$g gcauGcacuaugc gcg auacuccuau B | 1166 |

Lower Case = 2'-O-methyl
Upper Case = Ribo
s = phosphorothioate linkage
B = inverted deoxyabasic

What is claimed is:

1. A nucleic acid molecule with endonuclease activity to cleave a substrate RNA having the formula V:

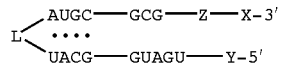

wherein, X and Y are independent oligonucleotides comprising 3 or more nucleotides; L is a linker which may be present or absent, wherein said linker, when present, is independently or in combination a nucleotide linker, or a non-nucleotide linker; Z is independently a nucleotide which is complementary to a nucleotide in the substrate RNA and C, G, A, and U represent cytidine, guanosine, adenosine, and uridine nucleotides, respectively, wherein each of said X and Y oligonucleotides independently comprises a sequence complementary to a portion of the substrate RNA.

2. The nucleic acid molecule with endonuclease activity of claim 1, wherein said L is a nucleotide linker.

3. The nucleic acid molecule with endonuclease activity of claim 2, wherein said nucleotide linker is a sequence selected from the group consisting of 5'-GCACU-3', 5'-GAACU-3', 5'-GCACC-3', 5'-GNACU-3', 5'-GNGCU-3', 5'-GNCCU-3', 5'-GNUCU-3', 5'-GNGUU-3', 5'-GNCUU-3', 5'-GNUUU-3', 5'-GNAUU-3', 5'-GNACA-3', 5'-GNGCA-3', 5'-GNCCA-3', and 5'-GNUCA-3', whereby N can be selected from the group consisting of A, G, C, or U.

4. The nucleic acid molecule with endonuclease activity of claim 2, wherein said nucleotide linker is a nucleic acid aptamer.

5. The nucleic acid molecule with endonuclease activity of claim 4, wherein said aptamer is an ATP aptamer.

6. The nucleic acid molecule with endonuclease activity of claim 1, wherein said L is non-nucleotide linker.

7. The nucleic acid molecule with endonuclease activity of claim 1, wherein said chemical linkage is independently or in combination selected from the group consisting of phosphate ester, amide, phosphorothioate, phosphorodithioate, arabino, and arabinofluoro linkages.

8. The nucleic acid molecule with endonuclease activity of claim 1, wherein said nucleic acid molecule is chemically synthesized.

9. The nucleic acid molecule with endonuclease activity of claim 1, wherein said nucleic acid molecule comprises at least four ribonucleotide residues.

10. The nucleic acid molecule with endonuclease activity of claim 1, wherein said nucleic acid molecule comprises at least five ribonucleotide residues.

11. The nucleic acid molecule with endonuclease activity of claim 1, wherein said nucleic acid molecule comprises at least one sugar modification.

12. The nucleic acid molecule with endonuclease activity of claim 1, wherein said nucleic acid molecule comprises at least one nucleic acid base modification.

13. The nucleic acid molecule with endonuclease activity of claim 1, wherein said nucleic acid molecule comprises at least one phosphate backbone modification.

14. The nucleic acid molecule with endonuclease activity of claim 11, wherein said sugar modification is selected from the group consisting of 2'-H, 2'-O-methyl, 2'-O-allyl, 2'-C-allyl, and 2'-deoxy-2'-amino.

15. The nucleic acid molecule with endonuclease activity of claim 13, wherein said phosphate backbone modification is selected from the group consisting of phosphorothioate, phosphorodithioate, and amide.

16. The nucleic acid molecule with endonuclease activity of claim 1, wherein said nucleic acid molecule comprises a 5'-cap or a 3'-cap or both a 5'-cap and a 3'-cap.

17. The nucleic acid molecule with endonuclease activity of claim 16, wherein said 5'-cap is a phosphorothioate modification of at least one 5'-terminal nucleotide in said nucleic acid molecule.

18. The nucleic acid molecule with endonuclease activity of claim 16, wherein said 5'-cap is a phosphorothioate modification of at least two 5'-terminal nucleotides in said nucleic acid molecule.

19. The nucleic acid molecule with endonuclease activity of claim 16, wherein said 5'-cap is a phosphorothioate modification of at least three 5'-terminal nucleotides in said nucleic acid molecule.

20. The nucleic acid molecule with endonuclease activity of claim 16, wherein said 5'-cap is a phosphorothioate modification of at least four 5'-terminal nucleotides in said nucleic acid molecule.

21. The nucleic acid molecule with endonuclease activity of claim 16, wherein said 3'-cap is a 3'-3' inverted riboabasic moiety.

22. The nucleic acid molecule with endonuclease activity of claim 16, wherein said 3'-cap is a 3'-3' inverted deoxyriboabasic moiety.

23. The nucleic acid molecule with endonuclease activity of claim 1, wherein said nucleic acid molecule with endonuclease activity cleaves a separate nucleic acid molecule.

24. The nucleic acid molecule with endonuclease activity of claim 23, wherein said separate nucleic acid molecule is RNA.

25. The nucleic acid molecule with endonuclease activity of claim 23, wherein said nucleic acid molecule with endonuclease activity comprises between 12 and 100 bases complementary to said separate nucleic acid molecule.

26. The nucleic acid molecule with endonuclease activity of claim 23, wherein said nucleic acid molecule with endonuclease activity comprises between 14 and 24 bases complementary to said separate nucleic acid molecule.

27. The nucleic acid molecule with endonuclease activity of claim 1, wherein the length of said X is equal to the length of said Y.

28. The nucleic acid molecule with endonuclease activity of claim 1, wherein the length of said X is not equal to the length of said Y.

29. The nucleic acid molecule with endonuclease activity of claim 28, wherein the length of said X is 10 nucleotides and the length of said Y is 5 nucleotides.

30. The nucleic acid molecule with endonuclease activity of claim 1, wherein said Z is selected from the group consisting of Adenosine, Uridine, Guanosine, Cytidine and Inosine.

31. A cell including the nucleic acid molecule with endonuclease activity of claim 1.

32. The cell of claim 31, wherein said cell is a mammalian cell.

33. The cell of claim 32, wherein said cell is a human cell.

34. An expression vector comprising nucleic acid sequence encoding at least one of the nucleic acid molecule with endonuclease activity of claim 1, in a manner which allows expression of that nucleic acid molecule with endonuclease activity.

35. A cell including the expression vector of claim 34.

36. The cell of claim 35, wherein said cell is a mammalian cell.

37. The cell of claim 36, wherein said cell is a human cell.

38. A method of cleaving a separate nucleic acid comprising, contacting the nucleic acid molecule of claim 1 with said separate nucleic acid molecule to achieve the cleavage of said separate nucleic acid molecule.

39. The method of claim 38, wherein said cleavage is carried out in the presence of a divalent cation.

40. The method of claim 39, wherein said divalent cation is $Mg^{2+}$.

41. The expression vector of claim 34, wherein said vector comprises:
   a) a transcription initiation region;
   b) a transcription termination region;
   c) a nucleic acid sequence encoding at least one said nucleic acid molecule; and
wherein said sequence is operably linked to said initiation region and said termination region, in a manner which allows expression and/or delivery of said nucleic acid molecule.

42. The expression vector of claim 34, wherein said vector comprises:
   a) a transcription initiation region;
   b) a transcription termination region;
   c) an open reading frame;
   d) a nucleic acid sequence encoding at least one said nucleic acid molecule, wherein said gene is operably linked to the 3'-end of said open reading frame; and
wherein said sequence is operably linked to said initiation region, said open reading frame and said termination region, in a manner which allows expression and/or delivery of said nucleic acid molecule.

43. The expression vector of claim 34, wherein said vector comprises:
   a) a transcription initiation region;
   b) a transcription termination region;
   c) an intron;
   d) a nucleic acid sequence encoding at least one said nucleic acid molecule; and
wherein said sequence is operably linked to said initiation region, said intron and said termination region, in a manner which allows expression and/or delivery of said nucleic acid molecule.

44. The expression vector of claim 34, wherein said vector comprises:
   a) a transcription initiation region;
   b) a transcription termination region;
   c) an intron;
   d) an open reading frame;
   e) a nucleic acid sequence encoding at least one said nucleic acids molecule, wherein said sequence is operably linked to the 3'-end, of said open reading frame; and
wherein said sequence is operably linked to said initiation region, said intron, said open reading frame and said termination region, in a manner which allows expression and/or delivery of said nucleic acid molecule.

45. The nucleic acid molecule of claim 23, wherein said nucleic acid molecule comprises at least five ribose residues; a phosphorothioate, phosphorodithioate, or 2'-C-allyl modification at position 6 of said nucleic acid; at least ten 2'-O-alkyl modifications, and a 3'- cap structure.

46. The nucleic acid molecule of claim 45, wherein said 2'-O-alkyl modifications is selected from the group consisting of 2'-O-methyl and 2'-O-allyl.

47. The nucleic acid molecule of claim 45, wherein said 3'-cap is 3'-3' inverted riboabasic moiety.

48. The nucleic acid molecule of claim 45, wherein said 3'-cap is 3'-3' inverted deoxyriboabasic moiety.

49. The nucleic acid molecule of claim 45, wherein said 3'-cap is 3'-3' inverted nucleotide.

50. The nucleic acid molecule of claim 45, wherein said nucleic acid comprises phosphorothioate linkages in at least two of the 5' terminal nucleotides.

* * * * *